United States Patent
Bloom

(10) Patent No.: US 10,125,182 B2
(45) Date of Patent: Nov. 13, 2018

(54) PEPTIDES HORMONE ANALOGUES DERIVABLE FROM PREPROGLUCAGON

(71) Applicant: IMPERIAL INNOVATIONS LIMITED, London (GB)

(72) Inventor: Stephen Robert Bloom, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 15/122,613

(22) PCT Filed: Mar. 5, 2015

(86) PCT No.: PCT/GB2015/050644
§ 371 (c)(1),
(2) Date: Aug. 30, 2016

(87) PCT Pub. No.: WO2015/132599
PCT Pub. Date: Sep. 11, 2015

(65) Prior Publication Data
US 2017/0058013 A1    Mar. 2, 2017

(30) Foreign Application Priority Data
Mar. 6, 2014 (GB) .................................. 1404002.6

(51) Int. Cl.
*A61K 38/00* (2006.01)
*C07K 14/605* (2006.01)

(52) U.S. Cl.
CPC ............ *C07K 14/605* (2013.01); *A61K 38/00* (2013.01)

(58) Field of Classification Search
None
See application file for complete search history.

(56) References Cited

FOREIGN PATENT DOCUMENTS

| WO | 2005035761 | | 4/2005 |
|---|---|---|---|
| WO | 2013004983 | | 1/2013 |
| WO | WO2013/004983 | * | 1/2013 |
| WO | 2014041375 | | 3/2014 |

OTHER PUBLICATIONS

Ueda et al. Analytical Sciences Aug. 1992, vol. 8 p. 487-489.*

* cited by examiner

*Primary Examiner* — Jeanette M Lieb
(74) *Attorney, Agent, or Firm* — Michael B. Rubin; Bozicevic, Field & Francis LLP

(57) ABSTRACT

Peptide hormone analogs of the formula X-V are provided herein, wherein X is a glucagon analog or a GLP1 analog, and V is a C-terminal extension amino acid sequence comprising at least four amino acid residues, at least three of said residues being His. Also provided herein are pharmaceutical compositions comprising said analogs, and methods of using said analogs for the treatment of conditions such as obesity and diabetes.

14 Claims, 79 Drawing Sheets
Specification includes a Sequence Listing.

FIG. 1A

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 1 | 1 | 1698 | His | Ser | Gln | Gly | Thr | Phe | Thr | Ser | Asp | Tyr | Ser | Lys | Tyr | Leu | Asp |
| 2 | 2 | 1700 | His | Ser | Gln | Gly | Thr | Phe | Thr | Ser | Asp | Tyr | Ser | Lys | Tyr | Leu | Asp |
| 3 | 3 | 1712 | His | Ser | Gln | Gly | Thr | Phe | Thr | Ser | Asp | Tyr | Ser | Lys | Tyr | Leu | Asp |
| 4 | 4 | 1713 | His | Ser | Gln | Gly | Thr | Phe | Thr | Ser | Asp | Tyr | Ser | His | Tyr | Leu | Asp |
| 5 | 5 | 1716 | His | Ser | Gln | Gly | Thr | Phe | Thr | Ser | Asp | Tyr | Ser | His | Tyr | Leu | Asp |
| 6 | 6 | 1718 | His | Ser | Gln | Gly | Thr | Phe | Thr | Ser | Asp | Tyr | Ser | His | Tyr | Leu | Asp |
| 7 | 7 | 1720 | His | Ser | Gln | Gly | Thr | Phe | Thr | Ser | Asp | Tyr | Ser | Lys | Tyr | Leu | Asp |
| 8 | 8 | 1722 | His | Ser | Gln | Gly | Thr | Phe | Thr | Ser | Asp | Tyr | Ser | His | Tyr | Leu | Asp |
| 9 | 9 | 1729 | His | Ser | Gln | Gly | Thr | Phe | Thr | Ser | Asp | Tyr | Ser | Lys | Tyr | Leu | Asp |
| 10 | 10 | 1730 | His | Ser | Gln | Gly | Thr | Phe | Thr | Ser | Asp | Tyr | Ser | Lys | Tyr | Leu | Asp |
| 11 | 11 | 1731 | His | Ser | Gln | Gly | Thr | Phe | Thr | Ser | Asp | Tyr | Ser | Lys | Tyr | Leu | Asp |
| 12 | 12 | 1735 | His | Ser | Gln | Gly | Thr | Phe | Thr | Ser | Asp | Tyr | Ser | Lys | Tyr | Leu | Asp |
| 13 | 13 | 1736 | His | Ser | Gln | Gly | Thr | Phe | Thr | Ser | Asp | Tyr | Ser | Lys | Tyr | Leu | Asp |
| 14 | 14 | 1741 | His | Ser | Gln | Gly | Thr | Phe | Thr | Ser | Asp | Tyr | Ser | His | Tyr | Leu | Asp |
| 15 | 15 | 1744 | His | Ser | Gln | Gly | Thr | Phe | Thr | Ser | Asp | Tyr | Ser | Lys | Tyr | Leu | Asp |
| 16 | 16 | 1745 | His | Ser | Gln | Gly | Thr | Phe | Thr | Ser | Asp | Tyr | Ser | Lys | Tyr | Leu | Asp |
| 17 | 17 | 1747 | His | Ser | Gln | Gly | Thr | Phe | Thr | Ser | Asp | Tyr | Ser | Lys | Tyr | Leu | Asp |

FIG. 1B

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 1 | 1 | 1698 | Glu | Arg | Arg | Ala | His | Glu | Phe | Ile | Glu | Trp | Leu | Leu | Asn | Gly |
| 2 | 2 | 1700 | Ser | Arg | Arg | Ala | His | Glu | Phe | Val | Gln | Trp | Leu | Leu | Asn | Gly |
| 3 | 3 | 1712 | Glu | Arg | Arg | Ala | His | Glu | Phe | Val | Glu | Trp | Leu | Leu | Asn | Gly |
| 4 | 4 | 1713 | Gln | Arg | Arg | Ala | His | Glu | Phe | Val | Glu | Trp | Leu | Leu | Asn | Gly |
| 5 | 5 | 1716 | Gln | Arg | Arg | Ala | His | Glu | Phe | Ile | Glu | Trp | Leu | Leu | Asn | Gly |
| 6 | 6 | 1718 | Gln | Arg | Arg | Ala | His | Glu | Phe | Ile | Gln | Trp | Leu | Leu | Asn | Gly |
| 7 | 7 | 1720 | Glu | Arg | Arg | Ala | His | Glu | Phe | Ile | Glu | Trp | Leu | Leu | Asn | Gly |
| 8 | 8 | 1722 | Ser | Lys | Arg | Ala | His | Glu | Phe | Ile | Gln | Trp | Leu | Leu | Asn | Gly |
| 9 | 9 | 1729 | Glu | Arg | Arg | Ala | His | Glu | Phe | Ile | Glu | Trp | Leu | Leu | Asn | Gly |
| 10 | 10 | 1730 | Glu | Arg | Arg | Ala | His | Glu | Phe | Ile | Gln | Trp | Leu | Leu | Asn | Thr |
| 11 | 11 | 1731 | Glu | Arg | Arg | Ala | His | Glu | Phe | Ile | Glu | Trp | Leu | Leu | Asn | Thr |
| 12 | 12 | 1735 | Glu | Lys | Arg | Ala | His | Glu | Phe | Ile | Gln | Trp | Leu | Leu | Asn | Thr |
| 13 | 13 | 1736 | Glu | Lys | Arg | Ala | His | Glu | Phe | Ile | Glu | Trp | Leu | Leu | Asn | Thr |
| 14 | 14 | 1741 | Ser | Lys | Arg | Ala | His | Glu | Phe | Ile | Gln | Trp | Leu | Leu | Asn | Thr |
| 15 | 15 | 1744 | Glu | Arg | Arg | Ala | His | Glu | Phe | Ile | Glu | Trp | Leu | Leu | Asn | Gly |
| 16 | 16 | 1745 | Glu | Arg | Arg | Ala | His | Glu | Phe | Ile | Glu | Trp | Leu | Leu | Asn | Gly |
| 17 | 17 | 1747 | Glu | Lys | Arg | Ala | His | Glu | Phe | Ile | Glu | Trp | Leu | Leu | Asn | Gly |

FIG. 1C

| Analogue no. | SEQ ID NO. | G no. | 30 | 31 | 32 | 33 | 34 | 35 | 36 | 37 |
|---|---|---|---|---|---|---|---|---|---|---|
| 1 | 1 | 1698 | His | His | His | His | | | | |
| 2 | 2 | 1700 | Gly | His | His | His | | | | |
| 3 | 3 | 1712 | His | His | His | His | | | | |
| 4 | 4 | 1713 | His | His | His | His | | | | |
| 5 | 5 | 1716 | His | His | His | His | | | | |
| 6 | 6 | 1718 | His | His | His | His | | | | |
| 7 | 7 | 1720 | His | His | His | His | | | | |
| 8 | 8 | 1722 | His | His | His | His | | | | |
| 9 | 9 | 1729 | Gly | His | His | His | His | | | |
| 10 | 10 | 1730 | Gly | His | His | His | His | | | |
| 11 | 11 | 1731 | Gly | His | His | His | NH2 | | | |
| 12 | 12 | 1735 | Gly | His | His | His | | | | |
| 13 | 13 | 1736 | Gly | His | His | His | NH2 | | | |
| 14 | 14 | 1741 | His | His | His | His | | | | |
| 15 | 15 | 1744 | His | His | His | His | His | | | |
| 16 | 16 | 1745 | His | His | His | His | Glu | | | |
| 17 | 17 | 1747 | His | His | His | His | | | | |

FIG. 1D

| Analogue no. | SEQ ID NO. | G no. | hGCGr cAMP | | hGLP-1r cAMP | | Mouse food intake inhibition (500nmol/kg) | | Rat food intake inhibition (500 nmol/kg with 1:1 Zn) |
|---|---|---|---|---|---|---|---|---|---|
| | | | n | vs hGCG | n | vs hGLP-1 | 0-24 | 0-48 | 0-24 |
| 1 | 1 | 1698 | 5 | 1.3 | 2 | 1.4 | 86 | 71 | 41 |
| 2 | 2 | 1700 | 2 | 0.7 | | | 72 | 51 | 42 |
| 3 | 3 | 1712 | 2 | 1.8 | | | 88 | 62 | 37 |
| 4 | 4 | 1713 | 2 | 2.0 | | | 45 | 27 | 13 |
| 5 | 5 | 1716 | 2 | 1.9 | | | 47 | 32 | 26 |
| 6 | 6 | 1718 | 2 | 4.6 | | | 70 | 46 | 7 |
| 7 | 7 | 1720 | 6 | 1.0 | 3 | 2.1 | 69 | 48 | 43 |
| 8 | 8 | 1722 | 1 | 5.3 | | | 58 | 45 | 5 |
| 9 | 9 | 1729 | 4 | 1.1 | 3 | 3.9 | 78 | 64 | 49 |
| 10 | 10 | 1730 | 4 | 1.8 | 3 | 4.3 | 69 | | 47 |
| 11 | 11 | 1731 | 4 | 1.3 | 1 | 5.1 | 65 | | 38 |
| 12 | 12 | 1735 | 2 | 2.7 | | | 58 | | 33 |
| 13 | 13 | 1736 | 1 | 3.6 | | | 77 | 45 | 36 |
| 14 | 14 | 1741 | 2 | 5.0 | | | 57 | | 25 |
| 15 | 15 | 1744 | 3 | 1.3 | 2 | 2.9 | 80 | 60 | 39 |
| 16 | 16 | 1745 | 4 | 1.5 | 3 | 1.8 | 51 | 36 | 26 |
| 17 | 17 | 1747 | 4 | 1.5 | 3 | 1.4 | 80 | 65 | 64 |

FIG. 1E

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 18 | 18 | 1748 | His | Ser | Gln | Gly | Thr | Phe | Thr | Ser | Asp | Tyr | Ser | Lys | Tyr | Leu | Asp |
| 19 | 19 | 1753 | His | Ser | Gln | Gly | Thr | Phe | Thr | Ser | Asp | Tyr | Ser | Lys | Tyr | Leu | Asp |
| 20 | 20 | 1755 | His | Ser | Gln | Gly | Thr | Phe | Thr | Ser | Asp | Tyr | Ser | His | Tyr | Leu | Asp |
| 21 | 21 | 1756 | His | Ser | Gln | Gly | Thr | Phe | Thr | Ser | Asp | Tyr | Ser | His | Tyr | Leu | Asp |
| 22 | 22 | 1757 | His | Ser | Gln | Gly | Thr | Phe | Thr | Ser | Asp | Tyr | Ser | Lys | Tyr | Leu | Asp |
| 23 | 23 | 1759 | His | Ser | Gln | Gly | Thr | Phe | Thr | Ser | Asp | Tyr | Ser | Lys | Tyr | Leu | Asp |
| 24 | 24 | 1761 | His | Ser | Gln | Gly | Thr | Phe | Thr | Ser | Asp | Tyr | Ser | Lys | Tyr | Leu | Asp |
| 25 | 25 | 1763 | His | Ser | Gln | Gly | Thr | Phe | Thr | Ser | Asp | Tyr | Ser | Lys | Tyr | Leu | Asp |
| 26 | 26 | 1765 | His | Ser | Gln | Gly | Thr | Phe | Thr | Ser | Asp | Tyr | Ser | Lys | Tyr | Leu | Asp |
| 27 | 27 | 1766 | His | Ser | Gln | Gly | Thr | Phe | Thr | Ser | Asp | Tyr | Ser | Lys | Tyr | Leu | Asp |
| 28 | 28 | 1773 | His | Ser | Gln | Gly | Thr | Phe | Thr | Ser | Asp | Tyr | Ser | His | Tyr | Leu | Asp |
| 29 | 29 | 1774 | His | Ser | Gln | Gly | Thr | Phe | Thr | Ser | Asp | Tyr | Ser | His | Tyr | Leu | Asp |
| 30 | 30 | 1776 | His | Ser | Gln | Gly | Thr | Phe | Thr | Ser | Asp | Tyr | Ser | His | Tyr | Leu | Asp |
| 31 | 31 | 1778 | His | Ser | Gln | Gly | Thr | Phe | Thr | Ser | Asp | Tyr | Ser | Lys | Tyr | Leu | Asp |
| 32 | 32 | 1779 | His | Ser | Gln | Gly | Thr | Phe | Thr | Ser | Asp | Tyr | Ser | Lys | Tyr | Leu | Asp |
| 33 | 33 | 1780 | His | Ser | Gln | Gly | Thr | Phe | Thr | Ser | Asp | Tyr | Ser | Lys | Tyr | Leu | Asp |
| 34 | 34 | 1781 | His | Ser | Gln | Gly | Thr | Phe | Thr | Ser | Asp | Tyr | Ser | Lys | Tyr | Leu | Asp |

FIG. 1F

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 18 | 18 | 1748 | Glu | Arg | Arg | Ala | His | Glu | Phe | Ile | Gln | Trp | Leu | Leu | Asn | Gly |
| 19 | 19 | 1753 | Glu | Lys | Arg | Ala | His | Glu | Phe | Ile | Glu | Trp | Leu | Leu | Asn | Gly |
| 20 | 20 | 1755 | Gln | Lys | Arg | Ala | His | Glu | Phe | Ile | Gln | Trp | Leu | Leu | Asn | Thr |
| 21 | 21 | 1756 | Gln | Lys | Arg | Ala | His | Glu | Phe | Ile | Glu | Trp | Leu | Leu | Asn | Gly |
| 22 | 22 | 1757 | Glu | Lys | Arg | Ala | His | Glu | Phe | Ile | Gln | Trp | Leu | Leu | Asn | Gly |
| 23 | 23 | 1759 | Ser | Arg | Arg | Ala | His | Glu | Phe | Val | Gln | Trp | Leu | Leu | Asn | Gly |
| 24 | 24 | 1761 | Glu | Arg | Arg | Ala | His | Glu | Phe | Ile | Glu | Trp | Leu | Leu | Asn | Thr |
| 25 | 25 | 1763 | Ser | Lys | Arg | Ala | His | Glu | Phe | Val | Gln | Trp | Leu | Leu | Asn | Gly |
| 26 | 26 | 1765 | Glu | Arg | Arg | Ala | His | Glu | Phe | Ile | Glu | Trp | Leu | Leu | Asn | Gly |
| 27 | 27 | 1766 | Glu | Lys | Arg | Ala | His | Glu | Phe | Ile | Gln | Trp | Leu | Leu | Asn | Gly |
| 28 | 28 | 1773 | Glu | Lys | Arg | Ala | His | Glu | Phe | Ile | Glu | Trp | Leu | Leu | Asn | Gly |
| 29 | 29 | 1774 | Glu | Lys | Arg | Ala | His | Glu | Phe | Val | Gln | Trp | Leu | Leu | Asn | Gly |
| 30 | 30 | 1776 | Ser | Lys | Arg | Ala | His | Glu | Phe | Ile | Gln | Trp | Leu | Leu | Asn | Gly |
| 31 | 31 | 1778 | Glu | Arg | Arg | Ala | His | Glu | Phe | Ile | Glu | Trp | Leu | Leu | Asn | Gly |
| 32 | 32 | 1779 | Glu | Arg | Arg | Ala | His | Glu | Phe | Ile | Glu | Trp | Leu | Leu | Asn | Gly |
| 33 | 33 | 1780 | Glu | Arg | Arg | Ala | His | Glu | Phe | Ile | Glu | Trp | Leu | Leu | Asn | Gly |
| 34 | 34 | 1781 | Glu | Arg | Arg | Ala | His | Glu | Phe | Ile | Glu | Trp | Leu | Leu | Asn | Gly |

FIG. 1G

| Analogue no. | SEQ ID NO. | G no. | 30 | 31 | 32 | 33 | 34 | 35 | 36 | 37 |
|---|---|---|---|---|---|---|---|---|---|---|
| 18 | 18 | 1748 | His | His | His | His | | | | |
| 19 | 19 | 1753 | His | His | His | His | | | | |
| 20 | 20 | 1755 | His | His | His | His | | | | |
| 21 | 21 | 1756 | His | His | His | His | | | | |
| 22 | 22 | 1757 | His | His | His | His | | | | |
| 23 | 23 | 1759 | Gly | His | His | His | His | | | |
| 24 | 24 | 1761 | His | His | His | His | | | | |
| 25 | 25 | 1763 | Gly | His | His | His | His | | | |
| 26 | 26 | 1765 | Gly | His | His | His | His | | | |
| 27 | 27 | 1766 | Gly | His | His | His | His | | | |
| 28 | 28 | 1773 | His | His | His | His | | | | |
| 29 | 29 | 1774 | His | His | His | His | Glu | | | |
| 30 | 30 | 1776 | His | His | His | His | | | | |
| 31 | 31 | 1778 | His | His | His | His | His | | | |
| 32 | 32 | 1779 | Gly | His | His | His | | | | |
| 33 | 33 | 1780 | Gly | His | His | His | NH2 | | | |
| 34 | 34 | 1781 | Gly | His | His | His | His | | | |

FIG. 1H

| Analogue no. | SEQ ID NO. | G no. | hGCGr cAMP | | | hGLP-1r cAMP | | Mouse food intake inhibition (500nmol/kg) | | Rat food intake inhibtion (500 nmol/kg with 1:1 Zn) |
|---|---|---|---|---|---|---|---|---|---|---|
| | | | n | vs hGCG | | n | vs hGLP-1 | 0-24 | 0-48 | 0-24 |
| 18 | 18 | 1748 | 4 | 1.5 | | 3 | 1.5 | 70 | 48 | 49 |
| 19 | 19 | 1753 | 4 | 1.5 | | 2 | 5.5 | 82 | 66 | 39 |
| 20 | 20 | 1755 | 3 | 2.8 | | 1 | 4.3 | 62 | 32 | 53 |
| 21 | 21 | 1756 | 2 | 2.4 | | 1 | 2.7 | 86 | 66 | 14 |
| 22 | 22 | 1757 | 2 | 5.5 | | | | 76 | 49 | 28 |
| 23 | 23 | 1759 | 2 | 1.3 | | | | 25 | 13 | 52 |
| 24 | 24 | 1761 | 2 | 2.4 | | | | 86 | 62 | 20 |
| 25 | 25 | 1763 | 1 | 2.1 | | | | 51 | 34 | 16 |
| 26 | 26 | 1765 | 6 | 7.0 | | 2 | 13.5 | 90 | 81 | 14 |
| 27 | 27 | 1766 | 6 | 5.1 | | 3 | 4.7 | 96 | 81 | 21 |
| 28 | 28 | 1773 | 4 | 2.2 | | | | 82 | 58 | 38 |
| 29 | 29 | 1774 | 2 | 2.1 | | | | 79 | 58 | 50 |
| 30 | 30 | 1776 | 3 | 2.1 | | | | 78 | 53 | 42 |
| 31 | 31 | 1778 | 4 | 1.3 | | 3 | 3.1 | 87 | 71 | 59 |
| 32 | 32 | 1779 | 3 | 1.0 | | | | 93 | 70 | 66 |
| 33 | 33 | 1780 | 2 | 1.3 | | | | 89 | 54 | 60 |
| 34 | 34 | 1781 | 4 | 1.3 | | 3 | 1.4 | 97 | 92 | 56 |

FIG. 1I

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 35 | 35 | 1782 | His | Ser | Gln | Gly | Thr | Phe | Thr | Ser | Asp | Tyr | Ser | His | Tyr | Leu | Asp |
| 36 | 36 | 1784 | His | Ser | Gln | Gly | Thr | Phe | Thr | Ser | Asp | Tyr | Ser | His | Tyr | Leu | Asp |
| 37 | 37 | 1785 | His | Ser | Gln | Gly | Thr | Phe | Thr | Ser | Asp | Tyr | Ser | Lys | Tyr | Leu | Asp |
| 38 | 38 | 1786 | His | Ser | Gln | Gly | Thr | Phe | Thr | Ser | Asp | Tyr | Ser | Lys | Tyr | Leu | Asp |
| 39 | 39 | 1789 | His | Ser | Gln | Gly | Thr | Phe | Thr | Ser | Asp | Tyr | Ser | Lys | Tyr | Leu | Asp |
| 40 | 40 | 1791 | His | Ser | Gln | Gly | Thr | Phe | Thr | Ser | Asp | Tyr | Ser | Lys | Tyr | Leu | Asp |
| 41 | 41 | 1792 | His | Ser | Gln | Gly | Thr | Phe | Thr | Ser | Asp | Tyr | Ser | Lys | Tyr | Leu | Asp |
| 42 | 42 | 1793 | His | Ser | Gln | Gly | Thr | Phe | Thr | Ser | Asp | Tyr | Ser | Lys | Tyr | Leu | Asp |
| 43 | 43 | 1794 | His | Ser | Gln | Gly | Thr | Phe | Thr | Ser | Asp | Tyr | Ser | Lys | Tyr | Leu | Asp |
| 44 | 44 | 1796 | His | Ser | Gln | Gly | Thr | Phe | Thr | Ser | Asp | Tyr | Ser | Lys | Tyr | Leu | Asp |
| 45 | 45 | 1797 | His | Ser | Gln | Gly | Thr | Phe | Thr | Ser | Asp | Tyr | Ser | Lys | Tyr | Leu | Asp |
| 46 | 46 | 1798 | His | Ser | Gln | Gly | Thr | Phe | Thr | Ser | Asp | Tyr | Ser | Lys | Tyr | Leu | Asp |
| 47 | 47 | 1802 | His | Ser | Gln | Gly | Thr | Phe | Thr | Ser | Asp | Tyr | Ser | Lys | Tyr | Leu | Asp |
| 48 | 48 | 1803 | His | Ser | Gln | Gly | Thr | Phe | Thr | Ser | Asp | Tyr | Ser | Lys | Tyr | Leu | Asp |
| 49 | 49 | 1804 | His | Ser | Gln | Gly | Thr | Phe | Thr | Ser | Asp | Tyr | Ser | Lys | Tyr | Leu | Asp |
| 50 | 50 | 1805 | His | Ser | Gln | Gly | Thr | Phe | Thr | Ser | Asp | Tyr | Ser | Lys | Tyr | Leu | Asp |
| 51 | 51 | 1808 | His | Ser | Gln | Gly | Thr | Phe | Thr | Ser | Asp | Tyr | Ser | Lys | Tyr | Leu | Asp |

FIG. 1J

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 35 | 35 | 1782 | Gln | Lys | Arg | Ala | His | Glu | Phe | Ile | Glu | Trp | Leu | Leu | Asn | Gly |
| 36 | 36 | 1784 | Gln | Lys | Arg | Ala | His | Glu | Phe | Ile | Glu | Trp | Leu | Leu | Asn | Gly |
| 37 | 37 | 1785 | Glu | Arg | Arg | Ala | His | Glu | Phe | Ile | Glu | Trp | Leu | Leu | Asn | Gly |
| 38 | 38 | 1786 | Glu | Arg | Arg | Ala | His | Glu | Phe | Val | Glu | Trp | Leu | Leu | Asn | Thr |
| 39 | 39 | 1789 | Glu | Arg | Arg | Ala | His | Glu | Phe | Val | Glu | Trp | Leu | Leu | Asn | Thr |
| 40 | 40 | 1791 | Gln | Arg | Arg | Ala | His | Glu | Phe | Ile | Glu | Trp | Leu | Leu | Asn | Thr |
| 41 | 41 | 1792 | Gln | Lys | Arg | Ala | His | Glu | Phe | Ile | Glu | Trp | Leu | Leu | Asn | Thr |
| 42 | 42 | 1793 | Gln | Arg | Arg | Ala | His | Glu | Phe | Ile | Glu | Trp | Leu | Leu | Asn | Thr |
| 43 | 43 | 1794 | Glu | Arg | Arg | Ala | His | Glu | Phe | Ile | Glu | Trp | Leu | Leu | Asn | Thr |
| 44 | 44 | 1796 | Gln | Arg | Arg | Ala | His | Glu | Phe | Ile | Glu | Trp | Leu | Leu | Asn | Thr |
| 45 | 45 | 1797 | Gln | Lys | Arg | Ala | His | Glu | Phe | Ile | Gln | Trp | Leu | Leu | Asn | Thr |
| 46 | 46 | 1798 | Gln | Arg | Arg | Ala | His | Glu | Phe | Ile | Gln | Trp | Leu | Leu | Asn | Gly |
| 47 | 47 | 1802 | Glu | Arg | Arg | Ala | His | Glu | Phe | Ile | Gln | Trp | Leu | Leu | Asn | Gly |
| 48 | 48 | 1803 | Glu | Arg | Arg | Ala | His | Glu | Phe | Ile | Gln | Trp | Leu | Leu | Asn | Gly |
| 49 | 49 | 1804 | Glu | Arg | Arg | Ala | His | Glu | Phe | Ile | Gln | Trp | Leu | Leu | Asn | Thr |
| 50 | 50 | 1805 | Glu | Arg | Arg | Ala | His | Glu | Phe | Ile | Glu | Trp | Leu | Leu | Asn | Gly |
| 51 | 51 | 1808 | Glu | Lys | Arg | Ala | His | Glu | Phe | Ile | Glu | Trp | Leu | Leu | Asn | Thr |

FIG. 1K

| Analogue no. | SEQ ID NO. | G no. | 30 | 31 | 32 | 33 | 34 | 35 | 36 | 37 |
|---|---|---|---|---|---|---|---|---|---|---|
| 35 | 35 | 1782 | Gly | His | His | His | Glu | | | |
| 36 | 36 | 1784 | Gly | His | His | His | NH2 | | | |
| 37 | 37 | 1785 | Gly | His | His | His | Glu | | | |
| 38 | 38 | 1786 | Gly | His | His | His | | | | |
| 39 | 39 | 1789 | Gly | His | His | His | NH2 | | | |
| 40 | 40 | 1791 | Gly | His | His | His | | | | |
| 41 | 41 | 1792 | Gly | His | His | His | His | | | |
| 42 | 42 | 1793 | Gly | His | His | His | Glu | | | |
| 43 | 43 | 1794 | Gly | His | His | His | | | | |
| 44 | 44 | 1796 | His | His | His | His | | | | |
| 45 | 45 | 1797 | His | His | His | His | | | | |
| 46 | 46 | 1798 | His | His | His | His | | | | |
| 47 | 47 | 1802 | Gly | His | His | His | His | | | |
| 48 | 48 | 1803 | Gly | His | His | His | His | His | Glu | |
| 49 | 49 | 1804 | Gly | His | His | His | His | His | Glu | |
| 50 | 50 | 1805 | Gly | His | His | His | His | | | |
| 51 | 51 | 1808 | Gly | His | His | His | His | | | |

FIG. 1L

| Analogue no. | SEQ ID NO. | G no. | hGCGr | | | hGLP-1r | | | Mouse food intake inhibition (500nmol/kg) | | Rat food intake inhibtion (500 nmol/kg with 1:1 Zn) |
|---|---|---|---|---|---|---|---|---|---|---|---|
| | | | n | cAMP vs hGCG | | n | cAMP vs hGLP-1 | | 0-24 | 0-48 | 0-24 |
| 35 | 35 | 1782 | 3 | 1.2 | | 2 | 1.2 | | 46 | 24 | 40 |
| 36 | 36 | 1784 | 4 | 1.3 | | 3 | 0.8 | | 82 | 53 | 47 |
| 37 | 37 | 1785 | 3 | 1.8 | | 1 | 1.5 | | 79 | 52 | 81 |
| 38 | 38 | 1786 | 3 | 3.5 | | | | | 69 | 47 | 31 |
| 39 | 39 | 1789 | 2 | 1.4 | | 2 | 5.8 | | 17 | 9 | 11 |
| 40 | 40 | 1791 | 2 | 1.4 | | 2 | 3.4 | | 77 | 56 | 51 |
| 41 | 41 | 1792 | 3 | 1.2 | | 3 | 6.5 | | 88 | 55 | 59 |
| 42 | 42 | 1793 | 6 | 1.8 | | 4 | 4.5 | | 56 | 39 | 24 |
| 43 | 43 | 1794 | 2 | 1.5 | | | | | 77 | 44 | 60 |
| 44 | 44 | 1796 | 3 | 2.1 | | 2 | 3.0 | | 69 | 55 | 31 |
| 45 | 45 | 1797 | 3 | 5.2 | | 1 | 4.0 | | 46 | 35 | 17 |
| 46 | 46 | 1798 | 3 | 9.1 | | | | | 59 | 42 | 26 |
| 47 | 47 | 1802 | 4 | 1.0 | | 6 | 3.5 | | 60 | 38 | 31 |
| 48 | 48 | 1803 | 4 | 1.4 | | 4 | 14.2 | | 60 | 41 | 15 |
| 49 | 49 | 1804 | 5 | 1.1 | | 3 | 0.8 | | 58 | 31 | 42 |
| 50 | 50 | 1805 | 5 | 1.7 | | 3 | 3.3 | | 80 | 60 | 54 |
| 51 | 51 | 1808 | 4 | 0.9 | | 3 | 2.0 | | 63 | 56 | 73 |

FIG. 1M

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 52 | 52 | 1811 | His | Ser | Gln | Gly | Thr | Phe | Thr | Ser | Asp | Tyr | Ser | Lys | Tyr | Leu | Asp |
| 53 | 53 | 1812 | His | Ser | Gln | Gly | Thr | Phe | Thr | Ser | Asp | Tyr | Ser | Lys | Tyr | Leu | Asp |
| 54 | 54 | 1814 | His | Ser | Gln | Gly | Thr | Phe | Thr | Ser | Asp | Tyr | Ser | Lys | Tyr | Leu | Asp |
| 55 | 55 | 1815 | His | Ser | Gln | Gly | Thr | Phe | Thr | Ser | Asp | Tyr | Ser | Lys | Tyr | Leu | Asp |
| 56 | 56 | 1825 | His | Ser | Gln | Gly | Thr | Phe | Thr | Ser | Asp | Tyr | Ser | Lys | Tyr | Leu | Asp |
| 57 | 57 | 1826 | His | Ser | Gln | Gly | Thr | Phe | Thr | Ser | Asp | Tyr | Ser | Lys | Tyr | Leu | Asp |
| 58 | 58 | 1827 | His | Ser | Gln | Gly | Thr | Phe | Thr | Ser | Asp | Tyr | Ser | Lys | Tyr | Leu | Asp |
| 59 | 59 | 1828 | His | Ser | Gln | Gly | Thr | Phe | Thr | Ser | Asp | Tyr | Ser | Lys | Tyr | Leu | Asp |
| 60 | 60 | 1829 | His | Ser | Gln | Gly | Thr | Phe | Thr | Ser | Asp | Tyr | Ser | Lys | Tyr | Leu | Asp |
| 61 | 61 | 1830 | His | Ser | Gln | Gly | Thr | Phe | Thr | Ser | Asp | Tyr | Ser | Lys | Tyr | Leu | Asp |
| 62 | 62 | 1831 | His | Ser | Gln | Gly | Thr | Phe | Thr | Ser | Asp | Tyr | Ser | Lys | Tyr | Leu | Asp |
| 63 | 63 | 1832 | His | Ser | Gln | Gly | Thr | Phe | Thr | Ser | Asp | Tyr | Ser | Lys | Tyr | Leu | Asp |
| 64 | 64 | 1833 | His | Ser | Gln | Gly | Thr | Phe | Thr | Ser | Asp | Tyr | Ser | Lys | Tyr | Leu | Asp |
| 65 | 65 | 1834 | His | Ser | Gln | Gly | Thr | Phe | Thr | Ser | Asp | Tyr | Ser | Lys | Tyr | Leu | Asp |
| 66 | 66 | 1835 | His | Ser | Gln | Gly | Thr | Phe | Thr | Ser | Asp | Tyr | Ser | Lys | Tyr | Leu | Asp |
| 67 | 67 | 1838 | His | Ser | Gln | Gly | Thr | Phe | Thr | Ser | Asp | Tyr | Ser | Lys | Tyr | Leu | Asp |
| 68 | 68 | 1839 | His | Ser | Gln | Gly | Thr | Phe | Thr | Ser | Asp | Tyr | Ser | Lys | Tyr | Leu | Asp |

FIG. 1N

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 52 | 52 | 1811 | Glu | Lys | Arg | Ala | His | Glu | Phe | Ile | Glu | Trp | Leu | Leu | Asn | Thr |
| 53 | 53 | 1812 | Glu | Lys | Arg | Ala | His | Glu | Phe | Ile | Glu | Trp | Leu | Leu | Asn | Thr |
| 54 | 54 | 1814 | Glu | Lys | Arg | Ala | His | Glu | Phe | Ile | Gln | Trp | Leu | Leu | Asn | Thr |
| 55 | 55 | 1815 | Glu | Lys | Arg | Ala | His | Glu | Phe | Ile | Gln | Trp | Leu | Leu | Asn | Thr |
| 56 | 56 | 1825 | Glu | Lys | Arg | Ala | His | Glu | Phe | Ile | Glu | Trp | Leu | Leu | Asn | Thr |
| 57 | 57 | 1826 | Glu | Lys | Arg | Ala | His | Glu | Phe | Ile | Glu | Trp | Leu | Leu | Asn | Gly |
| 58 | 58 | 1827 | Glu | Lys | Arg | Ala | His | Glu | Phe | Ile | Glu | Trp | Leu | Leu | Asn | Thr |
| 59 | 59 | 1828 | Glu | Lys | Arg | Ala | His | Glu | Phe | Ile | Glu | Trp | Leu | Leu | Asn | Gly |
| 60 | 60 | 1829 | Glu | Lys | Arg | Ala | His | Glu | Phe | Ile | Glu | Trp | Leu | Leu | Asn | Thr |
| 61 | 61 | 1830 | Glu | Lys | Arg | Ala | His | Glu | Phe | Ile | Glu | Trp | Leu | Leu | Asn | Thr |
| 62 | 62 | 1831 | Glu | Lys | Arg | Ala | His | Glu | Phe | Ile | Gln | Trp | Leu | Leu | Asn | Thr |
| 63 | 63 | 1832 | Glu | Lys | Arg | Ala | His | Glu | Phe | Ile | Glu | Trp | Leu | Leu | Asn | Gly |
| 64 | 64 | 1833 | Glu | Arg | Arg | Ala | His | Glu | Phe | Ile | Gln | Trp | Leu | Leu | Asn | Thr |
| 65 | 65 | 1834 | Glu | Lys | Arg | Ala | His | Glu | Phe | Ile | Glu | Trp | Leu | Leu | Asn | Thr |
| 66 | 66 | 1835 | Glu | Arg | Arg | Ala | His | Glu | Phe | Ile | Glu | Trp | Leu | Leu | Asn | Thr |
| 67 | 67 | 1838 | Glu | Arg | Arg | Ala | His | Glu | Phe | Ile | Glu | Trp | Leu | Leu | Asn | Gly |
| 68 | 68 | 1839 | Glu | Arg | Arg | Ala | His | Glu | Phe | Ile | Glu | Trp | Leu | Leu | Asn | Gly |

FIG. 10

| Analogue no. | SEQ ID NO. | G no. | 30 | 31 | 32 | 33 | 34 | 35 | 36 | 37 |
|---|---|---|---|---|---|---|---|---|---|---|
| 52 | 52 | 1811 | His | His | His | His | Glu | | | |
| 53 | 53 | 1812 | Gly | His | His | His | His | NH2 | | |
| 54 | 54 | 1814 | His | His | His | His | | | | |
| 55 | 55 | 1815 | Gly | His | His | His | His | | | |
| 56 | 56 | 1825 | Gly | His | His | His | His | NH2 | | |
| 57 | 57 | 1826 | Gly | His | His | His | Glu | | | |
| 58 | 58 | 1827 | Gly | His | His | His | Glu | | | |
| 59 | 59 | 1828 | His | His | His | His | NH2 | | | |
| 60 | 60 | 1829 | His | His | His | His | Gly | | | |
| 61 | 61 | 1830 | His | His | His | His | Gly | | | |
| 62 | 62 | 1831 | His | Gly | His | His | | | | |
| 63 | 63 | 1832 | His | Gly | His | His | NH2 | | | |
| 64 | 64 | 1833 | His | His | His | His | Gly | | | |
| 65 | 65 | 1834 | His | His | His | His | His | NH2 | | |
| 66 | 66 | 1835 | Gly | His | His | His | His | NH2 | | |
| 67 | 67 | 1838 | His | His | His | His | NH2 | | | |
| 68 | 68 | 1839 | His | His | His | His | Gly | | | |

FIG. 1P

| Analogue no. | SEQ ID NO. | G no. | hGCGr cAMP | | | hGLP-1r cAMP | | Mouse food intake inhibition (500nmol/kg) | | Rat food intake inhibition (500 nmol/kg with 1:1 Zn) |
|---|---|---|---|---|---|---|---|---|---|---|
| | | | n | vs hGCG | | n | vs hGLP-1 | 0-24 | 0-48 | 0-24 |
| 52 | 52 | 1811 | 2 | 1.4 | | | | 85 | 60 | 46 |
| 53 | 53 | 1812 | 2 | 1.3 | | | | 89 | 57 | 71 |
| 54 | 54 | 1814 | 2 | 0.9 | | | | 93 | 74 | 82 |
| 55 | 55 | 1815 | 2 | 1.5 | | | | 87 | 56 | 90 |
| 56 | 56 | 1825 | 4 | 1.3 | | 5 | 1.2 | 57 | 34 | 53 |
| 57 | 57 | 1826 | 2 | 1.2 | | | | 46 | 25 | 50 |
| 58 | 58 | 1827 | 2 | 2.8 | | | | 94 | 75 | 79 |
| 59 | 59 | 1828 | 3 | 0.8 | | 1 | 3.1 | 50 | 32 | 24 |
| 60 | 60 | 1829 | 2 | 1.7 | | | | 89 | 86 | 46 |
| 61 | 61 | 1830 | 2 | 1.2 | | | | 85 | 61 | 79 |
| 62 | 62 | 1831 | 2 | 1.6 | | 4 | 3.9 | 64 | 43 | 53 |
| 63 | 63 | 1832 | 4 | 1.1 | | 5 | 3.5 | 45 | 29 | 29 |
| 64 | 64 | 1833 | 7 | 1.7 | | 3 | 3.7 | 40 | 22 | 41 |
| 65 | 65 | 1834 | 4 | 0.9 | | | | 80 | 48 | 30 |
| 66 | 66 | 1835 | 2 | 1.1 | | | | 70 | 42 | 39 |
| 67 | 67 | 1838 | 2 | 1.6 | | | | 34 | 21 | 35 |
| 68 | 68 | 1839 | 4 | 1.6 | | 3 | 3.3 | 45 | 27 | 38 |

FIG. 1Q

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 69 | 69 | 1840 | His | Ser | Gln | Gly | Thr | Phe | Thr | Ser | Asp | Tyr | Ser | Lys | Tyr | Leu | Asp |
| 70 | 70 | 1841 | His | Ser | Gln | Gly | Thr | Phe | Thr | Ser | Asp | Tyr | Ser | Lys | Tyr | Leu | Asp |
| 71 | 71 | 1845 | His | Ser | Gln | Gly | Thr | Phe | Thr | Ser | Asp | Tyr | Ser | Lys | Tyr | Leu | Asp |
| 72 | 72 | 1846 | His | Ser | Gln | Gly | Thr | Phe | Thr | Ser | Asp | Tyr | Ser | Lys | Tyr | Leu | Asp |
| 73 | 73 | 1847 | His | Ser | Gln | Gly | Thr | Phe | Thr | Ser | Asp | Tyr | Ser | Lys | Tyr | Leu | Asp |
| 74 | 74 | 1848 | His | Ser | Gln | Gly | Thr | Phe | Thr | Ser | Asp | Tyr | Ser | His | Tyr | Leu | Asp |
| 75 | 75 | 1849 | His | Ser | Gln | Gly | Thr | Phe | Thr | Ser | Asp | Tyr | Ser | Lys | Tyr | Leu | Asp |
| 76 | 76 | 1850 | His | Ser | Gln | Gly | Thr | Phe | Thr | Ser | Asp | Tyr | Ser | Lys | Tyr | Leu | Asp |
| 77 | 77 | 1855 | His | Ser | Gln | Gly | Thr | Phe | Thr | Ser | Asp | Tyr | Ser | Lys | Tyr | Leu | Asp |
| 78 | 78 | 1856 | His | Ser | Gln | Gly | Thr | Phe | Thr | Ser | Asp | Tyr | Ser | His | Tyr | Leu | Asp |
| 79 | 79 | 1857 | His | Ser | Gln | Gly | Thr | Phe | Thr | Ser | Asp | Tyr | Ser | Lys | Tyr | Leu | Asp |
| 80 | 80 | 1859 | His | Ser | Gln | Gly | Thr | Phe | Thr | Ser | Asp | Tyr | Ser | Lys | Tyr | Leu | Asp |
| 81 | 81 | 1860 | His | Ser | Gln | Gly | Thr | Phe | Thr | Ser | Asp | Tyr | Ser | His | Tyr | Leu | Asp |
| 82 | 82 | 1861 | His | Ser | Gln | Gly | Thr | Phe | Thr | Ser | Asp | Tyr | Ser | Lys | Tyr | Leu | Asp |
| 83 | 83 | 1868 | His | Ser | Gln | Gly | Thr | Phe | Thr | Ser | Asp | Tyr | Ser | Lys | Tyr | Leu | Asp |
| 84 | 84 | 1869 | His | Ser | Gln | Gly | Thr | Phe | Thr | Ser | Asp | Tyr | Ser | Lys | Tyr | Leu | Asp |
| 85 | 85 | 1871 | His | Ser | Gln | Gly | Thr | Phe | Thr | Ser | Asp | Tyr | Ser | Lys | Tyr | Leu | Asp |

FIG. 1R

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 69 | 69 | 1840 | Glu | Lys | Arg | Ala | His | Glu | Phe | Ile | Glu | Trp | Leu | Leu | Asn | Gly |
| 70 | 70 | 1841 | Glu | Lys | Arg | Ala | His | Glu | Phe | Ile | Glu | Trp | Leu | Leu | Asn | Gly |
| 71 | 71 | 1845 | Glu | Lys | Arg | Ala | His | Glu | Phe | Ile | Glu | Trp | Leu | Leu | Asn | Gly |
| 72 | 72 | 1846 | Glu | Lys | Arg | Ala | His | Glu | Phe | Ile | Glu | Trp | Leu | Leu | Asn | Gly |
| 73 | 73 | 1847 | Glu | Lys | Arg | Ala | His | Glu | Phe | Ile | Glu | Trp | Leu | Leu | Asn | Thr |
| 74 | 74 | 1848 | Glu | Lys | Arg | Ala | His | Glu | Phe | Ile | Glu | Trp | Leu | Leu | Asn | Thr |
| 75 | 75 | 1849 | Glu | Arg | Arg | Ala | His | Glu | Phe | Ile | Gln | Trp | Leu | Leu | Asn | Gly |
| 76 | 76 | 1850 | Glu | Arg | Arg | Ala | His | Glu | Phe | Ile | Gln | Trp | Leu | Leu | Asn | Gly |
| 77 | 77 | 1855 | Glu | Lys | Arg | Ala | His | Glu | Phe | Ile | Gln | Trp | Leu | Leu | Asn | Gly |
| 78 | 78 | 1856 | Gln | Lys | Arg | Ala | His | Glu | Phe | Ile | Gln | Trp | Leu | Leu | Asn | Gly |
| 79 | 79 | 1857 | Gln | Lys | Arg | Ala | His | Glu | Phe | Ile | Gln | Trp | Leu | Leu | Asn | Gly |
| 80 | 80 | 1859 | Glu | Lys | Arg | Ala | His | Glu | Phe | Ile | Glu | Trp | Leu | Leu | Asn | Gly |
| 81 | 81 | 1860 | Glu | Lys | Arg | Ala | His | Glu | Phe | Ile | Gln | Trp | Leu | Leu | Asn | Gly |
| 82 | 82 | 1861 | Glu | Lys | Arg | Ala | His | Glu | Phe | Ile | Glu | Trp | Leu | Leu | Asn | Gly |
| 83 | 83 | 1868 | Glu | Lys | Arg | Ala | His | Glu | Phe | Ile | Glu | Trp | Leu | Leu | Asn | Gly |
| 84 | 84 | 1869 | Glu | Lys | Arg | Ala | His | Glu | Phe | Ile | Glu | Trp | Leu | Leu | Asn | Gly |
| 85 | 85 | 1871 | Glu | Lys | Arg | Ala | His | Glu | Phe | Ile | Glu | Trp | Leu | Leu | Asn | Gly |

FIG. 1S

| Analogue no. | SEQ ID NO. | G no. | 30 | 31 | 32 | 33 | 34 | 35 | 36 | 37 |
|---|---|---|---|---|---|---|---|---|---|---|
| 69 | 69 | 1840 | His | His | His | His | NH2 | | | |
| 70 | 70 | 1841 | His | His | His | His | Glu | | | |
| 71 | 71 | 1845 | His | His | His | His | His | NH2 | | |
| 72 | 72 | 1846 | His | His | His | His | Gly | NH2 | | |
| 73 | 73 | 1847 | His | His | His | His | Gly | NH2 | | |
| 74 | 74 | 1848 | His | His | His | His | Glu | | | |
| 75 | 75 | 1849 | His | His | His | His | Glu | | | |
| 76 | 76 | 1850 | His | His | His | His | NH2 | | | |
| 77 | 77 | 1855 | His | His | His | His | Glu | | | |
| 78 | 78 | 1856 | Gly | His | His | His | Glu | | | |
| 79 | 79 | 1857 | Gly | His | His | His | Glu | | | |
| 80 | 80 | 1859 | Gly | His | His | His | Glu | | | |
| 81 | 81 | 1860 | Gly | His | His | His | Glu | | | |
| 82 | 82 | 1861 | His | His | His | His | Glu | | | |
| 83 | 83 | 1868 | His | His | His | His | His | Ala | | |
| 84 | 84 | 1869 | His | His | His | His | His | Ser | | |
| 85 | 85 | 1871 | His | His | His | His | His | Ala | NH2 | |

FIG. 1T

| Analogue no. | SEQ ID NO. | G no. | hGCGr | | | hGLP-1r | | | Mouse food intake inhibition (500nmol/kg) | | Rat food intake inhibition (500 nmol/kg with 1:1 Zn) |
|---|---|---|---|---|---|---|---|---|---|---|---|
| | | | n | cAMP vs hGCG | | n | cAMP vs hGLP-1 | | 0-24 | 0-48 | 0-24 |
| 69 | 69 | 1840 | 6 | 1.8 | | 4 | 3.9 | | 44 | 26 | 36 |
| 70 | 70 | 1841 | 4 | 0.7 | | 3 | 1.6 | | 42 | 26 | 62 |
| 71 | 71 | 1845 | 2 | 1.8 | | | | | 28 | 13 | 31 |
| 72 | 72 | 1846 | 2 | 1.2 | | | | | 32 | 13 | 49 |
| 73 | 73 | 1847 | 2 | 1.9 | | | | | 66 | 39 | 46 |
| 74 | 74 | 1848 | 2 | 1.6 | | | | | 70 | 40 | 36 |
| 75 | 75 | 1849 | 3 | 1.3 | | 3 | 3.7 | | 52 | 29 | 48 |
| 76 | 76 | 1850 | 3 | 1.2 | | | | | 13 | 3 | 20 |
| 77 | 77 | 1855 | 2 | 3.5 | | | | | | | |
| 78 | 78 | 1856 | 2 | 2.7 | | | | | | | |
| 79 | 79 | 1857 | 3 | 1.7 | | | | | 25 | 9 | |
| 80 | 80 | 1859 | 2 | 7.7 | | | | | | | |
| 81 | 81 | 1860 | 2 | 1.6 | | | | | 28 | 14 | 51 |
| 82 | 82 | 1861 | 2 | 1.9 | | | | | 22 | 13 | |
| 83 | 83 | 1868 | 5 | 1.0 | | 3 | 2.8 | | 45 | 21 | 34 |
| 84 | 84 | 1869 | 4 | 1.3 | | 4 | 2.3 | | 69 | 44 | 31 |
| 85 | 85 | 1871 | 6 | 1.0 | | 6 | 1.6 | | 37 | 19 | 39 |

FIG. 1U

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 86 | 86 | 1872 | His | Ser | Gln | Gly | Thr | Phe | Thr | Ser | Asp | Tyr | Ser | Lys | Tyr | Leu | Asp |
| 87 | 87 | 1873 | His | Ser | Gln | Gly | Thr | Phe | Thr | Ser | Asp | Tyr | Ser | His | Tyr | Leu | Asp |
| 88 | 88 | 1874 | His | Ser | Gln | Gly | Thr | Phe | Thr | Ser | Asp | Tyr | Ser | His | Tyr | Leu | Asp |
| 89 | 89 | 1875 | His | Ser | Gln | Gly | Thr | Phe | Thr | Ser | Asp | Tyr | Ser | Lys | Tyr | Leu | Asp |
| 90 | 90 | 1878 | His | Ser | Gln | Gly | Thr | Phe | Thr | Ser | Asp | Tyr | Ser | Lys | Tyr | Leu | Asp |
| 91 | 91 | 1879 | His | Ser | Gln | Gly | Thr | Phe | Thr | Ser | Asp | Tyr | Ser | Lys | Tyr | Leu | Asp |
| 92 | 92 | 1880 | His | Ser | Gln | Gly | Thr | Phe | Thr | Ser | Asp | Tyr | Ser | Lys | Tyr | Leu | Asp |
| 93 | 93 | 1882 | His | Ser | Gln | Gly | Thr | Phe | Thr | Ser | Asp | Tyr | Ser | Lys | Tyr | Leu | Asp |
| 94 | 94 | 1884 | His | Ser | Gln | Gly | Thr | Phe | Thr | Ser | Asp | Tyr | Ser | Lys | Tyr | Leu | Asp |
| 95 | 95 | 1886 | His | Ser | Gln | Gly | Thr | Phe | Thr | Ser | Asp | Tyr | Ser | Lys | Tyr | Leu | Asp |
| 96 | 96 | 1887 | His | Ser | Gln | Gly | Thr | Phe | Thr | Ser | Asp | Tyr | Ser | Lys | Tyr | Leu | Asp |
| 97 | 97 | 1888 | His | Ser | Gln | Gly | Thr | Phe | Thr | Ser | Asp | Tyr | Ser | Lys | Tyr | Leu | Asp |
| 98 | 98 | 1889 | His | Ser | Gln | Gly | Thr | Phe | Thr | Ser | Asp | Tyr | Ser | Lys | Tyr | Leu | Asp |
| 99 | 99 | 1890 | His | Ser | Gln | Gly | Thr | Phe | Thr | Ser | Asp | Tyr | Ser | Lys | Tyr | Leu | Asp |
| 100 | 100 | 1891 | His | Ser | Gln | Gly | Thr | Phe | Thr | Ser | Asp | Tyr | Ser | Lys | Tyr | Leu | Asp |
| 101 | 101 | 1892 | His | Ser | Gln | Gly | Thr | Phe | Thr | Ser | Asp | Tyr | Ser | Lys | Tyr | Leu | Asp |
| 102 | 102 | 1893 | His | Ser | Gln | Gly | Thr | Phe | Thr | Ser | Asp | Tyr | Ser | Lys | Tyr | Leu | Asp |

FIG. 1V

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 86 | 86 | 1872 | Glu | Lys | Arg | Ala | His | Glu | Phe | Ile | Glu | Trp | Leu | Leu | Asn | Gly |
| 87 | 87 | 1873 | Gln | Lys | Arg | Ala | His | Glu | Phe | Ile | Glu | Trp | Leu | Leu | Asn | Gly |
| 88 | 88 | 1874 | Gln | Lys | Arg | Ala | His | Glu | Phe | Ile | Glu | Trp | Leu | Leu | Asn | Gly |
| 89 | 89 | 1875 | Glu | Lys | Arg | Ala | His | Glu | Phe | Ile | Glu | Trp | Leu | Leu | Asn | Gly |
| 90 | 90 | 1878 | Glu | Lys | Arg | Ala | His | Glu | Phe | Ile | Gln | Trp | Leu | Leu | Asn | Gly |
| 91 | 91 | 1879 | Glu | Arg | Arg | Ala | His | Glu | Phe | Ile | Glu | Trp | Leu | Leu | Asn | Gly |
| 92 | 92 | 1880 | Glu | Lys | Arg | Ala | His | Glu | Phe | Ile | Gln | Trp | Leu | Leu | Asn | Gly |
| 93 | 93 | 1882 | Glu | Lys | Arg | Ala | His | Glu | Phe | Ile | Glu | Trp | Leu | Leu | Asn | Gly |
| 94 | 94 | 1884 | Glu | Arg | Arg | Ala | His | Glu | Phe | Ile | Glu | Trp | Leu | Leu | Asn | Gly |
| 95 | 95 | 1886 | Gln | Arg | Arg | Ala | His | Glu | Phe | Ile | Gln | Trp | Leu | Leu | Asn | Thr |
| 96 | 96 | 1887 | Gln | Arg | Arg | Ala | His | Glu | Phe | Ile | Glu | Trp | Leu | Leu | Asn | Thr |
| 97 | 97 | 1888 | Gln | Arg | Arg | Ala | His | Glu | Phe | Ile | Glu | Trp | Leu | Leu | Asn | Thr |
| 98 | 98 | 1889 | Glu | Arg | Arg | Ala | His | Glu | Phe | Ile | Glu | Trp | Leu | Leu | Asn | Gly |
| 99 | 99 | 1890 | Glu | Arg | Arg | Ala | His | Glu | Phe | Ile | Glu | Trp | Leu | Leu | Asn | Gly |
| 100 | 100 | 1891 | Glu | Arg | Arg | Ala | His | Glu | Phe | Ile | Glu | Trp | Leu | Leu | Asn | Gly |
| 101 | 101 | 1892 | Gln | Lys | Arg | Ala | His | Glu | Phe | Ile | Glu | Trp | Leu | Leu | Asn | Thr |
| 102 | 102 | 1893 | Gln | Lys | Arg | Ala | His | Glu | Phe | Ile | Glu | Trp | Leu | Leu | Asn | Thr |

FIG. 1W

| Analogue no. | SEQ ID NO. | G no. | 30 | 31 | 32 | 33 | 34 | 35 | 36 | 37 |
|---|---|---|---|---|---|---|---|---|---|---|
| 86 | 86 | 1872 | Gly | His | His | His | His | Ala | | |
| 87 | 87 | 1873 | Gly | His | His | His | | | | |
| 88 | 88 | 1874 | Gly | His | His | His | Ala | | | |
| 89 | 89 | 1875 | His | His | His | His | His | Gln | | |
| 90 | 90 | 1878 | His | His | His | His | His | Gly | Glu | |
| 91 | 91 | 1879 | His | His | His | His | Ala | | | |
| 92 | 92 | 1880 | Gly | His | His | His | His | Gln | | |
| 93 | 93 | 1882 | His | His | His | His | Ala | | | |
| 94 | 94 | 1884 | Gly | His | His | His | His | Ala | | |
| 95 | 95 | 1886 | Gly | His | His | His | His | Ala | | |
| 96 | 96 | 1887 | Gly | His | His | His | His | Ala | NH2 | |
| 97 | 97 | 1888 | Gly | His | His | His | His | Gly | | |
| 98 | 98 | 1889 | Gly | His | His | His | His | Ala | | |
| 99 | 99 | 1890 | His | His | His | His | His | | | |
| 100 | 100 | 1891 | His | His | His | His | Ala | Ala | | |
| 101 | 101 | 1892 | Gly | His | His | His | Glu | | | |
| 102 | 102 | 1893 | Gly | His | His | His | Ala | | | |

FIG. 1X

| Analogue no. | SEQ ID NO. | G no. | hGCGr cAMP n | hGCGr cAMP vs hGCG | hGLP-1r cAMP n | hGLP-1r cAMP vs hGLP-1 | Mouse food intake inhibition (500nmol/kg) 0-24 | Mouse food intake inhibition 0-48 | Rat food intake inhibtion (500 nmol/kg with 1:1 Zn) 0-24 |
|---|---|---|---|---|---|---|---|---|---|
| 86 | 86 | 1872 | 3 | 1.3 | 1 | 5.2 | 57 | 39 | 62 |
| 87 | 87 | 1873 | 4 | 1.1 | 2 | 1.4 | 65 | 41 | 27 |
| 88 | 88 | 1874 | 2 | 2.2 |   |   | 36 | 27 |   |
| 89 | 89 | 1875 | 4 | 1.3 | 3 | 1.0 | 72 | 48 | 69 |
| 90 | 90 | 1878 | 1 | 2.4 |   |   | 93 | 74 | 49 |
| 91 | 91 | 1879 | 2 | 1.5 |   |   | 31 | 19 | 53 |
| 92 | 92 | 1880 | 2 | 1.9 |   |   | 50 | 27 | 71 |
| 93 | 93 | 1882 | 4 | 1.7 | 3 | 2.0 | 44 | 23 | 35 |
| 94 | 94 | 1884 | 2 | 1.7 |   |   | 39 | 21 | 34 |
| 95 | 95 | 1886 | 3 | 1.0 | 3 | 5.7 | 44 | 27 | 22 |
| 96 | 96 | 1887 | 2 | 1.3 |   |   | 26 | 12 | 3 |
| 97 | 97 | 1888 | 2 | 2.2 |   |   | 67 | 43 | 26 |
| 98 | 98 | 1889 | 2 | 2.3 | 2 | 2.4 | 49 | 45 | 25 |
| 99 | 99 | 1890 | 2 | 1.8 |   |   | 39 | 20 | 26 |
| 100 | 100 | 1891 | 3 | 2.9 |   |   |   |   | 59 |
| 101 | 101 | 1892 | 4 | 1.0 | 3 | 5.7 | 37 | 21 | 42 |
| 102 | 102 | 1893 | 2 | 1.5 |   |   | 38 | 23 | 75 |

FIG. 1Y

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 103 | 103 | 1894 | His | Ser | Gln | Gly | Thr | Phe | Thr | Ser | Asp | Tyr | Ser | His | Tyr | Leu | Asp |
| 104 | 104 | 1895 | His | Ser | Gln | Gly | Thr | Phe | Thr | Ser | Asp | Tyr | Ser | His | Tyr | Leu | Asp |
| 105 | 105 | 1896 | His | Ser | Gln | Gly | Thr | Phe | Thr | Ser | Asp | Tyr | Ser | His | Tyr | Leu | Asp |
| 106 | 106 | 1897 | His | Ser | Gln | Gly | Thr | Phe | Thr | Ser | Asp | Tyr | Ser | Lys | Tyr | Leu | Asp |
| 107 | 107 | 1898 | His | Ser | Gln | Gly | Thr | Phe | Thr | Ser | Asp | Tyr | Ser | Lys | Tyr | Leu | Asp |
| 108 | 108 | 1899 | His | Ser | Gln | Gly | Thr | Phe | Thr | Ser | Asp | Tyr | Ser | Lys | Tyr | Leu | Asp |
| 109 | 109 | 1900 | His | Ser | Gln | Gly | Thr | Phe | Thr | Ser | Asp | Tyr | Ser | Lys | Tyr | Leu | Asp |
| 110 | 110 | 1902 | His | Ser | Gln | Gly | Thr | Phe | Thr | Ser | Asp | Tyr | Ser | Lys | Tyr | Leu | Asp |
| 111 | 111 | 1903 | His | Ser | Gln | Gly | Thr | Phe | Thr | Ser | Asp | Tyr | Ser | Lys | Tyr | Leu | Asp |
| 112 | 112 | 1904 | His | Ser | Gln | Gly | Thr | Phe | Thr | Ser | Asp | Tyr | Ser | Lys | Tyr | Leu | Asp |
| 113 | 113 | 1905 | His | Ser | Gln | Gly | Thr | Phe | Thr | Ser | Asp | Tyr | Ser | Lys | Tyr | Leu | Asp |
| 114 | 114 | 1910 | His | Ser | Gln | Gly | Thr | Phe | Thr | Ser | Asp | Tyr | Ser | Lys | Tyr | Leu | Asp |
| 115 | 115 | 1911 | His | Ser | Gln | Gly | Thr | Phe | Thr | Ser | Asp | Tyr | Ser | Lys | Tyr | Leu | Asp |
| 116 | 116 | 1912 | His | Ser | Gln | Gly | Thr | Phe | Thr | Ser | Asp | Tyr | Ser | Lys | Tyr | Leu | Asp |
| 117 | 117 | 1913 | His | Ser | Gln | Gly | Thr | Phe | Thr | Ser | Asp | Tyr | Ser | Lys | Tyr | Leu | Asp |
| 118 | 118 | 1915 | His | Ser | Gln | Gly | Thr | Phe | Thr | Ser | Asp | Tyr | Ser | His | Tyr | Leu | Asp |
| 119 | 119 | 1916 | His | Ser | Gln | Gly | Thr | Phe | Thr | Ser | Asp | Tyr | Ser | His | Tyr | Leu | Asp |

FIG. 1Z

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 103 | 103 | 1894 | Gln | Lys | Arg | Ala | His | Glu | Phe | Ile | Glu | Trp | Leu | Leu | Asn | Gly |
| 104 | 104 | 1895 | Gln | Lys | Arg | Ala | His | Glu | Phe | Ile | Glu | Trp | Leu | Leu | Asn | Gly |
| 105 | 105 | 1896 | Gln | Lys | Arg | Ala | His | Glu | Phe | Ile | Glu | Trp | Leu | Leu | Asn | Gly |
| 106 | 106 | 1897 | Glu | Arg | Arg | Ala | His | Glu | Phe | Ile | Gln | Trp | Leu | Leu | Asn | Gly |
| 107 | 107 | 1898 | Glu | Arg | Arg | Ala | His | Glu | Phe | Ile | Gln | Trp | Leu | Leu | Asn | Gly |
| 108 | 108 | 1899 | Glu | Lys | Arg | Ala | His | Glu | Phe | Ile | Gln | Trp | Leu | Leu | Asn | Gly |
| 109 | 109 | 1900 | Glu | Arg | Arg | Ala | His | Glu | Phe | Ile | Glu | Trp | Leu | Leu | Asn | Gly |
| 110 | 110 | 1902 | Glu | Arg | Arg | Ala | His | Glu | Phe | Ile | Glu | Trp | Leu | Leu | Asn | Gly |
| 111 | 111 | 1903 | Glu | Arg | Arg | Ala | His | Glu | Phe | Ile | Glu | Trp | Leu | Leu | Asn | Gly |
| 112 | 112 | 1904 | Glu | Arg | Arg | Ala | His | Glu | Phe | Ile | Glu | Trp | Leu | Leu | Asn | Gly |
| 113 | 113 | 1905 | Glu | Arg | Arg | Ala | His | Glu | Phe | Ile | Glu | Trp | Leu | Leu | Asn | Gly |
| 114 | 114 | 1910 | Gln | Arg | Arg | Ala | His | Glu | Phe | Ile | Glu | Trp | Leu | Leu | Asn | Thr |
| 115 | 115 | 1911 | Gln | Arg | Arg | Ala | His | Glu | Phe | Ile | Glu | Trp | Leu | Leu | Asn | Thr |
| 116 | 116 | 1912 | Gln | Lys | Arg | Ala | His | Glu | Phe | Ile | Glu | Trp | Leu | Leu | Asn | Thr |
| 117 | 117 | 1913 | Gln | Lys | Arg | Ala | His | Glu | Phe | Ile | Glu | Trp | Leu | Leu | Asn | Thr |
| 118 | 118 | 1915 | Gln | Lys | Arg | Ala | His | Glu | Phe | Ile | Gln | Trp | Leu | Leu | Asn | Gly |
| 119 | 119 | 1916 | Gln | Lys | Arg | Ala | His | Glu | Phe | Ile | Gln | Trp | Leu | Leu | Asn | Gly |

FIG. 1AA

| Analogue no. | SEQ ID NO. | G no. | 30 | 31 | 32 | 33 | 34 | 35 | 36 | 37 |
|---|---|---|---|---|---|---|---|---|---|---|
| 103 | 103 | 1894 | Gly | His | His | His | His | Ala | | |
| 104 | 104 | 1895 | Gly | His | His | His | His | His | Ala | |
| 105 | 105 | 1896 | Gly | His | His | His | His | His | Glu | |
| 106 | 106 | 1897 | Gly | His | His | His | His | Ala | | |
| 107 | 107 | 1898 | Gly | His | His | His | His | His | Ala | |
| 108 | 108 | 1899 | Gly | His | His | His | His | Ala | | |
| 109 | 109 | 1900 | Gly | His | His | His | His | His | Glu | |
| 110 | 110 | 1902 | Gly | His | His | His | Ala | | | |
| 111 | 111 | 1903 | Gly | His | His | His | His | His | Gln | |
| 112 | 112 | 1904 | Gly | His | His | His | His | His | Ala | |
| 113 | 113 | 1905 | Gly | His | His | His | His | Gln | | |
| 114 | 114 | 1910 | Gly | His | His | His | His | Gln | | |
| 115 | 115 | 1911 | Gly | His | His | His | His | His | Glu | |
| 116 | 116 | 1912 | Gly | His | His | His | His | His | Ala | |
| 117 | 117 | 1913 | Gly | His | His | His | His | Ala | | |
| 118 | 118 | 1915 | Gly | His | His | His | His | Ala | | |
| 119 | 119 | 1916 | Gly | His | His | His | His | His | Ala | |

FIG. 1AB

| Analogue no. | SEQ ID NO. | G no. | hGCGr cAMP n | hGCGr cAMP vs hGCG | hGLP-1r cAMP n | hGLP-1r cAMP vs hGLP-1 | Mouse food intake inhibition (500nmol/kg) 0-24 | Mouse food intake inhibition (500nmol/kg) 0-48 | Rat food intake inhibtion (500 nmol/kg with 1:1 Zn) 0-24 |
|---|---|---|---|---|---|---|---|---|---|
| 103 | 103 | 1894 | 4 | 1.3 | | | 60 | 39 | 49 |
| 104 | 104 | 1895 | 2 | 1.3 | | | 80 | 61 | 45 |
| 105 | 105 | 1896 | 4 | 2.0 | 4 | 2.4 | 62 | 40 | 34 |
| 106 | 106 | 1897 | 3 | 0.9 | 1 | 1.4 | 40 | 21 | 50 |
| 107 | 107 | 1898 | 6 | 1.2 | 7 | 2.9 | 65 | 39 | 36 |
| 108 | 108 | 1899 | 2 | 1.4 | | | 42 | 23 | 59 |
| 109 | 109 | 1900 | 3 | 1.5 | 3 | 2.8 | 64 | 47 | 42 |
| 110 | 110 | 1902 | 3 | 1.4 | 2 | 1.0 | 48 | 28 | 44 |
| 111 | 111 | 1903 | 2 | 1.4 | | | 58 | 39 | 29 |
| 112 | 112 | 1904 | 2 | 1.5 | 1 | 1.7 | 60 | 38 | 58 |
| 113 | 113 | 1905 | 3 | 1.8 | | | 56 | 34 | 40 |
| 114 | 114 | 1910 | 5 | 2.3 | 4 | 5.0 | 47 | 29 | 16 |
| 115 | 115 | 1911 | 2 | 3.0 | | | | | |
| 116 | 116 | 1912 | 5 | 2.4 | | | 54 | 31 | 21 |
| 117 | 117 | 1913 | 1 | 1.7 | | | 48 | 30 | 64 |
| 118 | 118 | 1915 | 1 | 3.4 | | | 49 | 30 | 9 |
| 119 | 119 | 1916 | 3 | 2.0 | | | 64 | 47 | 34 |

FIG. 1AC

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 120 | 120 | 1917 | His | Ser | Gln | Gly | Thr | Phe | Thr | Ser | Asp | Tyr | Ser | Lys | Tyr | Leu | Asp |
| 121 | 121 | 1918 | His | Ser | Gln | Gly | Thr | Phe | Thr | Ser | Asp | Tyr | Ser | His | Tyr | Leu | Asp |
| 122 | 122 | 1921 | His | Ser | Gln | Gly | Thr | Phe | Thr | Ser | Asp | Tyr | Ser | Lys | Tyr | Leu | Asp |
| 123 | 123 | 1922 | His | Ser | Gln | Gly | Thr | Phe | Thr | Ser | Asp | Tyr | Ser | Lys | Tyr | Leu | Asp |
| 124 | 124 | 1923 | His | Ser | Gln | Gly | Thr | Phe | Thr | Ser | Asp | Tyr | Ser | Lys | Tyr | Leu | Asp |
| 125 | 125 | 1926 | His | Ser | Gln | Gly | Thr | Phe | Thr | Ser | Asp | Tyr | Ser | Lys | Tyr | Leu | Asp |
| 126 | 126 | 1927 | His | Ser | Gln | Gly | Thr | Phe | Thr | Ser | Asp | Tyr | Ser | Lys | Tyr | Leu | Asp |
| 127 | 127 | 1929 | His | Ser | Gln | Gly | Thr | Phe | Thr | Ser | Asp | Tyr | Ser | Lys | Tyr | Leu | Asp |
| 128 | 128 | 1930 | His | Ser | Gln | Gly | Thr | Phe | Thr | Ser | Asp | Tyr | Ser | Lys | Tyr | Leu | Asp |
| 129 | 129 | 1933 | His | Ser | Gln | Gly | Thr | Phe | Thr | Ser | Asp | Tyr | Ser | Lys | Tyr | Leu | Asp |
| 130 | 130 | 1934 | His | Ser | Gln | Gly | Thr | Phe | Thr | Ser | Asp | Tyr | Ser | Lys | Tyr | Leu | Asp |
| 131 | 131 | 1935 | His | Ser | Gln | Gly | Thr | Phe | Thr | Ser | Asp | Tyr | Ser | Lys | Tyr | Leu | Asp |
| 132 | 132 | 1936 | His | Ser | Gln | Gly | Thr | Phe | Thr | Ser | Asp | Tyr | Ser | His | Tyr | Leu | Asp |
| 133 | 133 | 1937 | His | Ser | Gln | Gly | Thr | Phe | Thr | Ser | Asp | Tyr | Ser | His | Tyr | Leu | Asp |
| 134 | 134 | 1938 | His | Ser | Gln | Gly | Thr | Phe | Thr | Ser | Asp | Tyr | Ser | Lys | Tyr | Leu | Asp |
| 135 | 135 | 1939 | His | Ser | Gln | Gly | Thr | Phe | Thr | Ser | Asp | Tyr | Ser | Lys | Tyr | Leu | Asp |
| 136 | 136 | 1940 | His | Ser | Gln | Gly | Thr | Phe | Thr | Ser | Asp | Tyr | Ser | Lys | Tyr | Leu | Asp |

FIG. 1AD

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 120 | 120 | 1917 | Glu | Arg | Arg | Ala | His | Glu | Phe | Ile | Gln | Trp | Leu | Leu | Asn | Gly |
| 121 | 121 | 1918 | Gln | Lys | Arg | Ala | His | Glu | Phe | Ile | Glu | Trp | Leu | Leu | Asn | Gly |
| 122 | 122 | 1921 | Glu | Arg | Arg | Ala | His | Glu | Phe | Ile | Gln | Trp | Leu | Leu | Asn | Gly |
| 123 | 123 | 1922 | Glu | Arg | Arg | Ala | His | Glu | Phe | Ile | Gln | Trp | Leu | Leu | Asn | Gly |
| 124 | 124 | 1923 | Glu | Arg | Arg | Ala | His | Glu | Phe | Ile | Glu | Trp | Leu | Leu | Asn | Gly |
| 125 | 125 | 1926 | Glu | Lys | Arg | Ala | His | Glu | Phe | Ile | Gln | Trp | Leu | Leu | Asn | Thr |
| 126 | 126 | 1927 | Glu | Lys | Arg | Ala | His | Glu | Phe | Ile | Gln | Trp | Leu | Leu | Asn | Thr |
| 127 | 127 | 1929 | Glu | Arg | Arg | Ala | His | Glu | Phe | Ile | Gln | Trp | Leu | Leu | Asn | Gly |
| 128 | 128 | 1930 | Glu | Arg | Arg | Ala | His | Glu | Phe | Ile | Gln | Trp | Leu | Leu | Asn | Gly |
| 129 | 129 | 1933 | Glu | Arg | Arg | Ala | His | Glu | Phe | Ile | Gln | Trp | Leu | Leu | Asn | Gly |
| 130 | 130 | 1934 | Glu | Lys | Arg | Ala | His | Glu | Phe | Ile | Gln | Trp | Leu | Leu | Asn | Gly |
| 131 | 131 | 1935 | Gln | Arg | Arg | Ala | His | Glu | Phe | Ile | Gln | Trp | Leu | Leu | Asn | Gly |
| 132 | 132 | 1936 | Gln | Lys | Arg | Ala | His | Glu | Phe | Ile | Gln | Trp | Leu | Leu | Asn | Gly |
| 133 | 133 | 1937 | Glu | Lys | Arg | Ala | His | Glu | Phe | Ile | Gln | Trp | Leu | Leu | Asn | Gly |
| 134 | 134 | 1938 | Glu | Lys | Arg | Ala | His | Glu | Phe | Ile | Glu | Trp | Leu | Leu | Asn | Gly |
| 135 | 135 | 1939 | Glu | Arg | Arg | Ala | His | Glu | Phe | Ile | Glu | Trp | Leu | Leu | Asn | Gly |
| 136 | 136 | 1940 | Ser | Lys | Arg | Ala | His | Glu | Phe | Ile | Glu | Trp | Leu | Leu | Asn | Gly |

FIG. 1AE

| Analogue no. | SEQ ID NO. | G no. | 30 | 31 | 32 | 33 | 34 | 35 | 36 | 37 |
|---|---|---|---|---|---|---|---|---|---|---|
| 120 | 120 | 1917 | Gly | His | His | His | His | Gly | NH2 | |
| 121 | 121 | 1918 | His | His | His | His | Glu | | | |
| 122 | 122 | 1921 | Gly | His | His | His | His | Gln | NH2 | |
| 123 | 123 | 1922 | Gly | His | His | His | His | His | Ala | NH2 |
| 124 | 124 | 1923 | Gly | His | His | His | His | Gly | NH2 | |
| 125 | 125 | 1926 | Gly | His | His | His | His | Ala | | |
| 126 | 126 | 1927 | His | His | His | His | Ala | | | |
| 127 | 127 | 1929 | Gly | His | His | His | His | Ala | Ala | NH2 |
| 128 | 128 | 1930 | Gly | His | His | His | His | Ala | Ala | NH2 |
| 129 | 129 | 1933 | Gly | His | His | His | His | Ala | NH2 | |
| 130 | 130 | 1934 | Gly | His | His | His | His | Ala | NH2 | |
| 131 | 131 | 1935 | Gly | His | His | His | His | Ala | NH2 | |
| 132 | 132 | 1936 | Gly | His | His | His | His | Ala | NH2 | |
| 133 | 133 | 1937 | Gly | His | His | His | His | Ala | NH2 | |
| 134 | 134 | 1938 | Gly | His | His | His | His | Ala | NH2 | |
| 135 | 135 | 1939 | His | His | His | His | His | His | Ala | NH2 |
| 136 | 136 | 1940 | His | His | His | His | His | Ala | | |

FIG. 1AF

| Analogue no. | SEQ ID NO. | G no. | hGCGr cAMP n | hGCGr cAMP vs hGCG | hGLP-1r cAMP n | hGLP-1r cAMP vs hGLP-1 | Mouse food intake inhibition (500nmol/kg) 0-24 | Mouse food intake inhibition (500nmol/kg) 0-48 | Rat food intake inhibtion (500 nmol/kg with 1:1 Zn) 0-24 |
|---|---|---|---|---|---|---|---|---|---|
| 120 | 120 | 1917 | 2 | 1.0 | 2 | 1.5 | 55 | 36 | 41 |
| 121 | 121 | 1918 | 3 | 1.1 | 3 | 3.7 | 60 | 36 | 39 |
| 122 | 122 | 1921 | 2 | 1.7 | | | 34 | 23 | 34 |
| 123 | 123 | 1922 | 3 | 1.0 | 3 | 1.7 | 53 | 32 | 35 |
| 124 | 124 | 1923 | 2 | 1.5 | | | 57 | 34 | 59 |
| 125 | 125 | 1926 | 3 | 2.4 | | | 68 | 41 | 54 |
| 126 | 126 | 1927 | 2 | 3.1 | | | 68 | 34 | |
| 127 | 127 | 1929 | 2 | 2.5 | | | 67 | 33 | 20 |
| 128 | 128 | 1930 | 5 | 1.3 | 6 | 1.5 | 42 | 26 | 46 |
| 129 | 129 | 1933 | | | | | 38 | 20 | 36 |
| 130 | 130 | 1934 | 3 | 2.0 | 3 | 4.6 | 40 | 23 | 43 |
| 131 | 131 | 1935 | 3 | 1.4 | | | 20 | 13 | -2 |
| 132 | 132 | 1936 | 1 | 2.1 | | | 35 | 21 | |
| 133 | 133 | 1937 | 3 | 3.0 | | | 35 | 20 | 13 |
| 134 | 134 | 1938 | 4 | 3.5 | | | | | |
| 135 | 135 | 1939 | 2 | 2.3 | | | 48 | 24 | 25 |
| 136 | 136 | 1940 | 4 | 1.7 | 4 | 3.3 | 60 | 39 | 35 |

FIG. 1AG

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 137 | 137 | 1941 | His | Ser | Gln | Gly | Thr | Phe | Thr | Ser | Asp | Tyr | Ser | Lys | Tyr | Leu | Asp |
| 138 | 138 | 1944 | His | Ser | Gln | Gly | Thr | Phe | Thr | Ser | Asp | Tyr | Ser | Lys | Tyr | Leu | Asp |
| 139 | 139 | 1945 | His | Ser | Gln | Gly | Thr | Phe | Thr | Ser | Asp | Tyr | Ser | Lys | Tyr | Leu | Asp |
| 140 | 140 | 1946 | His | Ser | Gln | Gly | Thr | Phe | Thr | Ser | Asp | Tyr | Ser | Lys | Tyr | Leu | Asp |
| 141 | 141 | 1948 | His | Ser | Gln | Gly | Thr | Phe | Thr | Ser | Asp | Tyr | Ser | Lys | Tyr | Leu | Asp |
| 142 | 142 | 1950 | His | Ser | Gln | Gly | Thr | Phe | Thr | Ser | Asp | Tyr | Ser | Lys | Tyr | Leu | Asp |
| 143 | 143 | 1952 | His | Ser | Gln | Gly | Thr | Phe | Thr | Ser | Asp | Tyr | Ser | Lys | Tyr | Leu | Asp |
| 144 | 144 | 1953 | His | Ser | Gln | Gly | Thr | Phe | Thr | Ser | Asp | Tyr | Ser | Lys | Tyr | Leu | Asp |
| 145 | 145 | 1954 | His | Ser | Gln | Gly | Thr | Phe | Thr | Ser | Asp | Tyr | Ser | Lys | Tyr | Leu | Asp |
| 146 | 146 | 1957 | His | Ser | Gln | Gly | Thr | Phe | Thr | Ser | Asp | Tyr | Ser | Lys | Tyr | Leu | Asp |
| 147 | 147 | 1958 | His | Ser | Gln | Gly | Thr | Phe | Thr | Ser | Asp | Tyr | Ser | Lys | Tyr | Leu | Asp |
| 148 | 148 | 1962 | His | Ser | Gln | Gly | Thr | Phe | Thr | Ser | Asp | Tyr | Ser | Lys | Tyr | Leu | Asp |
| 149 | 149 | 1963 | His | Ser | Gln | Gly | Thr | Phe | Thr | Ser | Asp | Tyr | Ser | His | Tyr | Leu | Asp |
| 150 | 150 | 1964 | His | Ser | Gln | Gly | Thr | Phe | Thr | Ser | Asp | Tyr | Ser | His | Tyr | Leu | Asp |
| 151 | 151 | 1966 | His | Ser | Gln | Gly | Thr | Phe | Thr | Ser | Asp | Tyr | Ser | Lys | Tyr | Leu | Asp |
| 152 | 152 | 1971 | His | Ser | Gln | Gly | Thr | Phe | Thr | Ser | Asp | Tyr | Ser | Lys | Tyr | Leu | Asp |
| 153 | 153 | 1972 | His | Ser | Gln | Gly | Thr | Phe | Thr | Ser | Asp | Tyr | Ser | Lys | Tyr | Leu | Asp |

FIG. 1AH

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 137 | 137 | 1941 | Ser | Lys | Arg | Ala | His | Glu | Phe | Ile | Glu | Trp | Leu | Leu | Asn | Gly |
| 138 | 138 | 1944 | Ser | Arg | Arg | Ala | His | Glu | Phe | Ile | Gln | Trp | Leu | Leu | Asn | Gly |
| 139 | 139 | 1945 | Glu | Lys | Arg | Ala | His | Asp | Phe | Ile | Glu | Trp | Leu | Leu | Asn | Gly |
| 140 | 140 | 1946 | Glu | Lys | Arg | Ala | His | Asp | Phe | Ile | Glu | Trp | Leu | Leu | Asn | Gly |
| 141 | 141 | 1948 | Glu | Lys | Arg | Ala | His | Glu | Phe | Ile | Glu | Trp | Leu | Leu | Asn | Thr |
| 142 | 142 | 1950 | Glu | Lys | Arg | Ala | His | Glu | Phe | Ile | Gln | Trp | Leu | Leu | Asn | Gly |
| 143 | 143 | 1952 | Glu | Arg | Arg | Ala | His | Glu | Phe | Ile | Gln | Trp | Leu | Leu | Asn | Gly |
| 144 | 144 | 1953 | Gln | Arg | Arg | Ala | His | Glu | Phe | Ile | Gln | Trp | Leu | Leu | Asn | Gly |
| 145 | 145 | 1954 | Gln | Arg | Arg | Ala | His | Glu | Phe | Ile | Gln | Trp | Leu | Leu | Asn | Thr |
| 146 | 146 | 1957 | Gln | Lys | Arg | Ala | His | Glu | Phe | Ile | Gln | Trp | Leu | Leu | Asn | Thr |
| 147 | 147 | 1958 | Gln | Arg | Arg | Ala | His | Glu | Phe | Ile | Glu | Trp | Leu | Leu | Asn | Gly |
| 148 | 148 | 1962 | Glu | Arg | Arg | Ala | His | Glu | Phe | Ile | Glu | Trp | Leu | Leu | Asn | Gly |
| 149 | 149 | 1963 | Glu | Arg | Arg | Ala | His | Glu | Phe | Ile | Glu | Trp | Leu | Leu | Asn | Gly |
| 150 | 150 | 1964 | Gln | Lys | Arg | Ala | His | Glu | Phe | Ile | Glu | Trp | Leu | Leu | Asn | Gly |
| 151 | 151 | 1966 | Gln | Lys | Arg | Ala | His | Glu | Phe | Ile | Glu | Trp | Leu | Leu | Asn | Gly |
| 152 | 152 | 1971 | Glu | Lys | Arg | Ala | His | Glu | Phe | Ile | Glu | Trp | Leu | Leu | Asn | Gly |
| 153 | 153 | 1972 | Glu | Lys | Arg | Ala | His | Glu | Phe | Ile | Glu | Trp | Leu | Leu | Asn | Thr |

FIG. 1AI

| Analogue no. | SEQ ID NO. | G no. | 30 | 31 | 32 | 33 | 34 | 35 | 36 | 37 |
|---|---|---|---|---|---|---|---|---|---|---|
| 137 | 137 | 1941 | His | His | His | His | His | Ala | NH2 | |
| 138 | 138 | 1944 | His | His | His | His | Glu | | | |
| 139 | 139 | 1945 | His | His | His | His | His | Ala | | |
| 140 | 140 | 1946 | His | His | His | His | His | Ala | NH2 | |
| 141 | 141 | 1948 | His | His | His | His | His | Ala | | |
| 142 | 142 | 1950 | His | His | His | His | His | Gln | NH2 | |
| 143 | 143 | 1952 | His | His | His | His | Glu | NH2 | | |
| 144 | 144 | 1953 | His | His | His | His | Glu | | | |
| 145 | 145 | 1954 | Gly | His | His | His | Gln | NH2 | | |
| 146 | 146 | 1957 | Gly | His | His | His | Gln | NH2 | | |
| 147 | 147 | 1958 | Gly | His | His | His | His | Gln | NH2 | |
| 148 | 148 | 1962 | Gly | His | His | His | His | Gln | Gln | |
| 149 | 149 | 1963 | Gly | His | His | His | Glu | Gln | Gln | NH2 |
| 150 | 150 | 1964 | Gly | His | His | His | Glu | NH2 | | |
| 151 | 151 | 1966 | His | His | His | His | Ala | NH2 | | |
| 152 | 152 | 1971 | His | His | His | His | Ala | NH2 | | |
| 153 | 153 | 1972 | His | His | His | His | Ala | | | |

FIG. 1AJ

| Analogue no. | SEQ ID NO. | G no. | hGCGr cAMP | | Mouse food intake inhibition (500nmol/kg) | | Rat food intake inhibition (500 nmol/kg with 1:1 Zn) |
|---|---|---|---|---|---|---|---|
| | | | n | cAMP vs hGCG | hGLP-1r cAMP n vs hGLP-1 | 0-24 0-48 | 0-24 |
| 137 | 137 | 1941 | 4 | 1.6 | 3 3.7 | 40 26 | 35 |
| 138 | 138 | 1944 | 2 | 3.3 | | 24 11 | 11 |
| 139 | 139 | 1945 | 3 | 2.0 | 2 3.5 | 80 50 | 16 |
| 140 | 140 | 1946 | 5 | 1.2 | 4 2.5 | 63 43 | 22 |
| 141 | 141 | 1948 | 3 | 2.4 | | 81 55 | 16 |
| 142 | 142 | 1950 | 3 | 1.0 | 2 2.4 | 72 47 | 54 |
| 143 | 143 | 1952 | 2 | 1.1 | | 50 26 | 27 |
| 144 | 144 | 1953 | 2 | 3.2 | | 47 29 | 20 |
| 145 | 145 | 1954 | 3 | 1.7 | | 32 21 | 17 |
| 146 | 146 | 1957 | 2 | 1.4 | | 28 18 | 35 |
| 147 | 147 | 1958 | 5 | 1.7 | 5 6.4 | 20 12 | 7 |
| 148 | 148 | 1962 | 4 | 1.5 | 4 2.1 | 47 28 | 49 |
| 149 | 149 | 1963 | 4 | 1.3 | 4 2.3 | 51 34 | 49 |
| 150 | 150 | 1964 | 3 | 1.1 | 3 1.6 | 34 24 | 61 |
| 151 | 151 | 1966 | 4 | 1.9 | 3 1.8 | 33 18 | 39 |
| 152 | 152 | 1971 | 3 | 1.5 | 3 3.7 | 54 34 | 34 |
| 153 | 153 | 1972 | 5 | 1.8 | 3 8.9 | 66 40 | 53 |

FIG. 1AK

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 154 | 154 | 1973 | His | Ser | Gln | Gly | Thr | Phe | Thr | Ser | Asp | Tyr | Ser | Lys | Tyr | Leu | Asp |
| 155 | 155 | 1975 | His | Ser | Gln | Gly | Thr | Phe | Thr | Ser | Asp | Tyr | Ser | Lys | Tyr | Leu | Asp |
| 156 | 156 | 1976 | His | Ser | Gln | Gly | Thr | Phe | Thr | Ser | Asp | Tyr | Ser | Lys | Tyr | Leu | Asp |
| 157 | 157 | 1977 | His | Ser | Gln | Gly | Thr | Phe | Thr | Ser | Asp | Tyr | Ser | Lys | Tyr | Leu | Asp |
| 158 | 158 | 1978 | His | Ser | Gln | Gly | Thr | Phe | Thr | Ser | Asp | Tyr | Ser | Lys | Tyr | Leu | Asp |
| 159 | 159 | 1979 | His | Ser | Gln | Gly | Thr | Phe | Thr | Ser | Asp | Tyr | Ser | Lys | Tyr | Leu | Asp |
| 160 | 160 | 1980 | His | Ser | Gln | Gly | Thr | Phe | Thr | Ser | Asp | Tyr | Ser | Lys | Tyr | Leu | Asp |
| 161 | 161 | 1981 | His | Ser | Gln | Gly | Thr | Phe | Thr | Ser | Asp | Tyr | Ser | His | Tyr | Leu | Asp |
| 162 | 162 | 1982 | His | Ser | Gln | Gly | Thr | Phe | Thr | Ser | Asp | Tyr | Ser | His | Tyr | Leu | Asp |
| 163 | 163 | 1983 | His | Ser | Gln | Gly | Thr | Phe | Thr | Ser | Asp | Tyr | Ser | His | Tyr | Leu | Asp |
| 164 | 164 | 1987 | His | Ser | Gln | Gly | Thr | Phe | Thr | Ser | Asp | Tyr | Ser | His | Gln | Leu | Asp |
| 165 | 165 | 1988 | His | Ser | Gln | Gly | Thr | Phe | Thr | Ser | Asp | Tyr | Ser | His | Tyr | Leu | Asp |
| 166 | 166 | 1989 | His | Ser | Gln | Gly | Thr | Phe | Thr | Ser | Asp | Tyr | Ser | His | Tyr | Leu | Asp |
| 167 | 167 | 1991 | His | Ser | Gln | Gly | Thr | Phe | Thr | Ser | Asp | Tyr | Ser | Lys | Tyr | Leu | Asp |
| 168 | 168 | 1992 | His | Ser | Gln | Gly | Thr | Phe | Thr | Ser | Asp | Tyr | Ser | Lys | Tyr | Leu | Asp |
| 169 | 169 | 1998 | His | Ser | Gln | Gly | Thr | Phe | Thr | Ser | Asp | Tyr | Ser | Lys | Tyr | Leu | Asp |
| 170 | 170 | 1999 | His | Ser | Gln | Gly | Thr | Phe | Thr | Ser | Asp | Tyr | Ser | Lys | Gln | Leu | Asp |

FIG. 1AL

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 154 | 154 | 1973 | Glu | Lys | Arg | Ala | His | Glu | Phe | Ile | Glu | Trp | Leu | Leu | Asn | Thr |
| 155 | 155 | 1975 | Glu | Lys | Arg | Ala | His | Glu | Phe | Ile | Glu | Trp | Leu | Leu | Asn | Thr |
| 156 | 156 | 1976 | Glu | Lys | Arg | Ala | His | Glu | Phe | Ile | Glu | Trp | Leu | Leu | Asn | Thr |
| 157 | 157 | 1977 | Glu | Lys | Arg | Ala | His | Glu | Phe | Ile | Glu | Trp | Leu | Leu | Asn | Thr |
| 158 | 158 | 1978 | Glu | Lys | Arg | Ala | His | Glu | Phe | Ile | Glu | Trp | Leu | Leu | Asn | Thr |
| 159 | 159 | 1979 | Glu | Lys | Arg | Ala | His | Glu | Phe | Ile | Glu | Trp | Leu | Leu | Asn | Gly |
| 160 | 160 | 1980 | Gln | Lys | Arg | Ala | His | Glu | Phe | Ile | Glu | Trp | Leu | Leu | Asn | Gly |
| 161 | 161 | 1981 | Gln | Lys | Arg | Ala | His | Glu | Phe | Ile | Glu | Trp | Leu | Leu | Asn | Gly |
| 162 | 162 | 1982 | Gln | Lys | Arg | Ala | His | Glu | Phe | Ile | Glu | Trp | Leu | Leu | Asn | Gly |
| 163 | 163 | 1983 | Gln | Lys | Arg | Ala | His | Glu | Phe | Ile | Glu | Trp | Leu | Leu | Asn | Gly |
| 164 | 164 | 1987 | Glu | Lys | Arg | Ala | His | Glu | Phe | Ile | Glu | Trp | Leu | Leu | Asn | Gly |
| 165 | 165 | 1988 | Gln | Lys | Arg | Ala | His | Glu | Phe | Ile | Glu | Trp | Leu | Leu | Asn | Gly |
| 166 | 166 | 1989 | Gln | Lys | Arg | Ala | His | Glu | Phe | Ile | Glu | Trp | Leu | Leu | Asn | Gly |
| 167 | 167 | 1991 | Glu | Arg | Arg | Ala | His | Glu | Phe | Ile | Glu | Trp | Leu | Leu | Asn | Gly |
| 168 | 168 | 1992 | Glu | Lys | Arg | Ala | His | Glu | Phe | Ile | Glu | Trp | Leu | Leu | Asn | Gly |
| 169 | 169 | 1998 | Ser | Arg | Arg | Ala | His | Glu | Phe | Ile | Glu | Trp | Leu | Leu | Asn | Gly |
| 170 | 170 | 1999 | Glu | Arg | Arg | Ala | His | Glu | Phe | Ile | Glu | Trp | Leu | Leu | Asn | Gly |

FIG. 1AM

| Analogue no. | SEQ ID NO. | G no. | 30 | 31 | 32 | 33 | 34 | 35 | 36 | 37 |
|---|---|---|---|---|---|---|---|---|---|---|
| 154 | 154 | 1973 | His | His | His | His | Glu | NH2 | | |
| 155 | 155 | 1975 | His | Gly | His | His | Ala | | | |
| 156 | 156 | 1976 | His | Gly | His | His | Ala | NH2 | | |
| 157 | 157 | 1977 | His | Gly | His | His | Glu | | | |
| 158 | 158 | 1978 | His | Gly | His | His | Glu | NH2 | | |
| 159 | 159 | 1979 | His | Gly | His | His | NH2 | | | |
| 160 | 160 | 1980 | Gly | His | His | His | Gly | | | |
| 161 | 161 | 1981 | Gly | His | His | His | Gly | NH2 | | |
| 162 | 162 | 1982 | Gly | His | His | His | His | Ala | NH2 | |
| 163 | 163 | 1983 | Gly | His | His | His | His | Gln | NH2 | |
| 164 | 164 | 1987 | Gly | His | His | His | His | Gln | | |
| 165 | 165 | 1988 | Gly | His | His | His | His | His | Ala | NH2 |
| 166 | 166 | 1989 | Gly | His | His | His | His | His | Glu | NH2 |
| 167 | 167 | 1991 | Gly | His | His | His | His | His | Glu | NH2 |
| 168 | 168 | 1992 | His | His | His | His | Glu | NH2 | | |
| 169 | 169 | 1998 | Gly | His | His | His | His | His | Glu | |
| 170 | 170 | 1999 | Gly | His | His | His | His | His | Glu | |

FIG. 1AN

| Analogue no. | SEQ ID NO. | G no. | hGCGr cAMP | | | hGLP-1r cAMP | | Mouse food intake inhibition (500nmol/kg) | | Rat food intake inhibtion (500 nmol/kg with 1:1 Zn) |
|---|---|---|---|---|---|---|---|---|---|---|
| | | | n | vs hGCG | | n | vs hGLP-1 | 0-24 | 0-48 | 0-24 |
| 154 | 154 | 1973 | 2 | 1.6 | | 2 | 11.3 | 62 | 41 | 39 |
| 155 | 155 | 1975 | 3 | 2.3 | | 2 | 4.9 | 48 | 27 | 49 |
| 156 | 156 | 1976 | 4 | 1.4 | | 4 | 4.7 | 46 | 29 | 30 |
| 157 | 157 | 1977 | 3 | 2.2 | | 2 | 6.5 | 45 | 25 | 51 |
| 158 | 158 | 1978 | 2 | 1.5 | | 2 | 5.6 | 48 | 26 | 43 |
| 159 | 159 | 1979 | 2 | 1.6 | | | | 29 | 17 | 56 |
| 160 | 160 | 1980 | 2 | 1.5 | | 1 | 2.6 | 36 | 20 | 33 |
| 161 | 161 | 1981 | 2 | 1.2 | | 2 | 1.6 | 37 | 18 | 41 |
| 162 | 162 | 1982 | 2 | 1.6 | | 2 | 1.4 | 66 | 36 | 46 |
| 163 | 163 | 1983 | 6 | 1.9 | | 3 | 1.8 | 43 | 26 | 32 |
| 164 | 164 | 1987 | 2 | 3.7 | | | | 34 | 17 | -0 |
| 165 | 165 | 1988 | 2 | 3.1 | | | | 53 | 28 | 29 |
| 166 | 166 | 1989 | 3 | 1.7 | | 3 | 2.6 | 58 | 32 | 36 |
| 167 | 167 | 1991 | 2 | 1.4 | | | | 41 | 31 | 37 |
| 168 | 168 | 1992 | 2 | 1.0 | | | | 65 | 36 | 48 |
| 169 | 169 | 1998 | 1 | 2.1 | | | | 35 | 43 | 15 |
| 170 | 170 | 1999 | 1 | 1.0 | | | | 37 | 22 | 3 |

FIG. 1AO

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 171 | 171 | 2000 | His | Ser | Gln | Gly | Thr | Phe | Thr | Ser | Asp | Tyr | Ser | Lys | Tyr | Leu | Asp |
| 172 | 172 | 2001 | His | Ser | Gln | Gly | Thr | Phe | Thr | Ser | Asp | Tyr | Ser | Lys | Gln | Leu | Asp |
| 173 | 173 | 2004 | His | Ser | Gln | Gly | Thr | Phe | Thr | Ser | Asp | Tyr | Ser | Lys | Tyr | Leu | Asp |
| 174 | 174 | 2012 | His | Ser | Gln | Gly | Thr | Phe | Thr | Ser | Asp | Tyr | Ser | Lys | Tyr | Leu | Asp |
| 175 | 175 | 2018 | His | Ser | Gln | Gly | Thr | Phe | Thr | Ser | Asp | Tyr | Ser | Lys | Tyr | Leu | Asp |
| 176 | 176 | 2022 | His | Ser | Gln | Gly | Thr | Phe | Thr | Ser | Asp | Tyr | Ser | Lys | Tyr | Leu | Asp |
| 177 | 177 | 2023 | His | Ser | Gln | Gly | Thr | Phe | Thr | Ser | Asp | Tyr | Ser | Lys | Gln | Leu | Asp |
| 178 | 178 | 2025 | His | Ser | Gln | Gly | Thr | Phe | Thr | Ser | Asp | Tyr | Ser | Lys | Tyr | Leu | Asp |
| 179 | 179 | 2026 | His | Ser | Gln | Gly | Thr | Phe | Thr | Ser | Asp | Tyr | Ser | Lys | Tyr | Leu | Asp |
| 180 | 180 | 2027 | His | Ser | Gln | Gly | Thr | Phe | Thr | Ser | Asp | Tyr | Ser | Lys | Tyr | Leu | Asp |
| 181 | 181 | 2028 | His | Ser | Gln | Gly | Thr | Phe | Thr | Ser | Asp | Tyr | Ser | Lys | Tyr | Leu | Asp |
| 182 | 182 | 2029 | His | Ser | Gln | Gly | Thr | Phe | Thr | Ser | Asp | Tyr | Ser | Lys | Tyr | Leu | Asp |
| 183 | 183 | 2030 | His | Ser | Gln | Gly | Thr | Phe | Thr | Ser | Asp | Tyr | Ser | Lys | Tyr | Leu | Asp |
| 184 | 184 | 2031 | His | Ser | Gln | Gly | Thr | Phe | Thr | Ser | Asp | Tyr | Ser | Lys | Gln | Leu | Asp |
| 185 | 185 | 2033 | His | Ser | Gln | Gly | Thr | Phe | Thr | Ser | Asp | Tyr | Ser | Lys | Tyr | Leu | Asp |
| 186 | 186 | 2036 | His | Ser | Gln | Gly | Thr | Phe | Thr | Ser | Asp | Tyr | Ser | Lys | Tyr | Leu | Asp |
| 187 | 187 | 2037 | His | Ser | Gln | Gly | Thr | Phe | Thr | Ser | Asp | Tyr | Ser | Lys | Gln | Leu | Asp |

FIG. 1AP

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 171 | 171 | 2000 | Ser | Arg | Arg | Ala | His | Glu | Phe | Ile | Glu | Trp | Leu | Leu | Asn | Gly |
| 172 | 172 | 2001 | Glu | Arg | Arg | Ala | His | Glu | Phe | Ile | Glu | Trp | Leu | Leu | Asn | Gly |
| 173 | 173 | 2004 | Ser | Lys | Arg | Ala | His | Glu | Phe | Ile | Glu | Trp | Leu | Leu | Asn | Gly |
| 174 | 174 | 2012 | Glu | Lys | Arg | Ala | His | Glu | Phe | Ile | Glu | Trp | Leu | Leu | Asn | Thr |
| 175 | 175 | 2018 | Glu | Arg | Arg | Ala | His | Glu | Phe | Ile | Gln | Trp | Leu | Leu | Asn | Gly |
| 176 | 176 | 2022 | Glu | Lys | Arg | Ala | His | Glu | Phe | Ile | Gln | Trp | Leu | Leu | Asn | Gly |
| 177 | 177 | 2023 | Glu | Arg | Arg | Ala | His | Glu | Phe | Ile | Gln | Trp | Leu | Leu | Asn | Gly |
| 178 | 178 | 2025 | Glu | Lys | Arg | Ala | His | Glu | Phe | Ile | Glu | Trp | Leu | Leu | Asn | Gly |
| 179 | 179 | 2026 | Glu | Lys | Arg | Ala | His | Glu | Phe | Ile | Gln | Trp | Leu | Leu | Asn | Gly |
| 180 | 180 | 2027 | Glu | Arg | Arg | Ala | His | Glu | Phe | Ile | Glu | Trp | Leu | Leu | Asn | Thr |
| 181 | 181 | 2028 | Glu | Arg | Arg | Ala | His | Glu | Phe | Ile | Gln | Trp | Leu | Leu | Asn | Thr |
| 182 | 182 | 2029 | Glu | Lys | Arg | Ala | His | Glu | Phe | Ile | Glu | Trp | Leu | Leu | Asn | Thr |
| 183 | 183 | 2030 | Glu | Arg | Arg | Ala | His | Glu | Phe | Ile | Gln | Trp | Leu | Leu | Asn | Thr |
| 184 | 184 | 2031 | Glu | Arg | Arg | Ala | His | Glu | Phe | Ile | Glu | Trp | Leu | Leu | Asn | Gly |
| 185 | 185 | 2033 | Glu | Arg | Arg | Ala | His | Glu | Phe | Ile | Glu | Trp | Leu | Leu | Asn | Thr |
| 186 | 186 | 2036 | Glu | Arg | Arg | Ala | His | Glu | Phe | Ile | Glu | Trp | Leu | Leu | Asn | Thr |
| 187 | 187 | 2037 | Glu | Arg | Arg | Ala | His | Glu | Phe | Ile | Glu | Trp | Leu | Leu | Asn | Thr |

FIG. 1AQ

| Analogue no. | SEQ ID NO. | G no. | 30 | 31 | 32 | 33 | 34 | 35 | 36 | 37 |
|---|---|---|---|---|---|---|---|---|---|---|
| 171 | 171 | 2000 | Gly | His | His | His | His | His | Glu | NH2 |
| 172 | 172 | 2001 | Gly | His | His | His | His | His | Glu | NH2 |
| 173 | 173 | 2004 | His | Gly | His | His | Glu | NH2 | | |
| 174 | 174 | 2012 | His | His | His | His | His | Ser | NH2 | |
| 175 | 175 | 2018 | Gly | His | His | His | His | Ser | Ala | NH2 |
| 176 | 176 | 2022 | Gly | His | His | His | His | Ala | Ala | NH2 |
| 177 | 177 | 2023 | Gly | His | His | His | His | Ala | Ala | NH2 |
| 178 | 178 | 2025 | His | His | His | His | His | Ser | Gln | NH2 |
| 179 | 179 | 2026 | Gly | His | His | His | His | His | Ala | NH2 |
| 180 | 180 | 2027 | Gly | His | His | His | His | His | Gln | |
| 181 | 181 | 2028 | Gly | His | His | His | His | His | Ala | NH2 |
| 182 | 182 | 2029 | Gly | His | His | His | His | His | Ala | NH2 |
| 183 | 183 | 2030 | Gly | His | His | His | His | Gln | Glu | NH2 |
| 184 | 184 | 2031 | Gly | His | His | His | His | His | Ala | NH2 |
| 185 | 185 | 2033 | Gly | His | His | His | His | Gln | Gln | |
| 186 | 186 | 2036 | Gly | His | His | His | His | His | Glu | NH2 |
| 187 | 187 | 2037 | Gly | His | His | His | His | His | Glu | NH2 |

FIG. 1AR

| Analogue no. | SEQ ID NO. | G no. | hGCGr n | hGCGr cAMP vs hGCG | hGLP-1r n | hGLP-1r cAMP vs hGLP-1 | Mouse food intake inhibition (500nmol/kg) 0-24 | Mouse food intake inhibition 0-48 | Rat food intake inhibition (500 nmol/kg with 1:1 Zn) 0-24 |
|---|---|---|---|---|---|---|---|---|---|
| 171 | 171 | 2000 | 2 | 1.3 | | | 35 | 23 | 19 |
| 172 | 172 | 2001 | 1 | 1.4 | 1 | 2.3 | 11 | 1 | 4 |
| 173 | 173 | 2004 | 1 | 2.3 | | | 19 | 6 | 29 |
| 174 | 174 | 2012 | 2 | 1.4 | | | 54 | 35 | 34 |
| 175 | 175 | 2018 | 2 | 2.2 | | | 27 | 13 | 39 |
| 176 | 176 | 2022 | 2 | 2.6 | | | 60 | 38 | 36 |
| 177 | 177 | 2023 | 2 | 2.6 | | | 3 | 4 | -16 |
| 178 | 178 | 2025 | 2 | 0.9 | | | 49 | 30 | 43 |
| 179 | 179 | 2026 | 2 | 1.6 | | | 44 | 27 | 38 |
| 180 | 180 | 2027 | 2 | 1.6 | | | 32 | 23 | 20 |
| 181 | 181 | 2028 | 2 | 1.7 | | | 22 | 9 | 13 |
| 182 | 182 | 2029 | 4 | 1.4 | 3 | 2.7 | 30 | 19 | 20 |
| 183 | 183 | 2030 | 2 | 1.9 | 1 | 1.0 | 46 | 27 | 29 |
| 184 | 184 | 2031 | 2 | 2.1 | | | 19 | 10 | -1 |
| 185 | 185 | 2033 | 2 | 1.2 | | | 28 | 19 | 29 |
| 186 | 186 | 2036 | 5 | 1.1 | 5 | 5.7 | 58 | 38 | 25 |
| 187 | 187 | 2037 | 2 | 1.4 | 1 | 4.3 | 15 | 8 | -0 |

FIG. 1AS

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 188 | 188 | 2038 | His | Ser | Gln | Gly | Thr | Phe | Thr | Ser | Asp | Tyr | Ser | Lys | Tyr | Leu | Asp |
| 189 | 189 | 2040 | His | Ser | Gln | Gly | Thr | Phe | Thr | Ser | Asp | Tyr | Ser | Lys | Tyr | Leu | Asp |
| 190 | 190 | 2041 | His | Ser | Gln | Gly | Thr | Phe | Thr | Ser | Asp | Tyr | Ser | Lys | Tyr | Leu | Asp |
| 191 | 191 | 2043 | His | Ser | Gln | Gly | Thr | Phe | Thr | Ser | Asp | Tyr | Ser | Lys | Tyr | Leu | Asp |
| 192 | 192 | 2044 | His | Ser | Gln | Gly | Thr | Phe | Thr | Ser | Asp | Tyr | Ser | Lys | Tyr | Leu | Asp |
| 193 | 193 | 2045 | His | Ser | Gln | Gly | Thr | Phe | Thr | Ser | Asp | Tyr | Ser | His | Tyr | Leu | Asp |
| 194 | 194 | 2046 | His | Ser | Gln | Gly | Thr | Phe | Thr | Ser | Asp | Tyr | Ser | His | Tyr | Leu | Asp |
| 195 | 195 | 2047 | His | Ser | Gln | Gly | Thr | Phe | Thr | Ser | Asp | Tyr | Ser | Lys | Tyr | Leu | Asp |
| 196 | 196 | 2050 | His | Ser | Gln | Gly | Thr | Phe | Thr | Ser | Asp | Tyr | Ser | Lys | Tyr | Leu | Asp |
| 197 | 197 | 2051 | His | Ser | Gln | Gly | Thr | Phe | Thr | Ser | Asp | Tyr | Ser | Lys | Tyr | Leu | Asp |
| 198 | 198 | 2052 | His | Ser | Gln | Gly | Thr | Phe | Thr | Ser | Asp | Tyr | Ser | Lys | Tyr | Leu | Asp |
| 199 | 199 | 2053 | His | Ser | Gln | Gly | Thr | Phe | Thr | Ser | Asp | Tyr | Ser | Lys | Tyr | Leu | Asp |
| 200 | 200 | 2054 | His | Ser | Gln | Gly | Thr | Phe | Thr | Ser | Asp | Tyr | Ser | Lys | Tyr | Leu | Asp |
| 201 | 201 | 2055 | His | Ser | Gln | Gly | Thr | Phe | Thr | Ser | Asp | Tyr | Ser | Lys | Tyr | Leu | Asp |
| 202 | 202 | 2056 | His | Ser | Gln | Gly | Thr | Phe | Thr | Ser | Asp | Tyr | Ser | Lys | Tyr | Leu | Asp |
| 203 | 203 | 2057 | His | Ser | Gln | Gly | Thr | Phe | Thr | Ser | Asp | Tyr | Ser | Lys | Tyr | Leu | Asp |
| 204 | 204 | 2059 | His | Ser | Gln | Gly | Thr | Phe | Thr | Ser | Asp | Tyr | Ser | Lys | Tyr | Leu | Asp |

FIG. 1AT

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 188 | 188 | 2038 | Glu | Arg | Arg | Ala | His | Glu | Phe | Ile | Gln | Trp | Leu | Leu | Asn | Thr |
| 189 | 189 | 2040 | Glu | Lys | Arg | Ala | His | Glu | Phe | Ile | Glu | Trp | Leu | Leu | Asn | Thr |
| 190 | 190 | 2041 | Glu | Lys | Arg | Ala | His | Glu | Phe | Ile | Glu | Trp | Leu | Leu | Asn | Thr |
| 191 | 191 | 2043 | Glu | Lys | Arg | Ala | His | Glu | Phe | Ile | Gln | Trp | Leu | Leu | Asn | Thr |
| 192 | 192 | 2044 | Glu | Lys | Arg | Ala | His | Glu | Phe | Ile | Glu | Trp | Leu | Leu | Asn | Thr |
| 193 | 193 | 2045 | Gln | Lys | Arg | Ala | His | Glu | Phe | Ile | Glu | Trp | Leu | Leu | Asn | Thr |
| 194 | 194 | 2046 | Gln | Lys | Arg | Ala | His | Glu | Phe | Ile | Gln | Trp | Leu | Leu | Asn | Thr |
| 195 | 195 | 2047 | Glu | Arg | Arg | Ala | His | Glu | Phe | Ile | Glu | Trp | Leu | Leu | Asn | Thr |
| 196 | 196 | 2050 | Glu | Arg | Arg | Ala | His | Glu | Phe | Ile | Glu | Trp | Leu | Leu | Asn | Thr |
| 197 | 197 | 2051 | Glu | Arg | Arg | Ala | His | Glu | Phe | Ile | Gln | Trp | Leu | Leu | Asn | Thr |
| 198 | 198 | 2052 | Glu | Arg | Arg | Ala | His | Glu | Phe | Ile | Gln | Trp | Leu | Leu | Asn | Thr |
| 199 | 199 | 2053 | Glu | Arg | Arg | Ala | His | Glu | Phe | Ile | Gln | Trp | Leu | Leu | Asn | Thr |
| 200 | 200 | 2054 | Glu | Arg | Arg | Ala | His | Glu | Phe | Ile | Glu | Trp | Leu | Leu | Asn | Thr |
| 201 | 201 | 2055 | Glu | Arg | Arg | Ala | His | Glu | Phe | Ile | Gln | Trp | Leu | Leu | Asn | Gly |
| 202 | 202 | 2056 | Glu | Lys | Arg | Ala | His | Glu | Phe | Ile | Gln | Trp | Leu | Leu | Asn | Gly |
| 203 | 203 | 2057 | Glu | Arg | Arg | Ala | His | Glu | Phe | Ile | Glu | Trp | Leu | Leu | Asn | Gly |
| 204 | 204 | 2059 | Ser | Arg | Arg | Ala | His | Glu | Phe | Ile | Glu | Trp | Leu | Leu | Asn | Gly |

FIG. 1AU

| Analogue no. | SEQ ID NO. | G no. | 30 | 31 | 32 | 33 | 34 | 35 | 36 | 37 |
|---|---|---|---|---|---|---|---|---|---|---|
| 188 | 188 | 2038 | Gly | His | His | His | His | His | Ala | |
| 189 | 189 | 2040 | His | His | His | His | His | Ser | | |
| 190 | 190 | 2041 | His | His | His | His | His | Ser | NH2 | |
| 191 | 191 | 2043 | His | His | His | His | His | Gln | | |
| 192 | 192 | 2044 | His | His | His | His | His | Gln | NH2 | |
| 193 | 193 | 2045 | Gly | His | His | His | Glu | | | |
| 194 | 194 | 2046 | Gly | His | His | His | Glu | NH2 | | |
| 195 | 195 | 2047 | Gly | His | His | His | His | Ala | Ala | NH2 |
| 196 | 196 | 2050 | Gly | His | His | His | His | Ser | NH2 | |
| 197 | 197 | 2051 | Gly | His | His | His | His | Ser | | |
| 198 | 198 | 2052 | Gly | His | His | His | His | Ser | NH2 | |
| 199 | 199 | 2053 | Gly | His | His | His | His | Gln | Gln | |
| 200 | 200 | 2054 | Gly | His | His | His | His | Gln | Gln | |
| 201 | 201 | 2055 | His | His | His | His | His | Ser | | |
| 202 | 202 | 2056 | His | His | His | His | His | Ser | | |
| 203 | 203 | 2057 | His | His | His | His | His | Ser | | |
| 204 | 204 | 2059 | His | His | His | His | His | Ser | | |

FIG. 1AV

| Analogue no. | SEQ ID NO. | G no. | hGCGr cAMP | | | hGLP-1r cAMP | | Mouse food intake inhibition (500nmol/kg) | | Rat food intake inhibtion (500 nmol/kg with 1:1 Zn) |
|---|---|---|---|---|---|---|---|---|---|---|
| | | | n | vs hGCG | n | vs hGLP-1 | 0-24 | 0-48 | 0-24 |
| 188 | 188 | 2038 | 3 | 2.6 | 2 | 4.7 | 55 | 32 | 12 |
| 189 | 189 | 2040 | 3 | 2.3 | 2 | 3.8 | 67 | 45 | 33 |
| 190 | 190 | 2041 | 3 | 1.6 | 2 | 5.4 | 66 | 42 | 32 |
| 191 | 191 | 2043 | 2 | 1.4 | | | 61 | 33 | 50 |
| 192 | 192 | 2044 | 3 | 1.6 | 1 | 3.1 | 59 | 39 | 47 |
| 193 | 193 | 2045 | 2 | 1.7 | | | 38 | 23 | 63 |
| 194 | 194 | 2046 | 2 | 1.6 | 2 | 4.6 | 36 | 21 | 38 |
| 195 | 195 | 2047 | 2 | 1.6 | | | 34 | 21 | -3 |
| 196 | 196 | 2050 | 2 | 2.1 | | | 72 | 47 | 19 |
| 197 | 197 | 2051 | 3 | 1.4 | 3 | 4.2 | 57 | 36 | 16 |
| 198 | 198 | 2052 | 2 | 1.8 | | | 77 | 45 | 1 |
| 199 | 199 | 2053 | 2 | 1.6 | | | 47 | 24 | 3 |
| 200 | 200 | 2054 | 2 | 2.0 | | | 49 | 25 | -2 |
| 201 | 201 | 2055 | 2 | 2.0 | | | 54 | 40 | 1 |
| 202 | 202 | 2056 | 2 | 1.6 | | | 81 | 46 | 22 |
| 203 | 203 | 2057 | 3 | 2.7 | 1 | 2.7 | 89 | 60 | -1 |
| 204 | 204 | 2059 | 3 | 2.5 | 1 | 3.0 | 52 | 35 | 13 |

FIG. 1AW

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 205 | 205 | 2060 | His | Ser | Gln | Gly | Thr | Phe | Thr | Ser | Asp | Tyr | Ser | Lys | Tyr | Leu | Asp |
| 206 | 206 | 2061 | His | Ser | Gln | Gly | Thr | Phe | Thr | Ser | Asp | Tyr | Ser | Lys | Tyr | Leu | Asp |
| 207 | 207 | 2062 | His | Ser | Gln | Gly | Thr | Phe | Thr | Ser | Asp | Tyr | Ser | Lys | Tyr | Leu | Asp |
| 208 | 208 | 2063 | His | Ser | Gln | Gly | Thr | Phe | Thr | Ser | Asp | Tyr | Ser | Lys | Tyr | Leu | Asp |
| 209 | 209 | 2064 | His | Ser | Gln | Gly | Thr | Phe | Thr | Ser | Asp | Tyr | Ser | Lys | Tyr | Leu | Asp |
| 210 | 210 | 2065 | His | Ser | Gln | Gly | Thr | Phe | Thr | Ser | Asp | Tyr | Ser | His | Tyr | Leu | Asp |
| 211 | 211 | 2067 | His | Ser | Gln | Gly | Thr | Phe | Thr | Ser | Asp | Tyr | Ser | Lys | Tyr | Leu | Asp |
| 212 | 212 | 2068 | His | Ser | Gln | Gly | Thr | Phe | Thr | Ser | Asp | Tyr | Ser | Lys | Tyr | Leu | Asp |
| 213 | 213 | 2069 | His | Ser | Gln | Gly | Thr | Phe | Thr | Ser | Asp | Tyr | Ser | Lys | Tyr | Leu | Asp |
| 214 | 214 | 2070 | His | Ser | Gln | Gly | Thr | Phe | Thr | Ser | Asp | Tyr | Ser | Lys | Tyr | Leu | Asp |
| 215 | 215 | 2071 | His | Ser | Gln | Gly | Thr | Phe | Thr | Ser | Asp | Tyr | Ser | His | Tyr | Leu | Asp |
| 216 | 216 | 2072 | His | Ser | Gln | Gly | Thr | Phe | Thr | Ser | Asp | Tyr | Ser | His | Tyr | Leu | Asp |
| 217 | 217 | 2073 | His | Ser | Gln | Gly | Thr | Phe | Thr | Ser | Asp | Tyr | Ser | Lys | Tyr | Leu | Asp |
| 218 | 218 | 2074 | His | Ser | Gln | Gly | Thr | Phe | Thr | Ser | Asp | Tyr | Ser | His | Tyr | Leu | Asp |
| 219 | 219 | 2077 | His | Ser | Gln | Gly | Thr | Phe | Thr | Ser | Asp | Tyr | Ser | Lys | Gln | Leu | Asp |
| 220 | 220 | 2079 | His | Ser | Gln | Gly | Thr | Phe | Thr | Ser | Asp | Tyr | Ser | Lys | Tyr | Leu | Asp |
| 221 | 221 | 2080 | His | Ser | Gln | Gly | Thr | Phe | Thr | Ser | Asp | Tyr | Ser | Lys | Tyr | Leu | Asp |

FIG. 1AX

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 205 | 205 | 2060 | Ser | Arg | Arg | Ala | His | Glu | Phe | Ile | Gln | Trp | Leu | Leu | Asn | Gly |
| 206 | 206 | 2061 | Ser | Arg | Arg | Ala | His | Glu | Phe | Ile | Gln | Trp | Leu | Leu | Asn | Thr |
| 207 | 207 | 2062 | Ser | Lys | Arg | Ala | His | Glu | Phe | Ile | Glu | Trp | Leu | Leu | Asn | Thr |
| 208 | 208 | 2063 | Ser | Lys | Arg | Ala | His | Glu | Phe | Ile | Glu | Trp | Leu | Leu | Asn | Thr |
| 209 | 209 | 2064 | Glu | Lys | Arg | Ala | His | Glu | Phe | Ile | Glu | Trp | Leu | Leu | Asn | Gly |
| 210 | 210 | 2065 | Gln | Lys | Arg | Ala | His | Glu | Phe | Ile | Glu | Trp | Leu | Leu | Asn | Gly |
| 211 | 211 | 2067 | Glu | Arg | Arg | Ala | His | Glu | Phe | Ile | Glu | Trp | Leu | Leu | Asn | Thr |
| 212 | 212 | 2068 | Glu | Lys | Arg | Ala | His | Glu | Phe | Ile | Glu | Trp | Leu | Leu | Asn | Thr |
| 213 | 213 | 2069 | Glu | Lys | Arg | Ala | His | Glu | Phe | Ile | Glu | Trp | Leu | Leu | Asn | Thr |
| 214 | 214 | 2070 | Glu | Lys | Arg | Ala | His | Glu | Phe | Ile | Glu | Trp | Leu | Leu | Asn | Thr |
| 215 | 215 | 2071 | Glu | Arg | Arg | Ala | His | Glu | Phe | Ile | Glu | Trp | Leu | Leu | Asn | Thr |
| 216 | 216 | 2072 | Gln | Lys | Arg | Ala | His | Glu | Phe | Ile | Glu | Trp | Leu | Leu | Asn | Thr |
| 217 | 217 | 2073 | Gln | Lys | Arg | Ala | His | Glu | Phe | Ile | Glu | Trp | Leu | Leu | Asn | Thr |
| 218 | 218 | 2074 | Glu | Arg | Arg | Ala | His | Glu | Phe | Ile | Gln | Trp | Leu | Leu | Asn | Gly |
| 219 | 219 | 2077 | Gln | Lys | Arg | Ala | His | Glu | Phe | Ile | Glu | Trp | Leu | Leu | Asn | Thr |
| 220 | 220 | 2079 | Glu | Arg | Arg | Ala | His | Glu | Phe | Ile | Glu | Trp | Leu | Leu | Asn | Gly |
| 221 | 221 | 2080 | Glu | Arg | Arg | Ala | His | Glu | Phe | Ile | Glu | Trp | Leu | Leu | Asn | Thr |

FIG. 1AY

| Analogue no. | SEQ ID NO. | G no. | 30 | 31 | 32 | 33 | 34 | 35 | 36 | 37 |
|---|---|---|---|---|---|---|---|---|---|---|
| 205 | 205 | 2060 | His | His | His | His | His | Ser | | |
| 206 | 206 | 2061 | His | His | His | His | His | Ser | | |
| 207 | 207 | 2062 | His | His | His | His | His | Ala | | |
| 208 | 208 | 2063 | His | His | His | His | His | Ser | | |
| 209 | 209 | 2064 | Gly | His | His | His | His | Ser | | |
| 210 | 210 | 2065 | Gly | His | His | His | His | His | Glu | NH2 |
| 211 | 211 | 2067 | Gly | His | His | His | His | Gln | Gln | NH2 |
| 212 | 212 | 2068 | Gly | His | His | His | His | Ser | NH2 | |
| 213 | 213 | 2069 | Gly | His | His | His | His | Gly | NH2 | |
| 214 | 214 | 2070 | Gly | His | His | His | His | Ser | | |
| 215 | 215 | 2071 | Gly | His | His | His | His | Ala | | |
| 216 | 216 | 2072 | Gly | His | His | His | His | Ala | | |
| 217 | 217 | 2073 | Gly | His | His | His | His | Ala | NH2 | |
| 218 | 218 | 2074 | His | His | His | His | Gly | NH2 | | |
| 219 | 219 | 2077 | Gly | His | His | His | NH2 | | | |
| 220 | 220 | 2079 | Gly | His | His | His | His | Gln | Gln | |
| 221 | 221 | 2080 | Gly | His | His | His | His | Ala | Ala | NH2 |

FIG. 1AZ

| Analogue no. | SEQ ID NO. | G no. | hGCGr | | hGLP-1r | | Mouse food intake inhibition (500nmol/kg) | | Rat food intake inhibtion (500 nmol/kg with 1:1 Zn) |
|---|---|---|---|---|---|---|---|---|---|
| | | | n | cAMP vs hGCG | n | cAMP vs hGLP-1 | 0-24 | 0-48 | 0-24 |
| 205 | 205 | 2060 | 2 | 1.3 | | | 39 | 23 | -1 |
| 206 | 206 | 2061 | 2 | 1.5 | 4 | 5.2 | 31 | 18 | 0 |
| 207 | 207 | 2062 | 3 | 2.4 | 2 | 5.3 | 41 | 21 | 5 |
| 208 | 208 | 2063 | 4 | 2.2 | 1 | 2.7 | 55 | 40 | 42 |
| 209 | 209 | 2064 | 2 | 1.4 | | | 61 | 40 | 58 |
| 210 | 210 | 2065 | 1 | 3.7 | | | 74 | 50 | 14 |
| 211 | 211 | 2067 | 2 | 1.3 | | | 58 | 30 | 35 |
| 212 | 212 | 2068 | 2 | 2.0 | | | 67 | 41 | 44 |
| 213 | 213 | 2069 | 2 | 1.3 | | | 46 | 29 | 65 |
| 214 | 214 | 2070 | 4 | 1.9 | 1 | 3.9 | 62 | 33 | 70 |
| 215 | 215 | 2071 | 3 | 2.4 | 2 | 6.3 | 42 | 26 | 17 |
| 216 | 216 | 2072 | 4 | 1.4 | 2 | 5.7 | 56 | 38 | 19 |
| 217 | 217 | 2073 | 1 | 2.1 | | | 54 | 29 | 11 |
| 218 | 218 | 2074 | 2 | 2.1 | | | 26 | 19 | 30 |
| 219 | 219 | 2077 | 1 | 1.6 | | | 50 | 27 | 14 |
| 220 | 220 | 2079 | 1 | 0.6 | | | 21 | 15 | -11 |
| 221 | 221 | 2080 | 5 | 2.5 | 3 | 4.6 | 57 | 37 | 33 |

FIG. 1AAA

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 222 | 222 | 2081 | His | Ser | Gln | Gly | Thr | Phe | Thr | Ser | Asp | Tyr | Ser | Lys | Tyr | Leu | Asp |
| 223 | 223 | 2082 | His | Ser | Gln | Gly | Thr | Phe | Thr | Ser | Asp | Tyr | Ser | Lys | Tyr | Leu | Asp |
| 224 | 224 | 2083 | His | Ser | Gln | Gly | Thr | Phe | Thr | Ser | Asp | Tyr | Ser | Lys | Tyr | Leu | Asp |
| 225 | 225 | 2084 | His | Ser | Gln | Gly | Thr | Phe | Thr | Ser | Asp | Tyr | Ser | Lys | Tyr | Leu | Asp |
| 226 | 226 | 2085 | His | Ser | Gln | Gly | Thr | Phe | Thr | Ser | Asp | Tyr | Ser | Lys | Tyr | Leu | Asp |
| 227 | 227 | 2086 | His | Ser | Gln | Gly | Thr | Phe | Thr | Ser | Asp | Tyr | Ser | Lys | Tyr | Leu | Asp |
| 228 | 228 | 2089 | His | Ser | Gln | Gly | Thr | Phe | Thr | Ser | Asp | Tyr | Ser | Lys | Tyr | Leu | Asp |
| 229 | 229 | 2093 | His | Ser | Gln | Gly | Thr | Phe | Thr | Ser | Asp | Tyr | Ser | Lys | Tyr | Leu | Asp |
| 230 | 230 | 2094 | His | Ser | Gln | Gly | Thr | Phe | Thr | Ser | Asp | Tyr | Ser | Lys | Tyr | Leu | Asp |
| 231 | 231 | 2095 | His | Ser | Gln | Gly | Thr | Phe | Thr | Ser | Asp | Tyr | Ser | Lys | Tyr | Leu | Asp |
| 232 | 232 | 2096 | His | Ser | Gln | Gly | Thr | Phe | Thr | Ser | Asp | Tyr | Ser | Lys | Tyr | Leu | Asp |
| 233 | 233 | 2098 | His | Ser | Gln | Gly | Thr | Phe | Thr | Ser | Asp | Tyr | Ser | Lys | Tyr | Leu | Asp |
| 234 | 234 | 2101 | His | Ser | Gln | Gly | Thr | Phe | Thr | Ser | Asp | Tyr | Ser | Lys | Tyr | Leu | Asp |
| 235 | 235 | 2102 | His | Ser | Gln | Gly | Thr | Phe | Thr | Ser | Asp | Tyr | Ser | Lys | Tyr | Leu | Asp |
| 236 | 236 | 2103 | His | Ser | Gln | Gly | Thr | Phe | Thr | Ser | Asp | Tyr | Ser | Lys | Tyr | Leu | Asp |
| 237 | 237 | 2104 | His | Ser | Gln | Gly | Thr | Phe | Thr | Ser | Asp | Tyr | Ser | Lys | Tyr | Leu | Asp |
| 238 | 238 | 2105 | His | Ser | Gln | Gly | Thr | Phe | Thr | Ser | Asp | Tyr | Ser | Lys | Tyr | Leu | Asp |

FIG. 1AAB

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 222 | 222 | 2081 | Ser | Arg | Arg | Ala | His | Glu | Phe | Ile | Gln | Trp | Leu | Leu | Asn | Gly |
| 223 | 223 | 2082 | Glu | Arg | Arg | Ala | His | Glu | Phe | Ile | Glu | Trp | Leu | Leu | Asn | Gly |
| 224 | 224 | 2083 | Glu | Arg | Arg | Ala | His | Glu | Phe | Ile | Glu | Trp | Leu | Leu | Asn | Thr |
| 225 | 225 | 2084 | Glu | Arg | Arg | Ala | His | Glu | Phe | Ile | Glu | Trp | Leu | Leu | Asn | Thr |
| 226 | 226 | 2085 | Ser | Arg | Arg | Ala | His | Glu | Phe | Ile | Gln | Trp | Leu | Leu | Asn | Thr |
| 227 | 227 | 2086 | Gln | Arg | Arg | Ala | His | Glu | Phe | Ile | Gln | Trp | Leu | Leu | Asn | Thr |
| 228 | 228 | 2089 | Glu | Arg | Arg | Ala | His | Glu | Phe | Ile | Gln | Trp | Leu | Leu | Asn | Thr |
| 229 | 229 | 2093 | Glu | Arg | Arg | Ala | His | Glu | Phe | Ile | Gln | Trp | Leu | Leu | Asn | Thr |
| 230 | 230 | 2094 | Glu | Arg | Arg | Ala | His | Glu | Phe | Ile | Gln | Trp | Leu | Leu | Asn | Gly |
| 231 | 231 | 2095 | Glu | Arg | Arg | Ala | His | Glu | Phe | Ile | Gln | Trp | Leu | Leu | Asn | Gly |
| 232 | 232 | 2096 | Glu | Arg | Arg | Ala | His | Glu | Phe | Ile | Gln | Trp | Leu | Leu | Asn | Gly |
| 233 | 233 | 2098 | Glu | Arg | Arg | Ala | His | Glu | Phe | Ile | Gln | Trp | Leu | Leu | Asn | Gly |
| 234 | 234 | 2101 | Glu | Arg | Arg | Ala | His | Glu | Phe | Ile | Gln | Trp | Leu | Leu | Asn | Gly |
| 235 | 235 | 2102 | Glu | Arg | Arg | Ala | His | Glu | Phe | Ile | Gln | Trp | Leu | Leu | Asn | Gly |
| 236 | 236 | 2103 | Glu | Arg | Arg | Ala | His | Glu | Phe | Ile | Gln | Trp | Leu | Leu | Asn | Gly |
| 237 | 237 | 2104 | Glu | Arg | Arg | Ala | His | Glu | Phe | Ile | Gln | Trp | Leu | Leu | Asn | Thr |
| 238 | 238 | 2105 | Glu | Arg | Arg | Ala | His | Glu | Phe | Ile | Gln | Trp | Leu | Leu | Asn | Thr |

FIG. 1AAC

| Analogue no. | SEQ ID NO. | G no. | 30 | 31 | 32 | 33 | 34 | 35 | 36 | 37 |
|---|---|---|---|---|---|---|---|---|---|---|
| 222 | 222 | 2081 | Gly | His | His | His | His | Ala | Ala | NH2 |
| 223 | 223 | 2082 | Gly | His | His | His | His | Ala | Ala | NH2 |
| 224 | 224 | 2083 | Gly | His | His | His | His | Gln | | |
| 225 | 225 | 2084 | Gly | His | His | His | His | Gln | NH2 | |
| 226 | 226 | 2085 | Gly | His | His | His | His | Gln | | |
| 227 | 227 | 2086 | Gly | His | His | His | His | Ser | | |
| 228 | 228 | 2089 | Gly | His | His | His | His | Ala | | |
| 229 | 229 | 2093 | Gly | His | His | His | Ala | Ala | Ala | Ala |
| 230 | 230 | 2094 | Gly | His | His | His | Gly | Ala | Ala | Ala |
| 231 | 231 | 2095 | Gly | His | His | Gly | His | Ala | Ala | NH2 |
| 232 | 232 | 2096 | Gly | His | His | His | His | Ala | Ala | NH2 |
| 233 | 233 | 2098 | Gly | His | His | His | His | Ala | Ala | NH2 |
| 234 | 234 | 2101 | Gly | His | His | His | His | Ala | Ala | NH2 |
| 235 | 235 | 2102 | Gly | His | His | His | His | His | Ala | Ala |
| 236 | 236 | 2103 | Gly | His | His | His | His | His | Ala | Ala |
| 237 | 237 | 2104 | Gly | His | His | His | His | His | Ala | Ala |
| 238 | 238 | 2105 | Gly | His | His | His | His | His | Ala | Ala |

FIG. 1AAD

| Analogue no. | SEQ ID NO. | G no. | hGCGr cAMP n | hGCGr cAMP vs hGCG | hGLP-1r cAMP n | hGLP-1r cAMP vs hGLP-1 | Mouse food intake inhibition (500nmol/kg) 0-24 | Mouse food intake inhibition 0-48 | Rat food intake inhibtion (500 nmol/kg with 1:1 Zn) 0-24 |
|---|---|---|---|---|---|---|---|---|---|
| 222 | 222 | 2081 | 1 | 1.5 | | | 66 | 44 | 13 |
| 223 | 223 | 2082 | 2 | 0.7 | | | 65 | 49 | 60 |
| 224 | 224 | 2083 | 1 | 1.0 | | | 59 | 36 | 33 |
| 225 | 225 | 2084 | 5 | 1.3 | 3 | 3.7 | 61 | 40 | 29 |
| 226 | 226 | 2085 | 1 | 1.2 | | | 62 | 41 | 29 |
| 227 | 227 | 2086 | 1 | 1.4 | | | 74 | 50 | 29 |
| 228 | 228 | 2089 | 4 | 1.9 | 3 | 4.1 | 59 | 38 | 45 |
| 229 | 229 | 2093 | 1 | 2.6 | | | 30 | 16 | 42 |
| 230 | 230 | 2094 | 1 | 1.2 | | | 28 | 15 | 42 |
| 231 | 231 | 2095 | 1 | 1.4 | | | 21 | 15 | 52 |
| 232 | 232 | 2096 | 1 | 1.3 | | | 5 | 10 | 49 |
| 233 | 233 | 2098 | 2 | 1.6 | 2 | 2.4 | 19 | 12 | 32 |
| 234 | 234 | 2101 | 1 | 2.9 | | | 14 | 13 | 59 |
| 235 | 235 | 2102 | 1 | 1.7 | | | 46 | 26 | 52 |
| 236 | 236 | 2103 | 1 | 2.2 | | | 39 | 30 | 36 |
| 237 | 237 | 2104 | 1 | 2.7 | | | 39 | 26 | 18 |
| 238 | 238 | 2105 | 3 | 2.8 | 1 | 3.2 | 33 | 25 | 22 |

FIG. 1AAE

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 239 | 239 | 2106 | His | Ser | Gln | Gly | Thr | Phe | Thr | Ser | Asp | Tyr | Ser | Lys | Tyr | Leu | Asp |
| 240 | 240 | 2107 | His | Ser | Gln | Gly | Thr | Phe | Thr | Ser | Asp | Tyr | Ser | Lys | Tyr | Leu | Asp |
| 241 | 241 | 2108 | His | Ser | Gln | Gly | Thr | Phe | Thr | Ser | Asp | Tyr | Ser | Lys | Tyr | Leu | Asp |
| 242 | 242 | 2109 | His | Ser | Gln | Gly | Thr | Phe | Thr | Ser | Asp | Tyr | Ser | Lys | Tyr | Leu | Asp |
| 243 | 243 | 2111 | His | Ser | Gln | Gly | Thr | Phe | Thr | Ser | Asp | Tyr | Ser | Lys | Tyr | Leu | Asp |
| 244 | 244 | 2112 | His | Ser | Gln | Gly | Thr | Phe | Thr | Ser | Asp | Tyr | Ser | Lys | Tyr | Leu | Asp |
| 245 | 245 | 2114 | His | Ser | Gln | Gly | Thr | Phe | Thr | Ser | Asp | Tyr | Ser | Lys | Tyr | Leu | Asp |
| 246 | 246 | 2115 | His | Ser | Gln | Gly | Thr | Phe | Thr | Ser | Asp | Tyr | Ser | Lys | Tyr | Leu | Asp |
| 247 | 247 | 2116 | His | Ser | Gln | Gly | Thr | Phe | Thr | Ser | Asp | Tyr | Ser | Lys | Tyr | Leu | Asp |
| 248 | 248 | 2117 | His | Ser | Gln | Gly | Thr | Phe | Thr | Ser | Asp | Tyr | Ser | Lys | Tyr | Leu | Asp |
| 249 | 249 | 2119 | His | Ser | Gln | Gly | Thr | Phe | Thr | Ser | Asp | Tyr | Ser | Lys | Tyr | Leu | Asp |
| 250 | 250 | 2120 | His | Ser | Gln | Gly | Thr | Phe | Thr | Ser | Asp | Tyr | Ser | Lys | Tyr | Leu | Asp |
| 251 | 251 | 2121 | His | Ser | Gln | Gly | Thr | Phe | Thr | Ser | Asp | Tyr | Ser | Lys | Tyr | Leu | Asp |
| 252 | 252 | 2122 | His | Ser | Gln | Gly | Thr | Phe | Thr | Ser | Asp | Tyr | Ser | Lys | Tyr | Leu | Asp |
| 253 | 253 | 2123 | His | Ser | Gln | Gly | Thr | Phe | Thr | Ser | Asp | Tyr | Ser | Lys | Tyr | Leu | Asp |
| 254 | 254 | 2128 | His | Ser | Gln | Gly | Thr | Phe | Thr | Ser | Asp | Tyr | Ser | Lys | Tyr | Leu | Asp |
| 255 | 255 | 2129 | His | Ser | Gln | Gly | Thr | Phe | Thr | Ser | Asp | Tyr | Ser | Lys | Tyr | Leu | Asp |

FIG. 1AAF

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 239 | 239 | 2106 | Glu | Arg | Arg | Ala | His | Glu | Phe | Ile | Gln | Trp | Leu | Leu | Asn | Gly |
| 240 | 240 | 2107 | Glu | Arg | Arg | Ala | His | Glu | Phe | Ile | Gln | Trp | Leu | Leu | Asn | Gly |
| 241 | 241 | 2108 | Glu | Arg | Arg | Ala | His | Glu | Phe | Ile | Gln | Trp | Leu | Leu | Asn | Gly |
| 242 | 242 | 2109 | Glu | Arg | Arg | Ala | His | Glu | Phe | Ile | Gln | Trp | Leu | Leu | Asn | Gly |
| 243 | 243 | 2111 | Glu | Arg | Arg | Ala | His | Glu | Phe | Ile | Gln | Trp | Leu | Leu | Asn | Gly |
| 244 | 244 | 2112 | Glu | Arg | Arg | Ala | His | Glu | Phe | Ile | Gln | Trp | Leu | Leu | Asn | Gly |
| 245 | 245 | 2114 | Glu | Arg | Arg | Ala | His | Glu | Phe | Ile | Gln | Trp | Leu | Leu | Asn | Gly |
| 246 | 246 | 2115 | Glu | Arg | Arg | Ala | His | Glu | Phe | Ile | Gln | Trp | Leu | Leu | Asn | Gly |
| 247 | 247 | 2116 | Glu | Arg | Arg | Ala | His | Glu | Phe | Ile | Gln | Trp | Leu | Leu | Asn | Thr |
| 248 | 248 | 2117 | Glu | Lys | Arg | Ala | His | Glu | Phe | Ile | Gln | Trp | Leu | Leu | Asn | Thr |
| 249 | 249 | 2119 | Glu | Lys | Arg | Ala | His | Glu | Phe | Ile | Glu | Trp | Leu | Leu | Asn | Thr |
| 250 | 250 | 2120 | Glu | Arg | Arg | Ala | His | Glu | Phe | Ile | Gln | Trp | Leu | Leu | Asn | Thr |
| 251 | 251 | 2121 | Glu | Arg | Arg | Ala | His | Glu | Phe | Ile | Gln | Trp | Leu | Leu | Asn | Thr |
| 252 | 252 | 2122 | Glu | Arg | Arg | Ala | His | Glu | Phe | Ile | Gln | Trp | Leu | Leu | Asn | Thr |
| 253 | 253 | 2123 | Glu | Arg | Arg | Ala | His | Glu | Phe | Ile | Gln | Trp | Leu | Leu | Asn | Thr |
| 254 | 254 | 2128 | Glu | Arg | Arg | Ala | His | Glu | Phe | Ile | Gln | Trp | Leu | Leu | Asn | Thr |
| 255 | 255 | 2129 | Glu | Arg | Arg | Ala | His | Glu | Phe | Ile | Gln | Trp | Leu | Leu | Asn | Thr |

FIG. 1AAG

| Analogue no. | SEQ ID NO. | G no. | 30 | 31 | 32 | 33 | 34 | 35 | 36 | 37 |
|---|---|---|---|---|---|---|---|---|---|---|
| 239 | 239 | 2106 | Gly | His | His | His | His | Gly | | |
| 240 | 240 | 2107 | His | His | His | His | His | Gly | | |
| 241 | 241 | 2108 | His | His | His | His | His | Gly | NH2 | |
| 242 | 242 | 2109 | Gly | His | His | His | His | Ala | Ala | Gly |
| 243 | 243 | 2111 | Gly | His | His | His | His | Gly | Ala | NH2 |
| 244 | 244 | 2112 | Gly | His | His | His | His | Ala | Ala | Gly |
| 245 | 245 | 2114 | Gly | His | His | His | His | Gln | Ala | NH2 |
| 246 | 246 | 2115 | Gly | His | His | His | His | Ala | Gln | NH2 |
| 247 | 247 | 2116 | Gly | His | His | His | His | Gln | Gln | NH2 |
| 248 | 248 | 2117 | His | His | His | His | Gly | | | |
| 249 | 249 | 2119 | His | His | His | His | Ala | | | |
| 250 | 250 | 2120 | His | Gly | His | His | Gly | Gly | | |
| 251 | 251 | 2121 | His | Gly | His | His | Gly | NH2 | | |
| 252 | 252 | 2122 | His | Gly | His | His | NH2 | | | |
| 253 | 253 | 2123 | His | His | His | His | NH2 | | | |
| 254 | 254 | 2128 | His | His | His | His | Ala | NH2 | | |
| 255 | 255 | 2129 | His | His | His | His | Ala | | | |

FIG. 1AAH

| Analogue no. | SEQ ID NO. | G no. | hGCGr cAMP n | hGCGr cAMP vs hGCG | hGLP-1r cAMP n | hGLP-1r cAMP vs hGLP-1 | Mouse food intake inhibition (500nmol/kg) 0-24 | Mouse food intake inhibition 0-48 | Rat food intake inhibition (500 nmol/kg with 1:1 Zn) 0-24 |
|---|---|---|---|---|---|---|---|---|---|
| 239 | 239 | 2106 | 1 | 2.6 | | | 25 | 17 | 16 |
| 240 | 240 | 2107 | 2 | 2.8 | | | 29 | 18 | 23 |
| 241 | 241 | 2108 | 1 | 3.2 | | | 17 | 12 | 29 |
| 242 | 242 | 2109 | 1 | 1.8 | | | 41 | 21 | 40 |
| 243 | 243 | 2111 | 1 | 3.5 | | | 6 | 4 | 18 |
| 244 | 244 | 2112 | 1 | 2.1 | | | 30 | 16 | 15 |
| 245 | 245 | 2114 | 2 | 1.3 | | | 34 | 21 | 61 |
| 246 | 246 | 2115 | 3 | 1.1 | 2 | 1.0 | 38 | 23 | 59 |
| 247 | 247 | 2116 | 3 | 1.3 | 4 | 3.3 | 28 | 15 | 38 |
| 248 | 248 | 2117 | 4 | 1.4 | 5 | 2.9 | 32 | 17 | 16 |
| 249 | 249 | 2119 | 4 | 0.9 | 4 | 2.5 | 33 | 18 | 23 |
| 250 | 250 | 2120 | 3 | 2.0 | 2 | 3.4 | 43 | 35 | 26 |
| 251 | 251 | 2121 | 3 | 1.4 | 2 | 3.3 | 44 | 27 | 31 |
| 252 | 252 | 2122 | 2 | 1.7 | 4 | 3.6 | 21 | 14 | 23 |
| 253 | 253 | 2123 | 4 | 1.3 | 4 | 3.4 | 23 | 10 | 24 |
| 254 | 254 | 2128 | 2 | 3.5 | | | 30 | 16 | 20 |
| 255 | 255 | 2129 | 2 | 3.4 | | | 57 | 34 | 14 |

FIG. 1AAI

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 256 | 256 | 2134 | His | Ser | Gln | Gly | Thr | Phe | Thr | Ser | Asp | Tyr | Ser | Lys | Tyr | Leu | Asp |
| 257 | 257 | 2136 | His | Ser | Gln | Gly | Thr | Phe | Thr | Ser | Asp | Tyr | Ser | Lys | Tyr | Leu | Asp |
| 258 | 258 | 2137 | His | Ser | Gln | Gly | Thr | Phe | Thr | Ser | Asp | Tyr | Ser | Lys | Tyr | Leu | Asp |
| 259 | 259 | 2138 | His | Ser | Gln | Gly | Thr | Phe | Thr | Ser | Asp | Tyr | Ser | Lys | Tyr | Leu | Asp |
| 260 | 260 | 2139 | His | Ser | Gln | Gly | Thr | Phe | Thr | Ser | Asp | Tyr | Ser | Lys | Tyr | Leu | Asp |
| 261 | 261 | 2140 | His | Ser | Gln | Gly | Thr | Phe | Thr | Ser | Asp | Tyr | Ser | Lys | Tyr | Leu | Asp |
| 262 | 262 | 2141 | His | Ser | Gln | Gly | Thr | Phe | Thr | Ser | Asp | Tyr | Ser | Lys | Tyr | Leu | Asp |
| 263 | 263 | 2142 | His | Ser | Gln | Gly | Thr | Phe | Thr | Ser | Asp | Tyr | Ser | Lys | Tyr | Leu | Asp |
| 264 | 264 | 2143 | His | Ser | Gln | Gly | Thr | Phe | Thr | Ser | Asp | Tyr | Ser | Lys | Tyr | Leu | Asp |
| 265 | 265 | 2144 | His | Ser | Gln | Gly | Thr | Phe | Thr | Ser | Asp | Tyr | Ser | Lys | Tyr | Leu | Asp |
| 266 | 266 | 2145 | His | Ser | Gln | Gly | Thr | Phe | Thr | Ser | Asp | Tyr | Ser | Lys | Tyr | Leu | Asp |
| 267 | 267 | 2147 | His | Ser | Gln | Gly | Thr | Phe | Thr | Ser | Asp | Tyr | Ser | Lys | Tyr | Leu | Asp |
| 268 | 268 | 2148 | His | Ser | Gln | Gly | Thr | Phe | Thr | Ser | Asp | Tyr | Ser | Lys | Tyr | Leu | Asp |
| 269 | 269 | 2150 | His | Ser | Gln | Gly | Thr | Phe | Thr | Ser | Asp | Tyr | Ser | Lys | Tyr | Leu | Asp |
| 270 | 270 | 2151 | His | Ser | Gln | Gly | Thr | Phe | Thr | Ser | Asp | Tyr | Ser | Lys | Tyr | Leu | Asp |
| 271 | 271 | 2152 | His | Ser | Gln | Gly | Thr | Phe | Thr | Ser | Asp | Tyr | Ser | His | Tyr | Leu | Asp |
| 272 | 272 | 2153 | His | Ser | Gln | Gly | Thr | Phe | Thr | Ser | Asp | Tyr | Ser | Lys | Tyr | Leu | Asp |

FIG. 1AAJ

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 256 | 256 | 2134 | Glu | Arg | Arg | Ala | His | Glu | Phe | Ile | Gln | Trp | Leu | Leu | Asn | Gly |
| 257 | 257 | 2136 | Glu | Arg | Arg | Ala | His | Glu | Phe | Ile | Gln | Trp | Leu | Leu | Asn | Thr |
| 258 | 258 | 2137 | Glu | Arg | Arg | Ala | His | Glu | Phe | Ile | Gln | Trp | Leu | Leu | Asn | Thr |
| 259 | 259 | 2138 | Glu | Arg | Arg | Ala | His | Glu | Phe | Ile | Gln | Trp | Leu | Leu | Asn | Gly |
| 260 | 260 | 2139 | Glu | Arg | Arg | Ala | His | Glu | Phe | Ile | Gln | Trp | Leu | Leu | Asn | Gly |
| 261 | 261 | 2140 | Glu | Arg | Arg | Ala | His | Glu | Phe | Ile | Gln | Trp | Leu | Leu | Asn | Gly |
| 262 | 262 | 2141 | Glu | Arg | Arg | Ala | His | Glu | Phe | Ile | Glu | Trp | Leu | Leu | Asn | Gly |
| 263 | 263 | 2142 | Gln | Arg | Arg | Ala | His | Glu | Phe | Ile | Gln | Trp | Leu | Leu | Asn | Thr |
| 264 | 264 | 2143 | Gln | Lys | Arg | Ala | His | Glu | Phe | Ile | Gln | Trp | Leu | Leu | Asn | Thr |
| 265 | 265 | 2144 | Glu | Arg | Arg | Ala | His | Glu | Phe | Ile | Glu | Trp | Leu | Leu | Asn | Gly |
| 266 | 266 | 2145 | Glu | Arg | Arg | Ala | His | Glu | Phe | Ile | Gln | Trp | Leu | Leu | Asn | Thr |
| 267 | 267 | 2147 | Glu | Arg | Arg | Ala | His | Glu | Phe | Ile | Gln | Trp | Leu | Leu | Asn | Gly |
| 268 | 268 | 2148 | Gln | Arg | Arg | Ala | His | Glu | Phe | Ile | Gln | Trp | Leu | Leu | Asn | Thr |
| 269 | 269 | 2150 | Glu | Arg | Arg | Ala | His | Glu | Phe | Ile | Gln | Trp | Leu | Leu | Asn | Gly |
| 270 | 270 | 2151 | Glu | Arg | Arg | Ala | His | Glu | Phe | Ile | Gln | Trp | Leu | Leu | Asn | Gly |
| 271 | 271 | 2152 | Gln | Lys | Arg | Ala | His | Glu | Phe | Ile | Gln | Trp | Leu | Leu | Asn | Thr |
| 272 | 272 | 2153 | Gln | Lys | Arg | Ala | His | Glu | Phe | Ile | Glu | Trp | Leu | Leu | Asn | Gly |

FIG. 1AAK

| Analogue no. | SEQ ID NO. | G no. | 30 | 31 | 32 | 33 | 34 | 35 | 36 | 37 |
|---|---|---|---|---|---|---|---|---|---|---|
| 256 | 256 | 2134 | His | His | His | His | Ala | NH2 | | |
| 257 | 257 | 2136 | His | Gly | His | His | NH2 | | | |
| 258 | 258 | 2137 | His | Gly | His | His | Gly | | | |
| 259 | 259 | 2138 | His | His | His | His | Gly | | | |
| 260 | 260 | 2139 | His | His | His | His | Gly | NH2 | | |
| 261 | 261 | 2140 | His | His | His | His | Ala | | | |
| 262 | 262 | 2141 | His | His | His | His | Ala | | | |
| 263 | 263 | 2142 | Gly | His | His | His | His | NH2 | | |
| 264 | 264 | 2143 | Gly | His | His | His | NH2 | | | |
| 265 | 265 | 2144 | His | His | His | Gly | | | | |
| 266 | 266 | 2145 | His | His | His | Gly | | | | |
| 267 | 267 | 2147 | His | His | His | His | His | Gly | | |
| 268 | 268 | 2148 | His | Gly | His | His | Gly | | | |
| 269 | 269 | 2150 | His | His | His | His | Gly | | | |
| 270 | 270 | 2151 | His | His | His | His | Gly | | | |
| 271 | 271 | 2152 | Gly | His | His | His | His | Gln | NH2 | |
| 272 | 272 | 2153 | Gly | His | His | His | His | Gln | NH2 | |

FIG. 1AAL

| Analogue no. | SEQ ID NO. | G no. | hGCGr cAMP | | Mouse food intake inhibition | Rat food intake inhibition |
| --- | --- | --- | --- | --- | --- | --- |
| | | | n | cAMP vs hGCG | hGLP-1r cAMP | |
| | | | | | n | cAMP vs hGLP-1 | (500nmol/kg) 0-24 | 0-48 | (500 nmol/kg with 1:1 Zn) 0-24 |

| Analogue no. | SEQ ID NO. | G no. | n | cAMP vs hGCG | n | cAMP vs hGLP-1 | 0-24 | 0-48 | 0-24 |
| --- | --- | --- | --- | --- | --- | --- | --- | --- | --- |
| 256 | 256 | 2134 | 3 | 2.9 | 2 | 4.5 | 27 | 13 | 9 |
| 257 | 257 | 2136 | 2 | 3.0 | | | 22 | 12 | -7 |
| 258 | 258 | 2137 | 2 | 3.6 | | | 36 | 20 | 25 |
| 259 | 259 | 2138 | 1 | 1.8 | | | 38 | 23 | 25 |
| 260 | 260 | 2139 | 3 | 2.8 | 3 | 3.5 | 29 | 16 | 25 |
| 261 | 261 | 2140 | 3 | 2.2 | 2 | 4.0 | 41 | 21 | 26 |
| 262 | 262 | 2141 | 3 | 2.0 | 1 | 3.3 | 31 | 18 | 14 |
| 263 | 263 | 2142 | 2 | 6.3 | | | 23 | 15 | -5 |
| 264 | 264 | 2143 | 3 | 2.7 | 3 | 6.0 | 14 | 5 | 16 |
| 265 | 265 | 2144 | 3 | 1.3 | 1 | 5.1 | 17 | 13 | 30 |
| 266 | 266 | 2145 | 2 | 1.1 | 4 | 4.2 | 25 | 7 | 10 |
| 267 | 267 | 2147 | 5 | 1.7 | 4 | 5.7 | 48 | 25 | 8 |
| 268 | 268 | 2148 | 3 | 0.9 | 3 | 3.3 | 24 | 15 | 27 |
| 269 | 269 | 2150 | 3 | 0.9 | 1 | 2.1 | 13 | 6 | 23 |
| 270 | 270 | 2151 | 3 | 1.0 | 2 | 2.9 | 31 | 14 | 34 |
| 271 | 271 | 2152 | 2 | 2.1 | | | 68 | 45 | 59 |
| 272 | 272 | 2153 | 3 | 1.6 | 2 | 2.8 | 17 | 5 | 47 |

FIG. 1AAM

| Analogue no. | SEQ ID NO. | G no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 273 | 273 | 2154 | His | Ser | Gln | Gly | Thr | Phe | Thr | Ser | Asp | Tyr | Ser | Lys | Tyr | Leu | Asp |
| 274 | 274 | 2155 | His | Ser | Gln | Gly | Thr | Phe | Thr | Ser | Asp | Tyr | Ser | Lys | Tyr | Leu | Asp |
| 275 | 275 | 2156 | His | Ser | Gln | Gly | Thr | Phe | Thr | Ser | Asp | Tyr | Ser | Lys | Tyr | Leu | Asp |
| 276 | 276 | 2157 | His | Ser | Gln | Gly | Thr | Phe | Thr | Ser | Asp | Tyr | Ser | Lys | Tyr | Leu | Asp |
| 277 | 277 | 2160 | His | Ser | Gln | Gly | Thr | Phe | Thr | Ser | Asp | Tyr | Ser | Lys | Tyr | Leu | Asp |
| 278 | 278 | 2161 | His | Ser | Gln | Gly | Thr | Phe | Thr | Ser | Asp | Tyr | Ser | Lys | Tyr | Leu | Asp |
| 279 | 279 | 2162 | His | Ser | Gln | Gly | Thr | Phe | Thr | Ser | Asp | Tyr | Ser | Lys | Tyr | Leu | Asp |
| 280 | 280 | 2163 | His | Ser | Gln | Gly | Thr | Phe | Thr | Ser | Asp | Tyr | Ser | Lys | Tyr | Leu | Asp |
| 281 | 281 | 2165 | His | Ser | Gln | Gly | Thr | Phe | Thr | Ser | Asp | Tyr | Ser | Lys | Tyr | Leu | Asp |
| 282 | 282 | 2170 | His | Ser | Gln | Gly | Thr | Phe | Thr | Ser | Asp | Tyr | Ser | His | Tyr | Leu | Asp |
| 283 | 283 | 2171 | His | Ser | Gln | Gly | Thr | Phe | Thr | Ser | Asp | Tyr | Ser | His | Tyr | Leu | Asp |
| 284 | 284 | 2172 | His | Ser | Gln | Gly | Thr | Phe | Thr | Ser | Asp | Tyr | Ser | His | Tyr | Leu | Asp |
| 285 | 285 | 2173 | His | Ser | Gln | Gly | Thr | Phe | Thr | Ser | Asp | Tyr | Ser | His | Tyr | Leu | Asp |
| 286 | 286 | 2174 | His | Ser | Gln | Gly | Thr | Phe | Thr | Ser | Asp | Tyr | Ser | His | Gln | Leu | Asp |
| 287 | 287 | 2175 | His | Ser | Gln | Gly | Thr | Phe | Thr | Ser | Asp | Tyr | Ser | His | Tyr | Leu | Asp |
| 288 | 288 | 2176 | His | Ser | Gln | Gly | Thr | Phe | Thr | Ser | Asp | Tyr | Ser | His | Tyr | Leu | Asp |

FIG. 1AAN

| Analogue no. | SEQ ID NO. | G no. | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|
| 273 | 273 | 2154 | Gln | Lys | Arg | Ala | His | Glu | Phe | Ile | Gln | Trp | Leu | Leu | Asn | Gly |
| 274 | 274 | 2155 | Glu | Arg | Arg | Ala | His | Glu | Phe | Val | Glu | Trp | Leu | Leu | Asn | Thr |
| 275 | 275 | 2156 | Glu | Arg | Arg | Ala | His | Glu | Phe | Val | Glu | Trp | Leu | Leu | Asn | Thr |
| 276 | 276 | 2157 | Glu | Arg | Arg | Ala | His | Glu | Phe | Val | Gln | Trp | Leu | Leu | Asn | Gly |
| 277 | 277 | 2160 | Glu | Arg | Arg | Ala | His | Glu | Phe | Val | Gln | Trp | Leu | Leu | Asn | Gly |
| 278 | 278 | 2161 | Glu | Arg | Arg | Ala | His | Glu | Phe | Val | Glu | Trp | Leu | Leu | Asn | Gly |
| 279 | 279 | 2162 | Glu | Arg | Arg | Ala | His | Glu | Phe | Val | Glu | Trp | Leu | Leu | Asn | Thr |
| 280 | 280 | 2163 | Glu | Lys | Arg | Ala | His | Glu | Phe | Ile | Gln | Trp | Leu | Leu | Asn | Thr |
| 281 | 281 | 2165 | Glu | Arg | Arg | Ala | His | Glu | Phe | Ile | Gln | Trp | Leu | Leu | Asn | Thr |
| 282 | 282 | 2170 | Gln | Lys | Arg | Ala | His | Glu | Phe | Ile | Glu | Trp | Leu | Leu | Asn | Gly |
| 283 | 283 | 2171 | Gln | Lys | Arg | Ala | His | Glu | Phe | Ile | Glu | Trp | Leu | Leu | Asn | Gly |
| 284 | 284 | 2172 | Gln | Lys | Arg | Ala | His | Glu | Phe | Ile | Glu | Trp | Leu | Leu | Asn | Thr |
| 285 | 285 | 2173 | Gln | Lys | Arg | Ala | His | Glu | Phe | Ile | Glu | Trp | Leu | Leu | Asn | Thr |
| 286 | 286 | 2174 | Gln | Lys | Arg | Ala | His | Glu | Phe | Ile | Glu | Trp | Leu | Leu | Asn | Gly |
| 287 | 287 | 2175 | Gln | Lys | Arg | Ala | His | Glu | Phe | Ile | Glu | Trp | Leu | Leu | Asn | Gly |
| 288 | 288 | 2176 | Gln | Lys | Arg | Ala | His | Glu | Phe | Ile | Gln | Trp | Leu | Leu | Asn | Gly |

FIG. 1AAO

| Analogue no. | SEQ ID NO. | G no. | 30 | 31 | 32 | 33 | 34 | 35 | 36 | 37 |
|---|---|---|---|---|---|---|---|---|---|---|
| 273 | 273 | 2154 | Gly | His | His | His | His | Gln | NH2 | |
| 274 | 274 | 2155 | His | His | His | Gly | | | | |
| 275 | 275 | 2156 | His | His | His | Gly | NH2 | | | |
| 276 | 276 | 2157 | Gly | His | His | His | His | Ala | Ala | NH2 |
| 277 | 277 | 2160 | His | His | His | His | Gly | | | |
| 278 | 278 | 2161 | Gly | His | His | His | His | Gln | Gln | NH2 |
| 279 | 279 | 2162 | His | His | His | His | Gly | | | |
| 280 | 280 | 2163 | His | His | His | His | Gly | | | |
| 281 | 281 | 2165 | His | His | His | Gly | | | | |
| 282 | 282 | 2170 | Gly | His | His | His | His | Gly | NH2 | |
| 283 | 283 | 2171 | Gly | His | His | His | His | Gly | | |
| 284 | 284 | 2172 | Gly | His | His | His | His | Gly | NH2 | |
| 285 | 285 | 2173 | Gly | His | His | His | His | Gly | | |
| 286 | 286 | 2174 | Gly | His | His | His | His | Gln | NH2 | |
| 287 | 287 | 2175 | Gly | His | His | His | His | NH2 | | |
| 288 | 288 | 2176 | Gly | His | His | His | His | Gln | NH2 | |

FIG. 1AAP

| Analogue no. | SEQ ID NO. | G no. | hGCGr cAMP | | hGLP-1r cAMP | | Mouse food intake inhibition (500nmol/kg) | | Rat food intake inhibtion (500 nmol/kg with 1:1 Zn) |
|---|---|---|---|---|---|---|---|---|---|
| | | | n | vs hGCG | n | vs hGLP-1 | 0-24 | 0-48 | 0-24 |
| 273 | 273 | 2154 | 2 | 1.7 | | | 17 | 2 | 30 |
| 274 | 274 | 2155 | 2 | 1.4 | | | 33 | 9 | 35 |
| 275 | 275 | 2156 | 2 | 2.3 | | | 49 | 19 | 28 |
| 276 | 276 | 2157 | 2 | 2.4 | | | 19 | -3 | 43 |
| 277 | 277 | 2160 | 3 | 1.3 | 3 | 5.9 | 19 | 8 | 45 |
| 278 | 278 | 2161 | 2 | 1.5 | | | 28 | 10 | 51 |
| 279 | 279 | 2162 | 1 | 2.0 | | | 37 | 6 | 23 |
| 280 | 280 | 2163 | 3 | 2.8 | 2 | 5.4 | 58 | 29 | 22 |
| 281 | 281 | 2165 | 1 | 1.5 | | | 48 | 23 | 32 |
| 282 | 282 | 2170 | 2 | 1.2 | 1 | 0.9 | 60 | 40 | 52 |
| 283 | 283 | 2171 | 2 | 1.2 | 1 | 1.7 | 62 | 42 | 56 |
| 284 | 284 | 2172 | 2 | 1.6 | 1 | 3.3 | 41 | 24 | 36 |
| 285 | 285 | 2173 | 1 | 1.1 | | | 39 | 20 | 35 |
| 286 | 286 | 2174 | 1 | 0.9 | | | 18 | 16 | -3 |
| 287 | 287 | 2175 | | | | | 38 | 20 | 10 |
| 288 | 288 | 2176 | 2 | 1.2 | 1 | 0.9 | 33 | 22 | 65 |

PEPTIDES HORMONE ANALOGUES DERIVABLE FROM PREPROGLUCAGON

FIELD OF THE INVENTION

This invention relates to analogues of peptide hormones derivable from preproglucagon, and in particular analogues of glucagon, which are useful in treating disorders such as diabetes and obesity.

BACKGROUND TO THE INVENTION

According to the National Health and Nutrition Examination Survey (NHANES, 1999 to 2008), over one half of adults in the United States are overweight or obese. In the United States, 72.3% percent of males and 64.1% percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. Recently it has been shown that considerable weight loss can effectively cure type 2 diabetes (Lim et al, Diabetologia June 2011).

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have proven to have serious adverse side effects, and have had to be withdrawn. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects as well as subjects who are of normal weight.

A number of approaches to the development of agents useful in effecting weight loss have involved gastrointestinal peptide hormones and their analogues. For example, derivatives of peptides deriving from the preproglucagon molecule have been proposed for use in treatment of obesity and/or diabetes. Preproglucagon is a precursor peptide of glucagon, as well as other hormones including glucagon-like peptide 1 (GLP1) and oxyntomodulin (OXM).

Glucagon is released in vivo when blood glucose levels fall low and has the activity of causing the liver to convert stored glycogen into glucose which is released into the bloodstream raising blood glucose levels. GLP1 is produced in vivo in the intestinal L cell in response to the presence of nutrients in the lumen of the gut. Once in the circulation, native GLP1 has a half-life of only a few minutes in humans due to rapid degradation by the enzyme dipeptidyl peptidase. GLP1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration. Peptide analogues of glucagon and GLP-1 useful in treating metabolic disorders are disclosed in, for example, WO2013/004983.

Oxyntomodulin (OCM) is a 37 amino acid peptide member of the glucagon superfamily (Sherwood et al, Endocrine Reviews, 2000, 21(6): 619-670) comprising the entire 29 amino acid sequence of glucagon, with an eight amino acid carboxy terminal extension, resulting from the tissue-specific processing of the pre-pro-glucagon precursor in the brain and gut (Holst, Ann Rev Physiol, 1997, 59:257-271). Administration of OCM to rats via intracerebroventricular injection and injection into the paraventricular and arcuate nuclei of the hypothalamus inhibits refeeding after a fast (Dakin et al, Endocrinology, 2001, 142:4244-4250; Dakin et al, Endocrinology, 2004, 145:2687-2695). Chronic central administration resulted in reduced weight gain consistent with a reduction in food intake (Dakin et al, Am J Physiol Endocrinol Metab, 2002, 283:E1173-E1177). Twice daily peripheral injections also resulted in reduced body weight gain and adiposity (Dakin et al, Endocrinology, 2004, 145: 2687-2695). Analogues of OCM useful in reducing food intake are disclosed in, for example, WO2006/134340 and WO2008/071972.

Despite significant advances, the process of identifying substances useful as drugs remains a complex and, in many cases, unpredictable field. In order to be useful as therapeutic agents, compounds must possess a suitable range of properties. For example, in addition to having efficacy at the biological target of interest, compounds must have good in vivo pharmacokinetic properties and low toxicity, and have appropriate physical properties (e.g. solubility).

In the field of peptide therapeutics, native peptides or analogues thereof often suffer from poor pharmacokinetic properties; it is often found that such compounds have a high clearance rate/and or are sensitive to degradation resulting in short duration of action. Research has led to the identification of peptide therapeutics having improved pharmacokinetic properties. For example, WO2011/075393 discloses peptides having activity at the GLP1 and/or glucagon receptors and teaches that, in order to achieve prolonged half-life/extended duration of action, the peptides may be derivatised, containing acylated or alkylated amino acids.

However, there remains a need for further compounds which have suitable properties so that they are effective as therapeutic agents; in particular having potent biological activity combined with improved pharmacokinetic properties.

SUMMARY OF THE INVENTION

The invention provides a peptide hormone analogue which is:
a compound comprising the formula (I)

$$X-V \quad \quad (I)$$

wherein X represents a peptide hormone derivable from preproglucagon or an analogue thereof; and
V represents a C-terminal extension amino acid sequence comprising at least four amino acid residues, at least three of said amino acid residues being His residues;
or a derivative of the compound;
or a pharmaceutically acceptable salt of the compound or the derivative.

The present inventors have identified peptide hormone analogues possessing C-terminal extension amino acid sequences which possess a range of excellent biological properties. The peptide hormone analogues have improved pharmacokinetic properties whilst retaining sufficient activity at the biological target of interest. In particular, the compounds exhibit potent and prolonged duration of action in vivo following subcutaneous administration. In addition, in contrast to peptides not having the C-terminal extension sequence of the invention, the present peptide hormone analogues of the present invention either do not display initial "spikes" or "bursts" in plasma concentration levels following subcutaneous administration or any such "burst" is significantly reduced. This reduces the likelihood and/or severity of possible side effects that may be associated with high circulating levels of the peptide hormone analogue. That the peptide hormone analogues possess such a range of properties is surprising given the presence of the highly polar C-terminal extension sequence which contains multiple charged residues concentrated in a single region of the peptide structure.

The invention also provides a pharmaceutical composition comprising a peptide hormone analogue according to the invention together with a pharmaceutically acceptable carrier and optionally a further therapeutic agent.

The invention also provides a peptide hormone analogue according to the invention or a pharmaceutical composition comprising the peptide hormone analogue for use as a medicament. Peptide hormone analogues or pharmaceutical compositions according to the invention find use in the prevention or treatment of obesity and/or diabetes, increasing the energy expenditure of a subject, improving insulin release in a subject, improving carbohydrate metabolism in a subject, improving the lipid profile of a subject, reducing appetite in a subject, reducing food intake in a subject, reducing calorie intake in a subject, improving carbohydrate tolerance in a subject, and/or as a cytoprotective agent.

The invention also provides a method of treating or preventing a disease or disorder or other non-desired physiological state in a subject comprising administration of a therapeutically effective amount of a peptide hormone analogue according to the invention, or a pharmaceutical composition comprising the peptide hormone analogue. There is also provided a method of treating or preventing obesity and/or diabetes in a subject, increasing energy expenditure in a subject, improving insulin release in a subject, improving carbohydrate metabolism in a subject, improving the lipid profile of a subject, reducing appetite in a subject, reducing food intake in a subject, reducing calorie intake in a subject, improving carbohydrate tolerance in a subject, and/or providing cytoprotection in a subject, comprising administration of a therapeutically effective amount of a peptide hormone analogue of the invention or a pharmaceutical composition comprising the peptide hormone analogue.

The invention also provides use of a peptide hormone analogue according to the invention for the manufacture of a medicament for the prevention or treatment of obesity and/or diabetes, increasing the energy expenditure of a subject, improving insulin release in a subject, improving carbohydrate metabolism in a subject, improving the lipid profile of a subject, reducing appetite in a subject, reducing food intake in a subject, reducing calorie intake in a subject, improving carbohydrate tolerance in a subject, and/or for use as a cytoprotective agent.

The invention also provides a method of causing weight loss or preventing weight gain in a subject for cosmetic purposes comprising administration of an effective amount of a peptide hormone analogue of the invention, or a composition comprising the peptide hormone analogue.

BRIEF DESCRIPTION OF THE DRAWINGS

FIGS. 1A-1AAP show the amino acid sequences of peptide hormone analogues of the invention. The peptide analogues in the table of FIGS. 1A-1AAP are presented with the N-terminal residue at the left hand side (signified by the column titled "1"). The amino acid sequence for each peptide hormone analogue is split between two pages, with residue nos. 1-16 on a first page, and the remaining residues on the next page). Analogues in the table containing the indication "NH2" next to the C-terminal amino acid residue have a C-terminal amide group (i.e. the C-terminal amino acid residue has a —$CONH_2$ group in place of a C-terminal carboxylic acid). FIGS. 1A-1AAP also show data relating to cAMP signaling in cells over-expressing the human glucagon receptor or the human GLP-1 receptor following contact with peptide hormone analogues of the invention. FIGS. 1A-1AAP also show summary food intake data for peptide hormone analogues of the invention in mice and rats.

As shown in FIG. 2, G1698 displays a more potent and more sustained reduction of cumulative food intake relative to saline control than the comparator compound.

As shown in FIG. 3, G1718 displays a more potent and more sustained reduction of cumulative food intake relative to saline control than the comparator compound.

As shown in FIG. 4, G1722 displays a more potent and more sustained reduction of body weight increase relative to saline control than the comparator compound.

As shown in FIG. 5, G1781 displays a more potent and more sustained reduction of body weight increase relative to saline control than the comparator compound.

SEQUENCE LISTING

Figure 2:
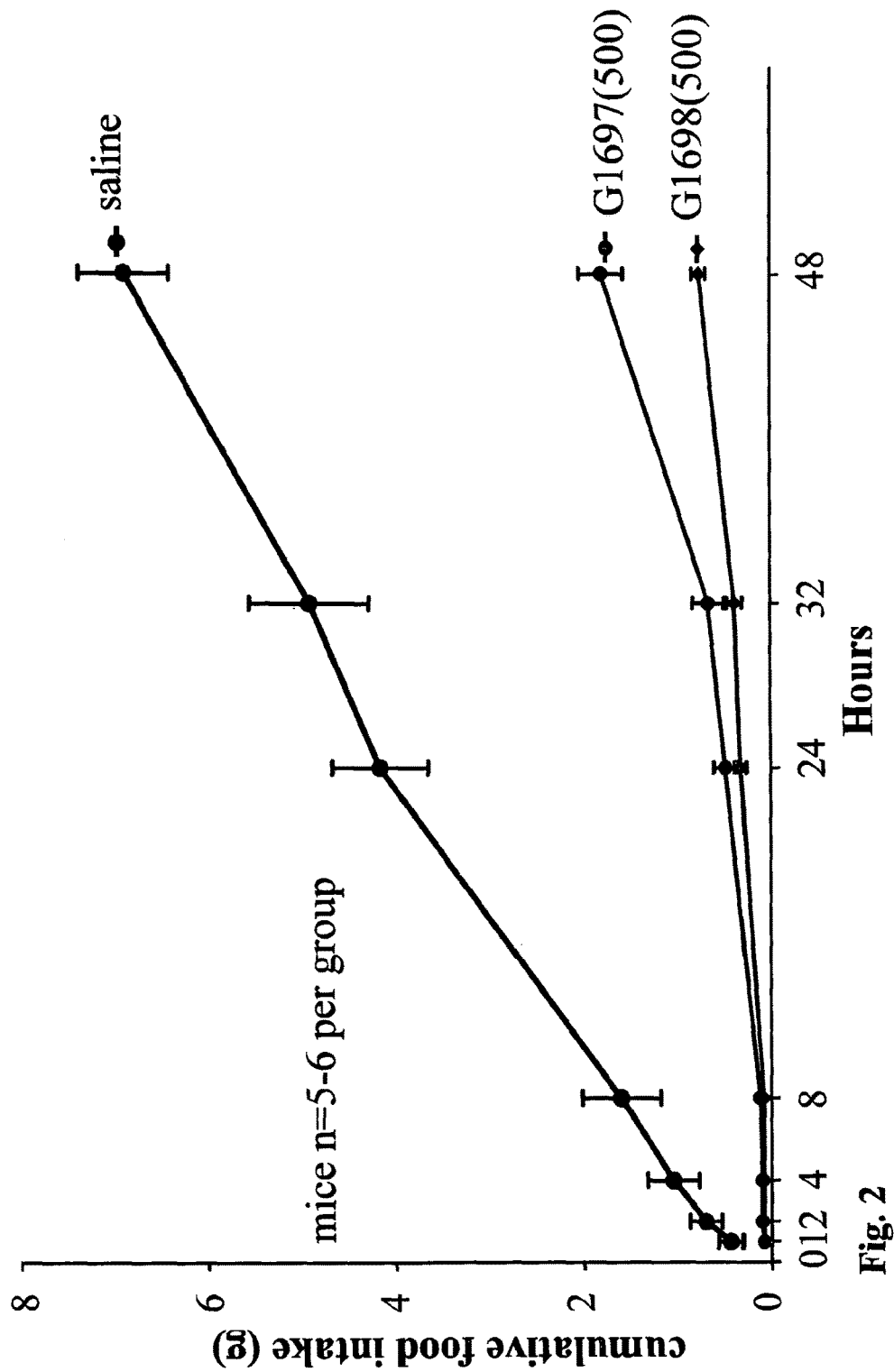
FIG. 2 shows the results of in vivo feeding studies in mice administered with a compound of the invention (G1698) and a comparator compound (G1697) not possessing a C-terminal extension amino acid sequence according to the invention.

The amino acid sequences listed in the application are shown using standard letter abbreviations for amino acids. The specific sequences given herein relate to specific preferred embodiments of the invention.

Definitions

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height (in meters). The current standards for both men and women accepted as "normal" are a BMI of 20-24.9 $kg/m^2$. In one embodiment, a BMI of greater than 25 $kg/m^2$ can be used to identify an obese subject. Grade I obesity (which is sometimes referred to as being "overweight" rather than obesity) corresponds to a BMI of 25-29.9 $kg/m^2$. Grade II obesity corresponds to a BMI of 30-40 $kg/m^2$; and Grade III obesity corresponds to a BMI greater than 40 $kg/m^2$ (Jequier, *Am. J Clin. Nutr.* 45:1035-47, 1987). Ideal body weight will vary among species and individuals based on height, body build, bone structure, and sex.

Cardioprotection refers to the protection of cardiac cells (and especially the myocardial cells) from apoptosis, necrotic cell death or degeneration (loss of function). Cardioprotection is most often required following myocardial infarction, but may also be used in subjects suffering from ischemic heart disease (for example angina)

Conservative substitutions: The replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide retains its activity or provided that antibodies raised to the substituted polypeptide also immunoreact with the unsubstituted polypeptide. Typical but not limiting conservative substitutions are the replacements, for one another, among the aliphatic amino acids Ala, Val, Leu and Ile; interchange of hydroxyl-containing residues Ser and Thr, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu.

TABLE 1

Non-limiting examples of conservative amino acid substitutions

| Original Residue | Conservative Substitutions |
|---|---|
| Ala | Gly, Val, Leu, Ile, Ser, Thr, Met |
| Arg | Lys |
| Asn | Asp, Gln, His |
| Asp | Glu, Asn |
| Cys | Ser |
| Gln | Asn, His, Lys, Glu |
| Glu | Asp, Gln |
| Gly | Ala, Ser, Thr, Met |
| His | Asn, Gln |
| Ile | Ala, Leu, Val, Met |
| Leu | Ala, Ile, Val, Met, |
| Lys | Arg |
| Met | Leu, Ile, Ala, Ser, Thr, Gly |
| Phe | Leu, Tyr, Trp |
| Ser | Thr, Cys, Ala, Met, Gly |
| Thr | Ser, Ala, Ser, Met, Gly |
| Trp | Tyr, Phe |
| Tyr | Trp; Phe |
| Val | Ala, Ile, Leu |

Non-conservative substitutions: The replacement, in a polypeptide, of an amino acid residue by another residue which is not biologically similar. For example, the replacement of an amino acid residue with another residue that has a substantially different charge, a substantially different hydrophobicity or a substantially different spatial or steric configuration.

The phrase "alternative amino acid" encompasses alternative amino acids that are the result of both conservative and non-conservative substitutions. In addition to the twenty commonly occurring amino acids that are typically found in naturally occurring polypeptides, rare amino acids, for example, canavanine, ornithine and 5-hydroxytryptophane, and artificial amino acids, that is to say amino acids not normally found in vivo, for example t-butylglycine, may be used as "alternative amino acids" in accordance with the invention. Any chiral form of an amino acid may be used.

Cytoprotection refers to the protection of cells from apoptosis, necrotic cell death or degeneration (loss of function).

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Energy Metabolism: The body has to expend a certain amount of energy to maintain normal metabolism. In civilized man this is often set at about 2,800 Calories daily. If food consumption does not provide this, weight loss results. However, energy metabolism is also regulated and, for example, administration of glucagon is thought to increase the metabolic rate so that a greater food intake is required to achieve energy balance and maintain weight. Thus, if food intake is maintained at the usual level, but energy metabolism is increased, weight loss will result.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

GLP1: Glucagon-like peptide 1 (GLP1) is derived from the transcription product of the proglucagon gene. The biologically active forms of GLP1 are truncated forms known as $GLP1_{(7-37)}$ and $GLP1_{(7-36)}$-$NH_2$ (i.e. the C-terminus has a —$CONH_2$ group in place of a carboxylic acid).

The sequence of human $GLP1_{(7-37)}$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly.

The sequence of human $GLP1_{(7-36)}$-$NH_2$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$CONH_2$.

Glucagon: Glucagon is a peptide derived from the proglucagon gene. It is a 29-amino acid polypeptide in humans and has the sequence:

```
His-Ser-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr.
```

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is uncharged, a hyperpolarized cell requires a stronger excitatory stimulus to reach threshold.

Neuroprotection refers to the protection of neurons within the nervous system (preferably within the central nervous system) from apoptosis, necrotic cell death or degeneration (loss of function). Neuroprotective treatments, including those relating to various aspects of the present invention may be required following a brain injury (for example those following physical trauma or non-traumatic injury such as stroke, brain tumours, infection, poisoning, hypoxia, ischemia, encephalopathy or substance abuse). Neuroprotective treatments, including those relating to various aspects of the present invention may also be indicated in subjects having a chronic neurodegenerative disease such as Alzheimer's disease, Parkinson's disease, Gehrig's disease or Huntington's disease.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 $kg/m^2$ to 29.9 $kg/m^2$ is overweight, while a BMI of 30 $kg/m^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 $kg/m^2$ to 29.9 $kg/m^2$.

Oxymtomodulin (OXM): Oxyntomodulin is a 37 amino acid peptide member of the glucagon superfamily comprising the entire 29 amino acid sequence of glucagon, with an eight amino acid carboxy terminal extension, resulting from the tissue-specific processing of the pre-pro-glucagon precursor in the brain and gut. The human OXM sequence (which is the same as the rat and hamster) is as follows:

His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr-Lys-Arg-Asn-Arg-Asn-Asn-Ile-

Ala.

PEGylated and PEGylation: the process of reacting a poly(alkylene glycol), preferably an activated poly(alkylene glycol) to form a covalent bond. A facilitator may be used, for example an amino acid, e.g. lysine. Although "PEGylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focusing which is an electrophoretic method that utilises a pH gradient contained within a polyacrylamide gel.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH 4 and pH 10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

DETAILED DESCRIPTION OF THE INVENTION

According to a first aspect of the invention there is provided a peptide hormone analogue which is: a compound comprising the formula (I)

$$X-V \qquad (I)$$

wherein
X represents a peptide hormone derivable from preproglucagon or an analogue thereof; and
V represents a C-terminal extension amino acid sequence comprising at least four amino acid residues, at least three of said amino acid residues being His residues;
or a derivative of the compound;
or a pharmaceutically acceptable salt of the compound or the derivative.

X is a peptide hormone derivable from preproglucagon or an analogue thereof. Preferably X is selected from the group consisting of glucagon or an analogue thereof, GLP1 or an analogue thereof and oxyntomodulin or an analogue thereof; more preferably glucagon or an analogue thereof or GLP1 or an analogue thereof; still more preferably glucagon or an analogue thereof.

In some embodiments, X is an analogue of a preproglucagon-derived peptide hormone. As defined herein, an analogue is a peptide sequence that contains at least 50% sequence homology with a native preproglucagon-derived peptide hormone, preferably at least 60% sequence homology, more preferably at least 70% sequence homology; still more preferably at least 80% sequence homology; yet more preferably at least 90% sequence homology. In some embodiments, an analogue contains an amino acid sequence that corresponds to the amino acid sequence of a native preproglucagon-derived peptide hormone except that the analogue contains from 1 to 14 amino acid modifications selected from substitutions, insertions and deletions, preferably the analogue contains from 1 to 13, from 1 to 12, from 1 to 11, from 1 to 10, from 1 to 9, from 1 to 8, from 1 to 7, from 1 to 6, from 1 to 5, from 1 to 4, from 1 to 3, or from 1 to 2 amino acid modifications from the amino acid sequence of a native preproglucagon-derived peptide hormone. Preferably the modifications are substitutions, i.e. the analogue contains from 1 to 14, from 1 to 13, from 1 to 12, from 1 to 11, from 1 to 10, from 1 to 9, from 1 to 8, from 1 to 7, from 1 to 6, from 1 to 5, from 1 to 4, from 1 to 3, or from 1 to 2 amino acid substitutions (more preferably conservative substitutions) from the amino acid sequence of a native preproglucagon-derived peptide hormone.

In one embodiment X is an analogue which contains amino acid sequence from more than one preproglucagon-derived peptide hormone, for example X may contain amino acid sequence from both glucagon and GLP-1.

In one preferred embodiment, X is an analogue of glucagon and represents an amino acid sequence having the formula (III):

(III)
[SEQ ID NO 289]
His-Ser-Gln-Gly-Thr-Phe-Thr-Ser-Asp-Xaa$^{10}$-Ser-Xaa$^{12}$-Xaa$^{13}$-Leu-Xaa$^{15}$-Xaa$^{16}$-Xaa$^{17}$-Xaa$^{18}$-Ala-Xaa$^{20}$-Xaa$^{21}$-Phe-Xaa$^{23}$-Xaa$^{24}$-Trp-Leu-Leu-Asn-Xaa$^{29}$ wherein
  Xaa$^{10}$ is selected from the group consisting of Tyr and Leu;
  Xaa$^{12}$ is selected from the group consisting of Lys, His and Arg;
  Xaa$^{13}$ is selected from the group consisting of Tyr, Gln and His;
  Xaa$^{15}$ is selected from the group consisting of Asp and Glu;
  Xaa$^{16}$ is selected from the group consisting of Glu, Gln and Ser;
  Xaa$^{18}$ is selected from the group consisting of Arg, His and Lys;
  Xaa$^{18}$ is selected from the group consisting of Arg and Lys;
  Xaa$^{20}$ is selected from the group consisting of His and Gln;
  Xaa$^{21}$ is selected from the group consisting of Glu, His and Asp;
  Xaa$^{23}$ is selected from the group consisting of Ile and Val;
  Xaa$^{24}$ is selected from the group consisting of Gln and Glu; and
  Xaa$^{29}$ is selected from the group consisting of Thr and Gly.

The amino acid sequence of formula (III) above is shown with the N-terminus to the top left. The C-terminal extension amino acid sequence (i.e. the V group) is attached to the residue at the bottom right of the sequence of formula (III). Unless indicated otherwise, the amino acid residues in the sequence of formula (III) are L-amino acids.

In formula (III), Xaa$^{10}$ is selected from the group consisting of Tyr and Leu. In one preferred embodiment Xaa$^{10}$ is Tyr. In one embodiment Xaa$^{10}$ is Leu.

In formula (III), Xaa$^{12}$ is selected from the group consisting of Lys, His and Arg. In one preferred embodiment Xaa$^{12}$ is Lys. In one embodiment Xaa$^{12}$ is His. In one embodiment Xaa$^{12}$ is Arg.

In formula (III), Xaa$^{13}$ is selected from the group consisting of Tyr, Gln and His. In one preferred embodiment Xaa$^{13}$ is Tyr. In one embodiment Xaa$^{13}$ is His. In one embodiment Xaa$^{13}$ is Gln. In one embodiment Xaa$^{13}$ is selected from the group consisting of Tyr and His.

In formula (III), Xaa$^{15}$ is selected from the group consisting of Asp and Glu. In one preferred embodiment Xaa$^{15}$ is Asp. In one embodiment Xaa$^{15}$ is Glu.

In formula (III), Xaa$^{16}$ is selected from the group consisting of Glu, Gln and Ser. In one embodiment Xaa$^{16}$ is Ser.

In one preferred embodiment Xaa$^{16}$ is Glu. In one preferred embodiment Xaa$^{16}$ is Gln. In one preferred embodiment Xaa$^{16}$ is selected from the group consisting of Glu and Gln.

In formula (III), Xaa$^{17}$ is selected from the group consisting of Arg, His and Lys. In one preferred embodiment Xaa$^{17}$ is Arg. In one preferred embodiment Xaa$^{17}$ is Lys. In one embodiment Xaa$^{17}$ is His. In one preferred embodiment Xaa$^{17}$ is selected from the group consisting of Arg and Lys.

In formula (III) Xaa$^{18}$ is selected from the group consisting of Arg and Lys. In one preferred embodiment Xaa$^{18}$ is Arg. In one embodiment Xaa$^{18}$ is Lys.

In formula (III), Xaa$^{20}$ is selected from the group consisting of His and Gln. In one preferred embodiment Xaa$^{20}$ is His. In one embodiment Xaa$^{20}$ is Gln.

In formula (III), Xaa$^{21}$ is selected from the group consisting of Glu, His and Asp. In one preferred embodiment Xaa$^{21}$ is Glu. In one embodiment Xaa$^{21}$ is Asp. In one embodiment Xaa$^{21}$ is His. In one embodiment Xaa$^{21}$ is selected from the group consisting of Glu and Asp.

In formula (III), Xaa$^{23}$ is selected from the group consisting of Ile and Val. In one embodiment Xaa$^{23}$ is Val. In one preferred embodiment Xaa$^{23}$ is Ile.

In formula (III), Xaa$^{24}$ is selected from the group consisting of Gln and Glu. In one preferred embodiment Xaa$^{24}$ is Gln. In one preferred embodiment Xaa$^{24}$ is Glu.

In formula (III), Xaa$^{29}$ is selected from the group consisting of Thr and Gly. In one preferred embodiment Xaa$^{29}$ is Thr. In one preferred embodiment Xaa$^{29}$ is Gly.

In one preferred embodiment, X has the formula (III), Xaa$^{10}$ is Tyr and Xaa$^{16}$ is Ser.

In one preferred embodiment, X has the formula (III), Xaa$^{10}$ is Tyr and Xaa$^{20}$ is His.

In one preferred embodiment, X has the formula (III), Xaa$^{16}$ is Ser and Xaa$^{20}$ is His.

In one preferred embodiment, X has the formula (III), Xaa$^{10}$ is Tyr, Xaa$^{16}$ is Ser and Xaa$^{20}$ is His.

In one preferred embodiment, X has the formula (III), Xaa$^{13}$ is Tyr and/or Xaa$^{15}$ is Asp and/or Xaa$^{17}$ is Arg and/or Xaa$^{18}$ is Arg and/or Xaa$^{21}$ is Glu and/or Xaa$^{23}$ is Val.

In one preferred embodiment, X has the formula (III), Xaa$^{13}$ is Tyr and Xaa$^{15}$ is Asp.

In one preferred embodiment, X has the formula (III), Xaa$^{13}$ is Tyr and Xaa$^{17}$ is Arg.

In one preferred embodiment, X has the formula (III), Xaa$^{13}$ is Tyr and Xaa$^{18}$ is Arg.

In one preferred embodiment, X has the formula (III), Xaa$^{13}$ is Tyr and Xaa$^{21}$ is Glu.

In one preferred embodiment, X has the formula (III), Xaa$^{13}$ is Tyr and Xaa$^{23}$ is Val.

In one preferred embodiment, X has the formula (III), Xaa$^{15}$ is Asp and Xaa$^{17}$ is Arg.

In one preferred embodiment, X has the formula (III), Xaa$^{15}$ is Asp and Xaa$^{18}$ is Arg.

In one preferred embodiment, X has the formula (III), Xaa$^{15}$ is Asp and Xaa$^{21}$ is Glu.

In one preferred embodiment, X has the formula (III), Xaa$^{15}$ is Asp and Xaa$^{23}$ is Val.

In one preferred embodiment, X has the formula (III), Xaa$^{17}$ is Arg and Xaa$^{18}$ is Arg.

In one preferred embodiment, X has the formula (III), Xaa$^{17}$ is Arg and Xaa$^{21}$ is Glu.

In one preferred embodiment, X has the formula (III), Xaa$^{17}$ is Arg and Xaa$^{23}$ is Val.

In one preferred embodiment, X has the formula (III), Xaa$^{18}$ is Arg and Xaa$^{21}$ is Glu.

In one preferred embodiment, X has the formula (III), Xaa$^{18}$ is Arg and Xaa$^{23}$ is Val.

In one preferred embodiment, X has the formula (III), $Xaa^{21}$ is Glu and $Xaa^{23}$ is Val.

In one preferred embodiment, X has the formula (III), $Xaa^{10}$ is Tyr, $Xaa^{12}$ is Lys, $Xaa^{16}$ is Ser and $Xaa^{20}$ is His.

In one preferred embodiment, X has the formula (III), $Xaa^{10}$ is Tyr, $Xaa^{12}$ is Arg, $Xaa^{16}$ is Ser and $Xaa^{20}$ is His.

In one preferred embodiment, X has the formula (III), $Xaa^{10}$ is Tyr, $Xaa^{12}$ is His, $Xaa^{16}$ is Ser and $Xaa^{20}$ is His.

In one preferred embodiment, X has the formula (III), $Xaa^{10}$ is Tyr, $Xaa^{13}$ is Tyr, $Xaa^{16}$ is Ser and $Xaa^{20}$ is His.

In one preferred embodiment, X has the formula (III), $Xaa^{10}$ is Tyr, $Xaa^{13}$ is His, $Xaa^{16}$ is Ser and $Xaa^{20}$ is His.

In one preferred embodiment, X has the formula (III), $Xaa^{10}$ is Tyr, $Xaa^{15}$ is Asp, $Xaa^{16}$ is Ser and $Xaa^{20}$ is His.

In one preferred embodiment, X has the formula (III), $Xaa^{10}$ is Tyr, $Xaa^{15}$ is Glu, $Xaa^{16}$ is Ser and $Xaa^{20}$ is His.

In one preferred embodiment, X has the formula (III), $Xaa^{10}$ is Tyr, $Xaa^{16}$ is Ser, $Xaa^{17}$ is Arg and $Xaa^{20}$ is His.

In one preferred embodiment, X has the formula (III), $Xaa^{10}$ is Tyr, $Xaa^{16}$ is Ser, $Xaa^{17}$ is Lys and $Xaa^{20}$ is His.

In one preferred embodiment, X has the formula (III), $Xaa^{10}$ is Tyr, $Xaa^{16}$ is Ser, $Xaa^{18}$ is Arg and $Xaa^{20}$ is His.

In one preferred embodiment, X has the formula (III), $Xaa^{10}$ is Tyr, $Xaa^{16}$ is Ser, $Xaa^{18}$ is Lys and $Xaa^{20}$ is His.

In one preferred embodiment, X has the formula (III), $Xaa^{10}$ is Tyr, $Xaa^{16}$ is Ser, $Xaa^{20}$ is His and $Xaa^{21}$ is Glu.

In one preferred embodiment, X has the formula (III), $Xaa^{10}$ is Tyr, $Xaa^{16}$ is Ser, $Xaa^{20}$ is His and $Xaa^{21}$ is Asp.

In one preferred embodiment, X has the formula (III), $Xaa^{10}$ is Tyr, $Xaa^{16}$ is Ser, $Xaa^{20}$ is His and $Xaa^{23}$ is Val.

In one preferred embodiment, X has the formula (III), $Xaa^{10}$ is Tyr, $Xaa^{16}$ is Ser, $Xaa^{20}$ is His and $Xaa^{23}$ is Ile.

In one preferred embodiment, X has the formula (III), $Xaa^{10}$ is Tyr, $Xaa^{16}$ is Ser, $Xaa^{20}$ is His and $Xaa^{24}$ is Gln.

In one preferred embodiment, X has the formula (III), $Xaa^{10}$ is Tyr, $Xaa^{16}$ is Ser, $Xaa^{20}$ is His and $Xaa^{24}$ is Glu.

In one preferred embodiment, X has the formula (III), $Xaa^{10}$ is Tyr, $Xaa^{16}$ is Ser, $Xaa^{20}$ is His and $Xaa^{29}$ is Thr.

In one preferred embodiment, X has the formula (III), $Xaa^{10}$ is Tyr, $Xaa^{16}$ is Ser, $Xaa^{20}$ is His and $Xaa^{29}$ is Gly.

In one preferred embodiment, X has the formula (III), $Xaa^{10}$ is Tyr, $Xaa^{13}$ is Tyr, $Xaa^{15}$ is Asp, $Xaa^{16}$ is Ser and $Xaa^{20}$ is His.

In one preferred embodiment, X has the formula (III), $Xaa^{10}$ is Tyr, $Xaa^{13}$ is Tyr, $Xaa^{16}$ is Ser, $Xaa^{17}$ is Arg and $Xaa^{20}$ is His.

In one preferred embodiment, X has the formula (III), $Xaa^{10}$ is Tyr, $Xaa^{13}$ is Tyr, $Xaa^{16}$ is Ser, $Xaa^{18}$ is Arg and $Xaa^{20}$ is His.

In one preferred embodiment, X has the formula (III), $Xaa^{10}$ is Tyr, $Xaa^{13}$ is Tyr, $Xaa^{16}$ is Ser, $Xaa^{20}$ is His and $Xaa^{21}$ is Glu.

In one preferred embodiment, X has the formula (III), $Xaa^{10}$ is Tyr, $Xaa^{13}$ is Tyr, $Xaa^{16}$ is Ser, $Xaa^{20}$ is His and $Xaa^{23}$ is Val.

In one preferred embodiment, X has the formula (III), $Xaa^{10}$ is Tyr, $Xaa^{15}$ is Asp, $Xaa^{16}$ is Ser, $Xaa^{17}$ is Arg and $Xaa^{20}$ is His.

In one preferred embodiment, X has the formula (III), $Xaa^{10}$ is Tyr, $Xaa^{15}$ is Asp, $Xaa^{16}$ is Ser, $Xaa^{18}$ is Arg and $Xaa^{20}$ is His.

In one preferred embodiment, X has the formula (III), $Xaa^{10}$ is Tyr, $Xaa^{15}$ is Asp, $Xaa^{16}$ is Ser, $Xaa^{20}$ is His and $Xaa^{21}$ is Glu.

In one preferred embodiment, X has the formula (III), $Xaa^{10}$ is Tyr, $Xaa^{15}$ is Asp, $Xaa^{16}$ is Ser, $Xaa^{20}$ is His and $Xaa^{23}$ is Val.

In one preferred embodiment, X has the formula (III), $Xaa^{10}$ is Tyr, $Xaa^{16}$ is Ser, $Xaa^{17}$ is Arg, $Xaa^{18}$ is Arg and $Xaa^{20}$ is His.

In one preferred embodiment, X has the formula (III), $Xaa^{10}$ is Tyr, $Xaa^{16}$ is Ser, $Xaa^{17}$ is Arg, $Xaa^{20}$ is His and $Xaa^{21}$ is Glu.

In one preferred embodiment, X has the formula (III), $Xaa^{10}$ is Tyr, $Xaa^{16}$ is Ser, $Xaa^{17}$ is Arg, $Xaa^{20}$ is His and $Xaa^{23}$ is Val.

In one preferred embodiment, X has the formula (III), $Xaa^{10}$ is Tyr, $Xaa^{16}$ is Ser, $Xaa^{18}$ is Arg, $Xaa^{20}$ is His and $Xaa^{21}$ is Glu.

In one preferred embodiment, X has the formula (III), $Xaa^{10}$ is Tyr, $Xaa^{16}$ is Ser, $Xaa^{18}$ is Arg, $Xaa^{20}$ is His and $Xaa^{23}$ is Val.

In one preferred embodiment, X has the formula (III), $Xaa^{10}$ is Tyr, $Xaa^{16}$ is Ser, $Xaa^{20}$ is His, $Xaa^{21}$ is Glu and $Xaa^{23}$ is Val.

In one preferred embodiment, X has the formula (III), $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred embodiment, X has the formula (III), $Xaa^{10}$ is Tyr, $Xaa^{12}$ is Lys, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred embodiment, X has the formula (III), $Xaa^{10}$ is Tyr, $Xaa^{12}$ is Arg, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu and $Xaa^{23}$ is Val.

In one preferred embodiment, X has the formula (III), $Xaa^{10}$ is Tyr, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu and $Xaa^{23}$ is Val.

In one preferred embodiment, X has the formula (III), $Xaa^{10}$ is Tyr, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu and $Xaa^{23}$ is Val.

In one preferred embodiment, X has the formula (III), $Xaa^{10}$ is Tyr, $Xaa^{13}$ is Tyr, $Xaa^{5}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{24}$ is Gln.

In one preferred embodiment, X has the formula (III), $Xaa^{10}$ is Tyr, $Xaa^{13}$ is Tyr, $Xaa^{5}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{24}$ is Glu.

In one preferred embodiment, X has the formula (III), $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{29}$ is Gly.

In one preferred embodiment, X has the formula (III), $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and $Xaa^{29}$ is Thr.

In one preferred embodiment, X has the formula (III), $Xaa^{10}$ is Tyr, $Xaa^{13}$ is Tyr, $Xaa^{5}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{24}$ is Gln and $Xaa^{23}$ is Val.

In one preferred embodiment, X has the formula (III), $Xaa^{10}$ is Tyr, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, $Xaa^{24}$ is Glu and $Xaa^{23}$ is Val.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys or Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Gln, $Xaa^{17}$ is Lys or Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, and $Xaa^{24}$ is Glu.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, and $Xaa^{24}$ is Gln.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{8}$ is Lys or Arg, $Xaa^{2}$ is Arg, $Xaa^{20}$ is His, $Xaa^{21}$ is Glu, $Xaa^{23}$ is Ile, and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, and $Xaa^{29}$ is Gly.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Gln, $Xaa^{17}$ is Arg, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Gln, $Xaa^{17}$ is Lys, $Xaa^{18}$ is Arg, $Xaa^{20}$ is His, $Xaa^{21}$ is Glu, and $Xaa^{23}$ is Ile.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys or Arg, $Xaa^{18}$ is Arg, $Xaa^{20}$ is His, $Xaa^{21}$ is Glu, $Xaa^{23}$ is Ile and $Xaa^{24}$ is Glu.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys or Arg, $Xaa^{18}$ is Arg, $Xaa^{20}$ is His, $Xaa^{21}$ is Glu, $Xaa^{23}$ is Ile and $Xaa^{24}$ is Gln.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Gln, $Xaa^{17}$ is Lys or Arg, $Xaa^{18}$ is Arg, $Xaa^{20}$ is His, $Xaa^{21}$ is Glu, $Xaa^{23}$ is Ile and $Xaa^{24}$ is Glu.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys or Arg, $Xaa^{18}$ is Arg, $Xaa^{20}$ is His, $Xaa^{21}$ is Glu, $Xaa^{23}$ is Ile and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Lys or Arg, $Xaa^{28}$ is Arg, $Xaa^{20}$ is His, $Xaa^{21}$ is Glu, $Xaa^{23}$ is Ile and $Xaa^{29}$ is Gly.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Gln, $Xaa^{17}$ is Lys or Arg, $Xaa^{18}$ is Arg, $Xaa^{20}$ is His, $Xaa^{21}$ is Glu, $Xaa^{23}$ is Ile and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys, $Xaa^{18}$ is Arg, $Xaa^{20}$ is His, $Xaa^{21}$ is Glu, $Xaa^{23}$ is Ile and $Xaa^{24}$ is Glu.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys, $Xaa^{18}$ is Arg, $Xaa^{20}$ is His, $Xaa^{21}$ is Glu, $Xaa^{23}$ is Ile and $Xaa^{24}$ is Gln.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Arg, $Xaa^{18}$ is Arg, $Xaa^{20}$ is His, $Xaa^{21}$ is Glu, $Xaa^{23}$ is Ile and $Xaa^{24}$ is Glu.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Arg, $Xaa^{18}$ is Arg, $Xaa^{20}$ is His, $Xaa^{21}$ is Glu, $Xaa^{23}$ is Ile and $Xaa^{24}$ is Gln.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys, $Xaa^{18}$ is Arg, $Xaa^{20}$ is His, $Xaa^{21}$ is Glu, $Xaa^{23}$ is Ile and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys, $Xaa^{18}$ is Arg, $Xaa^{20}$ is His, $Xaa^{21}$ is Glu, $Xaa^{23}$ is Ile and $Xaa^{29}$ is Gly.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Arg, $Xaa^{18}$ is Arg, $Xaa^{20}$ is His, $Xaa^{21}$ is Glu, $Xaa^{23}$ is Ile and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Arg, $Xaa^{18}$ is Arg, $Xaa^{20}$ is His, $Xaa^{21}$ is Glu, $Xaa^{23}$ is Ile and $Xaa^{29}$ is Gly.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{28}$ is Arg, $Xaa^{20}$ is His, $Xaa^{21}$ is Glu, $Xaa^{23}$ is Ile, $Xaa^{24}$ is Glu and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, $Xaa^{24}$ is Gln and $Xaa^{29}$ is Thr.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, $Xaa^{24}$ is Glu and $Xaa^{29}$ is Gly.

In one particularly preferred embodiment, X has the formula (III), $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, $Xaa^{23}$ is Ile, $Xaa^{24}$ is Gln and $Xaa^{29}$ is Gly.

In one embodiment, where X has the formula (III) and $Xaa^{12}$ is Lys, $Xaa^{13}$ is not His. In one embodiment, where X has the formula (III) and $Xaa^{13}$ is His, $Xaa^{17}$ is not His.

In one preferred embodiment, X is an analogue of GLP1 and represents an amino acid sequence having the formula (IV):

(IV)

[SEQ ID NO 290]
His-Xaa$^2$-Xaa$^3$-Gly-Thr-Phe-Thr-Ser-Asp-Xaa$^{10}$-Ser-Xaa$^{12}$-Xaa$^{13}$-Leu-Glu-Xaa$^{16}$-Xaa$^{17}$-Ala-Xaa$^{19}$-Xaa$^{20}$-Xaa$^{21}$-Phe-Xaa$^{23}$-Xaa$^{24}$-Trp-Leu-Xaa$^{27}$-Xaa$^{28}$-Xaa$^{29}$ wherein
- Xaa$^2$ is selected from the group consisting of Ser and Gly;
- Xaa$^3$ is selected from the group consisting of Glu and Gln;
- Xaa$^{10}$ is selected from the group consisting of Tyr and Leu;
- Xaa$^{12}$ is selected from the group consisting of Lys and His;
- Xaa$^{13}$ is selected from the group consisting of Tyr and Gln;
- Xaa$^{16}$ is selected from the group consisting of Glu, Ala and Ser;
- Xaa$^{17}$ is selected from the group consisting of Gln and Glu;
- Xaa$^{19}$ is selected from the group consisting of Val, Ala, Ile and Leu;
- Xaa$^{20}$ is selected from the group consisting of Arg and His;
- Xaa$^{21}$ is selected from the group consisting of Ile and Leu;
- Xaa$^{23}$ is selected from the group consisting of Ile and Val;
- Xaa$^{24}$ is selected from the group consisting of Glu and Gln;
- Xaa$^{27}$ is selected from the group consisting of Leu and Lys;
- Xaa$^{28}$ is selected from the group consisting of Asn, Lys and Gln; and
- Xaa$^{29}$ is selected from the group consisting of Gly and Thr.

The amino acid sequence of formula (IV) above is shown with the N-terminus to the top left. The C-terminal extension amino acid sequence (i.e. the V group) is attached to the residue at the bottom right of the sequence of formula (IV). Unless indicated otherwise, the amino acid residues in the sequence of formula (IV) are L-amino acids.

In formula (IV), Xaa$^2$ is selected from the group consisting of Ser and Gly. In one embodiment Xaa$^2$ is Ser. In one embodiment Xaa$^2$ is Gly.

In formula (IV), Xaa$^3$ is selected from the group consisting of Glu and Gln. In one embodiment Xaa$^3$ is Glu. In one embodiment Xaa$^3$ is Gln.

In formula (IV), Xaa$^{10}$ is selected from the group consisting of Tyr and Leu. In one embodiment Xaa$^{10}$ is Tyr. In one embodiment Xaa$^{10}$ is Leu.

In formula (IV), Xaa$^{12}$ is selected from the group consisting of Lys and His. In one embodiment Xaa$^{12}$ is Lys. In one embodiment Xaa$^{12}$ is His.

In formula (IV), Xaa$^{13}$ is selected from the group consisting of Tyr and Gln. In one embodiment Xaa$^{13}$ is Tyr. In one embodiment Xaa$^{13}$ is Gln.

In formula (IV), Xaa$^{16}$ is selected from the group consisting of Glu, Ala and Ser. In one embodiment Xaa$^{16}$ is Glu. In one embodiment Xaa$^{16}$ is Ala. In one embodiment Xaa$^{16}$ is Ser. In one embodiment Xaa$^{16}$ is selected from the group consisting of Glu and Ala.

In formula (IV) Xaa$^{17}$ is selected from the group consisting of Gln and Glu. In one embodiment Xaa$^{17}$ is Gln. In one embodiment Xaa$^{17}$ is Glu.

In formula (IV) Xaa$^{19}$ is selected from the group consisting of Val, Ala, Ile and Leu. In one embodiment Xaa$^{19}$ is Val. In one embodiment Xaa$^{19}$ is Leu. In one embodiment Xaa$^{19}$ is Ile.

In one embodiment Xaa$^{19}$ is Ala. In one embodiment Xaa$^{19}$ is selected from the group consisting of Val and Leu.

In formula (IV) Xaa$^{20}$ is selected from the group consisting of Arg and His. In one embodiment Xaa$^{20}$ is Arg. In one embodiment Xaa$^{20}$ is His.

In formula (IV) Xaa$^{21}$ is selected from the group consisting of Ile and Leu. In one embodiment Xaa$^{21}$ is Ile. In one embodiment Xaa$^{21}$ is Leu.

In formula (IV) Xaa$^{23}$ is selected from the group consisting of Ile and Val. In one embodiment Xaa$^{23}$ is Ile. In one embodiment Xaa$^{23}$ is Val.

In formula (IV) Xaa$^{24}$ is selected from the group consisting of Gln and Glu. In one embodiment Xaa$^{24}$ is Gln. In one embodiment Xaa$^{24}$ is Glu.

In formula (IV) Xaa$^{27}$ is selected from the group consisting of Leu and Lys. In one embodiment Xaa$^{27}$ is Leu. In one embodiment Xaa$^{27}$ is Lys.

In formula (IV) Xaa$^{28}$ is selected from the group consisting of Asn, Lys and Gln. In one embodiment Xaa$^{28}$ is Asn. In one embodiment Xaa$^{28}$ is Gln. In one embodiment Xaa$^{28}$ is Lys.

In formula (IV) Xaa$^{29}$ is selected from the group consisting of Gly and Thr. In one embodiment Xaa$^{29}$ is Gly. In one embodiment Xaa$^{29}$ is Thr.

In one preferred embodiment, X has the formula (IV), Xaa$^{12}$ is Lys, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^2$ is Ser, Xaa$^{12}$ is Lys, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^2$ is Gly, Xaa$^{12}$ is Lys, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{13}$ is Tyr, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{13}$ is Gln, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{16}$ is Glu, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{16}$ is Ala, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{16}$ is Ser, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{19}$ is Val, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{19}$ is Ala, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{19}$ is Ile, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{19}$ is Leu, Xaa$^{20}$ is Arg, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{20}$ is Arg, Xaa$^{21}$ is Ile, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{20}$ is Arg, Xaa$^{21}$ is Leu, Xaa$^{23}$ is Ile, Xaa$^{28}$ is Asn and Xaa$^{29}$ is Gly.

In one preferred embodiment, X has the formula (IV), Xaa$^{12}$ is Lys, Xaa$^{20}$ is Arg, Xaa$^{23}$ is Ile, Xaa$^{27}$ is Leu, Xaa$^{28}$ is Asn and Xaa$^{29}$ is Gly.

In one preferred embodiment, X has the formula (IV), Xaa$^{12}$ is Lys, Xaa$^{20}$ is Arg, Xaa$^{23}$ is Ile, Xaa$^{27}$ is Lys, Xaa$^{28}$ is Asn and Xaa$^{29}$ is Gly.

V represents a C-terminal extension amino acid sequence comprising at least four amino acid residues, at least three of said amino acid residues being His residues. For example, V may contain from 3 to 6 His residues; preferably 3, 4 or 5 His residues. Preferably V contains from 0 to 4 non-His residues; more preferably V contains 0, 1, 2 or 3 non-His residues.

In one preferred embodiment of the peptide hormone analogue of formula (I) V has the formula (II)

(II)
[SEQ ID NO 291]
Xaa$^{i}$-Xaa$^{ii}$-Xaa$^{iii}$-Xaa$^{iv}$-Xaa$^{v}$-Xaa$^{vi}$-Xaa$^{vii}$-Xaa$^{viii}$-Xaa$^{ix}$-Xaa$^{x}$ wherein
Xaa$^{i}$ is Gly or His;
Xaa$^{ii}$ is absent or selected from the group consisting of Gly and His;
Xaa$^{iii}$ is absent or selected from the group consisting of Gly and His;
Xaa$^{iv}$ is absent or selected from the group consisting of Gly and His;
Xaa$^{v}$ is absent or His;
Xaa$^{vi}$ is absent or His;
Xaa$^{vii}$ is absent or His;
Xaa$^{viii}$ is absent or is selected from the group consisting of Ala, Glu, Gly, Gln and Ser;
Xaa$^{ix}$ is absent or is selected from the group consisting of Ala, Glu, Gly, Gln and Ser;
Xaa$^{x}$ is absent or is selected from the group consisting of Ala, Glu, Gly, Gln and Ser; and
wherein the C-terminal residue may optionally terminate in a —CONH$_2$ group in place of a carboxylic acid group.

Unless indicated otherwise, the amino acid residues in the sequence of formula (II) are L-amino acids.

In one preferred embodiment V has the formula (II) and one of Xaa$^{i}$, Xaa$^{ii}$ and Xaa$^{iii}$ is Gly; more preferably one of Xaa$^{i}$ and Xaa$^{ii}$ is Gly.

In one preferred embodiment V has the formula (II), Xaa$^{i}$ is Gly and Xaa$^{i}$ and Xaa$^{iii}$ are each independently absent or His.

In one preferred embodiment V has the formula (II), Xaa$^{i}$ is His, Xaa$^{ii}$ is Gly and Xaa$^{iii}$ is His or absent.

In one preferred embodiment V has the formula (II) and V contains from 3 to 6 His residues, more preferably 3, 4 or 5 His residues.

In one preferred embodiment V has the formula (II) and V contains from 0 to 4 non-His residues; more preferably 0, 1, 2 or 3 non-His residues.

In one preferred embodiment V has the formula (II) and contains 3 His residues and 1, 2 or 3 non-His residues, or V has the formula (II) and contains 4 or 5 His residues and contains 0, 1, 2 or 3 non-His residues.

In one embodiment V is selected from the group consisting of Gly-His-His-His-His-Ala-CONH$_2$, Gly-His-His-His-Gln-CONH$_2$, Gly-His-His-His-His-Glu-CONH$_2$, Gly-His-His-His-His-Ser-CONH$_2$, Gly-His-His-His-His-Gln-Gln-CONH$_2$, His-His-His-His-Gly, His-His-His-Ala-Gly, Gly-His-His-His-CONH$_2$, His-Gly-His-His-NH$_2$, His-His-His-His-CONH$_2$, His-His-His-His-His-Gln-CONH$_2$, His-His-His-Gly and His-His-His-His-His-Gly.

For the avoidance of doubt, references to V groups containing a C-terminal —CONH$_2$ group will be understood as referring to peptides in which the carboxylic acid group of the C-terminal amino acid residue is replaced by a —CONH$_2$ group. For example, where V has the sequence His-His-His-His-His-Gln-CONH$_2$, the C-terminal Gln residue has a-CONH$_2$ group in place of the carboxylic acid (i.e. —CO$_2$H) group.

In one particularly preferred embodiment, X is a glucagon or an analogue thereof, and V has the formula (II). In one particularly preferred embodiment X represents an amino acid sequence having the formula (III) and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one particularly preferred embodiment X represents an amino acid sequence having the formula (III) and V is selected from the group consisting of Gly-His-His-His-His-Ala-CONH$_2$, Gly-His-His-His-His-Gln-CONH$_2$, Gly-His-His-His-His-His-Glu-CONH$_2$, Gly-His-His-His-His-Ser-CONH$_2$, Gly-His-His-His-His-Gln-Gln-CONH$_2$, His-His-His-His-Gly, His-His-His-Ala-Gly, Gly-His-His-His-CONH$_2$, His-Gly-His-His-CONH$_2$, His-His-His-His-CONH$_2$, His-His-His-His-His-Gln-CONH$_2$, His-His-His-His-Gly and His-His-His-His-His-Gly.

In one particularly preferred embodiment, X represents an amino acid sequence having the formula (III) in which Xaa$^{10}$ is Tyr, Xaa$^{12}$ is Lys, Xaa$^{13}$ is Tyr, Xaa$^{15}$ is Asp, Xaa$^{16}$ is Glu or Gln, Xaa$^{17}$ is Lys or Arg, Xaa$^{18}$ is Arg, Xaa$^{20}$ is His, Xaa$^{21}$ is Glu, Xaa$^{23}$ is Ile, and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one particularly preferred embodiment, X represents an amino acid sequence having the formula (III) in which Xaa$^{10}$ is Tyr, Xaa$^{12}$ is Lys, Xaa$^{13}$ is Tyr, Xaa$^{15}$ is Asp, Xaa$^{16}$ is Glu or Gln, Xaa$^{17}$ is Lys or Arg, Xaa$^{18}$ is Arg, Xaa$^{20}$ is His, Xaa$^{21}$ is Glu, and Xaa$^{23}$ is Ile; and V is selected from the group consisting of Gly-His-His-His-His-Ala-CONH$_2$, Gly-His-His-His-His-Gln-CONH$_2$, Gly-His-His-His-His-Glu-CONH$_2$, Gly-His-His-His-His-Ser-CONH$_2$, Gly-His-His-His-His-Gln-Gln-CONH$_2$, His-His-His-His-Gly, His-His-His-Ala-Gly, Gly-His-His-His-CONH$_2$, His-Gly-His-His-CONH$_2$, His-His-His-His-CONH$_2$, His-His-His-His-His-Gln-CONH$_2$, His-His-His-His-Gly and His-His-His-His-His-Gly.

In one preferred embodiment, X has the formula (III), Xaa$^{10}$ is Tyr, Xaa$^{16}$ is Ser, and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (III), Xaa$^{10}$ is Tyr, Xaa$^{20}$ is His, and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In another preferred group of glucagon analogues of the invention, Xaa$^{16}$ is Ser, Xaa$^{20}$ is His, and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, Xaa$^{10}$ is Tyr, Xaa$^{16}$ is Ser, Xaa$^{20}$ is His, and V has the formula (II); more preferably V has the formula (II) and contains 3 His residues and 1, 2 or 3 non-His residues, or V has the formula (II) and contains 4 or 5 His residues and 0, 1, 2 or 3 non-His residues. In one preferred group of glucagon analogues of the invention, $Xaa^{10}$ is Tyr, $Xaa^{16}$ is Ser, $Xaa^{20}$ is His, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Arg, $Xaa^{13}$ is His, $Xaa^{15}$ is Asp, $Xaa^{16}$ is Ser, $Xaa^{17}$ is Lys, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Lys, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Glu, $Xaa^{16}$ is Ser, $Xaa^{17}$ is Arg, $Xaa^{18}$ is Lys, $Xaa^{20}$ is His, $Xaa^{21}$ is Glu, $Xaa^{23}$ is Ile, $Xaa^{24}$ is Glu, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Asp, $Xaa^{23}$ is Val, $Xaa^{24}$ is Glu, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is His, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{13}$ is Tyr, $Xaa^{15}$ is Asp, $Xaa^{17}$ is Arg, $Xaa^{18}$ is Arg, $Xaa^{20}$ is His, $Xaa^{21}$ is Glu, $Xaa^{23}$ is Val and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Arg, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Thr and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is Lys, $Xaa^{13}$ is Tyr, $Xaa^{15}$ is Asp, $Xaa^{16}$ is Glu, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is His, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Glu, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred group of glucagon analogues of the invention, $Xaa^{10}$ is Tyr, $Xaa^{12}$ is His, $Xaa^{13}$ is Tyr, $Xaa^{15}$ is Asp, $Xaa^{16}$ is Ser, $Xaa^{17}$ is Arg, $Xaa^{18}$ is Arg, $Xaa^{20}$ is His, $Xaa^{21}$ is Glu, $Xaa^{23}$ is Val, $Xaa^{24}$ is Gln, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one particularly preferred embodiment, X is GLP1 or an analogue thereof, and V has the formula (II). In one particularly preferred embodiment X represents an amino acid sequence having the formula (IV) and V has the formula (II); more preferably V has the formula (II) and contains 3 His residues and 1, 2 or 3 non-His residues, or V has the formula (II) and contains 4 or 5 His residues and 0, 1, 2 or 3 non-His residues. In one particularly preferred embodiment X represents an amino acid sequence having the formula (IV) and V is selected from the group consisting of Gly-His-His-His-His-Ala-$CONH_2$, Gly-His-His-His-His-Gln-$CONH_2$, Gly-His-His-His-His-His-Glu-$CONH_2$, Gly-His-His-His-His-Ser-$CONH_2$, Gly-His-His-His-His-Gln-Gln-$CONH_2$, His-His-His-His-Gly, His-His-His-His-Ala-Gly, Gly-His-His-His-$CONH_2$, His-Gly-His-His-$CONH_2$, His-His-His-His-$CONH_2$, His-His-His-His-His-Gln-$CONH_2$, His-His-His-Gly and His-His-His-His-His-Gly.

In one preferred embodiment, X has the formula (IV), $Xaa^{12}$ is Lys, $Xaa^{20}$ is Arg, $Xaa^{23}$ is Ile, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Gly, $Xaa^3$ is Glu, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Gln, $Xaa^{10}$ is Tyr, $Xaa^{12}$ is Lys, $Xaa^{13}$ is Tyr, $Xaa^{16}$ is Glu, $Xaa^{17}$ is Glu, $Xaa^{19}$ is Leu, $Xaa^{20}$ is Arg, $Xaa^{21}$ is Leu, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Gly, $Xaa^3$ is Glu, $Xaa^{10}$ is Leu, $Xaa^{12}$ is Lys, $Xaa^{13}$ is Gln, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Leu, $Xaa^{23}$ is Ile, $Xaa^{24}$ is Glu, $Xaa^{27}$ is Lys, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Gly, $Xaa^3$ is Gln, $Xaa^{10}$ is Leu, $Xaa^{12}$ is Lys, $Xaa^{13}$ is Tyr, $Xaa^{16}$ is Glu, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Gly, $Xaa^3$ is Glu, $Xaa^{10}$ is Tyr, $Xaa^{12}$ is Lys, $Xaa^{13}$ is Tyr, $Xaa^{16}$ is Ala, $Xaa^{17}$ is Glu, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Gln, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one preferred embodiment, X has the formula (IV), $Xaa^2$ is Ser, $Xaa^3$ is Glu, $Xaa^{10}$ is Tyr, $Xaa^{12}$ is Lys, $Xaa^{13}$ is Tyr, $Xaa^{16}$ is Glu, $Xaa^{17}$ is Gln, $Xaa^{19}$ is Val, $Xaa^{20}$ is Arg, $Xaa^{21}$ is Ile, $Xaa^{23}$ is Ile, $Xaa^{24}$ is Glu, $Xaa^{27}$ is Leu, $Xaa^{28}$ is Asn, $Xaa^{29}$ is Gly and V has the formula (II); more preferably V has the formula (II) and contains 3 His residues and 1, 2 or 3 non-His residues, or V has the formula (II) and contains 4 or 5 His residues and 0, 1, 2 or 3 non-His residues.

In one particularly preferred embodiment, the peptide hormone analogue is a compound consisting of an amino acid sequence represented by formula (I) (e.g. in which X represents an amino acid sequence having the formula (III) and V represents an amino acid sequence having the formula (II); or in which X represents an amino acid sequence having the formula (IV) and V represents an amino acid sequence having the formula (II)), or a derivative of the compound, or a salt of the compound or the derivative.

In one particularly preferred embodiment the peptide hormone analogue is a compound consisting of an amino acid sequence represented by formula (I) (e.g. in which X represents an amino acid sequence having the formula (III) and V represents an amino acid sequence having the formula (II); or in which X represents an amino acid sequence having the formula (IV) and V represents an amino acid sequence having the formula (II)), or a salt of the compound.

In one particularly preferred embodiment, the peptide hormone analogue is a compound consisting of the amino acid sequence of any of analogue nos. 1 to 288, or a derivative of the compound, or a salt of the compound or the derivative. The amino acid sequences of analogue nos. 1 to 288 are provided in the Table of FIGS. 1A-1AAP. In one preferred embodiment the peptide hormone analogue is a compound consisting of the amino acid sequence of any of analogue nos. 1 to 288, or a salt of the compound. In one preferred embodiment the peptide hormone analogue is a compound consisting of the amino acid sequence of any of analogue nos. 1 to 288.

In one particularly preferred embodiment the peptide hormone analogue is a compound selected from the group consisting of:

analogue no. 63 (G1832) having the sequence His-Ser-Gln-Gly-Thr-Phe-Thr-Ser-Asp-Tyr-Ser-Lys-Tyr-Leu-Asp-Glu-Lys-Arg-Ala-His-Glu-Phe-Ile-Glu-Trp-Leu-Leu-Asn-Thr-His-Gly-His-His-$CONH_2$ [SEQ ID NO 63];

analogue no. 69 (G1840) having the sequence: His-Ser-Gln-Gly-Thr-Phe-Thr-Ser-Asp-Tyr-Ser-Lys-Tyr-Leu-Asp-Glu-Lys-Arg-Ala-His-Glu-Phe-Ile-Glu-Trp-Leu-Leu-Asn-Gly-His-His-His-His-$CONH_2$ [SEQ ID NO 69];

analogue no. 130 (G1934) having the sequence: His-Ser-Gln-Gly-Thr-Phe-Thr-Ser-Asp-Tyr-Ser-Lys-Tyr-Leu-Asp-Glu-Lys-Arg-Ala-His-Glu-Phe-Ile-Gln-Trp-Leu-Leu-Asn-Gly-Gly-His-His-His-His-Ala-$CONH_2$ [SEQ ID NO 130];

analogue no. 142 (G1950) having the sequence: His-Ser-Gln-Gly-Thr-Phe-Thr-Ser-Asp-Tyr-Ser-Lys-Tyr-Leu-Asp-Glu-Lys-Arg-Ala-His-Glu-Phe-Ile-Glu-Trp-Leu-Leu-Asn-Gly-His-His-His-His-His-Gln-$CONH_2$ [SEQ ID NO 142];

analogue no. 147 (G1958) having the sequence: His-Ser-Gln-Gly-Thr-Phe-Thr-Ser-Asp-Tyr-Ser-Lys-Tyr-Leu-Asp-Gln-Arg-Arg-Ala-His-Glu-Phe-Ile-Glu-Trp-Leu-Leu-Asn-Thr-His-His-His-His-His-Gln-$CONH_2$ [SEQ ID NO 147];

analogue no. 186 (G2036) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Glu-Trp-Leu-Leu-Asn-Thr-Gly-His-His-His-His-His-Glu-$CONH_2$ [SEQ ID NO 186];

analogue no. 197 (G2051) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Glu-Trp-Leu-Leu-Asn-Thr-Gly-His-His-His-His-Ser-$CONH_2$ [SEQ ID NO 197];

analogue no. 247 (G2116) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Gln-Trp-Leu-Leu-Asn-Gly-Gly-His-His-His-His-Gln-Gln-$CONH_2$ [SEQ ID NO 247];

analogue no. 248 (G2117) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Gln-Trp-Leu-Leu-Asn-Thr-His-His-His-His-Gly [SEQ ID NO 248];

analogue no. 249 (G2119) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Gln-Trp-Leu-Leu-Asn-Thr-His-His-His-His-Ala-Gly [SEQ ID NO 249];

analogue no. 252 (G2122) having the sequence: His-Ser-Gln-Gly-Thr-Phe-Thr-Ser-Asp-Tyr-Ser-Lys-Tyr-Leu-Asp- Glu-Lys-Arg-Ala-His-Glu-Phe-Ile-Gln-Trp-Leu-Leu-Asn-Thr-His-Gly-His-His-CONH$_2$ [SEQ ID NO 252];
analogue no. 253 (G2123) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Glu-Trp-Leu-Leu-Asn-Thr-His-Gly-His-His-CONH$_2$ [SEQ ID NO 253];
analogue no. 264 (G2143) having the sequence: His-Ser-Gln-Gly-Thr-Phe-Thr-Ser-Asp-Tyr-Ser-Lys-Tyr-Leu-Asp-Gln-Lys-Arg-Ala-His-Glu-Phe-Ile-Glu-Trp-Leu-Leu-Asn-Thr-Gly-His-His-His-CONH$_2$ [SEQ ID NO 264];
analogue no. 266 (G2145) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Gln-Trp-Leu-Leu-Asn-Thr-His-His-His-Gly [SEQ ID NO 266]; and
analogue no. 267 (G2147) having the sequence: His-Ser-Gln-Gly-Thr-Phe-Thr-Ser-Asp-Tyr-Ser-Lys-Tyr-Leu-Asp-Glu-Arg-Arg-Ala-His-Glu-Phe-Ile-Gln-Trp-Leu-Leu-Asn-Thr-His-His-His-His-Gly [SEQ ID NO 267];
or a derivative of the compound, or a salt of the compound or the derivative.

In one particularly preferred embodiment, the peptide hormone analogue is a compound selected from the group consisting of analogue nos. 63 (G1832) [SEQ ID NO 63], 69 (G1840) [SEQ ID NO 69], 130, (G1934) [SEQ ID NO 130], 142 (G1950) [SEQ ID NO 142], 147 (G1958) [SEQ ID NO 147], 186 (G2036) [SEQ ID NO 186], 197, (G2051) [SEQ ID NO 197], 247 (G2116) [SEQ ID NO 247], 248 (G2117) [SEQ ID NO 248], 249 (G2119) [SEQ ID NO 249], 252 (G2122) [SEQ ID NO 252], 253 (G2123) [SEQ ID NO 253], 264 (G2143) [SEQ ID NO 264], 266 (G2145) [SEQ ID NO 266] and 267 (G2147) [SEQ ID NO 267], or a salt of the compound.

In one particularly preferred embodiment, the peptide hormone analogue is a compound selected from the group consisting of analogue nos. 63 (G1832) [SEQ ID NO 63], 69 (G1840) [SEQ ID NO 69], 130, (G1934) [SEQ ID NO 130], 142 (G1950) [SEQ ID NO 142], 147 (G1958) [SEQ ID NO 147], 186 (G2036) [SEQ ID NO 186], 197, (G2051) [SEQ ID NO 197], 247 (G2116) [SEQ ID NO 247], 248 (G2117) [SEQ ID NO 248], 249 (G2119) [SEQ ID NO 249], 252 (G2122) [SEQ ID NO 252], 253 (G2123) [SEQ ID NO 253], 264 (G2143) [SEQ ID NO 64], 266 (G2145) [SEQ ID NO 266] and 267 (G2147) [SEQ ID NO 267].

Peptide hormone analogues of the invention may be produced by recombinant methods well known in the art or alternatively they may be produced by synthetic methods, again well known in the art.

Derivatives

A peptide hormone analogue of the invention may be a derivative which comprises the structure of formula (I) modified by well-known processes including amidation, glycosylation, carbamylation, acylation, for example acetylation, sulfation, phosphorylation, cyclization, lipidization and pegylation and fusion to another peptide or protein to form a fusion protein. The structure of formula (I) may be modified at random positions within the molecule, or at predetermined positions within the molecule and may include one, two, three or more attached chemical moieties.

A peptide hormone analogue of the invention may be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.).

Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y, G-P-R, A-G-G and H-P-F-H-L, which can be cleaved by enterokinase, thrombin, ubiquitin cleaving enzyme and renin, respectively. See, e.g., U.S. Pat. No. 6,410,707, the contents of which are incorporated herein by reference.

A peptide hormone analogue of the invention may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445, the contents of which are incorporated herein by reference. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in a lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A peptide hormone analogue of the invention may be a PEGylated structure of formula (I). PEGylated compounds of the invention may provide additional advantages such as increased solubility, stability and circulating time of the polypeptide, or decreased immunogenicity (see U.S. Pat. No. 4,179,337, the contents of which are incorporated herein by reference).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any, on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In one embodiment, the peptide hormone analogue of the invention is not a derivative.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". It will be understood by the skilled person that the invention also encompasses solvates of the compounds of formula (I), of derivatives of the compounds, and of salts of the compounds and derivatives.

Salts of compounds of formula (I) which are suitable for use in medicine are those wherein a counterion is pharmaceutically acceptable. However, salts having non-pharmaceutically acceptable counterions are within the scope of the present invention, for example, for use as intermediates in the preparation of the compounds of formula (I) and pharmaceutically acceptable salts and/or derivatives thereof.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Biological Activity

Where X is glucagon or an analogue thereof, for example where X represents an amino acid sequence of formula (III), the peptide hormone analogue will have activity at the human glucagon receptor and will be a glucagon receptor agonist. This may be assessed by, for example, an in vitro or cellular binding assay or by a reporter assay. Peptide hormone analogues of the invention where X is glucagon or an analogue thereof exhibit an activity at the human glucagon receptor which is at least $1/10^{th}$ that of human glucagon, preferably an activity which is at least $1/5^{th}$, $1/3^{rd}$ or $1/2$ that of human glucagon. More preferably peptide hormone analogues where X is glucagon or an analogue thereof exhibit an activity at the human glucagon receptor which is at least equivalent to that of human glucagon. Still more preferably, peptide hormone analogues where X is glucagon or an analogue thereof exhibit an activity at the human glucagon-receptor which is at least 2-fold, 5-fold, or 10-fold that of human glucagon. Methods of assessing activity at the glucagon receptor are well known. For example, Thermo Scientific (Lafayette, Colo., USA) market an in vitro glucagon receptor assay. Preferably, peptide hormone analogues where X is glucagon or an analogue thereof fulfil some or more preferably all, of the following criteria.

1) Sustained bioactivity at the human glucagon receptor resulting in enhancement of energy expenditure.
2) High solubility in aqueous solution at pH 5 to allow an effective dose to be administered in a low volume injection (thereby resulting in lower pain of injection). Solubility may be easily assessed by simple in vitro tests.
3) Long period of activity in vivo (as assessed in humans or an animal model) so as to permit injections no more frequently than daily and preferably no more than twice, or more preferably no more than once a week, whilst still producing acceptable therapeutic or cosmetic benefits.
4) Good weight loss (as assessed in human subjects or an animal model).
5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1): 181-6), or the PREDITOP algorithm (Pellequer & Westhof, (1993) J. Mol. Graph. 11(3):204-10, or using the methods of Kolaskar & Tongankar (1990) FEBS Leu. 10:276(1-2): 172-4, the contents of which are incorporated herein by reference).

According to certain embodiments of various aspects of the invention, especially embodiments relating to weight loss, obesity, carbohydrate metabolism and diabetes, peptide hormone analogues where X is glucagon or an analogue thereof have one, several or all of the following features:

A) Sufficient solubility between pH 4 and pH5 to permit an effective dose to be administered in a volume of less than 1 ml, less than 0.5 ml or less than 0.3 ml;
B) Activation of cAMP signaling in cells over-expressing the human glucagon receptor;

C) One, several or all of the further 1 to 5 features listed above for peptide hormone analogues where X is glucagon or an analogue thereof.

Where X is GLP1 or an analogue thereof, for example where X represents an amino acid sequence of formula (IV), the peptide hormone analogue will have activity at the human GLP1 receptor and will be a GLP1 receptor agonist. This may be assessed by, for example, an in vitro or cellular binding assay or by a reporter assay. Peptide hormone analogues where X is GLP or an analogue thereof exhibit an activity at the human GLP1 receptor that is at least $1/20^{th}$ that of human GLP1, preferably an activity which is at least $1/10^{th}$, $1/5^{th}$, $1/3^{rd}$ or $1/2$ that of human GLP1. More preferably, peptide hormone analogues where X is GLP or an analogue thereof exhibit an activity at the human GLP1 receptor that is at least equivalent to that of human GLP1. Still more preferably, peptide hormone analogues where X is GLP or an analogue thereof exhibit an activity at the human GLP1 receptor which is at least 2-fold, 5-fold, or 10-fold that of human GLP1. Methods of assessing activity at the GLP1 receptor are well known. For example, Mukai et al (2009) Biochem. Biophys. Re. Comm. 28993:523-6 discloses a method of assaying for GLP1 receptor binding.

Peptide hormone analogues where X is GLP1 or an analogue thereof preferably have a more sustained effect on food intake reduction or have a stronger effect on food intake reduction than human GLP1. Preferably they have an effect on food intake reduction which is at least as strong as native human GLP1 but which is more sustained. Increased duration of appetite suppression can be particularly important to avoid the effect known as "escape". A short duration of appetite suppressant may reduce appetite or the time covered by one meal and in that meal the subject typically eats less food. If, however, the appetite suppressant is then metabolized or otherwise removed from circulation then by the time of the next meal the subject can regain its "normal" appetite. In view of the subject having eaten a small meal at the previous mealtime, the subject may in fact have an increased appetite at the time of the second meal. If the subject satisfies that appetite it is possible for the food intake over the two meals in total to be no lower than the food intake would have been without the appetite suppressant. That is to say, the subject may have "escaped" from the effects of the appetite suppressant. "Escape" can be reduced by using additional doses of appetite suppressant or by using an appetite suppressant with a longer duration of action. If the subject has a reduced appetite for longer, then the degree to which it can make up the deficit from one meal in the next meal is reduced as there is a practical limit to total capacity in a particular single meal.

Preferably, peptide hormone analogues where X is GLP1 or an analogue thereof fulfil some or more preferably all, of the following criteria.

1) Sustained bioactivity at the human GLP1 receptor resulting in inhibition of appetite.
2) High solubility in aqueous solution at pH 5 to allow an effective dose to be administered in a low volume injection (thereby resulting in lower pain of injection). Solubility may be easily assessed by simple in vitro tests.
3) Long period of activity in vivo (as assessed in humans or an animal model) so as to permit injections no more frequently than daily and preferably no more than twice, or more preferably no more than once a week, whilst still producing acceptable therapeutic or cosmetic benefits.
4) Good weight loss or appetite suppression (as assessed in human subjects or an animal model).
5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1): 181-6), or the PREDITOP algorithm (Pellequer & Westhof, (1993) J. Mol. Graph. 11(3):204-10, or using the methods of Kolaskar & Tongankar (1990) FEBS Leu. 10:276(1-2): 172-4, the contents of which are incorporated herein by reference).

According to certain embodiments of various aspects of the invention, especially embodiments relating to weight loss, obesity, carbohydrate metabolism and diabetes, peptide hormone analogues where X is GLP1 or an analogue thereof have one, several or all of the following features:

A) Sufficient solubility between pH 4 and pH 5 to permit an effective dose to be administered in a volume of less than 1 ml, less than 0.5 ml or less than 0.3 ml;
B) Activation of cAMP signaling in human embryonic kidney cells over-expressing the human GLP1 Receptor;
C) One, several or all of the further 1 to 5 features listed above for peptide hormone analogues where X is GLP1 or an analogue thereof.

Pharmacokinetics, Duration of Action and Solubility

As discussed above, the peptide hormone analogues of the present invention exhibit potent and prolonged duration of action in vivo following subcutaneous administration. In order to achieve this the peptide hormone analogues are required to have both good activity at the biological target, and excellent pharmacokinetic properties.

Incorporation of His residue into peptides having poor aqueous solubility typically leads to peptides having enhanced solubility at acidic pH (e.g. pH 5) due to the presence of charged His side-chain groups, but which are less soluble at physiological pH (pH 7.4). The pI of the side-chain group of histidine is about 6.0. Such properties enable formulation of His-containing peptides in weakly acidic media. Upon subcutaneous injection of such formulations, the solubility falls leading to subcutaneous precipitation of peptide which resolubilises over time. Zinc-containing formulations of His-containing peptides enhance this effect, because at pH 7.4 but not at pH 5 zinc ions co-ordinate with histidine residues and result in a further reduction in solubility which can contribute to increased precipitation at a subcutaneous injection site, or which can contribute to increased stability of the precipitate. However, where precipitation of peptide is not sufficiently rapid following subcutaneous administration, there may still be an initial "spike" or "burst" in blood concentration levels of the peptide. Such properties are undesirable since they increase the possibility of subjects experiencing side effects associated with high concentration levels of the peptides, such as nausea, even if only temporary. In contrast to peptides not having the C-terminal extension sequence of the invention, the present peptide hormone analogues of the present invention either do not display initial "spikes" or "bursts" in plasma concentration levels following subcutaneous administration or any such "burst" is significantly reduced. This reduces the likelihood and/or severity of possible side effects associated with high circulating levels of the peptide hormone analogue.

Conditions

The invention also provides a peptide hormone analogue of the invention, or a pharmaceutical composition comprising the peptide hormone analogue of the invention, for use as a medicament.

The invention also provides a method of treating or preventing a disease or disorder or other non-desired physiological state in a subject comprising administration of a therapeutically effective amount of a peptide hormone analogue of the invention or of a pharmaceutical composition comprising a peptide hormone analogue of the invention. Preferably the peptide hormone analogue or pharmaceutical composition is administered subcutaneously.

According to certain embodiments the disease or disorder or other non-desired physiological state is obesity or diabetes. Accordingly, the invention also provides a method for treating obesity or diabetes in a subject comprising administering to the subject a therapeutically effective amount of a peptide hormone analogue of the invention or of a pharmaceutical composition comprising the peptide hormone analogue of the invention.

According to certain embodiments the disease or disorder or other non-desired physiological state may be being the physiological state of being overweight.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404:635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e. g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

According to certain embodiments the disease or disorder or other non-desired physiological state may be being of a non-desired weight despite not being obese or overweight. The subject may be of normal weight (this includes but is not limited to subjects who were previously overweight or obese and who wish to prevent a return to an unhealthy weight). A subject may be a subject who desires weight loss, for example female and male subjects who desire a change in their appearance. In some cases where the subject is of a normal weight, aspects of the invention may relate to cosmetic treatment rather than to therapeutic treatment.

The invention also provides a method of increasing the energy expenditure of a subject, reducing appetite in a subject, reducing food intake in a subject, reducing calorie intake in a subject, improving insulin release in a subject, improving carbohydrate metabolism in a subject, and/or improving carbohydrate tolerance in a subject, comprising administration of a therapeutically effective amount of a peptide hormone analogue of the invention, or of a pharmaceutical composition comprising the peptide hormone analogue of the invention. Such methods may relate to treating subjects having a pre-diabetic state such as insulin insensitivity or pre-diabetes.

Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry that alter food intake coordinately and reciprocally alter energy expenditure. Energy expenditure is a result of cellular metabolism, protein synthesis, metabolic rate, and calorie utilization. Thus, in this aspect of the invention, administration of a peptide hormone analogue of the invention results in increased energy expenditure, and decreased efficiency of calorie utilization.

The increase in energy expenditure may manifest as a lessening of the normal reduction in energy expenditure seen following reduced food intake, or it may manifest as an absolute increase in energy expenditure for example by the promotion of increased physical activity levels or by an increase in the basal metabolic rate.

The invention also provides a method for improving a lipid profile in a subject comprising administration of a therapeutically effective amount of a peptide hormone analogue of the invention, or of a pharmaceutical composition comprising the peptide hormone analogue of the invention. The invention also provides a method for alleviating a condition or disorder that can be alleviated by reducing nutrient availability comprising administration of a therapeutically effective amount of a peptide hormone analogue of the invention, or of a pharmaceutical composition comprising the peptide hormone analogue of the invention.

A peptide hormone analogue of the invention may be used for weight control and treatment, for example reduction or prevention of obesity, in particular any one or more of the following: preventing and reducing weight gain; inducing and promoting weight loss; and reducing obesity as measured by the Body Mass Index. A peptide hormone analogue of the invention may be used in maintaining any one or more of a desired body weight, a desired Body Mass Index, a desired appearance and good health.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

J. Cereb. Blood Flow Metab. 2011 Apr. 13 (Teramoto S et al) discusses the use of both GLP-1 and exendin-4 to confer cardioprotection after myocardial infarction, and demonstrates that exendin-4 may be used to provide neuroprotection against cerebral ischemia-reperfusion injury. The study showed that mice receiving a transvenous injection of exendin-4, after a 60-minute focal cerebral ischemia showed significantly reduced infarct volume and improved functional deficit as well as suppressed oxidative stress, inflammatory response, and cell death after reperfusion. The study provided evidence that the protective effect of exendin-4 is mediated through increased intracellular cAMP levels and suggested that exendin-4 is potentially useful in the treatment of acute ischemic stroke.

Accordingly, the invention also provides a method of providing cytoprotection in a subject, such as providing cardiac protection, providing neuroprotection and/or treating or preventing neurodegeneration, comprising administration of a therapeutically effective amount of a peptide hormone analogue of the invention, or of a pharmaceutical composition comprising the peptide hormone analogue of the invention.

In certain embodiments the disease or disorder or other non-desired physiological state which the peptide hormone analogue may be used to treat or prevent is neurodegeneration. Such neurodegeneration may be caused by apoptosis, necrosis or loss of function of neuronal cells, preferably in the CNS. Neurodegeneration treated or prevented may be that following a brain injury (for example following physical trauma or following a non-traumatic injury such a stroke, tumour, hypoxia, poisoning, infection, ischemia, encephalopathy or substance abuse.). Alternatively or additionally, neurodegeneration may be prevented or treated in a subject having (or diagnosed as having a predisposition to) a neurodegenerative disease such as Alzheimer's disease, Parkinson's disease, Gehrig's disease (Amyotrophic Lateral Sclerosis), Huntington's disease, Multiple Sclerosis, other demyelination related disorders, senile dementia, subcortical dementia, arteriosclerotic dementia, AIDS-associated dementia, other dementias, cerebral vasculitis, epilepsy, Tourette's syndrome, Guillain Barre Syndrome, Wilson's disease, Pick's disease, neuroinflammatory disorders, encephalitis, encephalomyelitis, meningitis, other central nervous system infections, prion diseases, cerebellar ataxias, cerebellar degeneration, spinocerebellar degeneration syndromes, Friedrich's ataxia, ataxia teangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis. Preferably, the neurodegenerative disease is selected from the group consisting of Alzheimer's disease, Parkinson's disease, Gehrig's disease (Amyotrophic Lateral Sclerosis) and Huntington's disease. In such circumstances the treatment would be regarded as neuroprotective. According to certain preferred embodiments, the treatment is neuroprotective following cerebral ischemia or neuroprotective in a subject having a neurodegenerative disease or diagnosed as having a predisposition to a neurodegenerative disease.

According to other embodiments the disease or disorder or other non-desired physiological state is cardiac degeneration (in particular myocardial degeneration by apoptosis, necrosis or loss of function of myocardial cells), in which case the peptide hormone analogue or pharmaceutical composition comprising the peptide hormone analogue provides cardiac protection. According to certain preferred embodiments that treatment is protective of myocardial function following myocardiac infarction.

The invention also provides a peptide hormone analogue of the invention, or a pharmaceutical composition comprising the peptide hormone analogue of the invention, for use in the treatment of obesity or diabetes.

The invention also provides a peptide hormone analogue of the invention or a pharmaceutical composition comprising the peptide hormone analogue of the invention for use in increasing energy expenditure of a subject, improving insulin release in a subject, improving carbohydrate tolerance in a subject and/or improving carbohydrate metabolism in a subject. Such use may relate to treating subjects having a pre-diabetic state such as insulin insensitivity or pre-diabetes.

The invention also provides a peptide hormone analogue of the invention or a pharmaceutical composition comprising the peptide hormone analogue of the invention for use in the reduction of appetite in a subject, use in the reduction of food intake in a subject, use in the reduction of calorie intake in a subject, use in improving insulin release in a subject, and/or use in improving carbohydrate tolerance in a subject. Such use may relate to treating subjects having a pre-diabetic state such as insulin insensitivity or pre-diabetes.

The invention also provides a peptide hormone analogue analogue of the invention, or a pharmaceutical composition comprising the peptide hormone analogue of the invention, for use as a cytoprotective agent (e.g. in treating or preventing neurodegeneration, providing neuroprotection and/or providing cardiac protection). For example, the peptide hormone analogue or pharmaceutical composition may be for use in myocardial protection in a subject following myocardial infarction, or for use in neuroprotection in a subject following cerebral ischemia or stroke, or for use in neuroprotection in a subject having a chronic neurodegenerative disease. Various features of neuroprotective or cardioprotective use of the peptide hormone analogue or pharmaceutical composition may be as outlined above in relation to methods of the invention.

In the case of neuroprotection the subject may have experienced previously a brain injury, stroke or other event causing cerebral ischemia. Alternatively, the subject may have or have been diagnosed with a predisposition to develop a chronic neurodegenerative disease. In the case of cardioprotection the subject may have experienced previously an event causing myocardial ischemia such as a myocardial infarction and angina. According to some embodiments a peptide hormone analogue or pharmaceutical composition comprising the peptide hormone analogue of the invention may be administered as soon as possible after the subject has experienced a suspected myocardial infarction. According to certain embodiments a peptide hormone analogue or pharmaceutical composition comprising the peptide hormone analogue of the invention may be administered as soon as possible after the subject has experienced as suspected stroke.

The invention also provides use of a peptide hormone analogue of the invention for the manufacture of a medicament for the treatment of obesity or diabetes, of a subject, who may be as described above in reference to other aspects of the invention.

The invention also provides use of a peptide hormone analogue of the invention for the manufacture of a medicament for increasing energy expenditure in a subject, for improving insulin release in a subject, for improving carbohydrate tolerance in a subject and/or improving carbohydrate metabolism in a subject. Such use may relate to treating subjects with a pre-diabetic state such as insulin insensitivity or pre-diabetes.

The invention also provides use of a peptide hormone analogue of the invention for the manufacture of a medicament for the reduction of appetite in a subject, reducing food intake in a subject, reducing calorie intake in a subject, improving insulin release in a subject, and/or use in improving carbohydrate tolerance in a subject.

The invention also provides use of a peptide hormone analogue of the invention for the manufacture of a medicament for providing cytoprotection (e.g. preventing or treating neurodegeneration, providing neuroprotection and/or providing cardiac protection) of a subject, who may be as described above in reference to other aspects of the invention.

According to certain embodiments the peptide hormone analogue or pharmaceutical composition is to be administered parentally. According to other embodiments the peptide hormone analogue or pharmaceutical composition is to be administered subcutaneously, intravenously, intramuscularly, intranasally, transdermally or sublingually. According to other embodiments the peptide hormone analogue or pharmaceutical composition is to be administered orally. In one preferred embodiment the peptide hormone analogue or pharmaceutical composition is administered subcutaneously.

According to the present invention, a peptide hormone analogue of the invention is preferably used in the treatment of a human. However, while the peptide hormone analogues of the invention will typically be used to treat human subjects they may also be used to treat similar or identical conditions in other vertebrates for example other primates; farm animals for example swine, cattle and poultry; sport animals for example horses; or companion animals for example dogs and cats.

Compositions

While it is possible for the active ingredient to be administered alone, it is preferable for it to be present in a pharmaceutical formulation or composition. Accordingly, the invention provides a pharmaceutical formulation comprising a peptide hormone analogue of the invention together with a pharmaceutically acceptable excipient and optionally other therapeutic ingredients. According to certain preferred embodiments the pharmaceutical composition is present in a syringe or other administration device for subcutaneous administration to humans. According to certain preferred embodiments the composition has a pH of less than 5 prior to administration and the composition comprises zinc ions. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intra-articular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988, the contents of which are incorporated herein by reference.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present peptide hormone analogues can, for example, be administered in a form suitable for immediate release or extended release. Immediate release or extended release can be achieved by the use of suitable pharmaceutical compositions comprising the present peptide hormone analogues, or, particularly in the case of extended release, by the use of devices such as subcutaneous implants or osmotic pumps. The present peptide hormone analogues can also be administered liposomally.

Preferably, compositions according to the invention are suitable for subcutaneous administration, for example by injection. According to certain embodiments the composition may contain metal ions, for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions (preferably at a molar ratio of 1:4, 1:2, 1:1, 2:1 or 4:1 of zinc ions to peptide hormone analogue, or at a ratio which is a range between any two of the whole number ratios given immediately above).

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The peptide hormone analogues of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to peptide hormone analogues of the invention and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The peptide hormone analogues of the invention may also be suitably administered as sustained-release systems. Suitable examples of sustained-release systems of the invention include suitable polymeric materials, for example semipermeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of peptide hormone analogues of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of particles of the peptide hormone analogues. These compositions exhibit certain biocompatibility features which allow a controlled release of the active substance, see U.S. Pat. No. 5,700,486, the contents of which are incorporated by reference.

Controlled release of peptide hormone analogues of the invention may also be achieved by the use of pharmaceutical compositions comprising the peptide hormone analogue and zinc ions. As described above, at pH 7.4 but not at pH 5 zinc ions co-ordinate with histidine residues and result in increased precipitation at a subcutaneous injection site. A zinc-containing precipitate will more gradually re-dissolve because the solubilisation is dependent on the zinc washing out of the injection site into the circulation and/or surrounding tissue fluid, increasing the longevity of the release into the circulation. The use of a controlled release composition is preferred for indications such as the treatment of obesity and/or diabetes, where maximising the time period between injections is desirable. However, for indications such as providing neuroprotection or cardiac protection (e.g. following suspected myocardial infarction or stroke), where it is desired to achieve a therapeutic plasma concentration of the peptide hormone analogue in as short a time period as possible, an immediate release formulation will be preferred. In such cases, a dosage regime comprising administration of a dose of an immediate release formulation of the peptide hormone analogue (i.e. as soon as possible after suspected myocardial infarction or stroke) and subsequent administration of a dose of a controlled release formulation of the peptide hormone analogue may be preferred.

A peptide hormone analogue of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusion, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990) which is incorporated herein by reference. In another aspect of the disclosure, peptide hormone analogues of the invention are delivered by way of an implanted pump, described, for example, in U.S. Pat. No. 6,436,091; U.S. Pat. No. 5,939,380; U.S. Pat. No. 5,993,414, the contents of which are incorporated herein by reference.

Implantable drug infusion devices are used to provide patients with a constant and long term dosage or infusion of a drug or any other therapeutic agent. Essentially such device may be categorized as either active or passive. A peptide hormone analogue of the present invention may be formulated as a depot preparation. Such a long acting depot formulation can be administered by implantation, for example subcutaneously or intramuscularly; or by intramuscular injection. Thus, for example, the peptide hormone analogues can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a peptide hormone analogue of the invention may be administered as a single pulse dose, as a bolus dose, or as pulse doses administered over time. Thus, in pulse doses, a bolus administration of a peptide hormone analogue of the invention is provided, followed by a time period wherein no peptide hormone analogue of the invention is administered to the subject, followed by a second bolus administration. In specific, non-limiting examples, pulse doses of a peptide hormone analogue of the invention are administered during the course of a day, during the course of a week, or during the course of a month.

In certain embodiments, a therapeutically effective amount of a peptide hormone analogue of the invention is administered with a therapeutically effective amount of a further agent. The peptide hormone analogue may be administered simultaneously with the further therapeutic agent, or it may be administered sequentially or separately. Accordingly, the invention provides a peptide hormone analogue of the invention for use as a medicament, wherein the peptide hormone analogue is for use with a therapeutically effective amount of a further therapeutic agent (e.g. for administration simultaneously, sequentially or separately). In certain embodiments, a peptide hormone analogue of the invention is formulated and administered with a further therapeutic agent as a single dose.

In certain embodiments, the further therapeutic agent is an additional anti-diabetic, appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, phendimetrazine, benzphetamine, sibutramine, rimonabant, topiramate, fluoxetine, bupropion, zonisamide, naltrexone, orlistat and cetilistat. Specific, non-limiting examples of an additional anti-diabetic agent include metformin, phenformin, rosiglitazone, pioglitazone, troglitazone, repaglinide, nateglinide, tolbutamide, acetohexamide, tolazamide, chlorpropamide, glipizide, glyburide, glimepiride, gliclazide, fibroblast growth factor 21, miglitol, acarbose, exenatide, pramlintide, vildagliptin and sitagliptin.

In alternative embodiments, the further therapeutic agent is an additional cardioprotective or neuroprotective agent. Specific, non-limiting, examples of additional cardioprotective agents include aspirin, N-acetylcysteine, phenethylamines, coenzyme Q10, vitamin E, vitamin C, L-carnitine, carvedilol and dexrazoxane. Specific, non-limiting examples of neuroprotective agents include statins such as simvastatin, steroids such as progesterone, minocycline, resveratrol and vitamin E. Examples of agents used for the treatment of Parkinson's disease include anticholinergics, pramipexole, bromocriptine, levodopa, carbidopa, rasagiline, amantadine and ropinirole.

A peptide hormone analogue of the invention may be administered whenever the effect, e.g., appetite suppression, decreased food intake, increased energy expenditure or decreased caloric intake, is desired, or slightly before to whenever the effect is desired, such as, but not limited to, about 10 minutes, about 15 minutes, about 30 minutes, about 60 minutes, about 90 minutes, or about 120 minutes, before the time the effect is desired.

The therapeutically effective amount of a peptide hormone analogue of the invention will be dependent on the molecule utilized, the subject being treated, the severity and type of the affliction, and the manner and route of administration. For example, a therapeutically effective amount of a peptide hormone analogue of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a peptide hormone analogue of the invention may be administered to a subject at from 4 to 1333 nmol per kg bodyweight, for example from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 300 nmol to 100 µmol, for example from 375 nmol to 75 µmol, for example from 750 nmol to 56.25 µmol, for example from 1.5 to 37.5 µmol, in particular from 2.25 to 18 µmol. The invention also contemplates dosages ranges bounded by any of the specific dosages mentioned herein.

In an alternative embodiment, a peptide hormone analogue of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a peptide hormone analogue of the invention is administered in a dose of about 1 nmol or more, 2 nmol or more, or 5 nmol or more. In this example, the dose of the peptide hormone analogue of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of peptide hormone analogues of the invention are within the range of from 1 to 100 nmol, from 2 to 90 mols, from 5 to 80 nmols.

In one specific, non-limiting example, from about 1 to about 50 nmol of a peptide hormone analogue of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

The doses discussed above may be given, for example, once, twice, three-times or four-times a day or once or twice a week. Preferably a dose may be given no more frequently than once a week. Alternatively, they may be given once every 2, 3 or 4 days. According to certain embodiments they may be administered once shortly before each meal to be taken.

The invention is illustrated by the following non-limiting Examples.

Materials and Methods:

Animals

Male C57BL/6 mice (Harlan) or male Wistar rats (Charles River Ltd, Margate, UK) were used for all animal experiments.

Peptide Synthesis

Peptides were made by a standard automated fluorenyl-methoxycarbonyl (Fmoc) solid phase peptide synthesis (SPPS) method. Peptide synthesis was carried out on a tricyclic amide linker resin. Amino acids were attached using the Fmoc strategy. Each amino acid was added sequentially from the C- to the N-termini. Peptide couplings were mediated by the reagent TBTU. Peptide cleavage from the resin was achieved with trifluoracetic acid in the presence of scavengers.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

Example 1

Cellular Assays

Cells (Chinese hamster ovary—hGCGr, or Human embryonic kidney—hGLP-1r) were plated at a density of 150000 cells/ml in 24 well plates. The cells were left for 18 hours, and were then serum starved for 1 hour by replacing with serum free media. The media was then replaced with that containing the example glucagon analogue at 12 concentrations in duplicate ranging from 0 up to 30 nM (1 analogue per 24 well plate). Each plate was incubated for exactly 30 minutes. The incubation media was removed, and replaced with 120 µl of lysis buffer (0.1M HCl 0.5% TritonX). 120 µl of sample (or a dilution thereof so as to hit ELISA standard curve) was added to an eppendorf tube, and was spun for 3 minutes at >5000 g to remove cell debris. 100 µl of sample was added to an ELISA plate (Direct cyclic AMP Enzyme Immunoassay Kit—Enzolifesciences). The ELISA assay was run as described in the manual.

Acute Feeding Studies in Mice

Mice were individually housed in IVC cages. Animals were randomised into treatment groups, with stratification by body weight. Mice were fasted overnight (16 hrs) prior to peptide or vehicle administration. All peptide solutions were prepared freshly, immediately prior to administration. The vehicle used for all studies was 5% v/v water and 95% v/v sodium chloride (0.9% w/v). Peptide and vehicle were administered by subcutaneous injection, with dosage corrected for bodyweight. The injection volume was 50 pl. Vehicle or peptide was administered at 09:00 and animals were returned to their home cage with a known amount of food. Food intake was measured at 24 and 48 hours post injection. All statistics are calculated using a one-way ANOVA with Dunnett's post-test or one-way ANOVA with Bonferroni post-test.

Acute Feeding Studies in Rats

Rats were individually housed in IVC cages. Animals were randomised into treatment groups, with stratification by body weight. Rats were fasted overnight (24 hrs) prior to peptide or vehicle administration. All peptide solutions were prepared freshly, immediately prior to administration. The vehicle used for all studies was 5% v/v water and 95% v/v sodium chloride (0.9% w/v) with zinc chloride added at a 1:1 molar ratio to the peptide. Peptide and vehicle were administered by subcutaneous injection, with dosage corrected for bodyweight. The injection volume was 50 µl. Vehicle or peptide was administered at 09:00 and animals were returned to their home cage with a known amount of food. Food intake was measured at 24 hours post injection. All statistics are calculated using a one-way ANOVA with Dunnett's post-test.

Results—Peptide Hormone Analogues

FIGS. 1A-1AAP show a table providing amino acid sequences of peptide hormone analogues of the invention (each compound is identified by a G no., as well as an analogue no.). The table also provides the results of cellular assay experiments, and the results of experiments in which appetite suppressant effects in mice and rats were determined.

The column headed "hGCGr cAMP vs hGCG" shows signaling in human embryonic kidney cells or Chinese hamster ovary cells over-expressing human glucagon receptor following administration of the example peptide hormone analogues. The values provided in the column are EC50 ratios relative to native glucagon (e.g. a value of 0.5 indicates that the concentration of the glucagon analogue required to stimulate 50% maximum release of cAMP is half the concentration of native glucagon that is required, and a value of 5 indicates that the concentration of the peptide hormone analogue required to stimulate 50% maximum release of cAMP is 5 times that of native glucagon). The figure provided in the column headed "hGCGr cAMP vs hGCG" is a mean value, with the preceding column (headed "n") indicating the number of times that the experiment was carried out.

The column headed "hGLP-1r cAMP vs hGLP-1" shows signaling in human embryonic kidney cells or Chinese hamster ovary cells over-expressing human GLP1 receptor. The values provided in the column are EC50 ratios relative to native GLP-1 (e.g. a value of 0.5 indicates that the concentration of the peptide hormone analogue required to stimulate 50% maximum release of cAMP is half the concentration of native GLP-1 that is required, and a value of 5 indicates that the concentration of the peptide hormone analogue required to stimulate 50% maximum release of cAMP is 5 times that of native GLP-1). The figure provided in the column headed "hGLP-1r cAMP vs hGLP-1" is a mean value, with the preceding column (headed "n") indicating the number of times that the experiment was carried out.

In the section of the table headed "Mouse food intake inhibition", the columns headed "0-24" and "0-48" show the reduction in food intake relative to saline during the indicated time periods (in hours) since administration of the peptide hormone analogue. A positive value indicates that less food was consumed by mice to which the peptide hormone analogue was administered compared with mice to which saline was administered during the relevant time period (a value of 100 indicates that nothing was eaten). A negative value indicates that more food was consumed by mice to whom the peptide hormone analogue was administered compared with mice to whom saline was administered during the relevant time period (e.g. a value of −5 indicates that the peptide hormone analogue mice consumed 5% more food (in grams) than the saline mice). A value of 0 indicates that the same quantity of food was consumed by the peptide hormone analogue mice and the saline mice.

In the section of the table headed "Rat food intake inhibition", the "0-24" shows the reduction in food intake relative to saline during the indicated time period (in hours) since administration of the peptide hormone analogue. A positive value indicates that less food was consumed by rats to which the peptide hormone analogue was administered compared with rats to which saline was administered during the relevant time period (a value of 100 indicates that nothing was eaten). A negative value indicates that more food was consumed by rats to whom the peptide hormone analogue was administered compared with rats to whom saline was administered during the relevant time period (e.g. a value of −5 indicates that the peptide hormone analogue rats consumed 5% more food (in grams) than the saline mice). A value of 0 indicates that the same quantity of food was consumed by the peptide hormone analogue rats and the saline rats.

Example 2—Mice Feeding Studies—Peptide Hormone Analogues

Peptide hormone analogues of the invention (G1698 [SEQ ID NO 1], 500 nmol/kg dosage, reconstituted in saline, and G1718 [SEQ ID NO 6], 200 nmol/kg dosage, reconstituted in saline), comparator compounds (G1697, 500 nmol/kg dosage, reconstituted in saline, and G1717, 200 nmol/kg dosage, reconstituted in saline), or saline (vehicle control group) were administered subcutaneously to mice (group size 4-6 animals). The animals had been fasted for 16 hours prior to administration. Food intake (in grams) was measured at time intervals over 48 hours.

G1697 has the same amino acid sequence as G1698 [SEQ ID NO 1] except that it has a C-terminal extension amino acid sequence which is $His^{30}$-$His^{31}$-$His^{32}$ whereas G1698 has a C-terminal extension amino acid sequence which is $His^{30}$-$His^{31}$-$His^{32}$-$His^{33}$.

G1717 has the same amino acid sequence as except that it has a C-terminal extension amino acid sequence which is $His^{30}$-$His^{31}$-$His^{32}$ whereas G1718 [SEQ ID NO 6] has a C-terminal extension amino acid sequence which is $His^{30}$-$His^{31}$-$His^{32}$-$His^{33}$.

Figure 3A:
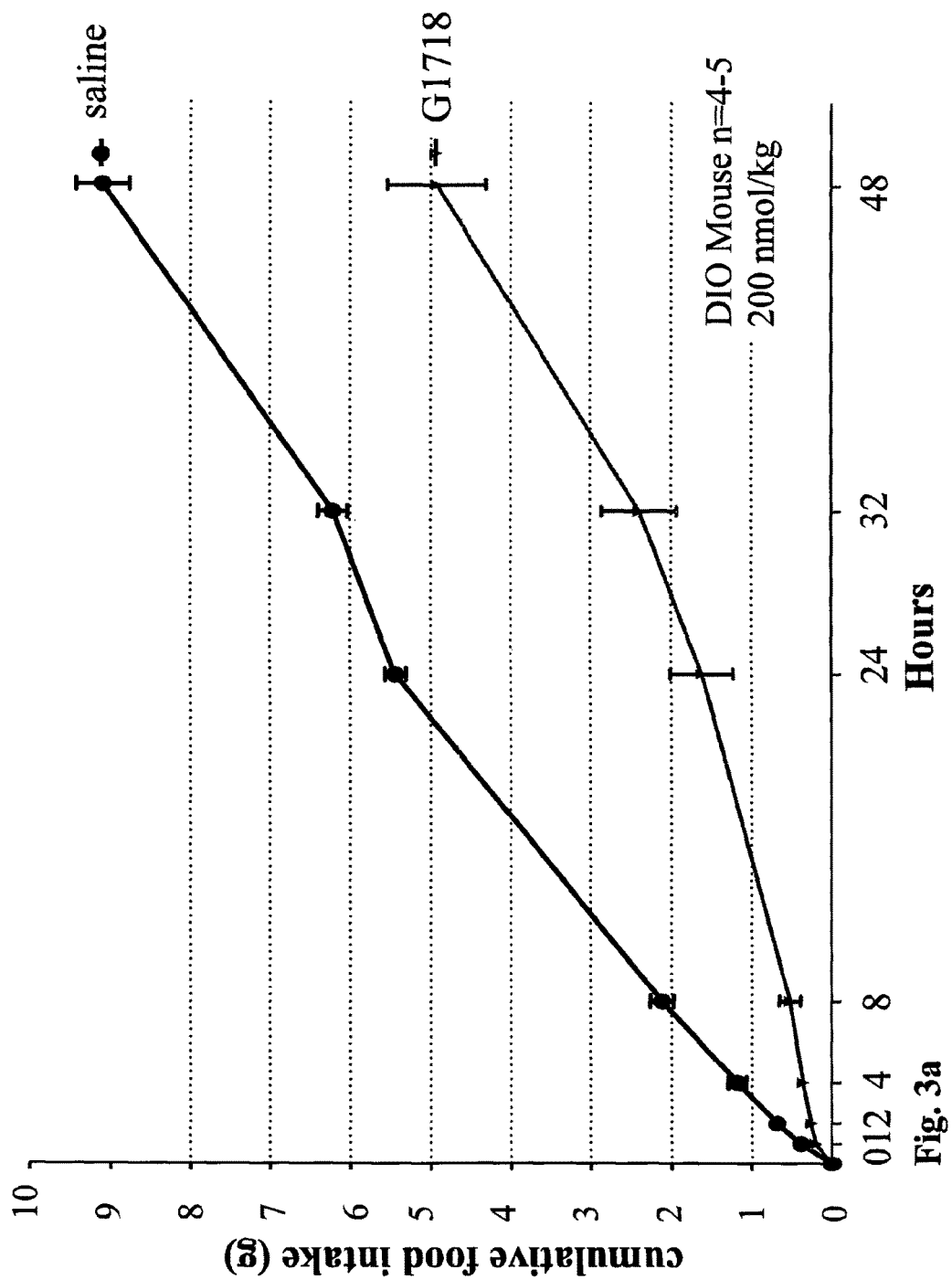
FIG. 3 shows the results of in vivo feeding studies in mice administered with (a) a compound of the invention (G1718) and (b) a comparator compound (G1717) not possessing a C-terminal extension amino acid sequence according to the invention.
Figure 3B:
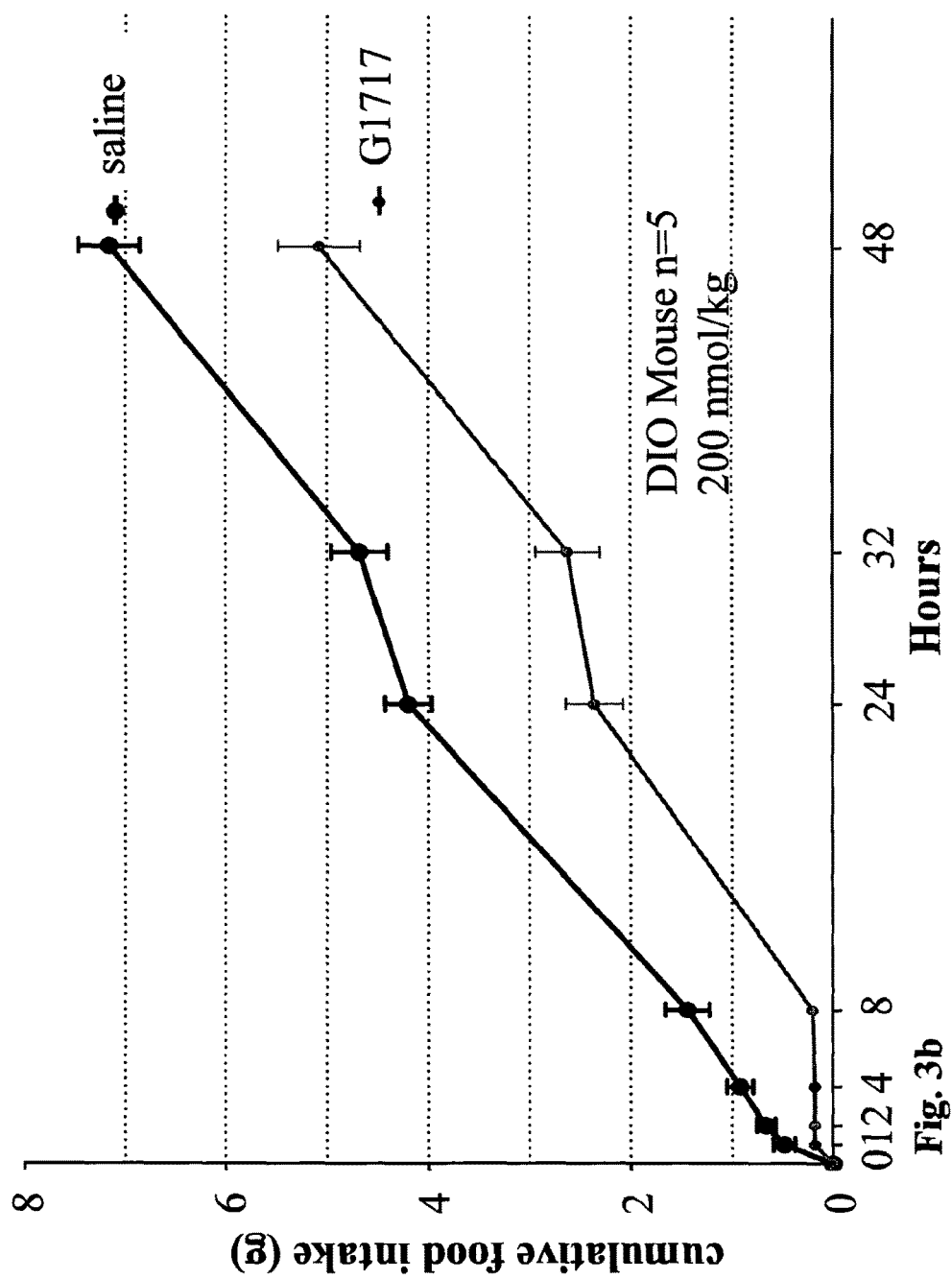

As shown in FIG. 2, G1698 [SEQ ID NO 1] displays a more potent and more sustained reduction of cumulative food intake relative to saline control than the comparator compound G1697, which does not possess a C-terminal extension amino acid sequence according to the invention. Similarly, as shown in FIG. 3, G1718 [SEQ ID NO 6] displays a more potent and more sustained reduction of cumulative food intake relative to saline control than the comparator compound G1717, which also does not possess the C-terminal extension sequence of the invention.

Example 3—Mice Feeding Studies—Peptide Hormone Analogues

Peptide hormone analogues of the invention (G1722 [SEQ ID NO 8], 200 nmol/kg dosage, reconstituted in saline) and G1781 [SEQ ID NO 34] (200 nmol/kg dosage, reconstituted in saline), comparator compounds (G1721, 200 nmol/kg dosage, reconstituted in saline) and G1779 [SEQ ID NO 32] (200 nmol/kg dosage, reconstituted in saline), or saline (vehicle control group) were administered subcutaneously to mice (group size 4-6 animals). The animals had been fasted for 16 hours prior to administration. Food intake (in grams) was measured at time intervals over 7 days.

G1721 has the same amino acid sequence as G1722 [SEQ ID NO 8] except that it has a C-terminal extension amino acid sequence which is $His^{30}$-$His^{31}$-$His^{32}$ whereas G1722 [SEQ ID NO 8] has a C-terminal extension amino acid sequence which is $His^{30}$-$His^{31}$-$His^{32}$-$His^{33}$. G1779 [SEQ ID NO 32] has the same amino acid sequence as G1781 [SEQ ID NO 34] except that it has a C-terminal extension amino acid sequence which is $His^{30}$-$His^{31}$-$His^{32}$ whereas G1722 [SEQ ID NO 8] has a C-terminal extension amino acid sequence which is $His^{30}$-$His^{31}$-$His^{32}$-$His^{33}$.

Figure 4A:
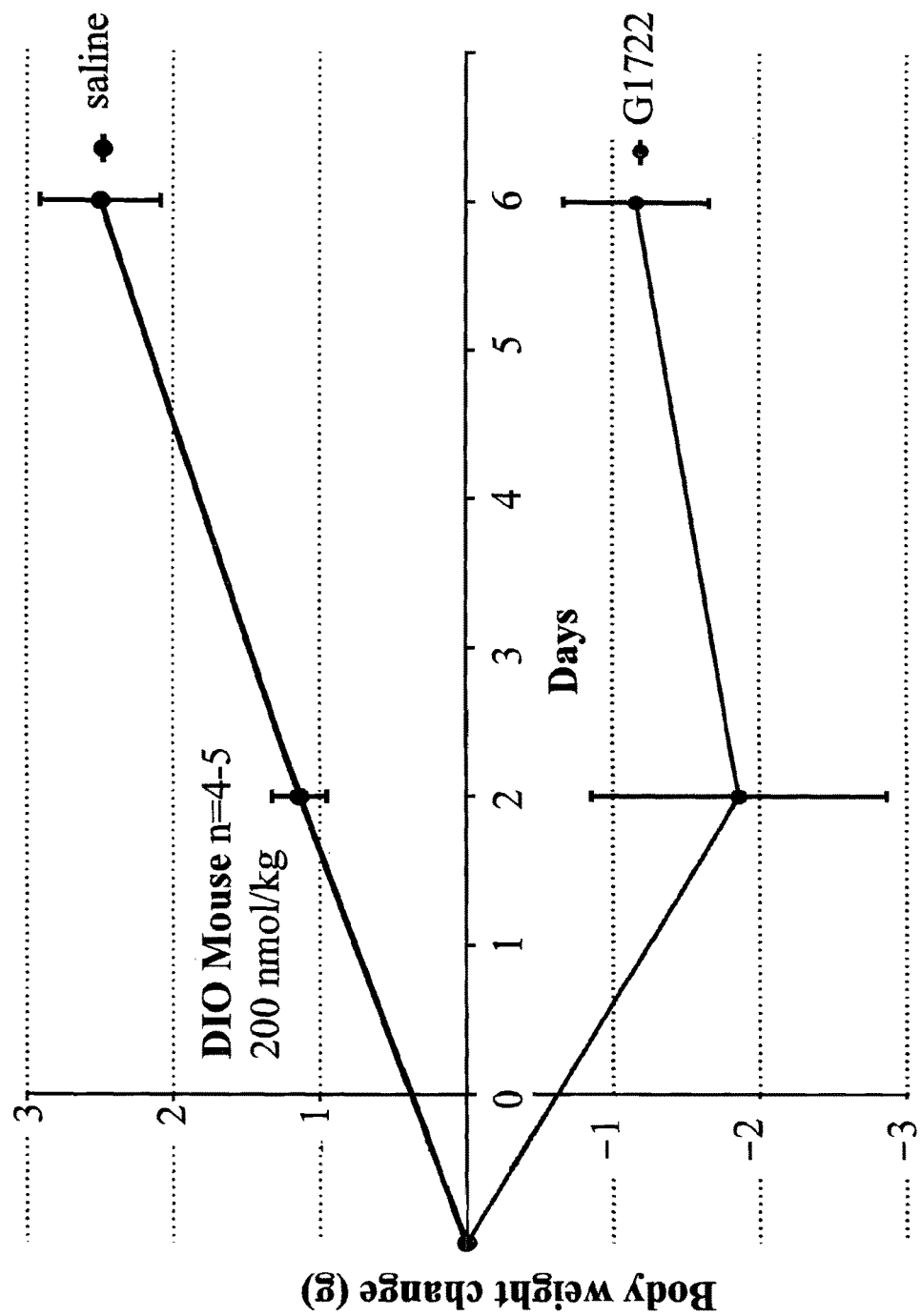
FIG. 4 shows the results of in vivo feeding studies in mice administered with (a) a compound of the invention (G1722) and (b) a comparator compound (G1721) not possessing a C-terminal extension amino acid sequence according to the invention.
Figure 4B:
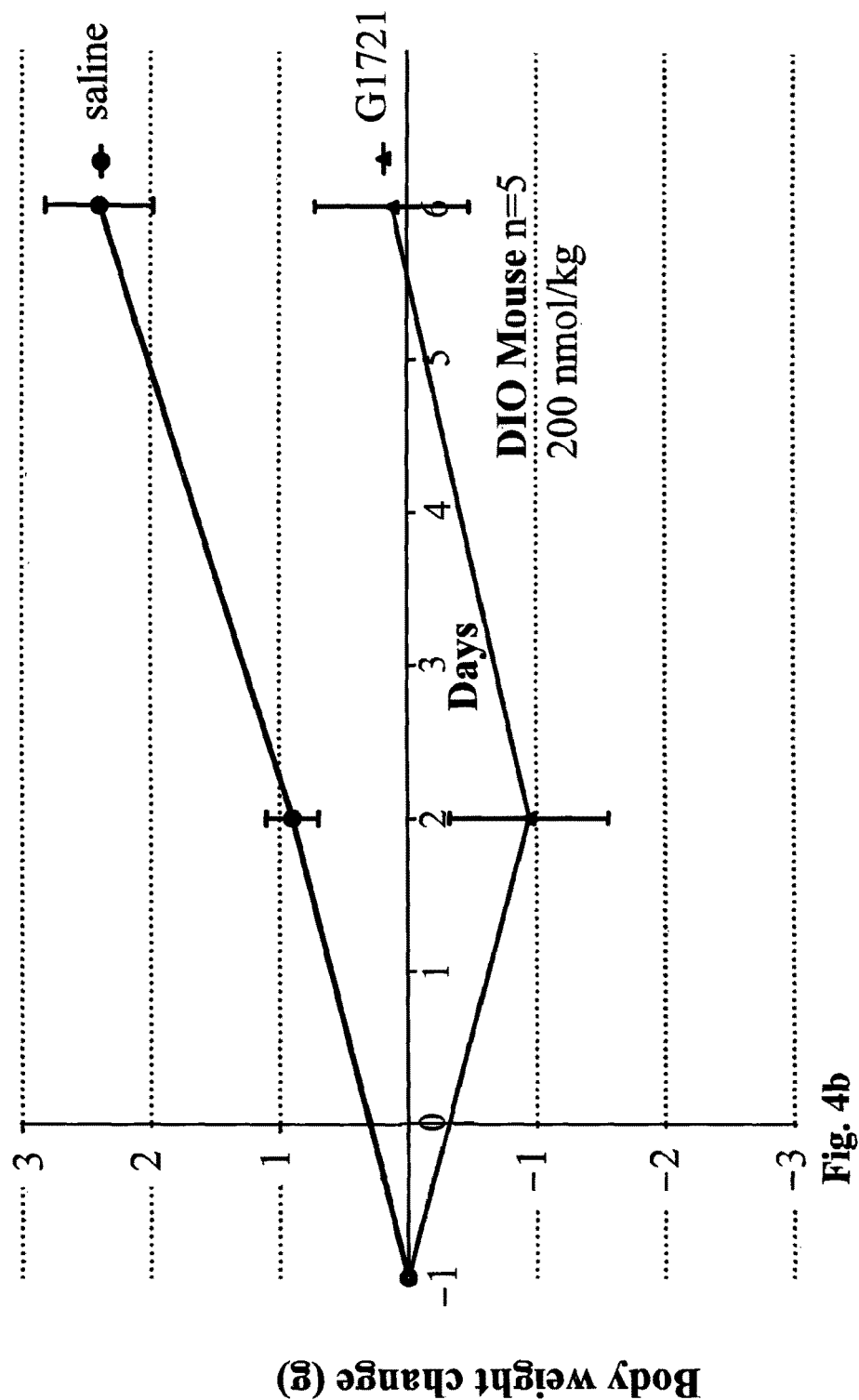
Figure 5:
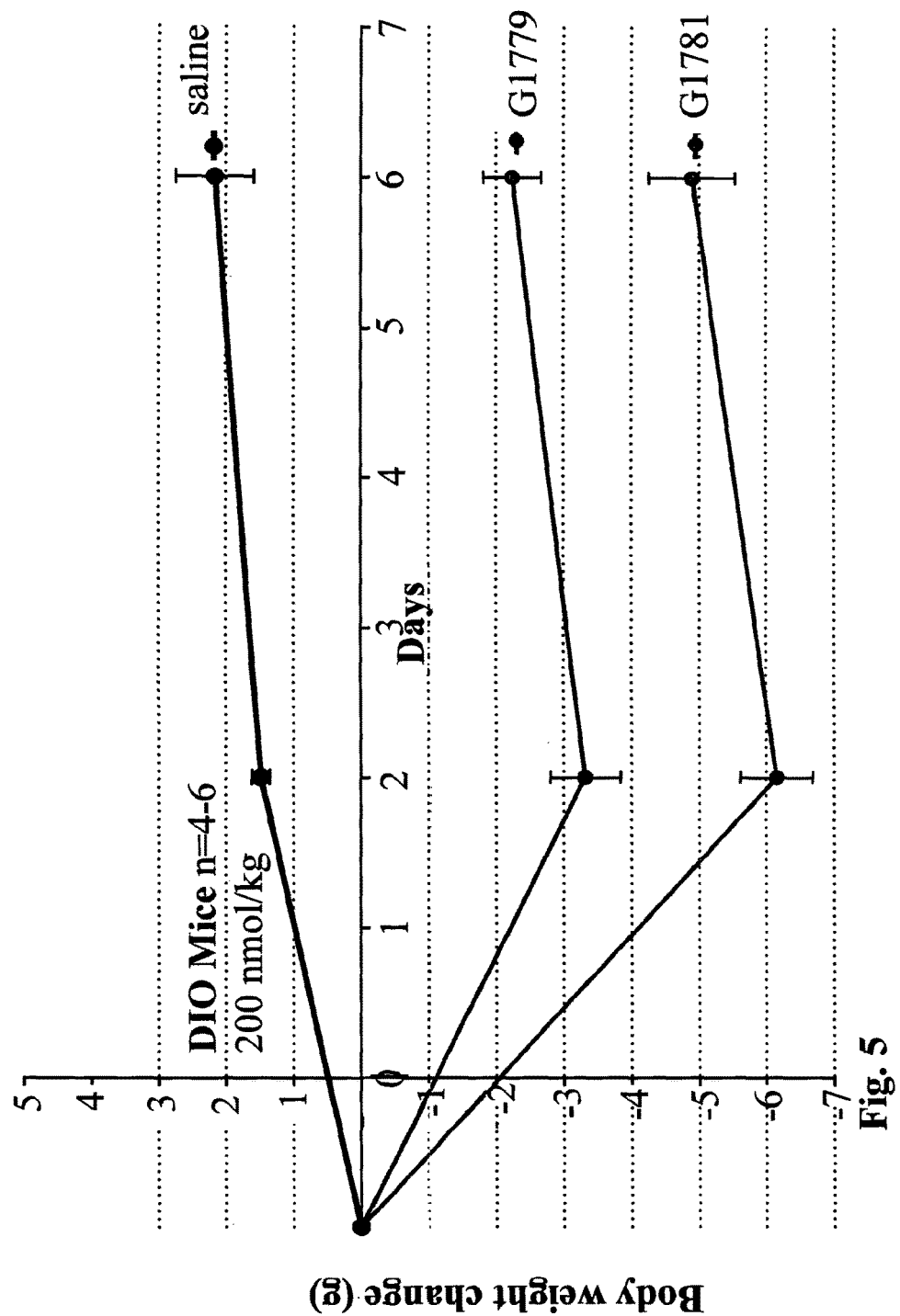
FIG. 5 shows the results of in vivo feeding studies in mice administered with a compound of the invention (G1781) and a comparator compound (G1779) not possessing a C-terminal extension amino acid sequence according to the invention.

As shown in FIG. 4, G1722 [SEQ ID NO 8] displays a more potent and more sustained reduction of body weight increase relative to saline control than the comparator compound G1721, which does not possess a C-terminal extension amino acid sequence according to the invention. Similarly, as shown in FIG. 5, G1781 [SEQ ID NO 34] displays a more potent and more sustained reduction of body weight increase relative to saline control than the comparator compound G1779 [SEQ ID NO 32], which also does not contain the C-terminal extension sequence of the invention.

Example 4—Rat Pharmacokinetic Studies—Peptide Hormone Analogues

Figure 6:
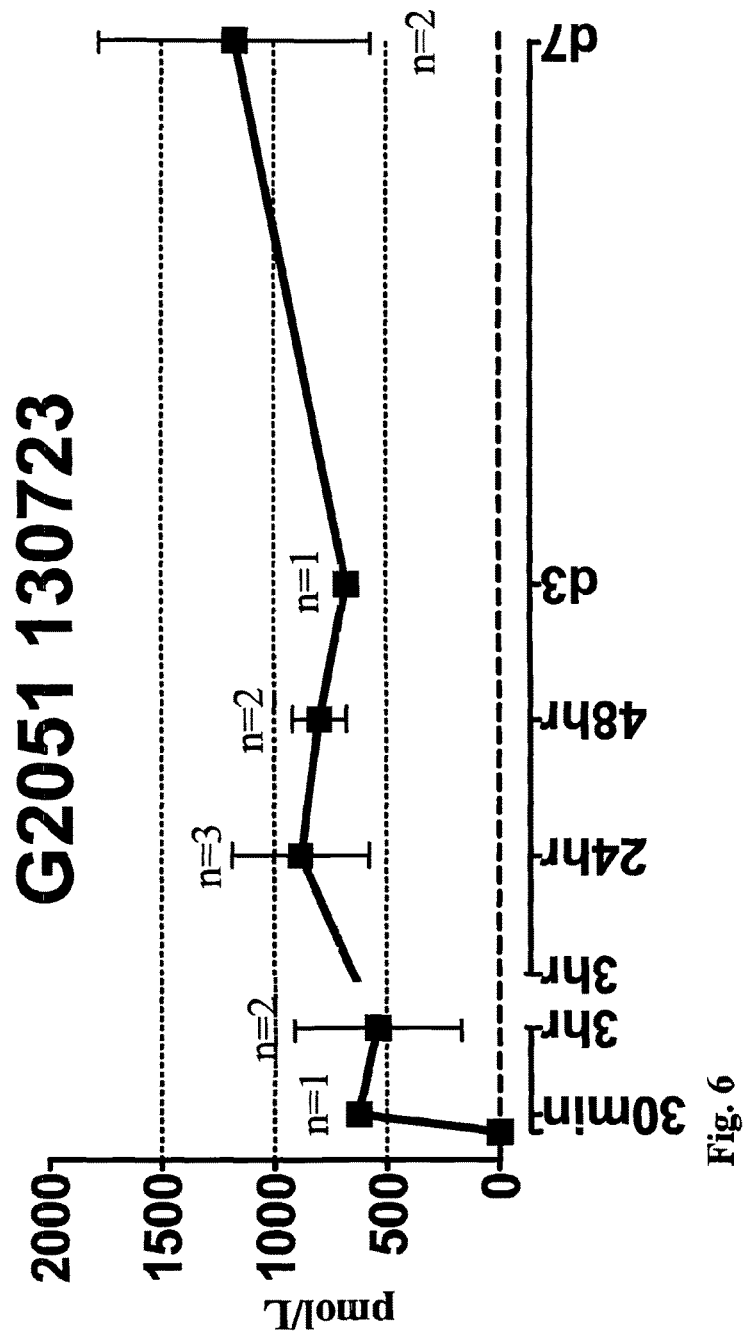
FIG. 6 shows the results of a 7 day in vivo pharmacokinetic study in rats with a compound of the invention (G2051), demonstrating that the plasma concentration of G2051 remains steady throughout the experiment and that no initial increase or "spike" in plasma concentration level is observed following subcutaneous administration to 4 rats of 2 mg of the compound in 10 µl aqueous $ZnCl_2$ solution at a 1.2:1 molar ratio.
Figure 7A:
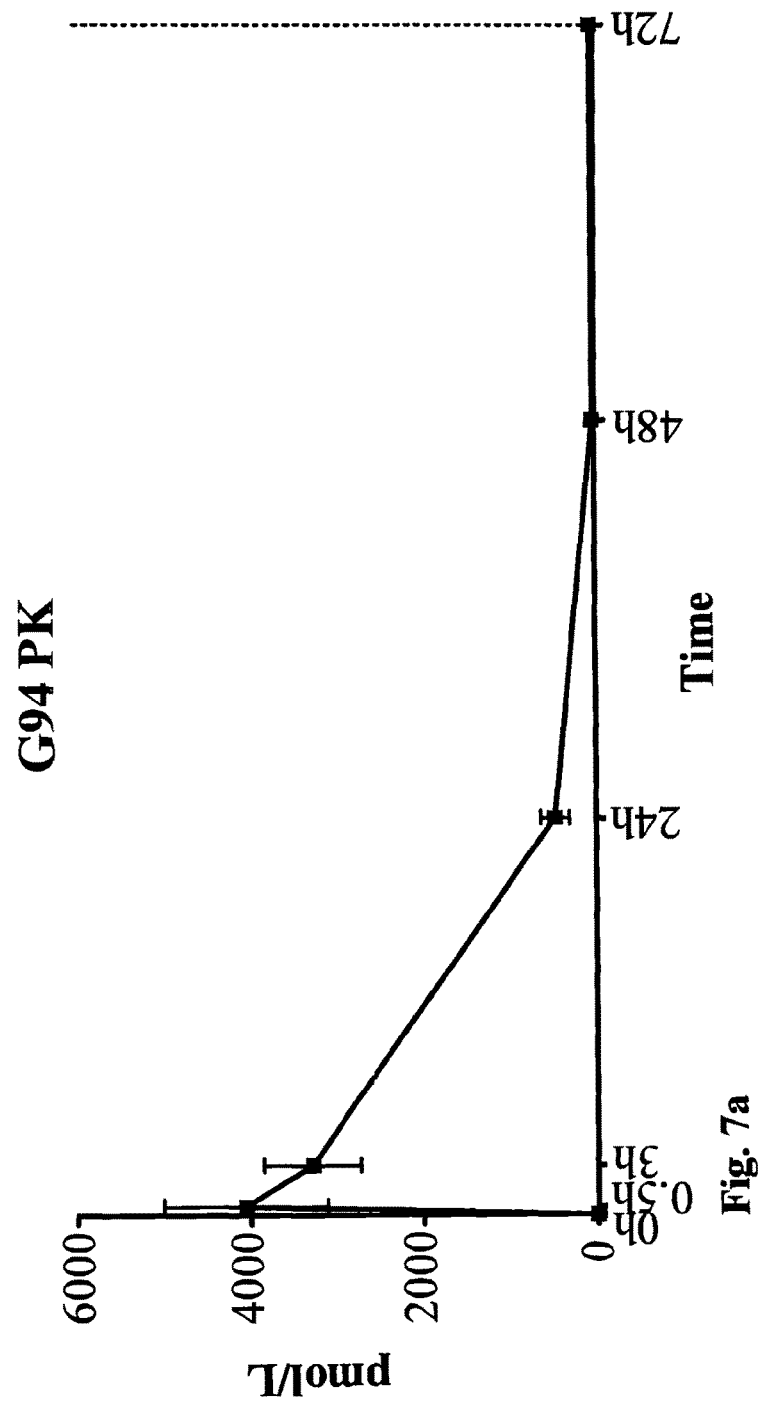
FIG. 7 shows the results of 3 day in vivo pharmacokinetic studies in rats with comparator compounds (G94, G162, G200, G202) not possessing a C-terminal extension amino acid sequence according to the invention. For each of those compounds, an initial increase or "spike" in plasma concentration level is observed following subcutaneous administration of 2 mg of each compound in 20 µl aqueous $ZnCl_2$ solution at a 1:1 molar ratio to 4 rats.
Figure 7B:
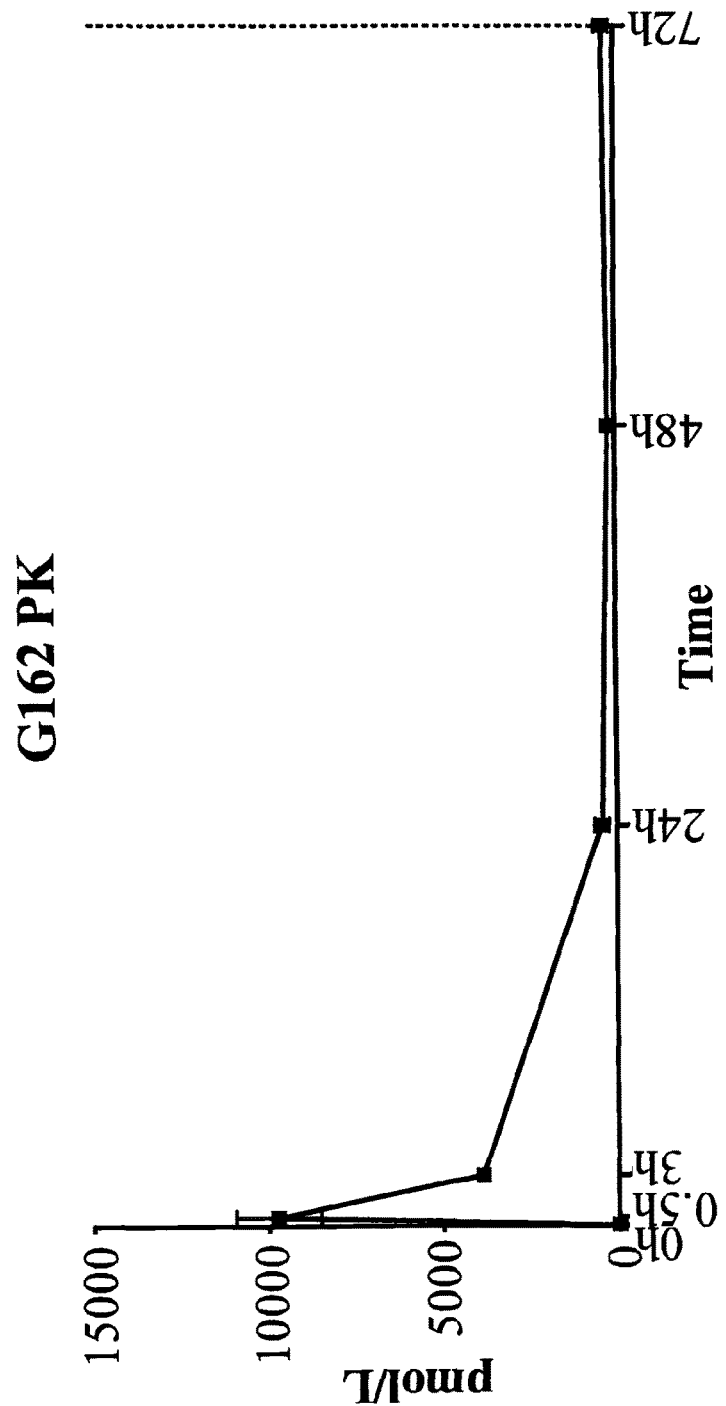
Figure 7C:
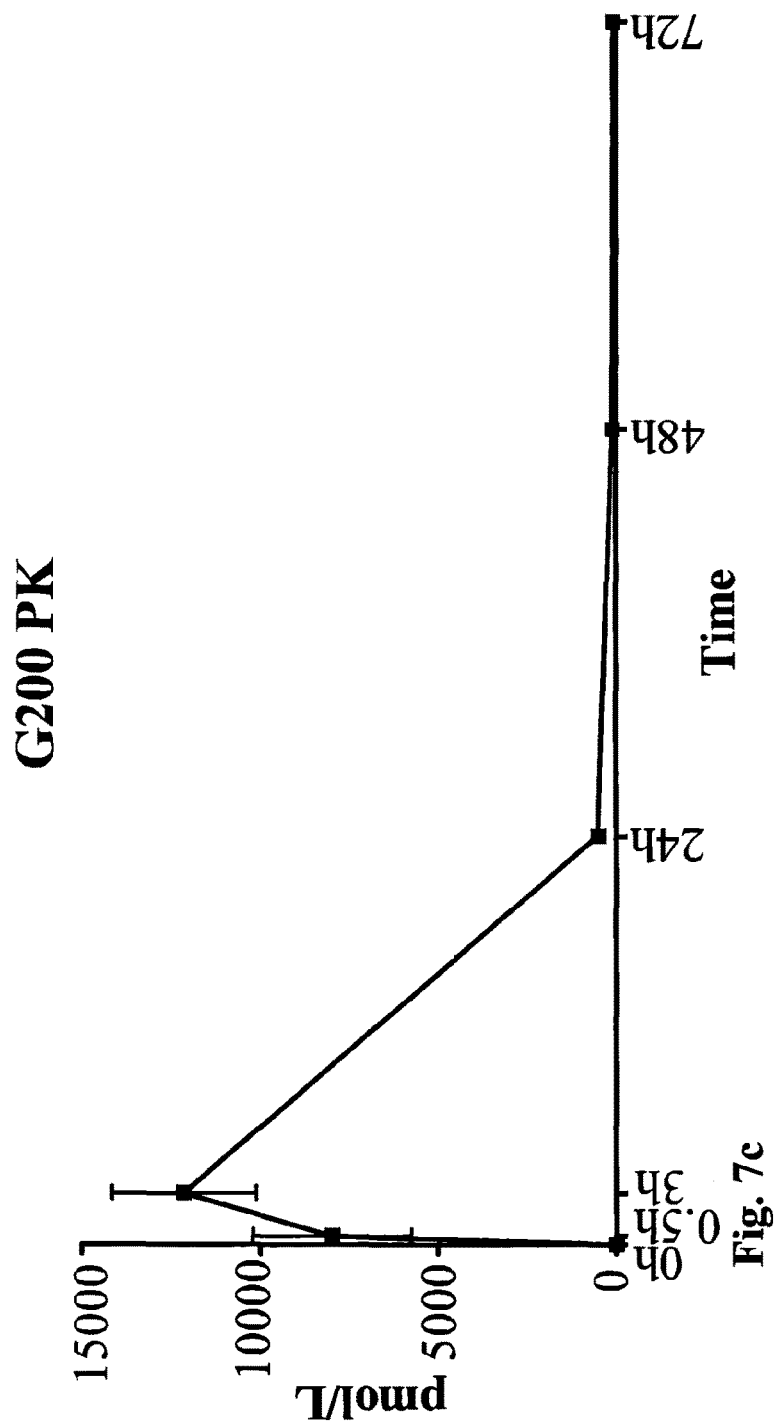
Figure 7D:
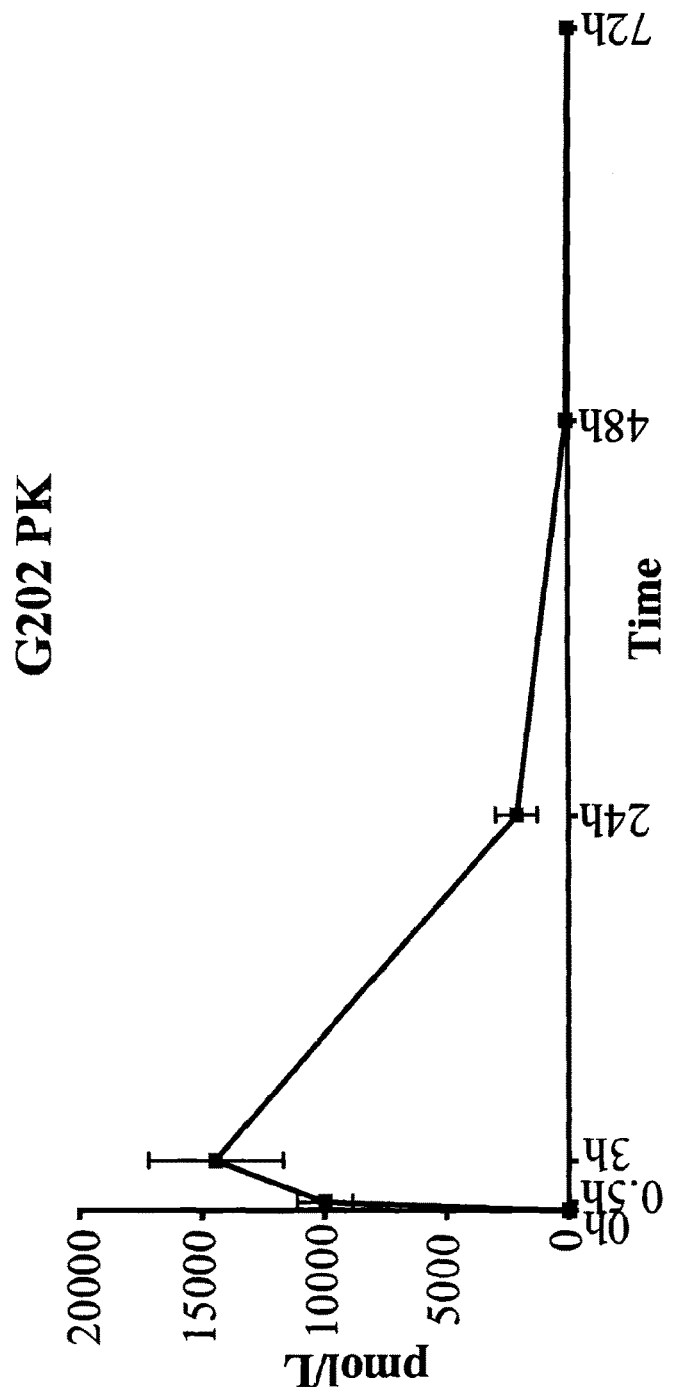

The pharmacokinetics of a peptide hormone analogue of the invention in rat was evaluated over 7 days. 4 rats were injected subcutaneously with the peptide hormone analogue G2051 [SEQ ID NO 197]. Each injection was of 10 μl total volume/rat containing 2 mg peptide and 1 zinc ion (as $ZnCl_2$) per peptide molecule. Blood was collected at the indicated time points, and the concentration of the peptide hormone analogue was determined. Peptide levels were assessed by/using radioimmunoassay using R4 exendin-4 antibody. The results are presented in FIG. 6, demonstrating that the plasma concentration of G2051 [SEQ ID NO 197] remains steady throughout the experiment and that no initial increase or "spike" in plasma concentration level is observed.

The pharmacokinetics of comparator compounds not possessing a C-terminal extension amino acid sequence according to the invention (G94, G162, G200, and G202) was evaluated over 3 days. 4 rats were injected subcutaneously with the peptide hormone analogue G2051 [SEQ ID NO 197]. Each injection was of 20 μl total volume/rat containing 2 mg peptide and 1 zinc ion (as $ZnCl_2$) per peptide molecule. Blood was collected at the indicated time points, and the concentration of the comparator compound was determined. Peptide levels were assessed by/using radioimmunoassay using R4 exendin-4 antibody.

The sequences of the comparator compounds were as follows:

G94:
[SEQ ID NO 309]
His-Ser-Gln-Gly-Thr-Phe-Thr-Ser-Asp-Tyr-Ser-Lys-Tyr-Leu-Asp-His-Arg-Arg-Ala-Lys-Asp-Phe-Val-Gln-Trp-Leu-Met-Asn-Thr-$CONH_2$;

G162:
[SEQ ID NO 310]
His-Ser-Gln-Gly-Thr-Phe-Thr-Ser-Asp-Tyr-Ser-Lys-Tyr-Leu-Asp-Ser-Lys-Lys-Ala-Gln-Glu-Phe-Val-Gln-Trp-Leu-Leu-Asn-Thr;

G200:
[SEQ ID NO 311]
His-Ser-Gln-Gly-Thr-Phe-Thr-Ser-Asp-Tyr-Ser-Lys-Tyr-Leu-Asp-Ser-Lys-Lys-Ala-Gln-Glu-Phe-Val-Gln-Trp-Leu-Met-Asn-Thr-$CONH_2$;

G202:
[SEQ ID NO 312]
His-Ser-Gln-Gly-Thr-Phe-Thr-Ser-Asp-Tyr-Ser-Lys-Tyr-Leu-Asp-Ser-Lys-Lys-Ala-Gln-Glu-Phe-Val-Glu-Trp-Leu-Met-Asn-Thr.

The results are presented in FIG. 7, which shows that, for each of those compounds, an initial increase or "spike" in plasma concentration level was observed following administration.

The invention claimed is:

1. A peptide hormone analogue which is:
a compound comprising the formula (I)

$$X\text{-}V \qquad (I)$$

wherein X represents an amino acid sequence having the formula (III);

(III)
[SEQ ID NO 289]
His-Ser-Gln-Gly-Thr-Phe-Thr-Ser-Asp-Xaa$^{10}$-Ser-Xaa$^{12}$-Xaa$^{13}$-Leu-Xaa$^{15}$-Xaa$^{16}$-Xaa$^{17}$-Xaa$^{18}$-Ala-Xaa$^{20}$-Xaa$^{21}$-Phe-Xaa$^{23}$-Xaa$^{24}$-Trp-Leu-Leu-Asn-Xaa$^{29}$ wherein Xaa$^{10}$ is selected from the group consisting of Tyr and Leu;
Xaa$^{12}$ is selected from the group consisting of Lys, His and Arg;
Xaa$^{13}$ is selected from the group consisting of Tyr, Gln and His;
Xaa$^{15}$ is selected from the group consisting of Asp and Glu;
Xaa$^{16}$ is selected from the group consisting of Glu, Gln and Ser;
Xaa$^{17}$ is selected from the group consisting of Arg, His and Lys;
Xaa$^{18}$ is selected from the group consisting of Arg and Lys;
Xaa$^{20}$ is selected from the group consisting of His and Gln;
Xaa$^{21}$ is selected from the group consisting of Glu, His and Asp;

Xaa$^{23}$ is selected from the group consisting of Ile and Val;
Xaa$^{24}$ is selected from the group consisting of Gln and Glu; and
Xaa$^{29}$ is selected from the group consisting of Thr and Gly; and
V represents a C-terminal extension amino acid sequence having the formula (II)

(II)
[SEQ ID NO 291]
Xaa$^{i}$-Xaa$^{ii}$-Xaa$^{iii}$-Xaa$^{iv}$-Xaa$^{v}$-Xaa$^{vi}$-Xaa$^{vii}$-Xaa$^{viii}$-Xaa$^{ix}$-Xaa$^{x}$ wherein Xaa$^{i}$ is Gly or His;
Xaa$^{ii}$ is absent or selected from the group consisting of Gly and His;
Xaa$^{iii}$ is absent or selected from the group consisting of Gly and His;
Xaa$^{iv}$ is absent or selected from the group consisting of Gly and His;
Xaa$^{v}$ is absent or His;
Xaa$^{vi}$ is absent or His;
Xaa$^{vii}$ is absent or His;
Xaa$^{viii}$ is absent or is selected from the group consisting of Ala, Glu, Gly, Gln and Ser;
Xaa$^{ix}$ is absent or is selected from the group consisting of Ala, Glu, Gly, Gln and Ser;
Xaa$^{x}$ is absent or is selected from the group consisting of Ala, Glu, Gly, Gln and Ser; and
wherein the C-terminal residue may optionally terminate in a —CONH$_2$ group in place of a carboxylic acid group; and
wherein V contains 4 or 5 His residues and 0, 1, 2 or 3 non-His residues;

or a derivative of the compound;

or a pharmaceutically acceptable salt of the compound or the derivative.

2. A peptide hormone analogue as claimed in claim 1, wherein V is selected from the group consisting of Gly-His-His-His-His-Ala-CONH2 [SEQ ID NO: 295], Gly-His-His-His-His-Gln-CONH2 [SEQ ID NO 296], Gly-His-His-His-His-His-Glu-CONH2 [SEQ ID NO: 297], Gly-His-His-His-His-His-Ser-CONH2 [SEQ ID NO: 298], Gly-His-His-His-His-Gln-Gln-CONH2 [SEQ ID NO: 299], His-His-His-His-Gly [SEQ ID NO: 300], His-His-His-His-Ala-Gly [SEQ ID NO: 301], His-His-His-His-CONH2 [SEQ ID NO: 304], His-His-His-His-His-Gln-NH2[SEQ ID NO: 305], and His-His-His-His-His-Gly [SEQ ID NO: 307].

3. A peptide hormone analogue as claimed in claim 1, wherein $Xaa^{10}$ is Tyr, $Xaa^{12}$ is Lys, $Xaa^{13}$ is Tyr, $Xaa^{15}$ is Asp, $Xaa^{16}$ is Glu or Gln, $Xaa^{17}$ is Lys or Arg, $Xaa^{18}$ is Arg, $Xaa^{20}$ is His, $Xaa^{21}$ is Glu, and $Xaa^{23}$ is Ile [SEQ ID NO: 308].

4. A peptide hormone analogue as claimed in claim 1, wherein the analogue is a compound consisting of an amino acid sequence represented by formula (I); or a derivative of the compound; or a pharmaceutically acceptable salt of the compound or the derivative.

5. A peptide hormone analogue as claimed in claim 1, wherein the compound is selected from the group consisting of analogue nos. 69 (G1840) [SEQ ID NO: 69], 130, (G1934) [SEQ ID NO: 130], 142 (G1950) [SEQ ID NO: 142], 147 (G1958) [SEQ ID NO: 147], 186 (G2036) [SEQ ID NO: 186], 197, (G2051) [SEQ ID NO: 197], 247 (G2116) [SEQ ID NO: 247], 248 (G2117) [SEQ ID NO: 248], 249 (G2119) [SEQ ID NO: 249] and 267 (G2147) [SEQ ID NO: 267].

6. A peptide hormone analogue as claimed in claim 1 which is a derivative that has been modified by one or more processes selected from amidation, glycosylation, carbamylation, acylation, sulfation, phosphorylation, cyclization, lipidization, pegylation and fusion to another peptide or protein to form a fusion protein.

7. A peptide hormone analogue as claimed in claim 1 together with a further therapeutic agent, for simultaneous, sequential or separate administration.

8. A pharmaceutical composition comprising a peptide hormone analogue as claimed in claim 1 together with a pharmaceutically acceptable carrier and optionally a further therapeutic agent.

9. The pharmaceutical composition as claimed in claim 8, present in a syringe or other administration device for subcutaneous administration to humans.

10. A method of treating or preventing a disease or disorder or other non-desired physiological state in a subject comprising, administration of an effective amount of a peptide hormone analogue as claimed in claim 1, wherein said administration is effective in treating or preventing obesity and/or-diabetes in the subject, increasing energy expenditure in the subject, improving insulin release in the subject, improving carbohydrate metabolism in the subject, improving the lipid profile of the subject, reducing appetite in the subject, reducing food intake in the subject, reducing calorie intake in the subject, improving carbohydrate tolerance in the subject, providing neuronal or cardiac cytoprotection in the subject, and/or causing weight loss or preventing weight gain in the subject for cosmetic purposes.

11. The method of claim 10, wherein the method is a method of providing cytoprotection in a subject, and wherein the method of providing cytoprotection is treating or preventing neurodegeneration, providing neuroprotection and/or providing cardiac protection.

12. The method of claim 11, wherein the method of providing cytoprotection is providing cardiac protection in a subject following a myocardial infarction; or providing neuroprotection in a subject having or diagnosed as being at risk of a chronic neurodegenerative disease.

13. The method of claim 12, wherein the chronic neurodegenerative disease is selected from the group consisting of Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Guillain Bane Syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis.

14. The method of claim 12, wherein the chronic neurodegenerative disease is selected from the group consisting of demyelination diseases, neuroinflammatory diseases and central nervous system infections.

* * * * *

SEQUENCE LISTING

```
<160> NUMBER OF SEQ ID NOS: 312

<210> SEQ ID NO 1
<211> LENGTH: 33
<212> TYPE: PRT
<213> ORGANISM: artificial sequence
<220> FEATURE:
<223> OTHER INFORMATION: hormone analogue

<400> SEQUENCE: 1

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His

<210> SEQ ID NO 2
<211> LENGTH: 33
<212> TYPE: PRT
<213> ORGANISM: artificial sequence
<220> FEATURE:
<223> OTHER INFORMATION: hormone analogue

<400> SEQUENCE: 2

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Gly His His
```

His

<210> SEQ ID NO 3
<211> LENGTH: 33
<212> TYPE: PRT
<213> ORGANISM: artificial sequence
<220> FEATURE:
<223> OTHER INFORMATION: hormone analogue

<400> SEQUENCE: 3

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Gly His His
            20                  25                  30

His

<210> SEQ ID NO 4
<211> LENGTH: 33
<212> TYPE: PRT
<213> ORGANISM: artificial sequence
<220> FEATURE:
<223> OTHER INFORMATION: hormone analogue

<400> SEQUENCE: 4

His Ser Gln Gly Thr Phe Thr Ser Asp Tyr Ser His Tyr Leu Asp Gln
1               5                   10                  15

Arg Arg Ala His Glu Phe Val Glu Trp Leu Leu Asn Gly His His His
            20                  25                  30

His

<210> SEQ ID NO 5
<211> LENGTH: 33
<212> TYPE: PRT
<213> ORGANISM: artificial sequence
<220> FEATURE:
<223> OTHER INFORMATION: hormone analogue

<400> SEQUENCE: 5

His Ser Gln Gly Thr Phe Thr Ser Asp Tyr Ser His Tyr Leu Asp Gln
1               5                   10                  15

Arg Arg Ala His Glu Phe Ile Glu Trp Leu Leu Asn Gly His His His
            20                  25                  30

His

<210> SEQ ID NO 6
<211> LENGTH: 33
<212> TYPE: PRT
<213> ORGANISM: artificial sequence
<220> FEATURE:
<223> OTHER INFORMATION: hormone analogue

<400> SEQUENCE: 6

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His His
            20                  25                  30

His

<210> SEQ ID NO 7
<211> LENGTH: 33

<212> TYPE: PRT
<213> ORGANISM: artificial sequence
<220> FEATURE:
<223> OTHER INFORMATION: hormone analogue

<400> SEQUENCE: 7

His Ser Gln Gly Thr Phe Thr Ser Asp Tyr Ser His Tyr Leu Asp Gln
1               5                   10                  15

Arg Arg Ala His Glu Phe Ile Gln Trp Leu Leu Asn Gly His His His
            20                  25                  30

His

<210> SEQ ID NO 8
<211> LENGTH: 33
<212> TYPE: PRT
<213> ORGANISM: artificial sequence
<220> FEATURE:
<223> OTHER INFORMATION: hormone analogue

<400> SEQUENCE: 8

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Gly His His His
            20                  25                  30

His

<210> SEQ ID NO 9
<211> LENGTH: 34
<212> TYPE: PRT
<213> ORGANISM: artificial sequence
<220> FEATURE:
<223> OTHER INFORMATION: hormone analogue

<400> SEQUENCE: 9

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His

<210> SEQ ID NO 10
<211> LENGTH: 33
<212> TYPE: PRT
<213> ORGANISM: artificial sequence
<220> FEATURE:
<223> OTHER INFORMATION: hormone analogue

<400> SEQUENCE: 10

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His

<210> SEQ ID NO 11
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)

```
<223> OTHER INFORMATION: AMIDATION

<400> SEQUENCE: 11

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His

<210> SEQ ID NO 12
<211> LENGTH: 33
<212> TYPE: PRT
<213> ORGANISM: artificial sequence
<220> FEATURE:
<223> OTHER INFORMATION: hormone analogue

<400> SEQUENCE: 12

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His

<210> SEQ ID NO 13
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 13

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His

<210> SEQ ID NO 14
<211> LENGTH: 33
<212> TYPE: PRT
<213> ORGANISM: artificial sequence
<220> FEATURE:
<223> OTHER INFORMATION: hormone analogue

<400> SEQUENCE: 14

His Ser Gln Gly Thr Phe Thr Ser Asp Tyr Ser His Tyr Leu Asp Ser
1               5                   10                  15

Lys Arg Ala His Glu Phe Ile Gln Trp Leu Leu Asn Thr Gly His His
            20                  25                  30

His

<210> SEQ ID NO 15
<211> LENGTH: 34
<212> TYPE: PRT
<213> ORGANISM: artificial sequence
<220> FEATURE:
<223> OTHER INFORMATION: hormone analogue

<400> SEQUENCE: 15
```

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
                20                  25                  30

His His

<210> SEQ ID NO 16
<211> LENGTH: 34
<212> TYPE: PRT
<213> ORGANISM: artificial sequence
<220> FEATURE:
<223> OTHER INFORMATION: hormone analogue

<400> SEQUENCE: 16

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
                20                  25                  30

His Glu

<210> SEQ ID NO 17
<211> LENGTH: 33
<212> TYPE: PRT
<213> ORGANISM: artificial sequence
<220> FEATURE:
<223> OTHER INFORMATION: hormone analogue

<400> SEQUENCE: 17

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
                20                  25                  30

His

<210> SEQ ID NO 18
<211> LENGTH: 33
<212> TYPE: PRT
<213> ORGANISM: artificial sequence
<220> FEATURE:
<223> OTHER INFORMATION: hormone analogue

<400> SEQUENCE: 18

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
                20                  25                  30

His

<210> SEQ ID NO 19
<211> LENGTH: 33
<212> TYPE: PRT
<213> ORGANISM: artificial sequence
<220> FEATURE:
<223> OTHER INFORMATION: hormone analogue

<400> SEQUENCE: 19

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
                20                  25                  30

His

```
<210> SEQ ID NO 20
<211> LENGTH: 33
<212> TYPE: PRT
<213> ORGANISM: artificial sequence
<220> FEATURE:
<223> OTHER INFORMATION: hormone analogue

<400> SEQUENCE: 20
```

His Ser Gln Gly Thr Phe Thr Ser Asp Tyr Ser His Tyr Leu Asp Gln
1               5                   10                  15

Lys Arg Ala His Glu Phe Ile Gln Trp Leu Leu Asn Gly His His His
            20                  25                  30

His

```
<210> SEQ ID NO 21
<211> LENGTH: 33
<212> TYPE: PRT
<213> ORGANISM: artificial sequence
<220> FEATURE:
<223> OTHER INFORMATION: hormone analogue

<400> SEQUENCE: 21
```

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly His His His
            20                  25                  30

His

```
<210> SEQ ID NO 22
<211> LENGTH: 33
<212> TYPE: PRT
<213> ORGANISM: artificial sequence
<220> FEATURE:
<223> OTHER INFORMATION: hormone analogue

<400> SEQUENCE: 22
```

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly His His His
            20                  25                  30

His

```
<210> SEQ ID NO 23
<211> LENGTH: 34
<212> TYPE: PRT
<213> ORGANISM: artificial sequence
<220> FEATURE:
<223> OTHER INFORMATION: hormone analogue

<400> SEQUENCE: 23
```

His Ser Gln Gly Thr Phe Thr Ser Asp Tyr Ser Lys Tyr Leu Asp Ser
1               5                   10                  15

Arg Arg Ala His Glu Phe Val Gln Trp Leu Leu Asn Gly Gly His His
            20                  25                  30

His His

```
<210> SEQ ID NO 24
<211> LENGTH: 33
<212> TYPE: PRT
<213> ORGANISM: artificial sequence
```

<220> FEATURE:
<223> OTHER INFORMATION: hormone analogue

<400> SEQUENCE: 24

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr His His His
            20                  25                  30

His

<210> SEQ ID NO 25
<211> LENGTH: 34
<212> TYPE: PRT
<213> ORGANISM: artificial sequence
<220> FEATURE:
<223> OTHER INFORMATION: hormone analogue

<400> SEQUENCE: 25

His Ser Gln Gly Thr Phe Thr Ser Asp Tyr Ser Lys Tyr Leu Asp Ser
1               5                   10                  15

Lys Arg Ala His Glu Phe Val Gln Trp Leu Leu Asn Gly Gly His His
            20                  25                  30

His His

<210> SEQ ID NO 26
<211> LENGTH: 34
<212> TYPE: PRT
<213> ORGANISM: artificial sequence
<220> FEATURE:
<223> OTHER INFORMATION: hormone analogue

<400> SEQUENCE: 26

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His

<210> SEQ ID NO 27
<211> LENGTH: 34
<212> TYPE: PRT
<213> ORGANISM: artificial sequence
<220> FEATURE:
<223> OTHER INFORMATION: hormone analogue

<400> SEQUENCE: 27

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His His
            20                  25                  30

His His

<210> SEQ ID NO 28
<211> LENGTH: 33
<212> TYPE: PRT
<213> ORGANISM: artificial sequence
<220> FEATURE:
<223> OTHER INFORMATION: hormone analogue

<400> SEQUENCE: 28

His Ser Gln Gly Thr Phe Thr Ser Asp Tyr Ser His Tyr Leu Asp Glu
1               5                   10                  15

-continued

Lys Arg Ala His Glu Phe Ile Glu Trp Leu Leu Asn Gly His His His
            20                  25                  30

His

<210> SEQ ID NO 29
<211> LENGTH: 34
<212> TYPE: PRT
<213> ORGANISM: artificial sequence
<220> FEATURE:
<223> OTHER INFORMATION: hormone analogue

<400> SEQUENCE: 29

His Ser Gln Gly Thr Phe Thr Ser Asp Tyr Ser His Tyr Leu Asp Glu
1               5                   10                  15

Lys Arg Ala His Glu Phe Ile Glu Trp Leu Leu Asn Gly His His His
            20                  25                  30

His Glu

<210> SEQ ID NO 30
<211> LENGTH: 33
<212> TYPE: PRT
<213> ORGANISM: artificial sequence
<220> FEATURE:
<223> OTHER INFORMATION: hormone analogue

<400> SEQUENCE: 30

His Ser Gln Gly Thr Phe Thr Ser Asp Tyr Ser His Tyr Leu Asp Ser
1               5                   10                  15

Lys Arg Ala His Glu Phe Val Gln Trp Leu Leu Asn Gly His His His
            20                  25                  30

His

<210> SEQ ID NO 31
<211> LENGTH: 34
<212> TYPE: PRT
<213> ORGANISM: artificial sequence
<220> FEATURE:
<223> OTHER INFORMATION: hormone analogue

<400> SEQUENCE: 31

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His

<210> SEQ ID NO 32
<211> LENGTH: 33
<212> TYPE: PRT
<213> ORGANISM: artificial sequence
<220> FEATURE:
<223> OTHER INFORMATION: hormone analogue

<400> SEQUENCE: 32

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His

<210> SEQ ID NO 33
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 33

His Ser Gln Gly Thr Phe Thr Ser Asp Tyr Ser Lys Tyr Leu Asp Glu
1               5                   10                  15
Arg Arg Ala His Glu Phe Ile Glu Trp Leu Leu Asn Gly Gly His His
            20                  25                  30
His

<210> SEQ ID NO 34
<211> LENGTH: 34
<212> TYPE: PRT
<213> ORGANISM: artificial sequence
<220> FEATURE:
<223> OTHER INFORMATION: hormone analogue

<400> SEQUENCE: 34

His Ser Gln Gly Thr Phe Thr Ser Asp Tyr Ser Lys Tyr Leu Asp Glu
1               5                   10                  15
Arg Arg Ala His Glu Phe Ile Glu Trp Leu Leu Asn Gly Gly His His
            20                  25                  30
His His

<210> SEQ ID NO 35
<211> LENGTH: 34
<212> TYPE: PRT
<213> ORGANISM: artificial sequence
<220> FEATURE:
<223> OTHER INFORMATION: hormone analogue

<400> SEQUENCE: 35

His Ser Gln Gly Thr Phe Thr Ser Asp Tyr Ser His Tyr Leu Asp Gln
1               5                   10                  15
Lys Arg Ala His Glu Phe Ile Glu Trp Leu Leu Asn Gly Gly His His
            20                  25                  30
His Glu

<210> SEQ ID NO 36
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 36

His Ser Gln Gly Thr Phe Thr Ser Asp Tyr Ser His Tyr Leu Asp Gln
1               5                   10                  15
Lys Arg Ala His Glu Phe Ile Glu Trp Leu Leu Asn Gly Gly His His
            20                  25                  30
His

<210> SEQ ID NO 37
<211> LENGTH: 34
<212> TYPE: PRT
<213> ORGANISM: artificial sequence
<220> FEATURE:
<223> OTHER INFORMATION: hormone analogue

<400> SEQUENCE: 37

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His Glu

<210> SEQ ID NO 38
<211> LENGTH: 33
<212> TYPE: PRT
<213> ORGANISM: artificial sequence
<220> FEATURE:
<223> OTHER INFORMATION: hormone analogue

<400> SEQUENCE: 38

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr Gly His His
            20                  25                  30

His

<210> SEQ ID NO 39
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 39

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Thr Gly His His
            20                  25                  30

His

<210> SEQ ID NO 40
<211> LENGTH: 33
<212> TYPE: PRT
<213> ORGANISM: artificial sequence
<220> FEATURE:
<223> OTHER INFORMATION: hormone analogue

<400> SEQUENCE: 40

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His

<210> SEQ ID NO 41
<211> LENGTH: 33

```
<212> TYPE: PRT
<213> ORGANISM: artificial sequence
<220> FEATURE:
<223> OTHER INFORMATION: hormone analogue

<400> SEQUENCE: 41

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr Gly His His
            20                  25                  30

His

<210> SEQ ID NO 42
<211> LENGTH: 34
<212> TYPE: PRT
<213> ORGANISM: artificial sequence
<220> FEATURE:
<223> OTHER INFORMATION: hormone analogue

<400> SEQUENCE: 42

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His

<210> SEQ ID NO 43
<211> LENGTH: 34
<212> TYPE: PRT
<213> ORGANISM: artificial sequence
<220> FEATURE:
<223> OTHER INFORMATION: hormone analogue

<400> SEQUENCE: 43

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His Glu

<210> SEQ ID NO 44
<211> LENGTH: 33
<212> TYPE: PRT
<213> ORGANISM: artificial sequence
<220> FEATURE:
<223> OTHER INFORMATION: hormone analogue

<400> SEQUENCE: 44

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Gly His His His
            20                  25                  30

His

<210> SEQ ID NO 45
<211> LENGTH: 33
<212> TYPE: PRT
<213> ORGANISM: artificial sequence
<220> FEATURE:
<223> OTHER INFORMATION: hormone analogue

<400> SEQUENCE: 45
```

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Gly His His His
            20                  25                  30

His

<210> SEQ ID NO 46
<211> LENGTH: 33
<212> TYPE: PRT
<213> ORGANISM: artificial sequence
<220> FEATURE:
<223> OTHER INFORMATION: hormone analogue

<400> SEQUENCE: 46

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly His His His
            20                  25                  30

His

<210> SEQ ID NO 47
<211> LENGTH: 36
<212> TYPE: PRT
<213> ORGANISM: artificial sequence
<220> FEATURE:
<223> OTHER INFORMATION: hormone analogue

<400> SEQUENCE: 47

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His His Glu
        35

<210> SEQ ID NO 48
<211> LENGTH: 36
<212> TYPE: PRT
<213> ORGANISM: artificial sequence
<220> FEATURE:
<223> OTHER INFORMATION: hormone analogue

<400> SEQUENCE: 48

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His His Glu
        35

<210> SEQ ID NO 49
<211> LENGTH: 34
<212> TYPE: PRT
<213> ORGANISM: artificial sequence
<220> FEATURE:
<223> OTHER INFORMATION: hormone analogue

<400> SEQUENCE: 49

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His

```
<210> SEQ ID NO 50
<211> LENGTH: 34
<212> TYPE: PRT
<213> ORGANISM: artificial sequence
<220> FEATURE:
<223> OTHER INFORMATION: hormone analogue

<400> SEQUENCE: 50
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
            20                  25                  30

His His

```
<210> SEQ ID NO 51
<211> LENGTH: 34
<212> TYPE: PRT
<213> ORGANISM: artificial sequence
<220> FEATURE:
<223> OTHER INFORMATION: hormone analogue

<400> SEQUENCE: 51
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His

```
<210> SEQ ID NO 52
<211> LENGTH: 34
<212> TYPE: PRT
<213> ORGANISM: artificial sequence
<220> FEATURE:
<223> OTHER INFORMATION: hormone analogue

<400> SEQUENCE: 52
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His Glu

```
<210> SEQ ID NO 53
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 53
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His

<210> SEQ ID NO 54
<211> LENGTH: 33
<212> TYPE: PRT
<213> ORGANISM: artificial sequence
<220> FEATURE:
<223> OTHER INFORMATION: hormone analogue

<400> SEQUENCE: 54

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr His His His
            20                  25                  30

His

<210> SEQ ID NO 55
<211> LENGTH: 34
<212> TYPE: PRT
<213> ORGANISM: artificial sequence
<220> FEATURE:
<223> OTHER INFORMATION: hormone analogue

<400> SEQUENCE: 55

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr Gly His His
            20                  25                  30

His His

<210> SEQ ID NO 56
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 56

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His His
            20                  25                  30

His His

<210> SEQ ID NO 57
<211> LENGTH: 34
<212> TYPE: PRT
<213> ORGANISM: artificial sequence
<220> FEATURE:
<223> OTHER INFORMATION: hormone analogue

<400> SEQUENCE: 57

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His Glu

<210> SEQ ID NO 58
<211> LENGTH: 34

<212> TYPE: PRT
<213> ORGANISM: artificial sequence
<220> FEATURE:
<223> OTHER INFORMATION: hormone analogue

<400> SEQUENCE: 58

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His His
            20                  25                  30

His Glu

<210> SEQ ID NO 59
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 59

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His

<210> SEQ ID NO 60
<211> LENGTH: 34
<212> TYPE: PRT
<213> ORGANISM: artificial sequence
<220> FEATURE:
<223> OTHER INFORMATION: hormone analogue

<400> SEQUENCE: 60

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His Gly

<210> SEQ ID NO 61
<211> LENGTH: 34
<212> TYPE: PRT
<213> ORGANISM: artificial sequence
<220> FEATURE:
<223> OTHER INFORMATION: hormone analogue

<400> SEQUENCE: 61

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His Gly

<210> SEQ ID NO 62
<211> LENGTH: 33
<212> TYPE: PRT
<213> ORGANISM: artificial sequence
<220> FEATURE:

<223> OTHER INFORMATION: hormone analogue

<400> SEQUENCE: 62

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His

<210> SEQ ID NO 63
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 63

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His

<210> SEQ ID NO 64
<211> LENGTH: 34
<212> TYPE: PRT
<213> ORGANISM: artificial sequence
<220> FEATURE:
<223> OTHER INFORMATION: hormone analogue

<400> SEQUENCE: 64

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Gly

<210> SEQ ID NO 65
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 65

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His His

<210> SEQ ID NO 66
<211> LENGTH: 34
<212> TYPE: PRT
<213> ORGANISM: artificial sequence

```
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 66

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His

<210> SEQ ID NO 67
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 67

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His

<210> SEQ ID NO 68
<211> LENGTH: 34
<212> TYPE: PRT
<213> ORGANISM: artificial sequence
<220> FEATURE:
<223> OTHER INFORMATION: hormone analogue

<400> SEQUENCE: 68

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His Gly

<210> SEQ ID NO 69
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 69

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His
```

```
<210> SEQ ID NO 70
<211> LENGTH: 34
<212> TYPE: PRT
<213> ORGANISM: artificial sequence
<220> FEATURE:
<223> OTHER INFORMATION: hormone analogue

<400> SEQUENCE: 70

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His Glu

<210> SEQ ID NO 71
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 71

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His

<210> SEQ ID NO 72
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 72

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His Gly

<210> SEQ ID NO 73
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 73

His Ser Gln Gly Thr Phe Thr Ser Asp Tyr Ser Lys Tyr Leu Asp Glu
1               5                   10                  15
```

```
Lys Arg Ala His Glu Phe Ile Glu Trp Leu Leu Asn Thr His His
            20                  25                  30

His Gly

<210> SEQ ID NO 74
<211> LENGTH: 34
<212> TYPE: PRT
<213> ORGANISM: artificial sequence
<220> FEATURE:
<223> OTHER INFORMATION: hormone analogue

<400> SEQUENCE: 74

His Ser Gln Gly Thr Phe Thr Ser Asp Tyr Ser His Tyr Leu Asp Glu
1               5                   10                  15

Lys Arg Ala His Glu Phe Ile Glu Trp Leu Leu Asn Thr His His His
            20                  25                  30

His Glu

<210> SEQ ID NO 75
<211> LENGTH: 34
<212> TYPE: PRT
<213> ORGANISM: artificial sequence
<220> FEATURE:
<223> OTHER INFORMATION: hormone analogue

<400> SEQUENCE: 75

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Glu

<210> SEQ ID NO 76
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 76

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His

<210> SEQ ID NO 77
<211> LENGTH: 34
<212> TYPE: PRT
<213> ORGANISM: artificial sequence
<220> FEATURE:
<223> OTHER INFORMATION: hormone analogue

<400> SEQUENCE: 77

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly His His His
            20                  25                  30
```

His Glu

<210> SEQ ID NO 78
<211> LENGTH: 34
<212> TYPE: PRT
<213> ORGANISM: artificial sequence
<220> FEATURE:
<223> OTHER INFORMATION: hormone analogue

<400> SEQUENCE: 78

His Ser Gln Gly Thr Phe Thr Ser Asp Tyr Ser His Tyr Leu Asp Gln
1               5                   10                  15

Lys Arg Ala His Glu Phe Ile Gln Trp Leu Leu Asn Gly Gly His His
            20                  25                  30

His Glu

<210> SEQ ID NO 79
<211> LENGTH: 34
<212> TYPE: PRT
<213> ORGANISM: artificial sequence
<220> FEATURE:
<223> OTHER INFORMATION: hormone analogue

<400> SEQUENCE: 79

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Gly Gly His His
            20                  25                  30

His Glu

<210> SEQ ID NO 80
<211> LENGTH: 34
<212> TYPE: PRT
<213> ORGANISM: artificial sequence
<220> FEATURE:
<223> OTHER INFORMATION: hormone analogue

<400> SEQUENCE: 80

His Ser Gln Gly Thr Phe Thr Ser Asp Tyr Ser Lys Tyr Leu Asp Gln
1               5                   10                  15

Lys Arg Ala His Glu Phe Ile Gln Trp Leu Leu Asn Gly Gly His His
            20                  25                  30

His Glu

<210> SEQ ID NO 81
<211> LENGTH: 34
<212> TYPE: PRT
<213> ORGANISM: artificial sequence
<220> FEATURE:
<223> OTHER INFORMATION: hormone analogue

<400> SEQUENCE: 81

His Ser Gln Gly Thr Phe Thr Ser Asp Tyr Ser His Tyr Leu Asp Glu
1               5                   10                  15

Lys Arg Ala His Glu Phe Ile Glu Trp Leu Leu Asn Gly Gly His His
            20                  25                  30

His Glu

<210> SEQ ID NO 82
<211> LENGTH: 34
<212> TYPE: PRT
<213> ORGANISM: artificial sequence

```
<220> FEATURE:
<223> OTHER INFORMATION: hormone analogue

<400> SEQUENCE: 82

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His Glu

<210> SEQ ID NO 83
<211> LENGTH: 35
<212> TYPE: PRT
<213> ORGANISM: artificial sequence
<220> FEATURE:
<223> OTHER INFORMATION: hormone analogue

<400> SEQUENCE: 83

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Ala
        35

<210> SEQ ID NO 84
<211> LENGTH: 35
<212> TYPE: PRT
<213> ORGANISM: artificial sequence
<220> FEATURE:
<223> OTHER INFORMATION: hormone analogue

<400> SEQUENCE: 84

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Ser
        35

<210> SEQ ID NO 85
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 85

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Ala
        35

<210> SEQ ID NO 86
<211> LENGTH: 35
<212> TYPE: PRT
<213> ORGANISM: artificial sequence
```

<220> FEATURE:
<223> OTHER INFORMATION: hormone analogue

<400> SEQUENCE: 86

His Ser Gln Gly Thr Phe Thr Ser Asp Tyr Ser Lys Tyr Leu Asp Glu
1               5                   10                  15
Lys Arg Ala His Glu Phe Ile Glu Trp Leu Leu Asn Gly Gly His His
            20                  25                  30
His His Ala
        35

<210> SEQ ID NO 87
<211> LENGTH: 33
<212> TYPE: PRT
<213> ORGANISM: artificial sequence
<220> FEATURE:
<223> OTHER INFORMATION: hormone analogue

<400> SEQUENCE: 87

His Ser Gln Gly Thr Phe Thr Ser Asp Tyr Ser His Tyr Leu Asp Gln
1               5                   10                  15
Lys Arg Ala His Glu Phe Ile Glu Trp Leu Leu Asn Gly Gly His His
            20                  25                  30
His

<210> SEQ ID NO 88
<211> LENGTH: 34
<212> TYPE: PRT
<213> ORGANISM: artificial sequence
<220> FEATURE:
<223> OTHER INFORMATION: hormone analogue

<400> SEQUENCE: 88

His Ser Gln Gly Thr Phe Thr Ser Asp Tyr Ser His Tyr Leu Asp Gln
1               5                   10                  15
Lys Arg Ala His Glu Phe Ile Glu Trp Leu Leu Asn Gly Gly His His
            20                  25                  30
His Ala

<210> SEQ ID NO 89
<211> LENGTH: 35
<212> TYPE: PRT
<213> ORGANISM: artificial sequence
<220> FEATURE:
<223> OTHER INFORMATION: hormone analogue

<400> SEQUENCE: 89

His Ser Gln Gly Thr Phe Thr Ser Asp Tyr Ser Lys Tyr Leu Asp Glu
1               5                   10                  15
Lys Arg Ala His Glu Phe Ile Glu Trp Leu Leu Asn Gly His His His
            20                  25                  30
His His Gln
        35

<210> SEQ ID NO 90
<211> LENGTH: 36
<212> TYPE: PRT
<213> ORGANISM: artificial sequence
<220> FEATURE:
<223> OTHER INFORMATION: hormone analogue

<400> SEQUENCE: 90

```
His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Gly Glu
        35
```

<210> SEQ ID NO 91
<211> LENGTH: 34
<212> TYPE: PRT
<213> ORGANISM: artificial sequence
<220> FEATURE:
<223> OTHER INFORMATION: hormone analogue

<400> SEQUENCE: 91

```
His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Ala
```

<210> SEQ ID NO 92
<211> LENGTH: 35
<212> TYPE: PRT
<213> ORGANISM: artificial sequence
<220> FEATURE:
<223> OTHER INFORMATION: hormone analogue

<400> SEQUENCE: 92

```
His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His His Gln
        35
```

<210> SEQ ID NO 93
<211> LENGTH: 34
<212> TYPE: PRT
<213> ORGANISM: artificial sequence
<220> FEATURE:
<223> OTHER INFORMATION: hormone analogue

<400> SEQUENCE: 93

```
His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His Ala
```

<210> SEQ ID NO 94
<211> LENGTH: 35
<212> TYPE: PRT
<213> ORGANISM: artificial sequence
<220> FEATURE:
<223> OTHER INFORMATION: hormone analogue

<400> SEQUENCE: 94

```
His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30
```

His His Ala
        35

<210> SEQ ID NO 95
<211> LENGTH: 35
<212> TYPE: PRT
<213> ORGANISM: artificial sequence
<220> FEATURE:
<223> OTHER INFORMATION: hormone analogue

<400> SEQUENCE: 95

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Ala
        35

<210> SEQ ID NO 96
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 96

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Ala
        35

<210> SEQ ID NO 97
<211> LENGTH: 35
<212> TYPE: PRT
<213> ORGANISM: artificial sequence
<220> FEATURE:
<223> OTHER INFORMATION: hormone analogue

<400> SEQUENCE: 97

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Gly
        35

<210> SEQ ID NO 98
<211> LENGTH: 35
<212> TYPE: PRT
<213> ORGANISM: artificial sequence
<220> FEATURE:
<223> OTHER INFORMATION: hormone analogue

<400> SEQUENCE: 98

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His

-continued

```
                  20                  25                  30

His His Ala
        35

<210> SEQ ID NO 99
<211> LENGTH: 34
<212> TYPE: PRT
<213> ORGANISM: artificial sequence
<220> FEATURE:
<223> OTHER INFORMATION: hormone analogue

<400> SEQUENCE: 99

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His Ala

<210> SEQ ID NO 100
<211> LENGTH: 35
<212> TYPE: PRT
<213> ORGANISM: artificial sequence
<220> FEATURE:
<223> OTHER INFORMATION: hormone analogue

<400> SEQUENCE: 100

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His His Ala
        35

<210> SEQ ID NO 101
<211> LENGTH: 34
<212> TYPE: PRT
<213> ORGANISM: artificial sequence
<220> FEATURE:
<223> OTHER INFORMATION: hormone analogue

<400> SEQUENCE: 101

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr Gly His His
            20                  25                  30

His Glu

<210> SEQ ID NO 102
<211> LENGTH: 34
<212> TYPE: PRT
<213> ORGANISM: artificial sequence
<220> FEATURE:
<223> OTHER INFORMATION: hormone analogue

<400> SEQUENCE: 102

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr Gly His His
            20                  25                  30

His Ala
```

```
<210> SEQ ID NO 103
<211> LENGTH: 35
<212> TYPE: PRT
<213> ORGANISM: artificial sequence
<220> FEATURE:
<223> OTHER INFORMATION: hormone analogue

<400> SEQUENCE: 103

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His Ala
        35

<210> SEQ ID NO 104
<211> LENGTH: 36
<212> TYPE: PRT
<213> ORGANISM: artificial sequence
<220> FEATURE:
<223> OTHER INFORMATION: hormone analogue

<400> SEQUENCE: 104

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His His Ala
        35

<210> SEQ ID NO 105
<211> LENGTH: 36
<212> TYPE: PRT
<213> ORGANISM: artificial sequence
<220> FEATURE:
<223> OTHER INFORMATION: hormone analogue

<400> SEQUENCE: 105

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His His Glu
        35

<210> SEQ ID NO 106
<211> LENGTH: 35
<212> TYPE: PRT
<213> ORGANISM: artificial sequence
<220> FEATURE:
<223> OTHER INFORMATION: hormone analogue

<400> SEQUENCE: 106

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala
        35

<210> SEQ ID NO 107
<211> LENGTH: 36
<212> TYPE: PRT
```

```
<213> ORGANISM: artificial sequence
<220> FEATURE:
<223> OTHER INFORMATION: hormone analogue

<400> SEQUENCE: 107
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His His Ala
        35

```
<210> SEQ ID NO 108
<211> LENGTH: 35
<212> TYPE: PRT
<213> ORGANISM: artificial sequence
<220> FEATURE:
<223> OTHER INFORMATION: hormone analogue

<400> SEQUENCE: 108
```

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His His Ala
        35

```
<210> SEQ ID NO 109
<211> LENGTH: 36
<212> TYPE: PRT
<213> ORGANISM: artificial sequence
<220> FEATURE:
<223> OTHER INFORMATION: hormone analogue

<400> SEQUENCE: 109
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His His Glu
        35

```
<210> SEQ ID NO 110
<211> LENGTH: 34
<212> TYPE: PRT
<213> ORGANISM: artificial sequence
<220> FEATURE:
<223> OTHER INFORMATION: hormone analogue

<400> SEQUENCE: 110
```

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His Ala

```
<210> SEQ ID NO 111
<211> LENGTH: 36
<212> TYPE: PRT
<213> ORGANISM: artificial sequence
<220> FEATURE:
<223> OTHER INFORMATION: hormone analogue
```

<400> SEQUENCE: 111

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His His Gln
        35

<210> SEQ ID NO 112
<211> LENGTH: 36
<212> TYPE: PRT
<213> ORGANISM: artificial sequence
<220> FEATURE:
<223> OTHER INFORMATION: hormone analogue

<400> SEQUENCE: 112

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His His Ala
        35

<210> SEQ ID NO 113
<211> LENGTH: 35
<212> TYPE: PRT
<213> ORGANISM: artificial sequence
<220> FEATURE:
<223> OTHER INFORMATION: hormone analogue

<400> SEQUENCE: 113

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gln
        35

<210> SEQ ID NO 114
<211> LENGTH: 35
<212> TYPE: PRT
<213> ORGANISM: artificial sequence
<220> FEATURE:
<223> OTHER INFORMATION: hormone analogue

<400> SEQUENCE: 114

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Gln
        35

<210> SEQ ID NO 115
<211> LENGTH: 36
<212> TYPE: PRT
<213> ORGANISM: artificial sequence
<220> FEATURE:
<223> OTHER INFORMATION: hormone analogue

<400> SEQUENCE: 115

His Ser Gln Gly Thr Phe Thr Ser Asp Tyr Ser Lys Tyr Leu Asp Gln

```
                1               5                  10                  15
Arg Arg Ala His Glu Phe Ile Glu Trp Leu Leu Asn Thr Gly His His
                20                  25                  30

His His His Glu
        35

<210> SEQ ID NO 116
<211> LENGTH: 36
<212> TYPE: PRT
<213> ORGANISM: artificial sequence
<220> FEATURE:
<223> OTHER INFORMATION: hormone analogue

<400> SEQUENCE: 116

His Ser Gln Gly Thr Phe Thr Ser Asp Tyr Ser Lys Tyr Leu Asp Gln
1               5                  10                  15

Arg Arg Ala His Glu Phe Ile Glu Trp Leu Leu Asn Thr Gly His His
                20                  25                  30

His His His Ala
        35

<210> SEQ ID NO 117
<211> LENGTH: 35
<212> TYPE: PRT
<213> ORGANISM: artificial sequence
<220> FEATURE:
<223> OTHER INFORMATION: hormone analogue

<400> SEQUENCE: 117

His Ser Gln Gly Thr Phe Thr Ser Asp Tyr Ser Lys Tyr Leu Asp Gln
1               5                  10                  15

Lys Arg Ala His Glu Phe Ile Glu Trp Leu Leu Asn Thr Gly His His
                20                  25                  30

His His Ala
        35

<210> SEQ ID NO 118
<211> LENGTH: 35
<212> TYPE: PRT
<213> ORGANISM: artificial sequence
<220> FEATURE:
<223> OTHER INFORMATION: hormone analogue

<400> SEQUENCE: 118

His Ser Gln Gly Thr Phe Thr Ser Asp Tyr Ser His Tyr Leu Asp Gln
1               5                  10                  15

Lys Arg Ala His Glu Phe Ile Gln Trp Leu Leu Asn Gly Gly His His
                20                  25                  30

His His Ala
        35

<210> SEQ ID NO 119
<211> LENGTH: 36
<212> TYPE: PRT
<213> ORGANISM: artificial sequence
<220> FEATURE:
<223> OTHER INFORMATION: hormone analogue

<400> SEQUENCE: 119

His Ser Gln Gly Thr Phe Thr Ser Asp Tyr Ser His Tyr Leu Asp Gln
1               5                  10                  15

Lys Arg Ala His Glu Phe Ile Gln Trp Leu Leu Asn Gly Gly His His
```

His His His Ala
        35

<210> SEQ ID NO 120
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 120

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gly
        35

<210> SEQ ID NO 121
<211> LENGTH: 34
<212> TYPE: PRT
<213> ORGANISM: artificial sequence
<220> FEATURE:
<223> OTHER INFORMATION: hormone analogue

<400> SEQUENCE: 121

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly His His His
            20                  25                  30

His Glu

<210> SEQ ID NO 122
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 122

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gln
        35

<210> SEQ ID NO 123
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)

<223> OTHER INFORMATION: AMIDATION

<400> SEQUENCE: 123

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His His Ala
        35

<210> SEQ ID NO 124
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 124

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His Gly
        35

<210> SEQ ID NO 125
<211> LENGTH: 35
<212> TYPE: PRT
<213> ORGANISM: artificial sequence
<220> FEATURE:
<223> OTHER INFORMATION: hormone analogue

<400> SEQUENCE: 125

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His Ala
        35

<210> SEQ ID NO 126
<211> LENGTH: 34
<212> TYPE: PRT
<213> ORGANISM: artificial sequence
<220> FEATURE:
<223> OTHER INFORMATION: hormone analogue

<400> SEQUENCE: 126

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr His His His
            20                  25                  30

His Ala

<210> SEQ ID NO 127
<211> LENGTH: 36
<212> TYPE: PRT
<213> ORGANISM: artificial sequence
<220> FEATURE:

<223> OTHER INFORMATION: hormone analogue

<400> SEQUENCE: 127

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala
        35

<210> SEQ ID NO 128
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 128

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala
        35

<210> SEQ ID NO 129
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 129

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala
        35

<210> SEQ ID NO 130
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 130

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His His Ala
        35

<210> SEQ ID NO 131
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 131

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly Gly His His
            20                  25                  30

His His Ala
        35

<210> SEQ ID NO 132
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 132

His Ser Gln Gly Thr Phe Thr Ser Asp Tyr Ser Lys Tyr Leu Asp Gln
1               5                   10                  15

Lys Arg Ala His Glu Phe Ile Gln Trp Leu Leu Asn Gly Gly His His
            20                  25                  30

His His Ala
        35

<210> SEQ ID NO 133
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 133

His Ser Gln Gly Thr Phe Thr Ser Asp Tyr Ser His Tyr Leu Asp Glu
1               5                   10                  15

Lys Arg Ala His Glu Phe Ile Gln Trp Leu Leu Asn Gly Gly His His
            20                  25                  30

His His Ala
        35

<210> SEQ ID NO 134
<211> LENGTH: 35
<212> TYPE: PRT
<213> ORGANISM: artificial sequence
<220> FEATURE:
<223> OTHER INFORMATION: hormone analogue

```
<220> FEATURE:
<221> NAME/KEY: MOD_RES
<222> LOCATION: (35)..(35)
<223> OTHER INFORMATION: AMIDATION

<400> SEQUENCE: 134

His Ser Gln Gly Thr Phe Thr Ser Asp Tyr Ser His Tyr Leu Asp Glu
1               5                   10                  15

Lys Arg Ala His Glu Phe Ile Glu Trp Leu Leu Asn Gly Gly His His
            20                  25                  30

His His Ala
        35

<210> SEQ ID NO 135
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 135

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His His Ala
        35

<210> SEQ ID NO 136
<211> LENGTH: 35
<212> TYPE: PRT
<213> ORGANISM: artificial sequence
<220> FEATURE:
<223> OTHER INFORMATION: hormone analogue

<400> SEQUENCE: 136

His Ser Gln Gly Thr Phe Thr Ser Asp Tyr Ser Lys Tyr Leu Asp Ser
1               5                   10                  15

Lys Arg Ala His Glu Phe Ile Glu Trp Leu Leu Asn Gly His His His
            20                  25                  30

His His Ala
        35

<210> SEQ ID NO 137
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 137

His Ser Gln Gly Thr Phe Thr Ser Asp Tyr Ser Lys Tyr Leu Asp Ser
1               5                   10                  15

Lys Arg Ala His Glu Phe Ile Glu Trp Leu Leu Asn Gly His His His
            20                  25                  30

His His Ala
```

<210> SEQ ID NO 138
<211> LENGTH: 34
<212> TYPE: PRT
<213> ORGANISM: artificial sequence
<220> FEATURE:
<223> OTHER INFORMATION: hormone analogue

<400> SEQUENCE: 138

His Ser Gln Gly Thr Phe Thr Ser Asp Tyr Ser Lys Tyr Leu Asp Ser
1               5                   10                  15
Arg Arg Ala His Glu Phe Ile Gln Trp Leu Leu Asn Gly His His His
            20                  25                  30
His Glu

<210> SEQ ID NO 139
<211> LENGTH: 35
<212> TYPE: PRT
<213> ORGANISM: artificial sequence
<220> FEATURE:
<223> OTHER INFORMATION: hormone analogue

<400> SEQUENCE: 139

His Ser Gln Gly Thr Phe Thr Ser Asp Tyr Ser Lys Tyr Leu Asp Glu
1               5                   10                  15
Lys Arg Ala His Asp Phe Ile Glu Trp Leu Leu Asn Gly His His His
            20                  25                  30
His His Ala
        35

<210> SEQ ID NO 140
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 140

His Ser Gln Gly Thr Phe Thr Ser Asp Tyr Ser Lys Tyr Leu Asp Glu
1               5                   10                  15
Lys Arg Ala His Asp Phe Ile Glu Trp Leu Leu Asn Gly His His His
            20                  25                  30
His His Ala
        35

<210> SEQ ID NO 141
<211> LENGTH: 35
<212> TYPE: PRT
<213> ORGANISM: artificial sequence
<220> FEATURE:
<223> OTHER INFORMATION: hormone analogue

<400> SEQUENCE: 141

His Ser Gln Gly Thr Phe Thr Ser Asp Tyr Ser Lys Tyr Leu Asp Glu
1               5                   10                  15
Lys Arg Ala His Glu Phe Ile Glu Trp Leu Leu Asn Thr His His His
            20                  25                  30
His His Ala

```
<210> SEQ ID NO 142
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 142
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Gln
        35

```
<210> SEQ ID NO 143
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 143
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Glu

```
<210> SEQ ID NO 144
<211> LENGTH: 34
<212> TYPE: PRT
<213> ORGANISM: artificial sequence
<220> FEATURE:
<223> OTHER INFORMATION: hormone analogue

<400> SEQUENCE: 144
```

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly His His His
            20                  25                  30

His Glu

```
<210> SEQ ID NO 145
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 145
```

-continued

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly His His His
            20                  25                  30

His Glu

<210> SEQ ID NO 146
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 146

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr Gly His His
            20                  25                  30

His Glu

<210> SEQ ID NO 147
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 147

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Gln
        35

<210> SEQ ID NO 148
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 148

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His Gln Gln
        35

<210> SEQ ID NO 149
<211> LENGTH: 36

```
<212> TYPE: PRT
<213> ORGANISM: artificial sequence
<220> FEATURE:
<223> OTHER INFORMATION: hormone analogue

<400> SEQUENCE: 149

His Ser Gln Gly Thr Phe Thr Ser Asp Tyr Ser Lys Tyr Leu Asp Glu
 1               5                  10                  15
Arg Arg Ala His Glu Phe Ile Glu Trp Leu Leu Asn Gly Gly His His
            20                  25                  30
His His Gln Gln
        35

<210> SEQ ID NO 150
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 150

His Ser Gln Gly Thr Phe Thr Ser Asp Tyr Ser His Tyr Leu Asp Gln
 1               5                  10                  15
Lys Arg Ala His Glu Phe Ile Glu Trp Leu Leu Asn Gly Gly His His
            20                  25                  30
His Glu

<210> SEQ ID NO 151
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 151

His Ser Gln Gly Thr Phe Thr Ser Asp Tyr Ser His Tyr Leu Asp Gln
 1               5                  10                  15
Lys Arg Ala His Glu Phe Ile Glu Trp Leu Leu Asn Gly Gly His His
            20                  25                  30
His Ala

<210> SEQ ID NO 152
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 152

His Ser Gln Gly Thr Phe Thr Ser Asp Tyr Ser Lys Tyr Leu Asp Glu
 1               5                  10                  15
Lys Arg Ala His Glu Phe Ile Glu Trp Leu Leu Asn Thr His His His
            20                  25                  30
```

His Ala

```
<210> SEQ ID NO 153
<211> LENGTH: 34
<212> TYPE: PRT
<213> ORGANISM: artificial sequence
<220> FEATURE:
<223> OTHER INFORMATION: hormone analogue

<400> SEQUENCE: 153
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His Ala

```
<210> SEQ ID NO 154
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 154
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His
            20                  25                  30

His Glu

```
<210> SEQ ID NO 155
<211> LENGTH: 34
<212> TYPE: PRT
<213> ORGANISM: artificial sequence
<220> FEATURE:
<223> OTHER INFORMATION: hormone analogue

<400> SEQUENCE: 155
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His Ala

```
<210> SEQ ID NO 156
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 156
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His

<210> SEQ ID NO 157
<211> LENGTH: 34
<212> TYPE: PRT
<213> ORGANISM: artificial sequence
<220> FEATURE:
<223> OTHER INFORMATION: hormone analogue

<400> SEQUENCE: 157

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His Glu

<210> SEQ ID NO 158
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 158

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His Glu

<210> SEQ ID NO 159
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 159

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His Gly His
            20                  25                  30

His

<210> SEQ ID NO 160
<211> LENGTH: 34
<212> TYPE: PRT
<213> ORGANISM: artificial sequence
<220> FEATURE:
<223> OTHER INFORMATION: hormone analogue

<400> SEQUENCE: 160

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His Gly

<210> SEQ ID NO 161
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 161

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His Gly

<210> SEQ ID NO 162
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 162

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His Ala
        35

<210> SEQ ID NO 163
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 163

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His Gln
        35

<210> SEQ ID NO 164
<211> LENGTH: 35
<212> TYPE: PRT
<213> ORGANISM: artificial sequence
<220> FEATURE:

<223> OTHER INFORMATION: hormone analogue

<400> SEQUENCE: 164

His Ser Gln Gly Thr Phe Thr Ser Asp Tyr Ser His Gln Leu Asp Gln
1               5                   10                  15

Lys Arg Ala His Glu Phe Ile Glu Trp Leu Leu Asn Gly Gly His His
            20                  25                  30

His His Gln
        35

<210> SEQ ID NO 165
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 165

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His His Ala
        35

<210> SEQ ID NO 166
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 166

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His His Glu
        35

<210> SEQ ID NO 167
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 167

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His His Glu
        35

<210> SEQ ID NO 168
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 168

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His Glu

<210> SEQ ID NO 169
<211> LENGTH: 36
<212> TYPE: PRT
<213> ORGANISM: artificial sequence
<220> FEATURE:
<223> OTHER INFORMATION: hormone analogue

<400> SEQUENCE: 169

His Ser Gln Gly Thr Phe Thr Ser Asp Tyr Ser Lys Tyr Leu Asp Ser
1               5                   10                  15

Arg Arg Ala His Glu Phe Ile Glu Trp Leu Leu Asn Gly Gly His His
            20                  25                  30

His His His Glu
        35

<210> SEQ ID NO 170
<211> LENGTH: 36
<212> TYPE: PRT
<213> ORGANISM: artificial sequence
<220> FEATURE:
<223> OTHER INFORMATION: hormone analogue

<400> SEQUENCE: 170

His Ser Gln Gly Thr Phe Thr Ser Asp Tyr Ser Lys Gln Leu Asp Glu
1               5                   10                  15

Arg Arg Ala His Glu Phe Ile Glu Trp Leu Leu Asn Gly Gly His His
            20                  25                  30

His His His Glu
        35

<210> SEQ ID NO 171
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 171

His Ser Gln Gly Thr Phe Thr Ser Asp Tyr Ser Lys Tyr Leu Asp Ser
1               5                   10                  15

```
Arg Arg Ala His Glu Phe Ile Glu Trp Leu Leu Asn Gly Gly His His
            20                  25                  30

His His His Glu
        35

<210> SEQ ID NO 172
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 172

His Ser Gln Gly Thr Phe Thr Ser Asp Tyr Ser Lys Gln Leu Asp Glu
1               5                   10                  15

Arg Arg Ala His Glu Phe Ile Glu Trp Leu Leu Asn Gly Gly His His
            20                  25                  30

His His His Glu
        35

<210> SEQ ID NO 173
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 173

His Ser Gln Gly Thr Phe Thr Ser Asp Tyr Ser Lys Tyr Leu Asp Ser
1               5                   10                  15

Lys Arg Ala His Glu Phe Ile Glu Trp Leu Leu Asn Thr His Gly His
            20                  25                  30

His Glu

<210> SEQ ID NO 174
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 174

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His
            20                  25                  30

His His Ser
        35

<210> SEQ ID NO 175
<211> LENGTH: 36
<212> TYPE: PRT
```

```
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 175
```

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ser Ala
        35

```
<210> SEQ ID NO 176
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 176
```

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His His Ala Ala
        35

```
<210> SEQ ID NO 177
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 177
```

His Ser Gln Gly Thr Phe Thr Ser Asp Tyr Ser Lys Gln Leu Asp Glu
1               5                   10                  15

Arg Arg Ala His Glu Phe Ile Gln Trp Leu Leu Asn Gly Gly His His
            20                  25                  30

His His Ala Ala
        35

```
<210> SEQ ID NO 178
<211> LENGTH: 36
<212> TYPE: PRT
<213> ORGANISM: artificial sequence
<220> FEATURE:
<223> OTHER INFORMATION: hormone analogue

<400> SEQUENCE: 178
```

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly His His His

His His Ser Gln
        35

<210> SEQ ID NO 179
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 179

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly Gly His His
            20                  25                  30

His His Ala
        35

<210> SEQ ID NO 180
<211> LENGTH: 36
<212> TYPE: PRT
<213> ORGANISM: artificial sequence
<220> FEATURE:
<223> OTHER INFORMATION: hormone analogue

<400> SEQUENCE: 180

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His His Gln
        35

<210> SEQ ID NO 181
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 181

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
            20                  25                  30

His His His Ala
        35

<210> SEQ ID NO 182
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES

```
<222> LOCATION: (36)..(36)
<223> OTHER INFORMATION: AMIDATION

<400> SEQUENCE: 182

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr Gly His His
            20                  25                  30

His His His Ala
        35

<210> SEQ ID NO 183
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 183

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Gln Glu
        35

<210> SEQ ID NO 184
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 184

His Ser Gln Gly Thr Phe Thr Ser Asp Tyr Ser Lys Gln Leu Asp Glu
1               5                   10                  15

Arg Arg Ala His Glu Phe Ile Gln Trp Leu Leu Asn Gly Gly His His
            20                  25                  30

His His His Ala
        35

<210> SEQ ID NO 185
<211> LENGTH: 36
<212> TYPE: PRT
<213> ORGANISM: artificial sequence
<220> FEATURE:
<223> OTHER INFORMATION: hormone analogue

<400> SEQUENCE: 185

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Gln Gln
        35
```

<210> SEQ ID NO 186
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 186

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His His Glu
        35

<210> SEQ ID NO 187
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 187

His Ser Gln Gly Thr Phe Thr Ser Asp Tyr Ser Lys Gln Leu Asp Glu
1               5                   10                  15

Arg Arg Ala His Glu Phe Ile Glu Trp Leu Leu Asn Thr Gly His His
            20                  25                  30

His His His Glu
        35

<210> SEQ ID NO 188
<211> LENGTH: 36
<212> TYPE: PRT
<213> ORGANISM: artificial sequence
<220> FEATURE:
<223> OTHER INFORMATION: hormone analogue

<400> SEQUENCE: 188

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
            20                  25                  30

His His His Ala
        35

<210> SEQ ID NO 189
<211> LENGTH: 35
<212> TYPE: PRT
<213> ORGANISM: artificial sequence
<220> FEATURE:
<223> OTHER INFORMATION: hormone analogue

<400> SEQUENCE: 189

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His His His

```
              20                  25                  30

His His Ser
        35

<210> SEQ ID NO 190
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 190

His Ser Gln Gly Thr Phe Thr Ser Asp Tyr Ser Lys Tyr Leu Asp Glu
1               5                  10                  15

Lys Arg Ala His Glu Phe Ile Glu Trp Leu Leu Asn Thr His His His
              20                  25                  30

His His Ser
        35

<210> SEQ ID NO 191
<211> LENGTH: 35
<212> TYPE: PRT
<213> ORGANISM: artificial sequence
<220> FEATURE:
<223> OTHER INFORMATION: hormone analogue

<400> SEQUENCE: 191

His Ser Gln Gly Thr Phe Thr Ser Asp Tyr Ser Lys Tyr Leu Asp Glu
1               5                  10                  15

Lys Arg Ala His Glu Phe Ile Glu Trp Leu Leu Asn Thr His His His
              20                  25                  30

His His Gln
        35

<210> SEQ ID NO 192
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 192

His Ser Gln Gly Thr Phe Thr Ser Asp Tyr Ser Lys Tyr Leu Asp Glu
1               5                  10                  15

Lys Arg Ala His Glu Phe Ile Glu Trp Leu Leu Asn Thr His His His
              20                  25                  30

His His Gln
        35

<210> SEQ ID NO 193
<211> LENGTH: 34
<212> TYPE: PRT
<213> ORGANISM: artificial sequence
<220> FEATURE:
<223> OTHER INFORMATION: hormone analogue

<400> SEQUENCE: 193
```

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His Glu

<210> SEQ ID NO 194
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 194

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His Glu

<210> SEQ ID NO 195
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 195

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
            20                  25                  30

His His Ala Ala
        35

<210> SEQ ID NO 196
<211> LENGTH: 35
<212> TYPE: PRT
<213> ORGANISM: artificial sequence
<220> FEATURE:
<223> OTHER INFORMATION: hormone analogue

<400> SEQUENCE: 196

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Ser
        35

<210> SEQ ID NO 197
<211> LENGTH: 35
<212> TYPE: PRT
<213> ORGANISM: artificial sequence
<220> FEATURE:

<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 197

His Ser Gln Gly Thr Phe Thr Ser Asp Tyr Ser Lys Tyr Leu Asp Glu
1               5                   10                  15
Arg Arg Ala His Glu Phe Ile Glu Trp Leu Leu Asn Thr Gly His His
            20                  25                  30
His His Ser
        35

<210> SEQ ID NO 198
<211> LENGTH: 35
<212> TYPE: PRT
<213> ORGANISM: artificial sequence
<220> FEATURE:
<223> OTHER INFORMATION: hormone analogue

<400> SEQUENCE: 198

His Ser Gln Gly Thr Phe Thr Ser Asp Tyr Ser Lys Tyr Leu Asp Glu
1               5                   10                  15
Arg Arg Ala His Glu Phe Ile Gln Trp Leu Leu Asn Thr Gly His His
            20                  25                  30
His His Ser
        35

<210> SEQ ID NO 199
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 199

His Ser Gln Gly Thr Phe Thr Ser Asp Tyr Ser Lys Tyr Leu Asp Glu
1               5                   10                  15
Arg Arg Ala His Glu Phe Ile Gln Trp Leu Leu Asn Thr Gly His His
            20                  25                  30
His His Ser
        35

<210> SEQ ID NO 200
<211> LENGTH: 36
<212> TYPE: PRT
<213> ORGANISM: artificial sequence
<220> FEATURE:
<223> OTHER INFORMATION: hormone analogue

<400> SEQUENCE: 200

His Ser Gln Gly Thr Phe Thr Ser Asp Tyr Ser Lys Tyr Leu Asp Glu
1               5                   10                  15
Arg Arg Ala His Glu Phe Ile Gln Trp Leu Leu Asn Thr Gly His His
            20                  25                  30
His His Gln Gln
        35

```
<210> SEQ ID NO 201
<211> LENGTH: 36
<212> TYPE: PRT
<213> ORGANISM: artificial sequence
<220> FEATURE:
<223> OTHER INFORMATION: hormone analogue

<400> SEQUENCE: 201

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gln Gln
        35

<210> SEQ ID NO 202
<211> LENGTH: 35
<212> TYPE: PRT
<213> ORGANISM: artificial sequence
<220> FEATURE:
<223> OTHER INFORMATION: hormone analogue

<400> SEQUENCE: 202

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Gly His His His
            20                  25                  30

His His Ser
        35

<210> SEQ ID NO 203
<211> LENGTH: 35
<212> TYPE: PRT
<213> ORGANISM: artificial sequence
<220> FEATURE:
<223> OTHER INFORMATION: hormone analogue

<400> SEQUENCE: 203

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly His His His
            20                  25                  30

His His Ser
        35

<210> SEQ ID NO 204
<211> LENGTH: 35
<212> TYPE: PRT
<213> ORGANISM: artificial sequence
<220> FEATURE:
<223> OTHER INFORMATION: hormone analogue

<400> SEQUENCE: 204

His Ser Gln Gly Thr Phe Thr Ser Asp Tyr Ser Lys Tyr Leu Asp Ser
1               5                   10                  15

Arg Arg Ala His Glu Phe Ile Glu Trp Leu Leu Asn Gly His His His
            20                  25                  30

His His Ser
        35

<210> SEQ ID NO 205
<211> LENGTH: 35
<212> TYPE: PRT
```

<213> ORGANISM: artificial sequence
<220> FEATURE:
<223> OTHER INFORMATION: hormone analogue

<400> SEQUENCE: 205

His Ser Gln Gly Thr Phe Thr Ser Asp Tyr Ser Lys Tyr Leu Asp Ser
1               5                   10                  15

Arg Arg Ala His Glu Phe Ile Gln Trp Leu Leu Asn Gly His His His
            20                  25                  30

His His Ser
        35

<210> SEQ ID NO 206
<211> LENGTH: 35
<212> TYPE: PRT
<213> ORGANISM: artificial sequence
<220> FEATURE:
<223> OTHER INFORMATION: hormone analogue

<400> SEQUENCE: 206

His Ser Gln Gly Thr Phe Thr Ser Asp Tyr Ser Lys Tyr Leu Asp Ser
1               5                   10                  15

Arg Arg Ala His Glu Phe Ile Gln Trp Leu Leu Asn Thr His His His
            20                  25                  30

His His Ser
        35

<210> SEQ ID NO 207
<211> LENGTH: 35
<212> TYPE: PRT
<213> ORGANISM: artificial sequence
<220> FEATURE:
<223> OTHER INFORMATION: hormone analogue

<400> SEQUENCE: 207

His Ser Gln Gly Thr Phe Thr Ser Asp Tyr Ser Lys Tyr Leu Asp Ser
1               5                   10                  15

Lys Arg Ala His Glu Phe Ile Glu Trp Leu Leu Asn Thr His His His
            20                  25                  30

His His Ala
        35

<210> SEQ ID NO 208
<211> LENGTH: 35
<212> TYPE: PRT
<213> ORGANISM: artificial sequence
<220> FEATURE:
<223> OTHER INFORMATION: hormone analogue

<400> SEQUENCE: 208

His Ser Gln Gly Thr Phe Thr Ser Asp Tyr Ser Lys Tyr Leu Asp Ser
1               5                   10                  15

Lys Arg Ala His Glu Phe Ile Glu Trp Leu Leu Asn Gly His His His
            20                  25                  30

His His Ser
        35

<210> SEQ ID NO 209
<211> LENGTH: 35
<212> TYPE: PRT
<213> ORGANISM: artificial sequence
<220> FEATURE:
<223> OTHER INFORMATION: hormone analogue

<400> SEQUENCE: 209

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Gly Gly His His
            20                  25                  30

His His Ser
        35

<210> SEQ ID NO 210
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 210

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His His His Glu
        35

<210> SEQ ID NO 211
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 211

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Gln Gln
        35

<210> SEQ ID NO 212
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 212

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His Ser

<210> SEQ ID NO 213
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 213

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His Gly
        35

<210> SEQ ID NO 214
<211> LENGTH: 35
<212> TYPE: PRT
<213> ORGANISM: artificial sequence
<220> FEATURE:
<223> OTHER INFORMATION: hormone analogue

<400> SEQUENCE: 214

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr Gly His His
            20                  25                  30

His His Ser
        35

<210> SEQ ID NO 215
<211> LENGTH: 35
<212> TYPE: PRT
<213> ORGANISM: artificial sequence
<220> FEATURE:
<223> OTHER INFORMATION: hormone analogue

<400> SEQUENCE: 215

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Ala
        35

<210> SEQ ID NO 216
<211> LENGTH: 35
<212> TYPE: PRT
<213> ORGANISM: artificial sequence
<220> FEATURE:
<223> OTHER INFORMATION: hormone analogue

<400> SEQUENCE: 216

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His His Ala
        35

<210> SEQ ID NO 217
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 217

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His His Ala
        35

<210> SEQ ID NO 218
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 218

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Gly

<210> SEQ ID NO 219
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 219

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His

<210> SEQ ID NO 220
<211> LENGTH: 36
<212> TYPE: PRT
<213> ORGANISM: artificial sequence
<220> FEATURE:
<223> OTHER INFORMATION: hormone analogue

<400> SEQUENCE: 220

His Ser Gln Gly Thr Phe Thr Ser Asp Tyr Ser Lys Gln Leu Asp Glu
1               5                   10                  15

Arg Arg Ala His Glu Phe Ile Glu Trp Leu Leu Asn Gly Gly His His
            20                  25                  30

His His Gln Gln
        35

<210> SEQ ID NO 221
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 221

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Ala Ala
        35

<210> SEQ ID NO 222
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 222

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Ala Ala
        35

<210> SEQ ID NO 223
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 223

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Gly Gly His His
            20                  25                  30

His His Ala Ala
        35

```
<210> SEQ ID NO 224
<211> LENGTH: 35
<212> TYPE: PRT
<213> ORGANISM: artificial sequence
<220> FEATURE:
<223> OTHER INFORMATION: hormone analogue

<400> SEQUENCE: 224

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Gln
        35

<210> SEQ ID NO 225
<211> LENGTH: 35
<212> TYPE: PRT
<213> ORGANISM: artificial sequence
<220> FEATURE:
<223> OTHER INFORMATION: hormone analogue

<400> SEQUENCE: 225

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr Gly His His
            20                  25                  30

His His Gln
        35

<210> SEQ ID NO 226
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 226

His Ser Gln Gly Thr Phe Thr Ser Asp Tyr Ser Lys Tyr Leu Asp Ser
1               5                   10                  15

Arg Arg Ala His Glu Phe Ile Glu Trp Leu Leu Asn Thr Gly His His
            20                  25                  30

His His Gln
        35

<210> SEQ ID NO 227
<211> LENGTH: 35
<212> TYPE: PRT
<213> ORGANISM: artificial sequence
<220> FEATURE:
<223> OTHER INFORMATION: hormone analogue

<400> SEQUENCE: 227

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His Ser
        35
```

<210> SEQ ID NO 228
<211> LENGTH: 35
<212> TYPE: PRT
<213> ORGANISM: artificial sequence
<220> FEATURE:
<223> OTHER INFORMATION: hormone analogue

<400> SEQUENCE: 228

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
            20                  25                  30

His His Ala
        35

<210> SEQ ID NO 229
<211> LENGTH: 37
<212> TYPE: PRT
<213> ORGANISM: artificial sequence
<220> FEATURE:
<223> OTHER INFORMATION: hormone analogue

<400> SEQUENCE: 229

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala Ala
        35

<210> SEQ ID NO 230
<211> LENGTH: 37
<212> TYPE: PRT
<213> ORGANISM: artificial sequence
<220> FEATURE:
<223> OTHER INFORMATION: hormone analogue

<400> SEQUENCE: 230

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala Ala
        35

<210> SEQ ID NO 231
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 231

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His Ala Ala Ala

<210> SEQ ID NO 232
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 232

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His Gly Ala Ala
        35

<210> SEQ ID NO 233
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 233

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

Gly His Ala Ala
        35

<210> SEQ ID NO 234
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 234

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala
        35

<210> SEQ ID NO 235
<211> LENGTH: 37
<212> TYPE: PRT
<213> ORGANISM: artificial sequence
<220> FEATURE:
<223> OTHER INFORMATION: hormone analogue

```
<400> SEQUENCE: 235

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
                20                  25                  30

His His His Ala Ala
        35

<210> SEQ ID NO 236
<211> LENGTH: 37
<212> TYPE: PRT
<213> ORGANISM: artificial sequence
<220> FEATURE:
<223> OTHER INFORMATION: hormone analogue

<400> SEQUENCE: 236

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
                20                  25                  30

His His His Ala Ala
        35

<210> SEQ ID NO 237
<211> LENGTH: 37
<212> TYPE: PRT
<213> ORGANISM: artificial sequence
<220> FEATURE:
<223> OTHER INFORMATION: hormone analogue

<400> SEQUENCE: 237

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
                20                  25                  30

His His His Ala Ala
        35

<210> SEQ ID NO 238
<211> LENGTH: 37
<212> TYPE: PRT
<213> ORGANISM: artificial sequence
<220> FEATURE:
<223> OTHER INFORMATION: hormone analogue

<400> SEQUENCE: 238

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr Gly His His
                20                  25                  30

His His His Ala Ala
        35

<210> SEQ ID NO 239
<211> LENGTH: 35
<212> TYPE: PRT
<213> ORGANISM: artificial sequence
<220> FEATURE:
<223> OTHER INFORMATION: hormone analogue

<400> SEQUENCE: 239

His Ser Gln Gly Thr Phe Thr Ser Asp Tyr Ser Lys Tyr Leu Asp Glu
```

```
                1               5                  10                 15
His Ser Gln Gly Thr Phe Thr Ser Asp Tyr Ser Lys Tyr Leu Asp Glu
                20                 25                 30
Arg Arg Ala His Glu Phe Ile Gln Trp Leu Leu Asn Gly Gly His His
                35
His His Gly

<210> SEQ ID NO 240
<211> LENGTH: 35
<212> TYPE: PRT
<213> ORGANISM: artificial sequence
<220> FEATURE:
<223> OTHER INFORMATION: hormone analogue

<400> SEQUENCE: 240

1               5                  10                 15
His Ser Gln Gly Thr Phe Thr Ser Asp Tyr Ser Lys Tyr Leu Asp Glu
                20                 25                 30
Arg Arg Ala His Glu Phe Ile Gln Trp Leu Leu Asn Gly His His His
                35
His His Gly

<210> SEQ ID NO 241
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 241

1               5                  10                 15
His Ser Gln Gly Thr Phe Thr Ser Asp Tyr Ser Lys Tyr Leu Asp Glu
                20                 25                 30
Arg Arg Ala His Glu Phe Ile Gln Trp Leu Leu Asn Gly His His His
                35
His His Gly

<210> SEQ ID NO 242
<211> LENGTH: 37
<212> TYPE: PRT
<213> ORGANISM: artificial sequence
<220> FEATURE:
<223> OTHER INFORMATION: hormone analogue

<400> SEQUENCE: 242

1               5                  10                 15
His Ser Gln Gly Thr Phe Thr Ser Asp Tyr Ser Lys Tyr Leu Asp Glu
                20                 25                 30
Arg Arg Ala His Glu Phe Ile Gln Trp Leu Leu Asn Gly Gly His His
                35
His His Ala Ala Gly

<210> SEQ ID NO 243
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
```

<223> OTHER INFORMATION: AMIDATION

<400> SEQUENCE: 243

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gly Ala
        35

<210> SEQ ID NO 244
<211> LENGTH: 37
<212> TYPE: PRT
<213> ORGANISM: artificial sequence
<220> FEATURE:
<223> OTHER INFORMATION: hormone analogue

<400> SEQUENCE: 244

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Ala Gly
        35

<210> SEQ ID NO 245
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 245

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gln Ala
        35

<210> SEQ ID NO 246
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 246

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Ala Gln
        35

```
<210> SEQ ID NO 247
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 247

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly Gly His His
            20                  25                  30

His His Gln Gln
        35

<210> SEQ ID NO 248
<211> LENGTH: 34
<212> TYPE: PRT
<213> ORGANISM: artificial sequence
<220> FEATURE:
<223> OTHER INFORMATION: hormone analogue

<400> SEQUENCE: 248

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30

His Gly

<210> SEQ ID NO 249
<211> LENGTH: 35
<212> TYPE: PRT
<213> ORGANISM: artificial sequence
<220> FEATURE:
<223> OTHER INFORMATION: hormone analogue

<400> SEQUENCE: 249

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30

His Ala Gly
        35

<210> SEQ ID NO 250
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 250

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30
```

His Gly

<210> SEQ ID NO 251
<211> LENGTH: 34
<212> TYPE: PRT
<213> ORGANISM: artificial sequence
<220> FEATURE:
<223> OTHER INFORMATION: hormone analogue

<400> SEQUENCE: 251

His Ser Gln Gly Thr Phe Thr Ser Asp Tyr Ser Lys Tyr Leu Asp Glu
1               5                   10                  15

Lys Arg Ala His Glu Phe Ile Glu Trp Leu Leu Asn Thr His Gly His
            20                  25                  30

His Gly

<210> SEQ ID NO 252
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 252

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr His Gly His
            20                  25                  30

His

<210> SEQ ID NO 253
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 253

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr His Gly His
            20                  25                  30

His

<210> SEQ ID NO 254
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 254

His Ser Gln Gly Thr Phe Thr Ser Asp Tyr Ser Lys Tyr Leu Asp Glu

```
1               5                   10                  15
Arg Arg Ala His Glu Phe Ile Gln Trp Leu Leu Asn Thr His His His
            20                  25                  30

His Ala

<210> SEQ ID NO 255
<211> LENGTH: 34
<212> TYPE: PRT
<213> ORGANISM: artificial sequence
<220> FEATURE:
<223> OTHER INFORMATION: hormone analogue

<400> SEQUENCE: 255

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30

His Ala

<210> SEQ ID NO 256
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 256

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Ala

<210> SEQ ID NO 257
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 257

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His Gly His
            20                  25                  30

His

<210> SEQ ID NO 258
<211> LENGTH: 34
<212> TYPE: PRT
<213> ORGANISM: artificial sequence
<220> FEATURE:
<223> OTHER INFORMATION: hormone analogue

<400> SEQUENCE: 258
```

```
His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His Gly His
            20                  25                  30

His Gly

<210> SEQ ID NO 259
<211> LENGTH: 35
<212> TYPE: PRT
<213> ORGANISM: artificial sequence
<220> FEATURE:
<223> OTHER INFORMATION: hormone analogue

<400> SEQUENCE: 259

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Gly Gly
        35

<210> SEQ ID NO 260
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 260

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Gly Gly
        35

<210> SEQ ID NO 261
<211> LENGTH: 35
<212> TYPE: PRT
<213> ORGANISM: artificial sequence
<220> FEATURE:
<223> OTHER INFORMATION: hormone analogue

<400> SEQUENCE: 261

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Ala Ala
        35

<210> SEQ ID NO 262
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
```

<223> OTHER INFORMATION: AMIDATION

<400> SEQUENCE: 262

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Ala Ala
        35

<210> SEQ ID NO 263
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 263

His Ser Gln Gly Thr Phe Thr Ser Asp Tyr Ser Lys Tyr Leu Asp Gln
1               5                   10                  15

Arg Arg Ala His Glu Phe Ile Glu Trp Leu Leu Asn Thr Gly His His
            20                  25                  30

His His

<210> SEQ ID NO 264
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 264

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Thr Gly His His
            20                  25                  30

His

<210> SEQ ID NO 265
<211> LENGTH: 33
<212> TYPE: PRT
<213> ORGANISM: artificial sequence
<220> FEATURE:
<223> OTHER INFORMATION: hormone analogue

<400> SEQUENCE: 265

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

Gly

<210> SEQ ID NO 266
<211> LENGTH: 33
<212> TYPE: PRT

<213> ORGANISM: artificial sequence
<220> FEATURE:
<223> OTHER INFORMATION: hormone analogue

<400> SEQUENCE: 266

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30

Gly

<210> SEQ ID NO 267
<211> LENGTH: 35
<212> TYPE: PRT
<213> ORGANISM: artificial sequence
<220> FEATURE:
<223> OTHER INFORMATION: hormone analogue

<400> SEQUENCE: 267

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Thr His His His
            20                  25                  30

His His Gly
        35

<210> SEQ ID NO 268
<211> LENGTH: 34
<212> TYPE: PRT
<213> ORGANISM: artificial sequence
<220> FEATURE:
<223> OTHER INFORMATION: hormone analogue

<400> SEQUENCE: 268

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly His His His
            20                  25                  30

His Gly

<210> SEQ ID NO 269
<211> LENGTH: 34
<212> TYPE: PRT
<213> ORGANISM: artificial sequence
<220> FEATURE:
<223> OTHER INFORMATION: hormone analogue

<400> SEQUENCE: 269

His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His Gly His
            20                  25                  30

His Gly

<210> SEQ ID NO 270
<211> LENGTH: 34
<212> TYPE: PRT
<213> ORGANISM: artificial sequence
<220> FEATURE:
<223> OTHER INFORMATION: hormone analogue

<400> SEQUENCE: 270

```
His Ser Gln Gly Thr Phe Thr Ser Asp Tyr Ser Lys Tyr Leu Asp Glu
1               5                   10                  15

Arg Arg Ala His Glu Phe Ile Gln Trp Leu Leu Asn Gly His His His
            20                  25                  30

His Gly

<210> SEQ ID NO 271
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 271

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His His Gln
        35

<210> SEQ ID NO 272
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 272

His Ser Gln Gly Thr Phe Thr Ser Asp Tyr Ser Lys Tyr Leu Asp Gln
1               5                   10                  15

Lys Arg Ala His Glu Phe Ile Glu Trp Leu Leu Asn Gly Gly His His
            20                  25                  30

His His Gln
        35

<210> SEQ ID NO 273
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 273

His Ser Gln Gly Thr Phe Thr Ser Asp Tyr Ser Lys Tyr Leu Asp Gln
1               5                   10                  15

Lys Arg Ala His Glu Phe Ile Gln Trp Leu Leu Asn Gly Gly His His
            20                  25                  30

His His Gln
        35

<210> SEQ ID NO 274
```

<211> LENGTH: 33
<212> TYPE: PRT
<213> ORGANISM: artificial sequence
<220> FEATURE:
<223> OTHER INFORMATION: hormone analogue

<400> SEQUENCE: 274

His Ser Gln Gly Thr Phe Thr Ser Asp Tyr Ser Lys Tyr Leu Asp Glu
1               5                   10                  15
Arg Arg Ala His Glu Phe Val Glu Trp Leu Leu Asn Thr His His His
            20                  25                  30
Gly

<210> SEQ ID NO 275
<211> LENGTH: 33
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (33)..(33)
<223> OTHER INFORMATION: AMIDATION

<400> SEQUENCE: 275

His Ser Gln Gly Thr Phe Thr Ser Asp Tyr Ser Lys Tyr Leu Asp Glu
1               5                   10                  15
Arg Arg Ala His Glu Phe Val Glu Trp Leu Leu Asn Thr His His His
            20                  25                  30
Gly

<210> SEQ ID NO 276
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 276

His Ser Gln Gly Thr Phe Thr Ser Asp Tyr Ser Lys Tyr Leu Asp Glu
1               5                   10                  15
Arg Arg Ala His Glu Phe Val Gln Trp Leu Leu Asn Gly Gly His His
            20                  25                  30
His His Ala Ala
        35

<210> SEQ ID NO 277
<211> LENGTH: 34
<212> TYPE: PRT
<213> ORGANISM: artificial sequence
<220> FEATURE:
<223> OTHER INFORMATION: hormone analogue

<400> SEQUENCE: 277

His Ser Gln Gly Thr Phe Thr Ser Asp Tyr Ser Lys Tyr Leu Asp Glu
1               5                   10                  15
Arg Arg Ala His Glu Phe Val Gln Trp Leu Leu Asn Gly His His His
            20                  25                  30
His Gly

```
<210> SEQ ID NO 278
<211> LENGTH: 36
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (36)..(36)
<223> OTHER INFORMATION: AMIDATION

<400> SEQUENCE: 278

His Ser Gln Gly Thr Phe Thr Ser Asp Tyr Ser Lys Tyr Leu Asp Glu
1               5                   10                  15

Arg Arg Ala His Glu Phe Val Glu Trp Leu Leu Asn Gly Gly His His
            20                  25                  30

His His Gln Gln
        35

<210> SEQ ID NO 279
<211> LENGTH: 34
<212> TYPE: PRT
<213> ORGANISM: artificial sequence
<220> FEATURE:
<223> OTHER INFORMATION: hormone analogue

<400> SEQUENCE: 279

His Ser Gln Gly Thr Phe Thr Ser Asp Tyr Ser Lys Tyr Leu Asp Glu
1               5                   10                  15

Arg Arg Ala His Glu Phe Val Gln Trp Leu Leu Asn Thr His His His
            20                  25                  30

His Gly

<210> SEQ ID NO 280
<211> LENGTH: 34
<212> TYPE: PRT
<213> ORGANISM: artificial sequence
<220> FEATURE:
<223> OTHER INFORMATION: hormone analogue

<400> SEQUENCE: 280

His Ser Gln Gly Thr Phe Thr Ser Asp Tyr Ser Lys Tyr Leu Asp Glu
1               5                   10                  15

Lys Arg Ala His Glu Phe Ile Gln Trp Leu Leu Asn Thr His His His
            20                  25                  30

His Gly

<210> SEQ ID NO 281
<211> LENGTH: 33
<212> TYPE: PRT
<213> ORGANISM: artificial sequence
<220> FEATURE:
<223> OTHER INFORMATION: hormone analogue

<400> SEQUENCE: 281

His Ser Gln Gly Thr Phe Thr Ser Asp Tyr Ser Lys Tyr Leu Asp Glu
1               5                   10                  15

Arg Arg Ala His Glu Phe Ile Glu Trp Leu Leu Asn Thr His His His
            20                  25                  30

Gly

<210> SEQ ID NO 282
```

```
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 282

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His Gly
        35

<210> SEQ ID NO 283
<211> LENGTH: 35
<212> TYPE: PRT
<213> ORGANISM: artificial sequence
<220> FEATURE:
<223> OTHER INFORMATION: hormone analogue

<400> SEQUENCE: 283

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His Gly
        35

<210> SEQ ID NO 284
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 284

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30

His His Gly
        35

<210> SEQ ID NO 285
<211> LENGTH: 35
<212> TYPE: PRT
<213> ORGANISM: artificial sequence
<220> FEATURE:
<223> OTHER INFORMATION: hormone analogue

<400> SEQUENCE: 285

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Thr Gly His His
            20                  25                  30
```

His His Gly
      35

<210> SEQ ID NO 286
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 286

His Ser Gln Gly Thr Phe Thr Ser Asp Tyr Ser His Gln Leu Asp Gln
1               5                   10                  15

Lys Arg Ala His Glu Phe Ile Glu Trp Leu Leu Asn Gly Gly His His
            20                  25                  30

His His Gln
      35

<210> SEQ ID NO 287
<211> LENGTH: 34
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (34)..(34)
<223> OTHER INFORMATION: AMIDATION

<400> SEQUENCE: 287

His Ser Gln Gly Thr Phe Thr Ser Asp Tyr Ser His Tyr Leu Asp Gln
1               5                   10                  15

Lys Arg Ala His Glu Phe Ile Glu Trp Leu Leu Asn Gly Gly His His
            20                  25                  30

His His

<210> SEQ ID NO 288
<211> LENGTH: 35
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (35)..(35)
<223> OTHER INFORMATION: AMIDATION

<400> SEQUENCE: 288

His Ser Gln Gly Thr Phe Thr Ser Asp Tyr Ser His Tyr Leu Asp Gln
1               5                   10                  15

Lys Arg Ala His Glu Phe Ile Gln Trp Leu Leu Asn Gly Gly His His
            20                  25                  30

His His Gln
      35

<210> SEQ ID NO 289
<211> LENGTH: 29
<212> TYPE: PRT
<213> ORGANISM: artificial sequence
<220> FEATURE:
<223> OTHER INFORMATION: glucagon analogue
<220> FEATURE:

```
<221> NAME/KEY: MISC_FEATURE
<222> LOCATION: (10)..(10)
<223> OTHER INFORMATION: The residue at this position is Leu or Tyr
<220> FEATURE:
<221> NAME/KEY: MISC_FEATURE
<222> LOCATION: (12)..(12)
<223> OTHER INFORMATION: The residue at this position is Arg, His or Lys
<220> FEATURE:
<221> NAME/KEY: MISC_FEATURE
<222> LOCATION: (13)..(13)
<223> OTHER INFORMATION: The residue at this position is Gln, His or Tyr
<220> FEATURE:
<221> NAME/KEY: MISC_FEATURE
<222> LOCATION: (15)..(15)
<223> OTHER INFORMATION: The residue at this position is Asp or Glu
<220> FEATURE:
<221> NAME/KEY: MISC_FEATURE
<222> LOCATION: (16)..(16)
<223> OTHER INFORMATION: The residue at this position is Gln, Glu or Ser
<220> FEATURE:
<221> NAME/KEY: MISC_FEATURE
<222> LOCATION: (17)..(17)
<223> OTHER INFORMATION: The residue at this position is Arg, His or Lys
<220> FEATURE:
<221> NAME/KEY: MISC_FEATURE
<222> LOCATION: (18)..(18)
<223> OTHER INFORMATION: The residue at this position is Arg or Lys
<220> FEATURE:
<221> NAME/KEY: MISC_FEATURE
<222> LOCATION: (20)..(20)
<223> OTHER INFORMATION: The residue at this position is Gln or His
<220> FEATURE:
<221> NAME/KEY: MISC_FEATURE
<222> LOCATION: (21)..(21)
<223> OTHER INFORMATION: The residue at this position is Asp, Glu or His
<220> FEATURE:
<221> NAME/KEY: MISC_FEATURE
<222> LOCATION: (23)..(23)
<223> OTHER INFORMATION: The residue at this position is Ile or Val
<220> FEATURE:
<221> NAME/KEY: MISC_FEATURE
<222> LOCATION: (24)..(24)
<223> OTHER INFORMATION: The residue at this position is Gln or Glu
<220> FEATURE:
<221> NAME/KEY: NON_TER
<222> LOCATION: (29)..(29)
<220> FEATURE:
<221> NAME/KEY: MISC_FEATURE
<222> LOCATION: (29)..(29)
<223> OTHER INFORMATION: The residue at this position is Gly or Thr

<400> SEQUENCE: 289

His Ser Gln Gly Thr Phe Thr Ser Asp Leu Ser Arg Gln Leu Asp Gln
1               5                   10                  15

Arg Arg Ala Gln Asp Phe Ile Gln Trp Leu Leu Asn Gly
            20                  25

<210> SEQ ID NO 290
<211> LENGTH: 29
<212> TYPE: PRT
<213> ORGANISM: artificial sequence
<220> FEATURE:
<223> OTHER INFORMATION: GLP1 analogue
<220> FEATURE:
<221> NAME/KEY: MISC_FEATURE
<222> LOCATION: (2)..(2)
<223> OTHER INFORMATION: The residue at this position is Gly or Ser
<220> FEATURE:
<221> NAME/KEY: MISC_FEATURE
<222> LOCATION: (3)..(3)
<223> OTHER INFORMATION: The residue at this position is Gln or Glu
<220> FEATURE:
<221> NAME/KEY: MISC_FEATURE
<222> LOCATION: (10)..(10)
<223> OTHER INFORMATION: The residue at this position is Leu or Tyr
<220> FEATURE:
```

```
<221> NAME/KEY: MISC_FEATURE
<222> LOCATION: (12)..(12)
<223> OTHER INFORMATION: The residue at this position is His or Lys
<220> FEATURE:
<221> NAME/KEY: MISC_FEATURE
<222> LOCATION: (13)..(13)
<223> OTHER INFORMATION: The residue at this position is Gln or Tyr
<220> FEATURE:
<221> NAME/KEY: MISC_FEATURE
<222> LOCATION: (16)..(16)
<223> OTHER INFORMATION: The residue at this position is Ala, Glu or Ser
<220> FEATURE:
<221> NAME/KEY: MISC_FEATURE
<222> LOCATION: (17)..(17)
<223> OTHER INFORMATION: The residue at this position is Gln or Glu
<220> FEATURE:
<221> NAME/KEY: MISC_FEATURE
<222> LOCATION: (19)..(19)
<223> OTHER INFORMATION: The residue at this position is Ala, Ile, Leu
      or Val
<220> FEATURE:
<221> NAME/KEY: MISC_FEATURE
<222> LOCATION: (20)..(20)
<223> OTHER INFORMATION: The residue at this position is Arg or His
<220> FEATURE:
<221> NAME/KEY: MISC_FEATURE
<222> LOCATION: (21)..(21)
<223> OTHER INFORMATION: The residue at this position is Ile or Leu
<220> FEATURE:
<221> NAME/KEY: MISC_FEATURE
<222> LOCATION: (23)..(23)
<223> OTHER INFORMATION: The residue at this position is Ile or Val
<220> FEATURE:
<221> NAME/KEY: MISC_FEATURE
<222> LOCATION: (24)..(24)
<223> OTHER INFORMATION: The residue at this position is Gln or Glu
<220> FEATURE:
<221> NAME/KEY: MISC_FEATURE
<222> LOCATION: (27)..(27)
<223> OTHER INFORMATION: The residue at this position is Leu or Lys
<220> FEATURE:
<221> NAME/KEY: MISC_FEATURE
<222> LOCATION: (28)..(28)
<223> OTHER INFORMATION: The residue at this position is Asn, Gln or Lys
<220> FEATURE:
<221> NAME/KEY: NON_TER
<222> LOCATION: (29)..(29)
<220> FEATURE:
<221> NAME/KEY: MISC_FEATURE
<222> LOCATION: (29)..(29)
<223> OTHER INFORMATION: The residue at this position is Gly or Thr

<400> SEQUENCE: 290

His Gly Gln Gly Thr Phe Thr Ser Asp Leu Ser His Gln Leu Glu Ala
1               5                   10                  15
Gln Ala Ala Arg Ile Phe Ile Gln Trp Leu Leu Asn Gly
            20                  25

<210> SEQ ID NO 291
<211> LENGTH: 10
<212> TYPE: PRT
<213> ORGANISM: artificial sequence
<220> FEATURE:
<223> OTHER INFORMATION: hormone analogue
<220> FEATURE:
<221> NAME/KEY: MISC_FEATURE
<222> LOCATION: (1)..(1)
<223> OTHER INFORMATION: The residue at this position is Gly or His
<220> FEATURE:
<221> NAME/KEY: MOD_RES
<222> LOCATION: (1)..(10)
<223> OTHER INFORMATION: AMIDATION - the C-terminal residue may be
      optionally amidated
<220> FEATURE:
<221> NAME/KEY: NON_TER
<222> LOCATION: (1)..(1)
```

```
<220> FEATURE:
<221> NAME/KEY: MISC_FEATURE
<222> LOCATION: (2)..(2)
<223> OTHER INFORMATION: The residue at this position is absent, or is
      Gly or His
<220> FEATURE:
<221> NAME/KEY: MISC_FEATURE
<222> LOCATION: (3)..(3)
<223> OTHER INFORMATION: The residue at this position is absent, or is
      Gly or His
<220> FEATURE:
<221> NAME/KEY: MISC_FEATURE
<222> LOCATION: (4)..(4)
<223> OTHER INFORMATION: The residue at this position is absent, or is
      Gly or His
<220> FEATURE:
<221> NAME/KEY: MISC_FEATURE
<222> LOCATION: (5)..(5)
<223> OTHER INFORMATION: The residue at this position is absent, or is
      His
<220> FEATURE:
<221> NAME/KEY: MISC_FEATURE
<222> LOCATION: (6)..(6)
<223> OTHER INFORMATION: The residue at this position is absent, or is
      His
<220> FEATURE:
<221> NAME/KEY: MISC_FEATURE
<222> LOCATION: (7)..(7)
<223> OTHER INFORMATION: The residue at this position is absent, or is
      His
<220> FEATURE:
<221> NAME/KEY: MISC_FEATURE
<222> LOCATION: (8)..(8)
<223> OTHER INFORMATION: The residue at this position is absent, or is
      Ala, Gln, Glu, Gly or Ser
<220> FEATURE:
<221> NAME/KEY: MISC_FEATURE
<222> LOCATION: (9)..(9)
<223> OTHER INFORMATION: The residue at this position is absent, or is
      Ala, Gln, Glu, Gly or Ser
<220> FEATURE:
<221> NAME/KEY: MISC_FEATURE
<222> LOCATION: (10)..(10)
<223> OTHER INFORMATION: The residue at this position is absent, or is
      Ala, Gln, Glu, Gly or Ser

<400> SEQUENCE: 291

Gly Gly Gly Gly His His His Ala Ala Ala
1               5                   10

<210> SEQ ID NO 292
<211> LENGTH: 10
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (1)..(10)
<223> OTHER INFORMATION: AMIDATION - the C-terminal residue may be
      optionally amidated
<220> FEATURE:
<221> NAME/KEY: MISC_FEATURE
<222> LOCATION: (2)..(2)
<223> OTHER INFORMATION: The residue at this position is absent, or is
      Gly or His
<220> FEATURE:
<221> NAME/KEY: MISC_FEATURE
<222> LOCATION: (3)..(3)
<223> OTHER INFORMATION: The residue at this position is absent, or is
      Gly or His
<220> FEATURE:
<221> NAME/KEY: MISC_FEATURE
<222> LOCATION: (4)..(4)
```

```
<223> OTHER INFORMATION: The residue at this position is absent, or is
      Gly or His
<220> FEATURE:
<221> NAME/KEY: MISC_FEATURE
<222> LOCATION: (5)..(5)
<223> OTHER INFORMATION: The residue at this position is absent, or is
      His
<220> FEATURE:
<221> NAME/KEY: MISC_FEATURE
<222> LOCATION: (6)..(6)
<223> OTHER INFORMATION: The residue at this position is absent, or is
      His
<220> FEATURE:
<221> NAME/KEY: MISC_FEATURE
<222> LOCATION: (7)..(7)
<223> OTHER INFORMATION: The residue at this position is absent, or is
      His
<220> FEATURE:
<221> NAME/KEY: MISC_FEATURE
<222> LOCATION: (8)..(8)
<223> OTHER INFORMATION: The residue at this position is absent, or is
      Ala, Gln, Glu, Gly or Ser
<220> FEATURE:
<221> NAME/KEY: MISC_FEATURE
<222> LOCATION: (9)..(9)
<223> OTHER INFORMATION: The residue at this position is absent, or is
      Ala, Gln, Glu, Gly or Ser
<220> FEATURE:
<221> NAME/KEY: MISC_FEATURE
<222> LOCATION: (10)..(10)
<223> OTHER INFORMATION: The residue at this position is absent, or is
      Ala, Gln, Glu, Gly or Ser

<400> SEQUENCE: 292

Gly Gly Gly Gly His His His Ala Ala Ala
1               5                   10

<210> SEQ ID NO 293
<211> LENGTH: 10
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (1)..(10)
<223> OTHER INFORMATION: AMIDATION - the C-terminal residue may be
      optionally amidated
<220> FEATURE:
<221> NAME/KEY: NON_TER
<222> LOCATION: (1)..(1)
<220> FEATURE:
<221> NAME/KEY: MISC_FEATURE
<222> LOCATION: (1)..(1)
<223> OTHER INFORMATION: The residue at this position is Gly or His
<220> FEATURE:
<221> NAME/KEY: MISC_FEATURE
<222> LOCATION: (3)..(3)
<223> OTHER INFORMATION: The residue at this position is absent, or is
      Gly or His
<220> FEATURE:
<221> NAME/KEY: MISC_FEATURE
<222> LOCATION: (4)..(4)
<223> OTHER INFORMATION: The residue at this position is absent, or is
      Gly or His
<220> FEATURE:
<221> NAME/KEY: MISC_FEATURE
<222> LOCATION: (5)..(5)
<223> OTHER INFORMATION: The residue at this position absent, or is His
<220> FEATURE:
<221> NAME/KEY: MISC_FEATURE
<222> LOCATION: (6)..(6)
<223> OTHER INFORMATION: The residue at this position absent, or is His
<220> FEATURE:
<221> NAME/KEY: MISC_FEATURE
<222> LOCATION: (7)..(7)
<223> OTHER INFORMATION: The residue at this position absent, or is His
```

```
<220> FEATURE:
<221> NAME/KEY: MISC_FEATURE
<222> LOCATION: (8)..(8)
<223> OTHER INFORMATION: The residue at this position absent, or is Ala,
      Gln, Glu, Gly or Ser
<220> FEATURE:
<221> NAME/KEY: MISC_FEATURE
<222> LOCATION: (9)..(9)
<223> OTHER INFORMATION: The residue at this position absent, or is Ala,
      Gln, Glu, Gly or Ser
<220> FEATURE:
<221> NAME/KEY: MISC_FEATURE
<222> LOCATION: (10)..(10)
<223> OTHER INFORMATION: The residue at this position absent, or is Ala,
      Gln, Glu, Gly or Ser

<400> SEQUENCE: 293

Gly Gly Gly Gly His His His Ala Ala Ala
1               5                   10

<210> SEQ ID NO 294
<211> LENGTH: 10
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (1)..(10)
<223> OTHER INFORMATION: AMIDATION - the C-terminal residue may be
      optionally amidated
<220> FEATURE:
<221> NAME/KEY: MISC_FEATURE
<222> LOCATION: (1)..(1)
<223> OTHER INFORMATION: The residue at this position is Gly or His
<220> FEATURE:
<221> NAME/KEY: MISC_FEATURE
<222> LOCATION: (2)..(2)
<223> OTHER INFORMATION: The residue at this position is Gly or His
<220> FEATURE:
<221> NAME/KEY: MISC_FEATURE
<222> LOCATION: (4)..(4)
<223> OTHER INFORMATION: The residue at this position absent, or is Gly
      or His
<220> FEATURE:
<221> NAME/KEY: MISC_FEATURE
<222> LOCATION: (5)..(5)
<223> OTHER INFORMATION: The residue at this position absent, or is His
<220> FEATURE:
<221> NAME/KEY: MISC_FEATURE
<222> LOCATION: (6)..(6)
<223> OTHER INFORMATION: The residue at this position absent, or is His
<220> FEATURE:
<221> NAME/KEY: MISC_FEATURE
<222> LOCATION: (7)..(7)
<223> OTHER INFORMATION: The residue at this position absent, or is His
<220> FEATURE:
<221> NAME/KEY: MISC_FEATURE
<222> LOCATION: (8)..(8)
<223> OTHER INFORMATION: The residue at this position absent, or is Ala,
      Gln, Glu, Gly or Ser
<220> FEATURE:
<221> NAME/KEY: MISC_FEATURE
<222> LOCATION: (9)..(9)
<223> OTHER INFORMATION: The residue at this position absent, or is Ala,
      Gln, Glu, Gly or Ser
<220> FEATURE:
<221> NAME/KEY: MISC_FEATURE
<222> LOCATION: (10)..(10)
<223> OTHER INFORMATION: The residue at this position absent, or is Ala,
      Gln, Glu, Gly or Ser

<400> SEQUENCE: 294
```

Gly Gly Gly Gly His His His Ala Ala Ala
1               5                   10

<210> SEQ ID NO 295
<211> LENGTH: 6
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (6)..(6)
<223> OTHER INFORMATION: AMIDATION

<400> SEQUENCE: 295

Gly His His His His Ala
1               5

<210> SEQ ID NO 296
<211> LENGTH: 6
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (6)..(6)
<223> OTHER INFORMATION: AMIDATION

<400> SEQUENCE: 296

Gly His His His His Gln
1               5

<210> SEQ ID NO 297
<211> LENGTH: 7
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (7)..(7)
<223> OTHER INFORMATION: AMIDATION

<400> SEQUENCE: 297

Gly His His His His His Glu
1               5

<210> SEQ ID NO 298
<211> LENGTH: 6
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (6)..(6)
<223> OTHER INFORMATION: AMIDATION

<400> SEQUENCE: 298

```
Gly His His His His Ser
1               5

<210> SEQ ID NO 299
<211> LENGTH: 7
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (7)..(7)
<223> OTHER INFORMATION: AMIDATION

<400> SEQUENCE: 299

Gly His His His His Gln Gln
1               5

<210> SEQ ID NO 300
<211> LENGTH: 5
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)

<400> SEQUENCE: 300

His His His His Gly
1               5

<210> SEQ ID NO 301
<211> LENGTH: 6
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)

<400> SEQUENCE: 301

His His His His Ala Gly
1               5

<210> SEQ ID NO 302
<211> LENGTH: 4
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (4)..(4)
<223> OTHER INFORMATION: AMIDATION

<400> SEQUENCE: 302

Gly His His His
1

<210> SEQ ID NO 303
<211> LENGTH: 4
```

```
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (4)..(4)
<223> OTHER INFORMATION: AMIDATION

<400> SEQUENCE: 303

His Gly His His
1

<210> SEQ ID NO 304
<211> LENGTH: 4
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (4)..(4)
<223> OTHER INFORMATION: AMIDATION

<400> SEQUENCE: 304

His His His His
1

<210> SEQ ID NO 305
<211> LENGTH: 6
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)
<220> FEATURE:
<221> NAME/KEY: MOD_RES
<222> LOCATION: (6)..(6)
<223> OTHER INFORMATION: AMIDATION

<400> SEQUENCE: 305

His His His His His Gln
1               5

<210> SEQ ID NO 306
<211> LENGTH: 4
<212> TYPE: PRT
<213> ORGANISM: artificial sequence
<220> FEATURE:
<223> OTHER INFORMATION: hormone analogue
<220> FEATURE:
<221> NAME/KEY: NON_TER
<222> LOCATION: (1)..(1)

<400> SEQUENCE: 306

His His His Gly
1

<210> SEQ ID NO 307
<211> LENGTH: 6
<212> TYPE: PRT
<213> ORGANISM: artificial sequence
<220> FEATURE:
```

```
<223> OTHER INFORMATION: hormone analogue
<220> FEATURE:
<221> NAME/KEY: NON_TER
<222> LOCATION: (1)..(1)

<400> SEQUENCE: 307

His His His His His Gly
1               5

<210> SEQ ID NO 308
<211> LENGTH: 29
<212> TYPE: PRT
<213> ORGANISM: artificial sequence
<220> FEATURE:
<223> OTHER INFORMATION: hormone analogue
<220> FEATURE:
<221> NAME/KEY: MISC_FEATURE
<222> LOCATION: (16)..(16)
<223> OTHER INFORMATION: The residue at this position is Gln or Glu
<220> FEATURE:
<221> NAME/KEY: MISC_FEATURE
<222> LOCATION: (17)..(17)
<223> OTHER INFORMATION: The residue at this position is Arg or Lys
<220> FEATURE:
<221> NAME/KEY: MISC_FEATURE
<222> LOCATION: (24)..(24)
<223> OTHER INFORMATION: The residue at this position is Gln or Glu
<220> FEATURE:
<221> NAME/KEY: NON_TER
<222> LOCATION: (29)..(29)
<220> FEATURE:
<221> NAME/KEY: MISC_FEATURE
<222> LOCATION: (29)..(29)
<223> OTHER INFORMATION: The residue at this position is Gly or Thr

<400> SEQUENCE: 308

His Ser Gln Gly Thr Phe Thr Ser Asp Tyr Ser Lys Tyr Leu Asp Gln
1               5                   10                  15

Arg Arg Ala His Glu Phe Ile Gln Trp Leu Leu Asn Gly
            20                  25

<210> SEQ ID NO 309
<211> LENGTH: 29
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (29)..(29)
<223> OTHER INFORMATION: AMIDATION

<400> SEQUENCE: 309

His Ser Gln Gly Thr Phe Thr Ser Asp Tyr Ser Lys Tyr Leu Asp His
1               5                   10                  15

Arg Arg Ala Lys Asp Phe Val Gln Trp Leu Met Asn Thr
            20                  25

<210> SEQ ID NO 310
<211> LENGTH: 29
<212> TYPE: PRT
<213> ORGANISM: artificial sequence
<220> FEATURE:
<223> OTHER INFORMATION: hormone analogue

<400> SEQUENCE: 310

His Ser Gln Gly Thr Phe Thr Ser Asp Tyr Ser Lys Tyr Leu Asp Ser
1               5                   10                  15

Lys Lys Ala Gln Glu Phe Val Gln Trp Leu Leu Asn Thr
```

```
<210> SEQ ID NO 311
<211> LENGTH: 29
<212> TYPE: PRT
<213> ORGANISM: artificial sequence
<220> FEATURE:
<223> OTHER INFORMATION: hormone analogue
<220> FEATURE:
<221> NAME/KEY: MOD_RES
<222> LOCATION: (29)..(29)
<223> OTHER INFORMATION: AMIDATION

<400> SEQUENCE: 311

His Ser Gln Gly Thr Phe Thr Ser Asp Tyr Ser Lys Tyr Leu Asp Ser
1               5                   10                  15

Lys Lys Ala Gln Glu Phe Val Gln Trp Leu Met Asn Thr
            20                  25

<210> SEQ ID NO 312
<211> LENGTH: 29
<212> TYPE: PRT
<213> ORGANISM: artificial sequence
<220> FEATURE:
<223> OTHER INFORMATION: hormone analogue

<400> SEQUENCE: 312

His Ser Gln Gly Thr Phe Thr Ser Asp Tyr Ser Lys Tyr Leu Asp Ser
1               5                   10                  15

Lys Lys Ala Gln Glu Phe Val Glu Trp Leu Met Asn Thr
            20                  25
```